(12) United States Patent
Takakura et al.

(10) Patent No.: US 8,298,819 B2
(45) Date of Patent: Oct. 30, 2012

(54) COSMID VECTOR FOR PLANT TRANSFORMATION AND USE THEREOF

(75) Inventors: Yoshimitsu Takakura, Iwata (JP); Toshihiko Komari, Iwata (JP); Yuji Ishida, Iwata (JP); Toshiyuki Komori, Iwata (JP); Yukoh Hiei, Iwata (JP); Toshiki Mine, Iwata (JP); Teruyuki Imayama, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 536 days.

(21) Appl. No.: 12/306,163

(22) PCT Filed: Jun. 25, 2007

(86) PCT No.: PCT/JP2007/062720
§ 371 (c)(1),
(2), (4) Date: Mar. 16, 2009

(87) PCT Pub. No.: WO2007/148819
PCT Pub. Date: Dec. 27, 2007

(65) Prior Publication Data
US 2010/0132068 A1    May 27, 2010

(30) Foreign Application Priority Data
Jun. 23, 2006  (WO) ................. PCT/JP2006/312633

(51) Int. Cl.
*C12N 15/82* (2006.01)
*C12N 15/19* (2006.01)
*C12N 15/00* (2006.01)

(52) U.S. Cl. ................... 435/320.1; 536/23.1; 536/24.2; 800/278; 800/294

(58) Field of Classification Search ........................ None
See application file for complete search history.

(56) References Cited

U.S. PATENT DOCUMENTS

| 5,733,744 A | 3/1998 | Hamilton | |
|---|---|---|---|
| 6,323,396 B1 * | 11/2001 | Dirks et al. | .................. 800/294 |
| 2003/0188344 A1 * | 10/2003 | Lynn et al. | .................... 800/294 |

FOREIGN PATENT DOCUMENTS

| EP | 0841402 A2 | 5/1998 |
|---|---|---|
| EP | 1 688 489 A1 | 8/2006 |
| JP | 10-155485 A | 6/1998 |
| WO | WO-2005/040374 A1 | 5/2005 |

OTHER PUBLICATIONS

Selvaraj et al 1985 Plasmid 13:70-74, provided by Applicant.*
Ma et al 1992 Gene 117:161-167, provided by Applicant.*
Komari et al 2006 Methods in Molecular Biology 343:15-41, provided by Applicant.*
G. Selvaraj and V. N. Iyer, Plasmid, 13, pp. 70-74 (1985).
Komari et al., The Plant Journal, 10(1), pp. 165-174 (1996).
Jin et al., Journal of Bacteriology, vol. 169, No. 10, pp. 4417-4425 (Oct. 1987).
Hauser et al., Development, vol. 127, pp. 2219-2226 (2000).
Kiyosue et al., Proc. Natl. Acad. Sci. USA, vol. 96, pp. 4186-4191 (Mar. 1999).
Schumacher et al., Proc. Natl. Acad Sci. USA, vol. 96, pp. 290-295 (Jan. 1999).
C. M. Hamilton, Gene, vol. 200, pp. 107-116 (1997).
Hansen et al., Proc. Natl. Acad. Sci. USA, vol. 91, pp. 7603-7607 (Aug. 1994).
van der Fits et al., Plant Molecular Biology, vol. 43, pp. 495-502, (2000).
Kikuchi et al., Plant Biotechnology, vol. 22, pp. 295-302 (2005).
C. M. Thomas, Plasmid, vol. 16, pp. 15-29 (1986).
Pansegrau et al., J. Mol. Biol., vol. 239, pp. 623-663 (1994).
S. B. Gelvin, Microbiology and Molecular Biology Reviews, vol. 67, No. 1, pp. 16-37 (Mar. 2003).
Chen et al., Mol. Gen. Genet, vol. 230, pp. 302-309 (1991).
Close et al., Plasmid, vol. 12, pp. 111-118 (1984).
An et al., "New Cloning Vehicles for Transformation of Higher Plants," The EMBO Journal, vol. 4, No. 2, 1985, pp. 277-284.
Jagura-Burdzy et al., "IncC of broad-host-range plasmid RK2 modulates KorB Transcriptional Repressor Activity in vivo and Operator Binding in vitro," Journal of Bacteriology, vol. 181, No. 9, May 1999, pp. 2807-2815.
Klee et al., "Plant Gene Vectors and Genetic Transformation: Plant Transformation Systems Based on the Use of *Agrobacterium-tumefaciens*," Cell Culture and Somatic Cell Genetics of Plants, Molecular Biology of Plant Nuclear Genes, vol. 6, Chapter 1, pp. 1-23, 1990.
Komari et al., "Binary Vectors and Super-binary Vectors," Methods in Molecular Biology, vol. 343: *Agrobacterium* Protocols, 2/e, vol. 1, 2006, pp. 15-41.
Lazo et al., "A DNA Transformation-Competent *Arabidopsis* Genomic Library in *Agrobacterium*," Bio/Technology, vol. 9, No. 10, Oct. 1, 1991, pp. 963-967.
Ma et al., "Use of cosmid libraries in plant transformations," Methods in Molecular Biology, vol. 44, 1995, pp. 351-367.

(Continued)

*Primary Examiner* — Brent T Page
(74) *Attorney, Agent, or Firm* — Birch, Stewart, Kolasch & Birch, LLP

(57) ABSTRACT

The present invention aims to provide novel vectors for plant transformation.
The vectors of the present invention are cosmid vectors having a full length of 15 kb or less characterized in that:
1) they contain an origin of replication of an IncP plasmid, but do not contain any origin of replication of other plasmid groups;
2) they contain the trfA1 gene of an IncP plasmid;
3) they contain an oriT of an IncP plasmid;
4) they contain the incC1 gene of an IncP plasmid;
5) they contain a cos site of lambda phage and the cos site is located outside the T-DNA;
6) they contain a drug resistance gene expressed in *E. coli* and a bacterium of the genus *Agrobacterium*;
7) they contain a T-DNA right border sequence of a bacterium of the genus *Agrobacterium*;
8) they contain a T-DNA left border sequence of a bacterium of the genus *Agrobacterium*;
9) they contain a selectable marker gene for plant transformation located between 7) and 8) and expressed in a plant; and
10) they contain restriction endonuclease recognition site(s) located between 7) and 8) for cloning a foreign gene.

12 Claims, 16 Drawing Sheets

OTHER PUBLICATIONS

Ma et al., "Vectors for plant transformation and cosmid libraries," Gene, vol. 117, No. 2, Aug. 15, 1992, pp. 161-167.

Olszewski et al., "Specialized Binary Vector for Plant Transformation: Expression of the *Arabidopsis-thaliana* AHAS Gene in *Nicotiana-tabacum*," Nucleic Acids Research, vol. 16, No. 22, 1988, pp. 10765-10782.

Supplementary European Search Report mailed Mar. 19, 2010 in European Application No. 07767526.2.

Tait et al., "Construction of Cloning Vectors From the Inc-W Plasmid PSA and Their Use in Analysis of Crown Gall Tumor Formation," 1983. NATO Advanced Science Institute Series: Series A, vol. 61, Genetic Engineering in Eukaryotes Symposium, Jul. 26-Aug. 6, 1982.

Bent et al., "RPS2 of *Arabidopsis thaliana*: A Leucine-Rich Repeat Class of Plant Disease Resistance Gene," Science, vol. 265, 1994, pp. 1856-1860.

Bilang et al., "The 3'-terminal region of the hygromycin-B-resistance gene is important for its activity in *Escherichia coli* and *Nicotiana tabacum*," Gene, vol. 100, 1991, pp. 247-250.

Christensen et al., "Maize polyubiquitin genes: structure, thermal perturbation of expression and transcript splicing, and promoter activity following transfer to protoplasts by electroporation," Plant Molecular Biology, vol. 18, 1992, pp. 675-689.

Ditta et al., "Broad host range DNA cloning system for Gram-negative bacteria: Construction of a gene bank of *Rhizobium meliloti*," Proc. Natl. Acad. Sci., USA, vol. 77, No. 12, Dec. 1980, pp. 7347-7351.

Frame et al., "*Agrobacterium tumefaciens*-Mediated Transformation of Maize Embryos Using a Standard Binary Vector System," Plant Physiol., vol. 129, 2002, pp. 13-22.

Hamilton et al., "Stable transfer of intact high molecular weight DNA into plant chromosomes," Proc. Natl. Acad. Sci., USA, vol. 93, 1996, pp. 9975-9979.

Hiei et al., "Efficient transformation of rice (*Oryza sativa* L.) mediated by *Agrobacterium* and sequence analysis of the boundaries of the T-DNA," The Plant Journal, 1994, No. 6, vol. 2, pp. 271-282.

Hiei et al., "Improved protocols for transformation of indica rice mediated by *Agrobacterium tumefaciens*," Plant Cell, Tissue and Organ Culture, vol. 85, 2006, pp. 271-283.

Hirsch et al., "Short Communication—A Physical Map of pPH1JI and pJB4JI," Plasmid, vol. 12, 1984, No. 139-141.

Ishida et al., "High efficiency transformation of maize (*Zea mays* L.) mediated by *Agrobacterium tumefaciens*," Nature Biotechnology, vol. 14, Jun. 1996, pp. 745-750.

Ishida et al., "Improved Protocol for Transformation of Maize (*Zea mays* L.) Mediated by *Agrobacterium tumefaciens*," Plant Biotechnology, vol. 20, No. 1, 2003, pp. 57-66.

Kazama et al., "A pentatricopeptide repeat-containing gene that promotes the processing of aberrant atp6 RNA of cytoplasmic male-sterile rice," FEBS Letters, vol. 544, 2003, pp. 99-102.

Klee et al., "Gene rescue in plants: A model system for "shotgun" cloning by retransformation," Mol. Gen. Genet., 1987, vol. 210, pp. 282-287.

Knauf et al., "Wide Host Range Closing Vectors: A Cosmid Clone Bank of an *Agrobacterium* Ti Plasmid," Plasmid, No. 8, 1982, pp. 45-54.

Komori et al., "Map-based cloning of a fertility restorer gene, Rf-1, in rice (*Oryza sativa* L.)," The Plant Journal, vol. 37, 2004, pp. 315-325.

Konieczny et al., "A procedure for mapping *Arabidopsis* mutations using co-dominant ecotype-specific PCR-based markers," The Plant Journal, vol. 4, No. 2, 1993, pp. 403-410.

Lin et al., "Efficient linking and transfer of multiple genes by a multigene assembly and transformation vector system," PNAS, vol. 100, No. 10, May 13, 2003, pp. 5962-5967.

Liu et al, "Complementation of plant mutants with large genomic DNA fragments by a transformation-competent artificial chromosome vector accelerates positional cloning," Proc. Natl. Acad. Sci., USA, vol. 96, 1999, pp. 6535-6540.

Nakano et al., "Rearrangements of large-insert T-DNAs in transgenic rice," Mol. Gen. Genomics, 2005, vol. 273: pp. 123-129.

Okumura et al., "The region essential for efficient autonomous replication of pSa in *Escherichia coli*," Mol. Gen. Genet., vol. 235, 1992, pp. 55-63.

Pansegrau et al., "Complete Nucleotide Sequence of Birmingham IncPa Plasmids—Compilation and Comparative Analysis," J. Mol. Biol., 1994, vol. 239, pp. 623-663.

Pazour et al., "Constitutive Mutations of *Agrobacterium tumefaciens* Transcriptional Activator virG," Journal of Bacteriology, vol. 174, No. 12, Jun. 1992, pp. 4169-4174.

Schmidhauser et al., "Regions of Broad-Host-Range Plasmid RK2 Involved in Replication and Stable Maintenance in Nine Species of Gram-Negative Bacteria," Journal of Bacteriology, vol. 164, No. 1, Oct. 1985, pp. 446-455.

Shibata et al., "Trends in Plant Science, *Agrobacterium*-mediated plant transformation with large DNA fragments," vol. 5, No. 8, Aug. 2000, pp. 354-357.

Simoens et al., "A binary vector for transferring genomic libraries to plants," vol. 14, No. 20, 1986, pp. 8073-8090.

Tao et al., "Cloning and stable maintenance of DNA fragments over 300 kb in *Escherichia coli* with conventional plasmid-based vectors," Nucleic Acids Research, 1998, vol. 26, No. 21, pp. 4901-4909.

Wang et al., "Construction of an efficient expression system for *Agrobacterium tumefaciens* based on the coliphage T5 promoter," Gene 242, 2000, pp. 105-114.

Ward et al., "Characterization of the virB Operon from an *Agrobacterium tumefaciens* Ti Plasmid," The Journal of Biological Chemistry, vol. 263, No. 12, Issue of Apr. 25, 1988, pp. 5804-5814.

Winans et al., "A gene essential for *Agrobacterium* virulence is homologous to a family of positive regulatory loci," Proc. Natl. Acad. Sci., USA, vol. 83, Nov. 1986, pp. 8278-8282.

Zambryski et al., "Tumor DNA Structure in Plant Cells Transformed by *A. tumefaciens*," Science, vol. 209, Sep. 19, 1980, pp. 1385-1391.

* cited by examiner

4. T-DNA insertion

COSMID VECTOR FOR PLANT TRANSFORMATION AND USE THEREOF

TECHNICAL FIELD

The present invention relates to novel cosmid vectors for transforming plant and use thereof.

BACKGROUND ART

Various vectors have been previously developed for the purpose of plant transformation.

Recently, the entire genome sequences of *Arabidopsis thaliana* and rice (*Oryza sativa*) were elucidated, which moved the focus of plant genome studies from the accumulation of nucleotide sequence information to the elucidation of gene functions. For the elucidation of gene functions, experiments are absolutely necessary in which cloned DNA is transferred into a plant to analyze changes in the phenotype. If large DNA could be transferred in this operation, the study efficiency would be dramatically improved.

Thus, a number of vectors intended to transfer large DNA fragments into plants were developed. As typical examples, cosmid vectors for plant transformation were prepared, such as pOCA18 (Olszewski et al., 1988, Nucleic Acids Res. 16: 10765-10782) and pLZO3 (Lazo et al., 1991, Bio/Technology 9: 963-967). The use of a cosmid has the advantage that a lambda phage packaging reaction can be used, which allows easy cloning of relatively large genomic fragments (Sambrook J. and Russell D. W. 2001. Molecular Cloning, A Laboratory Manual, 3rd edn. Cold Spring Harbor Laboratory Press, Cold Spring Harbor, N.Y., USA.). In cloning with a cosmid vector and a packaging reaction, the total size of the vector and the insert fragment is 40 kb-50 kb so that the size of the insert fragment is restricted within a certain range by the size of the vector and the sizes of the vector and the insert fragment inversely correlate with each other.

Vectors such as pOCA18 and pLZO3 contain elements for plant transformation such as T-DNA border sequences and a selectable marker (kanamycin resistance gene) in pRK290 (Ditta et al., 1980, Proc. Natl. Acad. Sci. USA 77: 7347-7351) which is a typical vector having an origin of replication (oriV) of an IncP plasmid that is functional in both *E. coli* and *Agrobacterium*. These vectors per se had a size of 24.3-30.1 kb, and therefore, the size of DNA that can be cloned using a packaging reaction was about 20 kb (pOCA18), or about 13-22 kb (pLZO3) on average. These vectors have an origin of replication (oriV) of an IncP plasmid, but other vectors such as pCIT103 and pCIT104 (Ma et al. 1992 Gene 117: 161-167) have an origin of replication from ColE1 in addition to an origin of replication (oriV) of an IncP plasmid. On the other hand, pC22 (Simoens et al. 1986 Nucleic Acids Res 14: 8073-8090) is a vector having an origin of replication from ColE1 and an origin of replication from an Ri plasmid. Other cosmid vectors capable of plant transformation include pMON565 (Klee et al. 1987 Mol Gen Genet 210: 282-287) and pCLD04541 (Bent et al. 1994 Science 265: 1856-1860), but they are not suitable for cloning DNA fragments of 25 kb or more because their own sizes are 24 kb and 29 kb, respectively. Other examples such as pE4 cos(16 kb, Klee et al. 1987 Mol Gen Genet 210: 282-287), pMON565, pLZ03, pOCA18, pCLD04541, pC22 and the like had a structure containing a cos site within the T-DNA.

Subsequently, the BIBAC vector (binary bacterial artificial chromosome, Hamilton U.S. Pat. No. 5,733,744, Hamilton et al., 1996, Proc. Natl. Acad. Sci. USA 93:9975-9979, Hamilton, 1997, Gene 200:107-116) was developed, which is capable of cloning DNA fragments of up to about 150 kb and transferring them into plants. This vector is based on a BAC vector capable of carrying large DNA fragments and further contains elements for plant transformation such as T-DNA border sequences and a selectable marker as well as an origin of replication for *Agrobacterium*. The TAC vector (transformation-competent bacterial artificial chromosome) pYL-TAC7 (Liu et al., 1999, Proc. Natl. Acad. Sci. USA 96: 6535-6540.) was also developed, which is capable of cloning DNA of up to about 80 kb and transferring it into plants. This vector is based on a high-capacity PAC vector (P1-derived artificial chromosome) using the replication mechanism of P1 phage and contains elements for plant transformation such as T-DNA border sequences and a selectable marker as well as an origin of replication for *Agrobacterium*. These vectors contain an origin of replication of (ori) from a plasmid existing as a single copy per cell in *E. coli* and *Agrobacterium* for the purpose of stably maintaining a large foreign gene. That is, they use an F factor on (BIBAC) or a P1 phage ori (TAC) as ori for *E. coli* and an Ri on from *Agrobacterium rhizogenes* (both BIBAC and TAC) as on for *Agrobacterium*. However, the use of an origin of replication from a single-copy plasmid is not necessarily essential, and vectors having an origin of replication (oriV) of an IncP plasmid known to exist as a few copies per cell such as pSLJ1711 and pCLD04541 were reported to be capable of stably maintaining plant genomic DNA fragments of more than 100 kb in size (Tao and Zhang (1998) Nucleic Acids Res 26: 4901-4909). In addition, pBIGRZ was also reported, which contains Ri ori in the versatile binary plasmid vector pBI121 (JPA Hei-10-155485).

Such vectors can be used to clone large DNA fragments far exceeding 50 kb, but involve complicated cloning operations. Cloning of large DNA requires skilled techniques and a considerable amount of time and labor. Transformation with BIBAC requires special *Agrobacterium* cells overexpressing virG or the like and results in a much lower transformation efficiency (the number of selected calli/inoculated leaf section) for fragments of 150 kb as compared with those of normal small vectors (Hamiltin et al., 1996, Proc Natl Acad Sci USA 93: 9975-9979, Shibata and Liu, 2000, Trend Plant Sci 5: 354-357). Thus, transformation of large fragments into plants with BIBAC or TAC is limited to a few specific examples of large fragments (e.g., Hamiltin et al., 1996, Proc Natl Acad Sci USA 93: 9975-9979, Liu et al., 1999, Proc Natl Acad Sci USA 96: 6535-6540, Lin et al., 2003, Proc Natl Acad Sci USA 100: 5962-5967, Nakano et al., 2005, Mol Gen Genomics 273: 123-129).

As described above, pCLD04541 is a cosmid of 29 kb in size, and therefore, the size of DNA fragments that can be cloned using a lambda phage packaging reaction is 10-20 kb. If cloning of larger DNA fragments is intended, a packaging reaction cannot be used as described above, and thus complicated cloning operations and a considerable amount of time and labor are required.

Recently, genetic markers based on DNA sequence polymorphisms or so-called DNA markers are used more and more frequently with the advance in genome studies of higher plants. Many attempts have been made to clone unknown genes of higher plants known only by their phenotypes on the basis of genetic map information using DNA markers, i.e., so-called map-based cloning. Generally, the basic protocol of map-based cloning is as follows.

1. Examine a relatively small segregating population with a set of DNA markers widely used for rough mapping of a candidate region on a chromosome.

2. Screen a large segregating population with a set of DNA markers newly designed for the particular region of the genome to narrow down the candidate region.

3. Determine the nucleotide sequence of the genetic region and guess a candidate gene.

4. Transfer a DNA fragment containing the candidate gene into a plant and determine the effect/function of the gene on the basis of the phenotype.

Many previous successful cases often involve narrowing down the genetic region to about 1-3 genes in step 3 and transferring several DNA fragments of several kilobases or less in step 4. However, it is not always easy to narrow down the genetic region. For example, it is often impossible to narrow down the genetic region to 150 kb or less in chromosomal regions near centromeres because of the low frequency of genetic recombination upon cross-hybridization. Even cases where narrowing down is possible often require repeating the operation of step 2 and therefore enormous amounts of time. Even if narrowing down to about 50 kb were possible, it would be very difficult to guess a candidate gene without strong information linking the phenotype to the gene sequence in step 3.

Thus, map-based cloning is relatively easy until the step of defining a candidate region including one to a few DNA fragments cloned by a BAC vector by narrowing down to some extent (to 50 kb to several hundreds of kilobases), but it is often technically difficult to further pursue the analysis to practically identify a gene, and even if it is possible, enormous amounts of labor and time are often required.

REFERENCES

Patent Publication No. 1: U.S. Pat. No. 5,733,744
Patent Publication No. 2: Japanese Patent Laid-open Publication No. H10-155485
Patent Publication No. 3: WO2005/040374
Non-patent Publication No. 1: Olszewski et al., 1988, Nucleic Acids Res. 16: 10765-10782
Non-patent Publication No. 2: Lazo et al., 1991, Bio/Technology 9: 963-967
Non-patent Publication No. 3: Ditta et al., 1980, Proc. Natl. Acad. Sci. USA 77: 7347-7351
Non-patent Publication No. 4: Ma at al. 1992 Gene 117: 161-167
Non-patent Publication No. 5: Simoens et al. 1986 Nucleic Acids Res 14: 8073-8090
Non-patent Publication No. 6: Klee at al. 1987 Mol Gen Genet 210: 282-287
Non-patent Publication No. 7: Bent et al. 1994 Science 265: 1856-1860
Non-patent Publication No. 8: Hamilton et al., 1996, Proc. Natl. Acad. Sci. USA 93:9975-9979,
Non-patent Publication No. 9: Hamilton, 1997, Gene 200: 107-116
Non-patent Publication No. 10: Liu et al., 1999, Proc. Natl. Acad. Sci. USA 96: 6535-6540
Non-patent Publication No. 11: Tao and Zhang, 1998, Nucleic Acids Res 26: 4901-4909
Non-patent Publication No. 12: Shibata and Liu, 2000, Trend Plant Sci 5: 354-357
Non-patent Publication No. 13: Lin et al., 2003, Proc Natl Acad Sci USA 100: 5962-5967,
Non-patent Publication No. 14: Nakano et al., 2005, Mol Gen Genomics 273: 123-129
Non-patent Publication No. 15: Pansegrau et al. (1994) J Mol Biol 239: 623-663
Non-patent Publication No. 16: Knauf and Nester 1982 Plasmid 8: 45-54
Non-patent Publication No. 17: Komari et al. 1996 Plant J 10:165-174
Non-patent Publication No. 18: Zambryski et al. 1980 Science 209: 1385-1391
Non-patent Publication No. 19: Schmidhauser and Helinski, J. Bacteriol. 164:446-455, 1985
Non-patent Publication No. 20: Winans et al. 1986 Proc. Natl. Acad. Sci. USA 83: 8278-8282
Non-patent Publication No. 21: Pazour et al. 1992 J. Bac 174:4169-4174
Non-patent Publication No. 22: Ward et al. (1988) J Biol Chem 263: 5804-5814
Non-patent Publication No. 23: Frame et al. 2002 Plant Physiol 129: 13-22
Non-patent Publication No. 24: Hansen et al. 1994 ProNAS 91:7603-7607
Non-patent Publication No. 25: Ishida et al. 1996 Nat Biotechnol 14:745-50
Non-patent Publication No. 26: Close et al. 1984 Plasmid 12: 111-118
Non-patent Publication No. 27: Jin et al. 1987 J Bacteriol 169: 4417-4425
Non-patent Publication No. 28: Wang et al. 2000 Gene 242: 105-114
Non-patent Publication No. 29: Okumura and Kado (1992) Mol Gen Genet 235: 55-63
Non-patent Publication No. 30: Christensen et al. 1992 Plant Mol Biol 18: 675-689
Non-patent Publication No. 31: Bilang et al. (1991) Gene 100: 247-250
Non-patent Publication No. 32: Hirsch and Beringer 1984 Plasmid 12: 139-141
Non-patent Publication No. 33: Konieczny and Ausubel 1993 Plant Journal 4: 403-410
Non-patent Publication No. 34: Hiei et al. (1994) Plant J 6: 271-282
Non-patent Publication No. 35: Ishida et al. (2003) Plant Biotechnology 20:57-66
Non-patent Publication No. 36: Hiei and Komari (2006) Plant Cell, Tissue and Organ Culture 85: 271-283
Non-patent Publication No. 37: Komori et al. (2004) Plant J 37: 315-325
Non-patent Publication No. 38: Kazama and Toriyama (2003) FEBS lett 544: 99-102.

DISCLOSURE OF THE INVENTION

Problems to be Solved by the Invention

WO2005/040374, which is incorporated by reference herein in its entirety, discloses a method for efficiently selecting and preparing a number of genomic DNA fragments capable of improving traits expressed in heterosis or quantitative traits as cloned DNA fragments. We have selected large genomic DNA fragments capable of introducing agriculturally useful mutations by using the method described in WO2005/040374. However, the success rate of transferring clones carried in *E. coli* into *Agrobacterium* was about 80%. Moreover, only about 60% of *Agrobacterium* strains harboring clones was able to transform plants. In view of this result, we examined whether or not the efficiency of the method of WO2005/040374 could be significantly improved by changing the vector used. However, the efficiency of this method could not be improved by any vector ever known.

Thus, an object of the present invention is to provide a novel vector capable of improving the efficiency of selecting and cloning relatively large genomic DNA fragments, e.g., in the method described in WO2005/040374.

Another object of the present invention is to provide a vector preferably fulfilling all of the requirements below:

it allows efficient cloning of DNA fragments of about 25-40 kb in size;

it is stably maintained in *E. coli* and *Agrobacterium* cells;

it can be efficiently introduced into *Agrobacterium*;

the copy number per cell in *E. coli* and *Agrobacterium* is 4-5; and it allows efficient transfer of only cloned DNA fragments of interest into plants, preferably monocotyledons.

Still another object of the present invention is to provide a gene transfer method for transferring a gene into a plant at a very high efficiency using such a vector.

Still another object of the present invention is to provide a method for rapidly narrowing down a gene region for completing map-based cloning with ease in a short time using such a vector.

Still another object of the present invention is to provide a plasmid capable of further improving the transformation efficiency by combining it with said vector.

Means for Solving the Problems

Cosmid Vectors

The cosmid vectors of the present invention are vectors having a full length of 15 kb or less satisfying all of the following criteria (hereinafter referred to as "pLC vectors"):

1) they contain an origin of replication (oriV) of an IncP plasmid, but do not contain any origin of replication of other plasmid groups;

2) they contain the trfA1 gene of an IncP plasmid;

3) they contain an origin of conjugative transfer (oriT) of an IncP plasmid;

4) they contain the incC1 gene of an IncP plasmid;

5) they contain a cos site of lambda phage and the cos site is located outside the T-DNA;

6) they contain a drug resistance gene expressed in *E. coli* and a bacterium of the genus *Agrobacterium*;

7) they contain a T-DNA right border sequence of a bacterium of the genus *Agrobacterium*;

8) they contain a T-DNA left border sequence of a bacterium of the genus *Agrobacterium*;

9) they contain a selectable marker gene for plant transformation located between 7) and 8) and expressed in a plant; and 10) they contain restriction endonuclease recognition site(s) located between 7) and 8) for cloning a foreign gene.

The vectors of the present invention are cosmid vector containing a cos site of lambda phage. This allows cloning of relatively large genomic fragments by a packaging reaction (Sambrook J. and Russell D. W. 2001. Molecular Cloning, A Laboratory Manual, 3rd edn. Cold Spring Harbor Laboratory Press, Cold Spring Harbor, N.Y., USA.). In cloning using a packaging reaction of a cosmid vector, the total size of the vector and the insert fragment is around 40 kb-50 kb so that the size of the insert fragment is restricted within a certain range by the size of the vector. The vectors of the present invention have a full length of 15 kb or less, preferably 12-14 kb because they are intended to clone a DNA fragment of up to about 25-40 kb, preferably 30-40 kb.

1) An origin of replication (oriV) of an IncP plasmid: The oriV is functional in both *E. coli* and *Agrobacterium*. The nucleotide sequence of the oriV of the present invention is not specifically limited so far as it has the function of oriV, i.e., the function of an origin of replication of an IncP plasmid.

The oriV has molecular biological properties described in detail in Pansegrau et al. (1994) J Mol Biol 239: 623-663, and it is defined as nucleotides 12200-12750 of the sequence of Genbank/EMBL Accession Number L27758 (full length 60099 bp). This corresponds to nucleotides 3451-4002 of SEQ ID NO: 1 (core sequence of oriV).

The oriV can be conventionally prepared from an IncP plasmid such as pVK102 (Knauf and Nester 1982 Plasmid 8: 45-54). For example, a 0.9 kb DNA (nucleotides 3345-4247 of SEQ ID NO: 1) amplified by PCR from pVK102 can be used as the oriV.

Alternatively, a nucleic acid containing a nucleotide sequence hybridizing to a complementary strand of the nucleotide sequence of nucleotides 3451-4002, more preferably 3345-4247 of SEQ ID NO: 1 described above under stringent conditions and having the function of oriV can also be used. Alternatively, a nucleic acid containing a nucleotide sequence having an identity of at least 95%, more preferably 97%, still more preferably 99% to the nucleotide sequence of nucleotides 3451-4002, more preferably 3345-4247 of SEQ ID NO: 1 described above and having the function of oriV can also be used.

It will be recognized by those skilled in the art that a shorter region in nucleotides 3451-4002 of SEQ ID NO: 1 may be selected as a sequence having a similar function. We investigated from various viewpoints the reason why the final transformation efficiency was only about 50% (80%×60%=48%) when the method described in WO2005/040374 was used, and concluded that this might be ascribable to the use of the cloning vector pSB200.

A replication origin of pSB200 is from ColE1, and plasmids having an origin of replication from ColE1 exist in a relatively high copy number, i.e., 30-40 copies per *E. coli* cell. Tao and Zhang (1998, Nucleic Acids Res 26: 4901-4909) assume that *E. coli* can stably maintain 1200-1500 kb of foreign DNA per cell. If 30-40 kb of DNA is cloned by pSB200, the total DNA amount including the vector size reaches 1200-2000 kb per cell, which may exceed the range assumed above. Another possible reason is that pSB200 is a plasmid that is not replicated alone in *Agrobacterium*. Thus, a vector having an origin of replication (oriV) of an IncP plasmid called pSB1 is preliminarily introduced into *Agrobacterium*, and a cointegrate between pSB200 and pSB1 is prepared via homologous recombination between DNA sequences contained in both pSB200 and pSB1, thereby introducing pSB200 into *Agrobacterium*. It is undeniable that some adverse phenomenon could occur during such an operation to result in the failure in the transfer of pSB200.

If the copy number in *E. coli* and *Agrobacterium* is too low, however, the analysis of DNA or the like will be inefficient.

Based on the foregoing discussion, we prepared and tested vectors containing an origin of replication (oriV) of an IncP plasmid that is functional in both *E. coli* and *Agrobacterium* but not any origin of replication of other plasmid groups and existing in 4-5 copies in these bacteria. As a result, we found that the transformation efficiency is improved by using such vectors in plant transformation, specifically e.g., in the method described in WO2005/040374, and thus achieved the present invention.

2) The trfA1 gene of an IncP plasmid: The trfA1 gene is important as a transacting replication factor of IncP plasmids and necessary for an oriV to perform its function. The nucleotide sequence of the trfA1 gene of the present invention is not specifically limited so far as it has the function of trfA1, i.e. the function of a transacting replication factor.

It has molecular biological properties described in detail in Pansegrau et al. (1994) J Mol Biol 239: 623-663, and it is defined as nucleotides 16521-17669 of the sequence of Genbank/EMBL Accession Number L27758 (full length 60099 bp). This corresponds to nucleotides 6323-7471 of SEQ ID NO: 1 (core sequence of trfA1).

TrfA1 can be conventionally prepared from an IncP plasmid such as pVK102 (Knauf and Nester 1982 Plasmid 8: 45-54). For example, a 3.2 kb DNA fragment (nucleotides 5341-8507 of SEQ ID NO: 1) amplified by PCR from pVK102 can be used as the trfA1 gene.

Alternatively, a nucleic acid containing a nucleotide sequence hybridizing to a complementary strand of the nucleotide sequence of nucleotides 6323-7471, more preferably 5341-8507 of SEQ ID NO: 1 described above under stringent conditions and having the function of the trfA1 gene can also be used. Alternatively, a nucleic acid containing a nucleotide sequence having an identity of at least 95%, more preferably 97%, still more preferably 99% to the nucleotide sequence of nucleotides 6323-7471, more preferably 5341-8507 of SEQ ID NO: 1 described above and having the function of the trfA1 gene can also be used.

It will be recognized by those skilled in the art that a shorter region in nucleotides 6323-7471 of SEQ ID NO: 1 may be selected as a sequence having a similar function.

3) An origin of conjugative transfer (oriT) of an IncP plasmid: oriT is an element responsible for conjugation (mating). One of the purposes of the vectors of the present invention is to perform large-scale and high-efficient transformation. For that purpose, conjugation (mating) between *E. coli* and *Agrobacterium* is necessary, and oriT contributes to the conjugation (mating). The sequence of the oriT of the present invention is not specifically limited so far as it has the function of oriT, i.e. the function of an element responsible for conjugation (mating).

The oriT has molecular biological properties described in detail in Pansegrau et al. (1994) J Mol Biol 239: 623-663, and it is defined as nucleotides 51097-51463 of the sequence of Genbank/EMBL Accession Number L27758 (full length 60099 bp). The oriT can be conventionally prepared from an IncP plasmid such as pVK102 (Knauf and Nester 1982 Plasmid 8: 45-54). For example, a 0.8 kb DNA fragment (nucleotides 1-816 of SEQ ID NO: 1) amplified by PCR from pVK102 can be used as the oriT.

Alternatively, a nucleic acid containing a nucleotide sequence hybridizing to a complementary strand of the nucleotide sequence of nucleotides 1-816 of SEQ ID NO: 1 described above under stringent conditions and having the function of oriT can also be used. Alternatively, a nucleic acid containing a nucleotide sequence having an identity of at least 95%, more preferably 97%, still more preferably 99% to the nucleotide sequence of nucleotides 1-816 of SEQ ID NO: 1 described above and having the function of oriT can also be used.

It will be recognized by those skilled in the art that a shorter region in nucleotides 1-816 of SEQ ID NO: 1 may be selected as a sequence having a similar function.

4) The incC1 gene of an IncP plasmid: The incC1 gene contributes to the stability of IncP plasmids. The nucleotide sequence of the incC1 gene of the present invention is not specifically limited so far as it has the function of the incC1 gene contributing the stability of IncP plasmids.

This gene has molecular biological properties described in detail in Pansegrau et al. (1994) J Mol Biol 239: 623-663, and it is defined as nucleotides 58260-59354 of the sequence of Genbank/EMBL Accession Number L27758 (full length 60099 bp). This corresponds to nucleotides 1179-2273 of SEQ ID NO: 1 (core sequence of the incC1 gene).

IncC1 can be conventionally prepared from an IncP plasmid such as pVK102 (Knauf and Nester 1982 Plasmid 8: 45-54). For example, a 2.1 kb DNA fragment (nucleotides 817-2935 of SEQ ID NO: 1) amplified by PCR from pVK102 can be used as the incC1 gene.

Alternatively, a nucleic acid containing a nucleotide sequence hybridizing to a complementary strand of the nucleotide sequence of nucleotides 1179-2273, more preferably 817-2935 of SEQ ID NO: 1 described above under stringent conditions and having the function of the incC1 gene can also be used. Alternatively, a nucleic acid containing a nucleotide sequence having an identity of at least 95%, more preferably 97%, still more preferably 99% to the nucleotide sequence of nucleotides 1179-2273, more preferably 817-2935 of SEQ ID NO: 1 described above and having the function of the incC1 gene can also be used.

It will be recognized by those skilled in the art that a shorter region in nucleotides 1179-2273 of SEQ ID NO: 1 may be selected as a sequence having a similar function.

5) A cos site of lambda phage: The vectors of the present invention contain a cos site of lambda phage to utilize the packaging reaction of cosmid vectors. The nucleotide sequence of the cos site of lambda phage of the present invention is not specifically limited so far as it has the function of a cos site of lambda phage, i.e. the function contributing to the packaging reaction of cosmid vectors.

The cos site of lambda phage has molecular biological properties described in detail in Sambrook J. and Russell D. W. (2001), and it has the sequence 5'-aggtcgccgccc-3' (SEQ ID NO: 9) (the core sequence of a cos site of lambda phage). The cos can be conventionally prepared from a plasmid such as pSB11 (Komari et al. 1996 Plant J 10:165-174). For example, a 0.4 kb DNA fragment (nucleotides 2936-3344 of SEQ ID NO: 1) amplified by PCR from pSB11 can be used.

Alternatively, a nucleic acid containing a nucleotide sequence hybridizing to a complementary strand of the nucleotide sequence of SEQ ID NO: 9 described above, more preferably the nucleotide sequence of nucleotides 2936-3344 of SEQ ID NO: 1 under stringent conditions and having the function of a cos site of lambda phage can also be used. Alternatively, a nucleic acid containing a nucleotide sequence having an identity of at least 95%, more preferably 97%, still more preferably 99% to the nucleotide sequence of SEQ ID NO: 9 described above, more preferably the nucleotide sequence of nucleotides 2936-3344 of SEQ ID NO: 1 and having the function of a cos site of lambda phage can also be used.

The cos site should be located outside the T-DNA because undesired DNA will be introduced into plants if the cos site is located inside the T-DNA.

6) The drug resistance gene expressed in *E. coli* and a bacterium of the genus *Agrobacterium* is used as a selectable marker for transformation. This drug resistance gene confers e.g., antibiotic resistance or autotrophy, including, but not limited to, a kanamycin resistance gene, a spectinomycin resistance gene, an ampicillin resistance gene, a tetracycline resistance gene, a gentamycin resistance gene, a hygromycin resistance gene, etc.

7), 8) T-DNA right border sequence (RB) and left border sequence (LB) of a bacterium of the genus *Agrobacterium* are essential for transformation (Zambryski et al. 1980 Science 209: 1385-1391), and a cloning site for a foreign gene is located between them. The nucleotide sequences of the RB and LB of the present invention are not specifically limited so far as they have the function of T-DNA right border sequence (RB) and left border sequence (LB) of a bacterium of the genus *Agrobacterium*. They can be each conventionally prepared from a plasmid such as pSB11 (Komari et al. 1996 Plant J 10:165-174). For example, nucleotides 13253-13277 and 3479-3503 of SEQ ID NO: 2 can be used, respectively.

Alternatively, nucleic acids containing nucleotide sequences hybridizing to complementary strands of the nucleotide sequences of nucleotides 13253-13277 and 3479-3503 of SEQ ID NO: 2 described above under stringent conditions and having the functions of the RB and LB, respectively, can also be used. Alternatively, nucleic acids containing nucleotide sequences having an identity of at least 95%, more preferably 97%, still more preferably 99% to the nucleotide sequences of nucleotides 13253-13277 and 3479-3503 of SEQ ID NO: 2 described above and having the functions of the RB and LB, respectively, can also be used.

It will be recognized by those skilled in the art that shorter regions in nucleotides 13253-13277 and 3479-3503 of SEQ ID NO: 2 may be selected as sequences having similar functions.

9) A selectable marker gene for plant transformation expressed in a plant cell and located between 7) and 8) is included. The selectable marker gene for plant transformation is not specifically limited, and known selectable marker genes can be used. Preferably, it is any one of a hygromycin resistance gene, a phosphinotricin resistance gene, and a kanamycin resistance gene. For use in transformation of monocotyledons, a hygromycin resistance gene or a phosphinotricin resistance gene is preferred.

10) Restriction endonuclease recognition site(s) located between 7) and 8) for cloning a foreign gene are included. The restriction endonuclease recognition sites for cloning a foreign gene are not specifically limited, and known restriction endonuclease recognition sites can be used, but the same recognition sites are desirably absent elsewhere on the vectors.

In the cosmid vector constructs of the present invention, the order of all of the seven elements consisting of elements 1)-6) and a unit of 7)-10) is not limited. Moreover, the order of 9) and 10) located between 7) and 8) is not limited.

The cosmid vectors of the present invention preferably satisfy one or more of the following criteria A-G.

A. The nucleotide sequence of oriV in 1) comprises the following nucleotide sequence:
  i) the nucleotide sequence of nucleotides 3451-4002, more preferably 3345-4247 of SEQ ID NO: 1;
  ii) a nucleotide sequence containing a nucleotide sequence hybridizing to a complementary strand of the nucleotide sequence of nucleotides 3451-4002, more preferably 3345-4247 of SEQ ID NO: 1 under stringent conditions and having the function of oriV; or
  iii) a nucleotide sequence containing a nucleotide sequence having an identity of at least 95%, more preferably 97%, still more preferably 99% to the nucleotide sequence of nucleotides 3451-4002, more preferably 3345-4247 of SEQ ID NO: 1 and having the function of oriV.

B. The trfA1 gene in 2) comprises the following nucleotide sequence:
  i) the nucleotide sequence of nucleotides 6323-7471, more preferably 5341-8507 of SEQ ID NO: 1;
  ii) a nucleotide sequence containing a nucleotide sequence hybridizing to a complementary strand of the nucleotide sequence of nucleotides 6323-7471, more preferably 5341-8507 of SEQ ID NO: 1 under stringent conditions and having the function of the trfA1 gene;
  iii) a nucleotide sequence containing a nucleotide sequence having an identity of at least 95%, more preferably 97%, still more preferably 99% to the nucleotide sequence of nucleotides 6323-7471, more preferably 5341-8507 of SEQ ID NO: 1 and having the function of the trfA1 gene.

C. The oriT in 3) comprises the following nucleotide sequence:
  i) the nucleotide sequence of nucleotides 1-816 of SEQ ID NO: 1;
  ii) a nucleotide sequence containing a nucleotide sequence hybridizing to a complementary strand of the nucleotide sequence of nucleotides 1-816 of SEQ ID NO: 1 under stringent conditions and having the function of oriT;
  iii) a nucleotide sequence containing a nucleotide sequence having an identity of at least 95%, more preferably 97%, still more preferably 99% to the nucleotide sequence of nucleotides 1-816 of SEQ ID NO: 1 and having the function of oriT.

D. The incC1 gene in 4) comprises the following nucleotide sequence:
  i) the nucleotide sequence of nucleotides 1179-2273, more preferably 817-2935 of SEQ ID NO: 1;
  ii) a nucleotide sequence containing a nucleotide sequence hybridizing to a complementary strand of the nucleotide sequence of nucleotides 1179-2273, more preferably 817-2935 of SEQ ID NO: 1 under stringent conditions and having the function of the incC1 gene;
  iii) a nucleotide sequence containing a nucleotide sequence having an identity of at least 95%, more preferably 97%, still more preferably 99% to the nucleotide sequence of nucleotides 1179-2273, more preferably 817-2935 of SEQ ID NO: 1 and having the function of the incC1 gene.

E. The cos site of lambda phage in 5) comprises the following nucleotide sequence:
  i) the nucleotide sequence of SEQ ID NO: 9, more preferably the nucleotide sequence of nucleotides 2936-3344 of SEQ ID NO: 1;
  ii) a nucleotide sequence containing a nucleotide sequence hybridizing to a complementary strand of the nucleotide sequence of SEQ ID NO: 9, more preferably the nucleotide sequence of nucleotides 2936-3344 of SEQ ID NO: 1 under stringent conditions and having the function of a cos site of lambda phage;
  iii) a nucleotide sequence containing a nucleotide sequence having an identity of at least 95%, more preferably 97%, still more preferably 99% to the nucleotide sequence of SEQ ID NO: 9, more preferably the nucleotide sequence of nucleotides 2936-3344 of SEQ ID NO: 1 and having the function of a cos site of lambda phage.

F. The T-DNA right border sequence (RB) of a bacterium of the genus *Agrobacterium* in 7) comprises the following nucleotide sequence:
  i) the nucleotide sequence of nucleotides 13253-13277 of SEQ ID NO: 2;
  ii) a nucleotide sequence containing a nucleotide sequence hybridizing to a complementary strand of the nucleotide sequence of nucleotides 13253-13277 of SEQ ID NO: 2 under stringent conditions and having the function of RB;
  iii) a nucleotide sequence containing a nucleotide sequence having an identity of at least 95%, more preferably 97%, still more preferably 99% to the nucleotide sequence of nucleotides 13253-13277 of SEQ ID NO: 2 and having the function of RB.

G. The T-DNA left border sequence (LB) of a bacterium of the genus *Agrobacterium* in 8) comprises the following nucleotide sequence:
  i) the nucleotide sequence of nucleotides 3479-3503 of SEQ ID NO: 2;
  ii) a nucleotide sequence containing a nucleotide sequence hybridizing to a complementary strand of the nucleotide sequence of nucleotides 3479-3503 of SEQ ID NO: 2 under stringent conditions and having the function of LB;

iii) a nucleotide sequence containing a nucleotide sequence having an identity of at least 95%, more preferably 97%, still more preferably 99% to the nucleotide sequence of nucleotides 3479-3503 of SEQ ID NO: 2 and having the function of LB.

By satisfying all of the criteria 1)-10) above for the cosmid vectors of the present invention, a vector fulfilling all of the requirements below can be prepared:

it allows efficient cloning of DNA fragments of about 25-40 kb in size, preferably 30-40 kb;

it is stably maintained in *E. coli* and *Agrobacterium* cells;

it can be efficiently introduced into *Agrobacterium*;

the copy number per cell in *E. coli* and *Agrobacterium* is 4-5; and it allows efficient transfer of only cloned DNA fragments of interest into plants, preferably monocotyledons.

However, the development of such a vector was not straightforward even after the requirements above had been defined. This is partially due to the very complex control mechanism of plasmid replication. Specifically, the most suitable vector backbone for the requirements above is a small plasmid (in the order of 12 kb to 15 kb) having an origin of replication (oriV) of an IncP plasmid. However, the backbone 60 kb IncP plasmid has many genes involved in the replication of the plasmid and partitioning during cell division, resulting in a very complex mechanism, though its entire nucleotide sequence has been determined (Pansegrau et al. J. Mol. Biol. 239:623-663, 1994). Thus, it is not easy to prepare a small vector having an origin of replication (only) of an IncP plasmid and stably maintained in bacteria. In fact, plasmids of various sizes derived from IncP plasmids have been studied, but small plasmids are generally unstable and widely differ in stability depending on the bacterial species (Schmidhauser and Helinski, J. Bacteriol. 164:446-455, 1985). pE4 cos is an example of the plasmid which has lost stability in *Agrobacterium* by size reduction. The reasons for this have been discussed to a certain extent (Klee et al. 1987 Mol Gen Genet 210: 282-287), but it can be hardly said that they have been clarified.

Schmidhauser and Helinski (J. Bacteriol. 164:446-455, 1985) say that "there is no universal set of genetic determinants in plasmid RK2 that accounts for stable maintenance in all gram-negative bacteria", indicating great difficulty in the preparation of a small and stable vector. The plasmid RK2 here (also often designated as pRK2) is one of typical IncP plasmids. The procedure for constructing such a vector often uses the step of cloning elements of a backbone plasmid using another vector. However, DNA fragments involved in the replication of bacterial plasmids or chromosomes are sometimes difficult to clone. If such a problem occurs, a means to solve it must be developed, which contributes to the difficulty in the construction of novel vectors.

Non-limitative examples of the cosmid vectors (pLC series) of the present invention are as follows.

i) pLC40 (SEQ ID NO: 2, FIG. 6)

A binary cosmid vector having a full length of 13429 bp characterized in that:

1) it contains an origin of replication (oriV) of an IncP plasmid, but does not contain any origin of replication of other plasmid groups;

2) it contains the trfA1 gene, 3) oriT, and 4) the incC1 gene of an IncP plasmid;

5) it contains a cos site of lambda phage and the cos site is located outside the T-DNA;

6) it contains the drug resistance gene nptIII (kanamycin resistance gene) expressed in *E. coli* and a bacterium of the genus *Agrobacterium*;

7) it contains a T-DNA right border sequence of a bacterium of the genus *Agrobacterium*;

8) it contains a T-DNA left border sequence of a bacterium of the genus *Agrobacterium*;

9) it contains the selectable marker gene for plant transformation hpt (hygromycin resistance gene) located between 7) and 8) and expressed in a plant; and 10) it contains restriction endonuclease recognition site(s) located between 7) and 8) for cloning a foreign gene, e.g., an NspV site.

pLC40 was prepared by inserting a region containing the T-DNA region of pSB200PcHm (FIG. 1) into p6FRG. It should be noted that p6FRG is a cosmid vector of 8507 bp in full length having the structure shown in FIG. 5 (SEQ ID NO: 1 in the Sequence Listing) characterized in that:

1) it contains an origin of replication (oriV) of an IncP plasmid, but does not contain any origin of replication of other plasmid groups;

2) it contains the trfA1 gene, oriT and the incC1 gene of an IncP plasmid, and a cos site of lambda phage;

3) it contains the drug resistance gene nptIII (kanamycin resistance gene) expressed in *E. coli* and a bacterium of the genus *Agrobacterium*.

ii) pLC40GWH (SEQ ID NO: 3, FIG. 7)

A binary cosmid vector of 13174 bp in full length. It differs from pLC40 by an insertion of attB1, 2 sequences and a deletion of a 317 bp SspI-BalI region upstream of the RB. It was prepared by inserting a region containing the T-DNA region of pSB200PcHmGWH (FIG. 3) into p6FRG.

iii) pLC40 bar (SEQ ID NO: 4, FIG. 8)

A binary cosmid vector of 12884 bp in full length.

Principal differences of pLC40 bar from pLC40 are in that the selectable marker gene for plant transformation is bar (phosphinotricin resistance gene), and that the orientation of the selectable marker unit (ubiquitin promoter-ubiquitin intron-selectable marker gene for plant transformation) on the T-DNA is opposite. It was prepared by inserting a region containing the T-DNA region of pSB25UNpHm (FIG. 2) into p6FRG.

iv) pLC40GWB (SEQ ID NO: 5, FIG. 9)

A binary cosmid vector of 13026 bp in full length. It differs from pLC40 in that the selectable marker gene for plant transformation is bar (phosphinotricin resistance gene) and that attB1, 2 sequences have been inserted. It was prepared by inserting a region containing the T-DNA region of pSB200PcHmGWB (FIG. 4) into p6FRG.

v) pLC40GWHkorB (SEQ ID NO: 65, FIG. 10)

A binary cosmid vector of 14120 bp in full length. It differs from pLC40GWH in that it contains the nucleotide sequence of the korB gene. The korB gene is located near IncC1 described above, and contributes to the stability of IncP plasmids as IncC1 does. The nucleotide sequence of the korB gene of the present invention is not specifically limited so far as it has the function of the korB gene contributing to the stability of IncP plasmids.

This sequence has molecular biological properties described in detail in Pansegrau et al. (1994) J Mol Biol 239: 623-663, and it is defined as nucleotides 57187-58263 of the sequence of Genbank/EMBL Accession Number L27758 (full length 60099 bp). This corresponds to nucleotides 6306-7382 of SEQ ID NO: 65.

The korB can be conventionally prepared from an IncP plasmid such as pVK102 (Knauf and Nester 1982 Plasmid 8:

45-54). For example, a sequence amplified by PCR from pVK102 (nucleotides 6306-7382 of SEQ ID NO: 65) can be used as the korB gene.

Alternatively, a nucleic acid containing a nucleotide sequence hybridizing to a complementary strand of the nucleotide sequence of nucleotides 6306-7382 of SEQ ID NO: 65 under stringent conditions and having the function of the korB gene can be used. Alternatively, a nucleic acid containing a nucleotide sequence having an identity of at least 95%, more preferably 97%, still more preferably 99% to the nucleotide sequence of nucleotides 6306-7382 of SEQ ID NO: 65 and having the function of the korB gene can also be used.

vi) pLCleo (SEQ ID NO: 66, FIG. 11)

A binary cosmid vector of 14195 bp in full length. It differs from pLC40GWHkorB in that it contains a PspOMI site in the multicloning site, a PI-SceI upstream of it, and an attB3 site upstream of the ubiquitin promoter.

vii) pLC40GWHvG1 (SEQ ID NO: 7, FIG. 13)

A binary cosmid vector of 14222 bp in full length. It differs from pLC40GWH in that the virG gene has been inserted. It was prepared by inserting the virG gene outside the T-DNA of pPLC40GWH.

Those skilled in the art can readily derive equivalents to the seven cosmid vectors described above, i.e., i) the cosmid vector pLC40 consisting of the nucleotide sequence of SEQ ID NO: 2;

ii) the cosmid vector pLC40GWH consisting of the nucleotide sequence of SEQ ID NO: 3;

iii) the cosmid vector pLC40 bar consisting of the nucleotide sequence of SEQ ID NO: 4;

iv) the cosmid vector pLC40GWB consisting of the nucleotide sequence of SEQ ID NO: 5;

v) the cosmid vector pLC40GWHKorB consisting of the nucleotide sequence of SEQ ID NO: 65;

vi) the cosmid vector pLCleo consisting of the nucleotide sequence of SEQ ID NO: 66; and vii) the cosmid vector pLC40GWHvG1 consisting of the nucleotide sequence of SEQ ID NO: 7;

said equivalents having similar functions to those of these vectors even if the nucleotide sequences are not completely identical. Thus, these "equivalents" are also included as preferred embodiments of the cosmid vectors of the present invention.

For example, it is thought that even if the nucleotide sequences of the cosmid vectors of the present invention i)-vii) above are modified especially in parts other than the elements related to criteria 1)-10) above (e.g., oriV in criterion 1), or the trfA1 gene in criterion 2)), they perform similar functions to those of the original vectors as cosmid vectors. Moreover, more than one genes or restriction endonuclease sites having similar functions to those of the drug resistance gene in 6), the selectable marker gene for plant transformation in 9), and the restriction endonuclease recognition site(s) in 10) among criteria 1)-10) are known even if the nucleotide sequences are not completely identical to the nucleotide sequences in the cosmid vectors i)-vii), and those skilled in the art can modify these parts as appropriate.

Therefore, an "equivalent" to each of the cosmid vectors of the present invention i)-vii) preferably refers to a nucleotide sequence identical to or having an identity of at least 95% or more, 97% or more, 98% or more or 99% or more, more preferably 99.5% or more to the nucleotide sequence of each cosmid vector in the nucleotide sequences of the elements related to criteria 1)-5) and 7)-8) of the cosmid vectors of the present invention, especially the core sequences in these criteria or refers to a nucleotide sequence hybridizing to a complementary strand of the nucleotide sequence of each cosmid vector under stringent conditions, said equivalent containing a mutation elsewhere in the nucleotide sequence while having similar function and effect to those of each vector. More preferably, it refers to a nucleotide sequence identical to the nucleotide sequence of each cosmid vector in the nucleotide sequences of the elements related to criteria 1)-10) of the cosmid vectors of the present invention, especially the core sequences in these criteria and containing a mutation elsewhere in the nucleotide sequence while having similar function and effect to those of each vector.

The degree of mutation is not specifically limited, but the "equivalent" preferably consists of a nucleotide sequence hybridizing to a complementary strand of the nucleotide sequence of each of cosmid vectors i)-vii) under stringent conditions. The number of nucleotides that can be mutated is more preferably one or more, still more preferably one to a few (e.g., to the extent at which a mutation can be introduced by known site-directed mutagenesis).

The "equivalent" also preferably consists of a nucleotide sequence having an identity of 95% or more, 97% or more, 98% or more or 99% or more, more preferably 99.5% or more to a nucleotide sequence selected from the nucleotide sequences of cosmid vectors i)-vii).

The percent identity of two nucleic acid sequences can be determined by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, "GAP" (Devereux et al., 1984, Nucl. Acids Res. 12: 387). This "GAP" program can be used to compare not only two nucleic acid sequences but also two amino acid sequences or a nucleic acid sequence and an amino acid sequence. The preferred default parameters for the "GAP" program include (1) The GCG implementation of a unary comparison matrix (containing a value of 1 for identities and 0 for non-identities) for nucleotides, and the weighted amino acid comparison matrix of Gribskov and Burgess, Nucl. Acids Res. 14: 6745, 1986 as described by Schwartz and Dayhoff, eds., "Atlas of Polypeptide Sequence and Structure", National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website: http://www.ncbi.nlm.nih.gov/blast/bl2seq/bls.html, or the UW-BLAST 2.0 algorithm. Standard default parameter settings for UW-BLAST 2.0 are described at the following Internet site: http://blast.wustl.edu. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, Analysis of compositionally biased regions in sequence databases, Methods Enzymol. 266: 554-71) or segments consisting of short-periodicity internal repeats (as determined by the XNU program of Claverie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

Plant Transformation Methods

The present invention also provides a plant transformation method using a cosmid vector of the present invention. Specifically, the plant transformation method of the present invention comprises transforming a plant with a bacterium of the genus *Agrobacterium* harboring a vector containing a nucleic acid fragment of a plant inserted into a cosmid vector of the present invention.

The type of the nucleic acid fragment inserted into the cosmid vector is not specifically limited, and any fragment can be used, such as a genomic DNA fragment, a cDNA fragment, etc. The nucleic acid fragment is preferably a genomic DNA fragment, more preferably a genomic DNA fragment derived from a plant. The size of the DNA fragment inserted is preferably 1 kb or more, more preferably 10 kb or more, still more preferably 20 kb or more, still more preferably 25-40 kb, still more preferably 30-40 kb.

The preparation and introduction of the nucleic acid fragment into the cosmid vector and other operations can be performed by a known method, e.g., the method described in WO2005/040374.

The source of the nucleic acid fragment are not specifically limited. In the case of plant genomic DNA fragments, preferred examples include plants in which heterosis may occur by cross with recipient plants of genomic DNA fragments. When the recipient plant is Japonica rice, for example, the donor is preferably a wild species of rice *Oryza rufipogon* or Indica rice. When the recipient plant is a specific variety of maize, preferred examples of donor plants include the other varieties of maize and wild species of teosinte. In general, higher heterosis has been observed between more distantly related plants.

The recipient plant used for transformation may belong to a different species from that of the donor plant of the genomic DNA or a different variety of the same species or the same variety of the same species. Preferred examples of plants include substantially unrestricted wide range of plants, e.g., cereals such as rice, barley, wheat, maize, sorghum, or millet such as an extremely early maturing variety of Italian millet or pearl millet; industrial crops such as sugar cane; pasture grasses such as Sudan grass or rose grass; plants for producing luxury grocery items such as coffee, cocoa, tea and tobacco; vegetables; fruits; ornamental plants such as flowers; weeds such as *Arabidopsis*, etc.

The cosmid vectors of the present invention were obtained especially to improve the efficiency of *Agrobacterium*-mediated transformation among biological transfer methods. Therefore, the plant transformation method is preferably *Agrobacterium*-mediated. However, other known plant transformation methods are not excluded. For example, known methods include physical transfer methods such as microinjection, electroporation, particle gun, silicon carbide-mediated method and air injection; and chemical transfer methods such as polyethylene glycol-mediated method.

The type of *Agrobacterium* strain is not specifically limited so far as it has an antibiotic resistance other than the antibiotic resistance (gene) for the bacterium used for the construction of the vector, and known strains such as LBA4404, A281, EHA105, PC2760, etc. can be used.

Map-Based Cloning Method

The present invention also provides an efficient map-based cloning method using a cosmid vector of the present invention as described above. The map-based cloning method is characterized in that it comprises the steps of:

1) partially or completely digesting BAC clones containing candidate genes responsible for a plant phenotype with a restriction endonuclease;

2) subcloning DNA fragments obtained in step 1) using a cosmid vector to construct a library; and 3) individually transferring clones constituting the library into a plant to evaluate the phenotypes of transformed plants.

In this map-based cloning method, the DNA fragments obtained in step 1) preferably have a size of, but not limited to, 25-40 kb. More preferably, the cosmid vector in 2) is a cosmid vector as described in the section "Cosmid vectors" above.

The "candidate genes" refer to a group of genes including genes likely to be responsible for a plant phenotype. The "plant phenotype" is not specifically limited, but includes various agriculturally useful phenotypes such as high vigor of the whole plant, large sizes of the plant and organs, high yield, high growth speed, disease and insect resistance, resistance to various environmental stresses such as drought, high temperature, low temperature, etc., an increase or decrease of a specific component, an increase or decrease of a specific enzyme activity, dwarfness, etc.

For example, suppose that candidate genes were found to be contained in DNA fragments carried by more than one BAC clones of 100-200 kb. Then, these cloned DNAs are partially or completely digested with an appropriate restriction endonuclease to prepare overlapping fragments of about 40 kb, which are then subcloned using a transformation vector of the present invention. It is not necessary to investigate in detail the relative positions and the overlapping of the subcloned DNA fragments. According to a statistical calculation, any site on original fragments in 200 kb clones is maintained by randomized 21 subclones with a 99% probability (e.g., see [0043]-[0047] in WO2005/040374).

Then, each subclone is transferred into a plant to prepare about 10 independent transformants per subclone, and the effect of the gene is analyzed. According to this operation, the candidate region can be first narrowed down to 40 kb by identifying subclones containing candidate genes, and then the candidate region can be further restricted to a very narrow region by comparing the experimental results between adjacent subclones. Thus, the efficiency of identifying candidate genes greatly improves.

Transformation Method Additionally Using the virG Gene (and the virB Gene)

In a preferred embodiment, the plant transformation method of the present invention is characterized in that it uses a bacterium of the genus *Agrobacterium* harboring the following elements:

1a) a vector containing a nucleic acid fragment of a plant and the virG gene of a bacterium of the genus *Agrobacterium* inserted into the cosmid vector of the present invention; or 1b) a vector containing a nucleic acid fragment of a plant inserted into the cosmid vector of the present invention, and a plasmid capable of coexisting with an IncP plasmid in a cell of a bacterium of the genus *Agrobacterium* and containing the virG gene of a bacterium of the genus *Agrobacterium*, and 2) a Ti plasmid or Ri plasmid of a bacterium of the genus *Agrobacterium*.

virG is one of vir genes of *Agrobacterium* that play a role in the transfer of the T-DNA into plants, and it is regarded as a transcription factor of the virB gene or the like (Winans et al. 1986 Proc. Natl. Acad. Sci. USA 83: 8278-8282). As an example of virG, virGN54D is a variant in which the amino acid at position 54 of the virG protein is changed from asparagine to aspartic acid to increase the expression of the virB gene as compared with the wild-type virG (Pazour et al. 1992 J. Bac 174:4169-4174). In the present transformation method, the virG gene is preferably virGN54D.

In an embodiment of the present invention 1a), the virG gene may be further inserted into a cosmid vector of the present invention containing a nucleic acid fragment of a plant. In embodiments where a cosmid vector of the present invention already carries the virG gene (e.g., pLC40GWHvG1), the virG gene need not be further inserted.

Alternatively, the virG gene may exist in an independent plasmid separate from a cosmid vector of the present invention. In this case, *Agrobacterium* in the method of the present invention harbors a plasmid capable of coexisting with an IncP plasmid in *Agrobacterium* cells and containing the virG gene of a bacterium of the genus *Agrobacterium*, in addition to the cosmid vector (embodiment 1b).

The Ti plasmid or Ri plasmid is not specifically limited, but preferably disarmed by deleting the T-DNA.

The plasmid containing the virG gene of a bacterium of the genus *Agrobacterium* in 1b) may contain an origin of replication of an IncW plasmid. Preferably, it is pVGW having the structure shown in FIG. 14. More preferably, it is pVGW2 having the structure shown in FIG. 15.

The plasmid containing the virG gene of a bacterium of the genus *Agrobacterium* in 1b) may further contain the virB gene of a bacterium of the genus *Agrobacterium*. Here again, the plasmid may contain an origin of replication of an IncW plasmid. Such a plasmid is preferably pTOK47.

The virB gene of a bacterium of the genus *Agrobacterium* is described in detail in Ward et al. (1988) J Biol Chem 263: 5804-5814. For example, it can be conventionally prepared from a plasmid such as pSB1 (Komari et al. 1996 Plant J 10: 165-174). The nucleotide sequence of virB is defined as, e.g., nucleotides 3416-12851 of the nucleotide sequence of Genbank/EMBL Accession Number: AB027255 (pSB1). As a non-limitative example, a DNA containing a nucleotide sequence hybridizing to this sequence or a complementary strand thereto under stringent conditions can be used as the virB gene.

These transformation methods are more effective for plants normally associated with low efficiency of *Agrobacterium*-mediated transformation, e.g., including, but not limited to, maize and soybean. When the nucleic acid fragment to be transferred is large (e.g., 25-40 kb as a non-limitative example) or has a complex structure (e.g., a highly repeated sequence as a non-limitative example), pVGW described below is preferably used as a plasmid containing the virG gene of a bacterium of the genus *Agrobacterium*.

Plasmid Vectors

In plants such as maize, wherein transformation is difficult to occur, the efficiency of *Agrobacterium*-mediated transformation with standard binary vectors containing the T-DNA is very low except for special cases (Frame et al. 2002 Plant Physiol 129: 13-22). Previous reports show an increase in the efficiency of transient expression in maize by the coexistence of a binary vector with another plasmid containing the virGN54D gene, a variant of the virG gene in *Agrobacterium* (Hansen et al. 1994 ProNAS 91:7603-7607), and a high efficiency maize transformation system with a binary vector containing virG and virB (Ishida et al. 1996 Nat Biotechnol 14:745-50).

However, no report has shown that the maize transformation efficiency was increased by the coexistence of a binary vector with a plasmid containing virG or virGN54D in *Agrobacterium*.

The cosmid vectors of the present invention (pLC vectors) (IncP plasmids) are also expected to further improve the maize transformation efficiency. Plasmids capable of coexisting with an IncP plasmid include e.g., IncW plasmids (Close et al. 1984 Plasmid 12: 111-118). Previously reported IncW vectors containing virG are large because they contain origins of replication of other plasmids such as pBR322 ori. For example, pTOK47 contains IncW (pSa) on and pBR322 ori (as well as not only virG but also virB) and it has a full length of about 28 kb (Jin et al. 1987 J Bacteriol 169: 4417-4425). pYW48 contains IncW (pSa) on and pBR322 on (as well as not only virG but also virA) and it has a full length of 15.5 kb (Wang et al. 2000 Gene 242: 105-114). Such vectors can also be used in the transformation methods of the present invention. However, these vectors are so long that they may cause problems in stability in bacteria when they coexist with a pLC vector containing a large fragment, and therefore, small vectors capable of coexisting with a pLC vector and containing virG are desirable.

As a means to solve these problems, the present invention provides a small plasmid vector capable of further improving the transformation efficiency by the coexistence with the cosmid vectors of the present invention described above.

The plasmid vector of the present invention satisfies all of the criteria below.

1) it contains an origin of replication of an IncW plasmid, but does not contain any origin of replication of other plasmid groups;

2) it contains the repA gene necessary for the replication of an IncW plasmid;

3) it contains a drug resistance gene expressed in *E. coli* and a bacterium of the genus *Agrobacterium*; and 4) it contains the virG gene of a bacterium of the genus *Agrobacterium*.

1) The nucleotide sequence of the origin of replication of an IncW plasmid of the present invention is not specifically limited so far as it has the function as an origin of replication of an IncW plasmid.

The origin of replication of an IncW plasmid has molecular biological properties described in detail in Okumura and Kado (1992 Mol Gen Genet 235: 55-63), and it is defined as nucleotides 2170-2552 of Genbank/EMBL Accession Number: U30471 (full length 5500 bp). This corresponds to nucleotides 2832-3214 of SEQ ID NO: 8.

The origin of replication of an IncW plasmid can be conventionally prepared from an IncW plasmid such as pTOK47 (Jin et al. 1987 J Bacteriol 169: 4417-4425). For example, nucleotides 2832-3214 of SEQ ID NO: 8 in a 2.7 kb DNA amplified by PCR from pTOK47 with repA necessary for the replication of an IncW plasmid described below can be used.

Alternatively, a nucleic acid containing a nucleotide sequence hybridizing to a complementary strand of the nucleotide sequence of nucleotides 2832-3214 of SEQ ID NO: 8 described above under stringent conditions and having the function of an origin of replication of an IncW plasmid can also be used. Alternatively, a nucleic acid containing a nucleotide sequence having an identity of at least 95%, more preferably 97%, still more preferably 99% to the nucleotide sequence of nucleotides 2832-3214 of SEQ ID NO: 8 described above and having the function of an origin of replication of an IncW plasmid can also be used.

It will be recognized by those skilled in the art that a shorter region in nucleotides 2832-3214 of SEQ ID NO: 8 may be selected as a sequence having a similar function.

2) The nucleotide sequence of the repA gene of the present invention is not specifically limited so far as it has the function as the repA gene necessary for the replication of an IncW plasmid.

The repA necessary for the replication of an IncW plasmid has molecular biological properties described in detail in Okumura and Kado (1992 Mol Gen Genet 235: 55-63), and it is defined as nucleotides 1108-2079 of Genbank/EMBL Accession Number:U30471 (full length 5500 bp). This corresponds to nucleotides 1770-2741 of SEQ ID NO: 8.

The repA necessary for the replication of an IncW plasmid can be conventionally prepared from an IncW plasmid such as pTOK47 (Jin et al. 1987 J Bacteriol 169: 4417-4425). For example, nucleotides 1770-2741 of SEQ ID NO: 8 in a 2.7 kb DNA amplified by PCR from pTOK47 with an origin of replication of an IncW plasmid described above can be used.

Alternatively, a nucleic acid containing a nucleotide sequence hybridizing to a complementary strand of the nucleotide sequence of nucleotides 1770-2741 of SEQ ID NO: 8 described above under stringent conditions and having the function of the repA gene necessary for the replication of an IncW plasmid can also be used. Alternatively, a nucleic acid containing a nucleotide sequence having an identity of at least 95%, more preferably 97%, still more preferably 99% to the nucleotide sequence of nucleotides 1770-2741 of SEQ ID NO: 8 described above and having the function of the repA gene necessary for the replication of an IncW plasmid can also be used.

It will be recognized by those skilled in the art that a shorter region in nucleotides 1770-2741 of SEQ ID NO: 8 may be selected as a sequence having a similar function.

3) The drug resistance gene expressed in *E. coli* and a bacterium of the genus *Agrobacterium* is used as a selectable marker for transformation. This drug resistance gene confers e.g., antibiotic resistance or autotrophy, including, but not limited to, a kanamycin resistance gene, a spectinomycin resistance gene, an ampicillin resistance gene, a tetracycline resistance gene, a gentamycin resistance gene, a hygromycin resistance gene, etc.

4) The virG gene of a bacterium of the genus *Agrobacterium* and virGN54D have molecular biological properties described in detail in Winans et al. (1986) Proc. Natl. Acad. Sci. USA 83: 8278-8282 and Pazour et al. (1992) J. Bacteriol. 174: 4169-4174, Hansen et al. 1994 Proc. Natl. Acad. Sci. USA 91: 7603-7607, respectively. virG is a transcription regulator (activator) of other vir genes such as virB and virE. virG is activated upon regulation (phosphorylation) by virA, whereas virGN54D is a variant in a permanently activated state without this regulation. The virG gene can be prepared by conventional procedure and virGN54D can be prepared by mutagenesis both from a plasmid such as pTOK47 (Jin et al. 1987 J Bacteriol 169: 4417-4425). For example, 1 kb virG DNA (nucleotides 4024-5069 of SEQ ID NO: 7) amplified by PCR from pTOK47 and 1 kb virGN54D DNA (nucleotides 1-1080 of SEQ ID NO: 8) amplified and prepared by PCR mutagenesis can be used.

Alternatively, a nucleic acid containing a nucleotide sequence hybridizing to a complementary strand of these nucleotide sequences under stringent conditions and having the function of the virG gene of a bacterium of the genus *Agrobacterium* or a nucleic acid containing a nucleotide sequence having an identity of at least 95%, more preferably 97%, still more preferably 99% to these nucleotide sequences and having the function of the virG gene of a bacterium of the genus *Agrobacterium* can also be used.

The plasmid vector of the present invention preferably has a full length of 10 kb or less, more preferably 5 kb or less.

The plasmid vector of the present invention is preferably the pVGW vector having the structure shown in FIG. 14. More preferably, it is pVGW2 having the structure shown in FIG. 15. pVGW and pVGW2 are vectors satisfying all of criteria 1)-4) above. pVGW shown as SEQ ID NO: 8 has a full length of 4531 bp, and pVGW2 shown as SEQ ID NO: 67 has a full length of 4836 bp, and they are characterized in that:

1) they contain an origin of replication of an IncW plasmid, but do not contain any origin of replication of other plasmid groups;

2) they contain the repA gene necessary for the replication of an IncW plasmid;

3) they contain a gentamycin resistance gene as a drug resistance gene expressed in *E. coli* and a bacterium of the genus *Agrobacterium*; and 4) they contain the virGN54D gene of a bacterium of the genus *Agrobacterium*.

Among these components, the origin of replication of an IncW plasmid and the repA gene necessary for the replication of an IncW plasmid were simultaneously cloned and the gentamycin resistance gene and the virGN54D gene were separately cloned, after which all of the three DNA fragments (four components) were assembled.

Those skilled in the art can readily derive equivalents to the two plasmid vectors pVGW, pVGW2 of the present invention described above, said equivalents having similar functions to those of these vectors even if the nucleotide sequences are not completely identical. Thus, these "equivalents" are also included as preferred embodiments of the plasmid vectors of the present invention.

For example, it is thought that even if the nucleotide sequences of the plasmid vectors of the present invention are modified especially in parts other than the elements related to criteria 1)-4) above (e.g., the origin of replication of an IncW plasmid in criterion 1)), they perform similar functions to those of the original vectors as plasmid vectors. Moreover, more than one genes having similar functions to those of the drug resistance gene in 3) among criteria 1)-4) are known even if the nucleotide sequences are not completely identical to the nucleotide sequences in the plasmid vectors, and those skilled in the art can modify these parts as appropriate.

Therefore, an "equivalent" to each of the plasmid vectors of the present invention preferably refers to a nucleotide sequence identical to or having an identity of at least 95% or more, 97% or more, 98% or more or 99% or more, more preferably 99.5% or more to the nucleotide sequence of each plasmid vector in the nucleotide sequences of the elements related to criteria 1)-2) and 4) of the plasmid vectors of the present invention or refers to a nucleotide sequence hybridizing to a complementary strand of the nucleotide sequence of each plasmid vector under stringent conditions, said equivalent containing a mutation elsewhere in the nucleotide sequence while having similar function and effect to those of each vector. More preferably, it refers to a nucleotide sequence identical to the nucleotide sequence of each plasmid vector in the nucleotide sequences of the elements related to criteria 1)-4) of the plasmid vectors of the present invention and containing a mutation elsewhere in the nucleotide sequence while having similar function and effect to those of each vector.

The degree of mutation is not specifically limited, but the "equivalent" preferably consists of a nucleotide sequence hybridizing to a complementary strand of the nucleotide sequence of each plasmid vector under stringent conditions. The number of nucleotides that can be mutated is more preferably one or more, still more preferably one to a few (e.g., to the extent at which a mutation can be introduced by known site-directed mutagenesis).

The "equivalent" also preferably consists of a nucleotide sequence having an identity of 95% or more, 97% or more, 98% or more or 99% or more, more preferably 99.5% or more to a nucleotide sequence selected from the nucleotide sequences of the plasmid vectors.

As used herein, the expression "under stringent conditions" refers to hybridization under conditions of moderate or high stringency. Specifically, conditions of moderate stringency can be readily determined by those having ordinary skill in the art based on, for example, the length of the DNA. The basic conditions are set forth by Sambrook et al. Molecular Cloning: A Laboratory Manual, 3rd Ed., Chapters 6-7, Cold Spring Harbor Laboratory Press, 2001, and include use of a prewashing solution for the nitrocellulose filters containing 5×SSC, 0.5% SDS, 1.0 mM EDTA (pH 8.0), hybridization conditions of 2×SSC to 6×SSC with or without about 50% formamide at about 40° C. to 50° C. (or other similar hybridization solution, such as Stark's solution, in about 50% formamide at about 42° C.), and washing conditions of 0.5 to 6×SSC, 0.1% SDS at about 40° C. to 60° C. Preferably, conditions of moderate stringency include hybridization conditions (and washing conditions) of 6×SSC at about 50° C. Conditions of high stringency can also be readily determined by the skilled artisan based on, for example, the length of the DNA.

Generally, such conditions include hybridization and/or washing at higher temperatures and/or lower salt concentrations than in the conditions of moderate stringency (e.g., hybridization in 6×SSC to 0.2×SSC, preferably 6×SSC, more preferably 2×SSC, most preferably 0.2×SSC at about 65° C.), and are defined to involve hybridization conditions as above and washing in 0.2×SSC, 0.1% SDS at about 65° C. to 68° C. SSPE (1×SSPE=0.15 M NaCl, 10 mM $NaH_2PO_4$, and 1.25 mM EDTA, pH 7.4) can be substituted for SSC (1×SSC=0.15 M NaCl and 15 mM sodium citrate) for use as hybridization and washing buffers, and washing is continued for 15 minutes after completion of hybridization.

Commercially available hybridization kits not using radioactive substances as probes can also be used. Specifically, hybridization can be performed by using ECL direct labeling & detection system (from Amersham), etc. Stringent hybridization conditions include hybridization in the hybridization buffer included in the kit containing 5% (w/v) Blocking reagent and 0.5 M NaCl at 42° C. for 4 hours, followed by washing twice in 0.4% SDS, 0.5×SSC at 55° C. for 20 minutes, and once in 2×SSC at room temperature for 5 minutes.

pVGW is characterized in that it is small and stable. Specifically, it is effective for improving the transformation efficiency by the coexistence with pLC especially when large fragments are used and/or when maize is used as a host. It is also effective for improving the efficiency of transformation of maize or the like by the coexistence with an ordinary vector other than pLC.

Effects of the Invention

The vectors (pLC vectors) of the present invention provide the following advantages that could not be achieved by known vectors:
they allow efficient cloning of DNA fragments of about 25-40 kb in size, preferably 30-40 kb;

they are stably maintained in *E. coli* and *Agrobacterium* cells;
they can be efficiently introduced in *Agrobacterium*;
the copy number per cell in *E. coli* and *Agrobacterium* is 4-5; and
they allow efficient transfer of only cloned DNA fragments of interest into plants, preferably monocotyledons (the transformation efficiency of pLC vectors is 90%, in contrast to the transformation efficiency of pSB vectors 60%).

The combined use of the pLC vectors of the present invention and the pVGW vector allows efficient gene transfer into even plants that are relatively difficult to transform such as maize.

Candidate gene sites can be narrowed down with little expenditure of labor and time by map-based cloning with the pLC vectors of the present invention.

The present invention is significantly effective even if mapping information is very limited. For example, suppose that nothing is known except for the presence of candidate genes at an end region of a chromosome. If the entire length of one chromosome is 40 Mb, for example, its end region may be assumed to be 2 Mb. This region can be covered by about 20 BAC clones carrying an insert fragment of 150 kb on average by constructing a library of aligned BACs (BAC contig). Therefore, if 20 subclones are prepared from each BAC, almost all candidate genes can be rapidly identified by preparing a total of 400 fragments and 4000 recombinants. Thus, genes can be identified with little expenditure of labor and time unimaginable from conventional techniques by using the technique of the present invention.

EMBODIMENTS OF THE PRESENT INVENTION

The present invention preferably the following embodiments.

Embodiment 1

A cosmid vector having a full length of 15 kb or less characterized in that:
1) it contains an origin of replication (oriV) of an IncP plasmid, but does not contain any origin of replication of other plasmid groups;
2) it contains the trfA1 gene of an IncP plasmid;
3) it contains an origin of conjugative transfer (oriT) of an IncP plasmid;
4) it contains the incC1 gene of an IncP plasmid;
5) it contains a cos site of lambda phage and the cos site is located outside the T-DNA;
6) it contains a drug resistance gene expressed in *E. coli* and a bacterium of the genus *Agrobacterium*;
7) it contains a T-DNA right border sequence of a bacterium of the genus *Agrobacterium*;
8) it contains a T-DNA left border sequence of a bacterium of the genus *Agrobacterium*;
9) it contains a selectable marker gene for plant transformation located between 7) and 8) and expressed in a plant; and
10) it contains restriction endonuclease recognition site(s) located between 7) and 8) for cloning a foreign gene.

Embodiment 2

The cosmid vector of Embodiment 1 wherein the selectable marker gene for plant transformation is selected from the group consisting of a hygromycin resistance gene, a phosphinotricin resistance gene and a kanamycin resistance gene.

Embodiment 3

The cosmid vector of Embodiment 1 or 2, which contains the korB gene of an IncP plasmid.

Embodiment 4

The cosmid vector of any one of Embodiments 1 to 3 selected from the group consisting of:
the cosmid vector pLC40 consisting of the nucleotide sequence of SEQ ID NO: 2 or an equivalent thereof;
the cosmid vector pLC40GWH consisting of the nucleotide sequence of SEQ ID NO: 3 or an equivalent thereof;
the cosmid vector pLC40 bar consisting of the nucleotide sequence of SEQ ID NO: 4 or an equivalent thereof;
the cosmid vector pLC40GWB consisting of the nucleotide sequence of SEQ ID NO: 5 or an equivalent thereof;
the cosmid vector pLC40GWHKorB consisting of the nucleotide sequence of SEQ ID NO: 65 or an equivalent thereof;
the cosmid vector pLCleo consisting of the nucleotide sequence of SEQ ID NO: 66 or an equivalent thereof; and
the cosmid vector pLC40GWHvG1 consisting of the nucleotide sequence of SEQ ID NO: 7 or an equivalent thereof.

Embodiment 5

The cosmid vector of Embodiment 4 selected from the group consisting of:
the cosmid vector pLC40 consisting of the nucleotide sequence of SEQ ID NO: 2;
the cosmid vector pLC40GWH consisting of the nucleotide sequence of SEQ ID NO: 3;
the cosmid vector pLC40 bar consisting of the nucleotide sequence of SEQ ID NO: 4;
the cosmid vector pLC40GWB consisting of the nucleotide sequence of SEQ ID NO: 5;
the cosmid vector pLC40GWHKorB consisting of the nucleotide sequence of SEQ ID NO: 65;
the cosmid vector pLCleo consisting of the nucleotide sequence of SEQ ID NO: 66; and
the cosmid vector pLC40GWHvG1 consisting of the nucleotide sequence of SEQ ID NO: 7.

Embodiment 6

A method for transforming a plant, comprising transforming the plant with a bacterium of the genus *Agrobacterium* harboring an expression vector containing a nucleic acid fragment of a plant inserted into the cosmid vector of any one of Embodiments 1 to 5.

Embodiment 7

The method of Embodiment 6 wherein the nucleic acid fragment inserted has a size of 25-40 kb.

Embodiment 8

The method of Embodiment 6 or 7 characterized in that it uses a bacterium of the genus *Agrobacterium* harboring the following elements for transforming the plant:

1a) a vector containing a nucleic acid fragment of a plant and the virG gene of a bacterium of the genus *Agrobacterium* inserted into the cosmid vector of any one of Embodiments 1 to 5; or
1b) a vector containing a nucleic acid fragment of a plant inserted into the cosmid vector of any one of Embodiments 1 to 5, and a plasmid capable of coexisting with an IncP plasmid in a cell of a bacterium of the genus *Agrobacterium* and containing the virG gene of a bacterium of the genus *Agrobacterium*, and
2) a Ti plasmid or Ri plasmid of a bacterium of the genus *Agrobacterium*.

Embodiment 9

The method of Embodiment 8 wherein the virG gene of a bacterium of the genus *Agrobacterium* in 1a) or 1b) is virGN54D.

Embodiment 10

The method of Embodiment 8 wherein the plasmid containing the virG gene of a bacterium of the genus *Agrobacterium* in 1b) contains an origin of replication of an IncW plasmid.

Embodiment 11

The method of Embodiment 10 wherein the plasmid containing the virG gene of a bacterium of the genus *Agrobacterium* in 1b) is pVGW having the structure shown in FIG. 14 or pVGW2 having the structure shown in FIG. 15.

Embodiment 12

The method of Embodiment 8 wherein the plasmid containing the virG gene of a bacterium of the genus *Agrobacterium* in 1b) further contains the virB gene of a bacterium of the genus *Agrobacterium*.

Embodiment 13

The method of Embodiment 12 wherein the plasmid containing the virG gene of a bacterium of the genus *Agrobacterium* in 1b) contains an origin of replication of an IncW plasmid.

Embodiment 14

The method of Embodiment 13 wherein the plasmid containing the virG gene of a bacterium of the genus *Agrobacterium* in 1b) is pTOK47.

Embodiment 15

A map-based cloning method comprising the steps of:
1) partially or completely digesting BAC clones containing candidate genes responsible for a plant phenotype with a restriction endonuclease;
2) subcloning DNA fragments obtained in step 1) using a cosmid vector to construct a library; and
3) individually transferring clones constituting the library into a plant to evaluate the phenotypes of transformed plants.

Embodiment 16

The map-based cloning method of Embodiment 15 wherein the DNA fragments obtained in step 1) have a size of 25-40 kb.

Embodiment 17

The map-based cloning method of Embodiment 16 wherein the cosmid vector in 2) is the cosmid vector of any one of Embodiments 1 to 5.

Embodiment 18

A plasmid vector characterized in that:
1) it contains an element necessary for the replication of an IncW plasmid, but does not contain any origin of replication of other plasmid groups;
2) it contains the repA gene necessary for the replication of an IncW plasmid;
3) it contains a drug resistance gene expressed in *E. coli* and a bacterium of the genus *Agrobacterium*; and
4) the virG gene of a bacterium of the genus *Agrobacterium*.

Embodiment 19

The plasmid vector of Embodiment 18, which has a full length of 10 kb or less.

Embodiment 20

The plasmid vector of Embodiment 19 wherein the virG gene of a bacterium of the genus *Agrobacterium* is virGN54D.

Embodiment 21

The plasmid vector of any one of Embodiments 18 to 20 selected from the group consisting of:
the plasmid vector pVGW consisting of the nucleotide sequence of SEQ ID NO: 8 or an equivalent thereof; and
the plasmid vector pVGW2 consisting of the nucleotide sequence of SEQ ID NO: 67 or an equivalent thereof.

Embodiment 22

The plasmid vector pVGW consisting of the nucleotide sequence of SEQ ID NO: 8.

Embodiment 23

The plasmid vector pVGW2 consisting of the nucleotide sequence of SEQ ID NO: 67.

Embodiment 24

A method for transforming a plant, comprising transforming the plant with a bacterium of the genus *Agrobacterium* harboring the plasmid vector of any one of Embodiments 18 to 23.

EXAMPLES

The following examples further illustrate the present invention but are not intended to limit the technical scope of the invention. Those skilled in the art can readily add modifications/changes to the present invention in the light of the description herein, and those modifications/changes are also included in the technical scope of the present invention.

Example 1

Construction of pLC Series Cosmid Vectors

In the following procedures, molecular biological experimental methods were performed as described in Sambrook J. and Russell D. W. 2001. Molecular Cloning, A Laboratory Manual, 3rd edn. Cold Spring Harbor Laboratory Press, Cold Spring Harbor, N.Y., USA., unless otherwise specified.

1) Construction of T-DNA Regions

A PacI linker (gttaattaac) (SEQ ID NO: 10) was inserted into the EcoRV site of pSB200 (WO2005/040374) to construct pSB200 PacI. The cauliflower mosaic virus 35S promoter in pSB25 (Ishida et al. 1996) was replaced by the ubiquitin promoter of maize (Christensen et al. 1992 Plant Mol Biol 18: 675-689) to construct pSB25U. The adapters HinNspISceRV and HinNspISceFW (Table 1) having recognition sites for the restriction endonuclease NspV and the homing endonuclease I-SceI were annealed. A part of the annealed adapters were phosphorylated with a polynucleotide kinase (PNK, Amersham). The phosphorylated adapters were cloned into the SacI site of pSB200 PacI and the HindIII site of pSB25U. The resulting plasmids were designated as pSB200 PacHm1 and pSB25UNpHm1, respectively.

Figure 1:
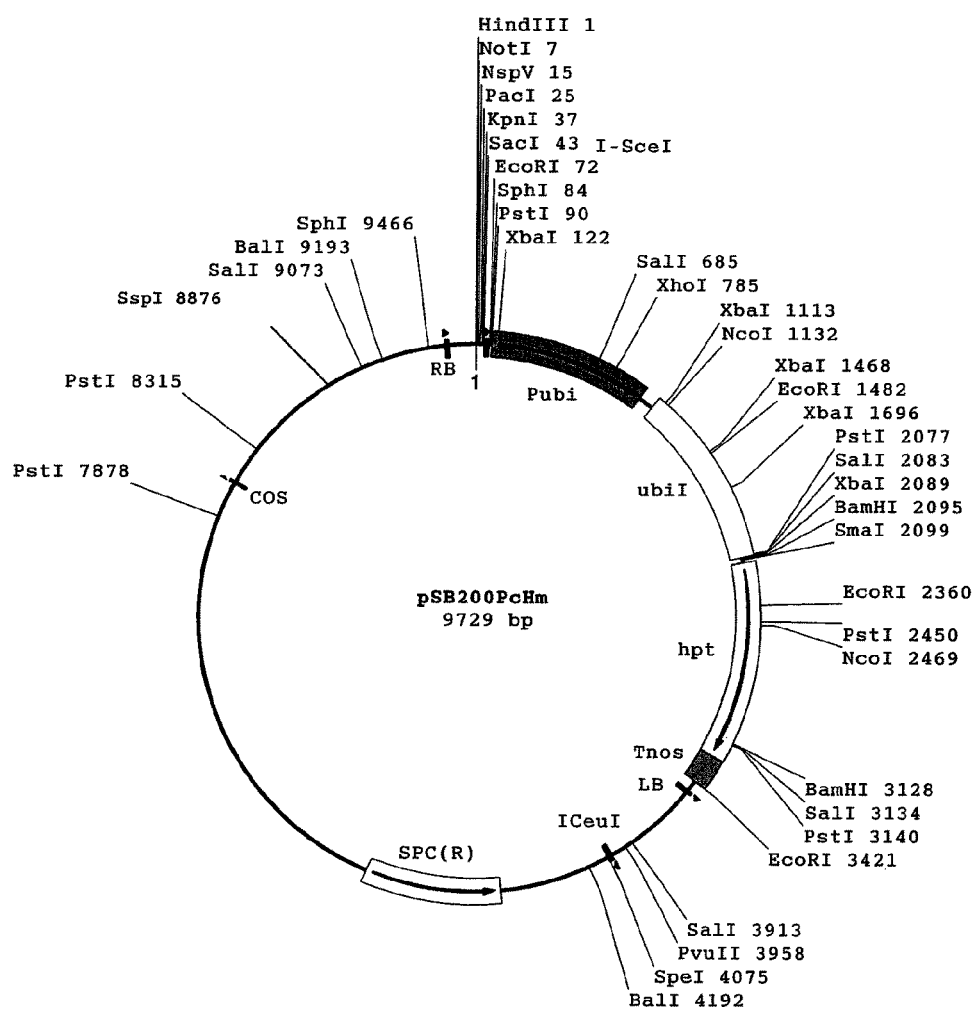
FIG. 1 is a schematic diagram of the vector pSB200PcHm.
Figure 2:
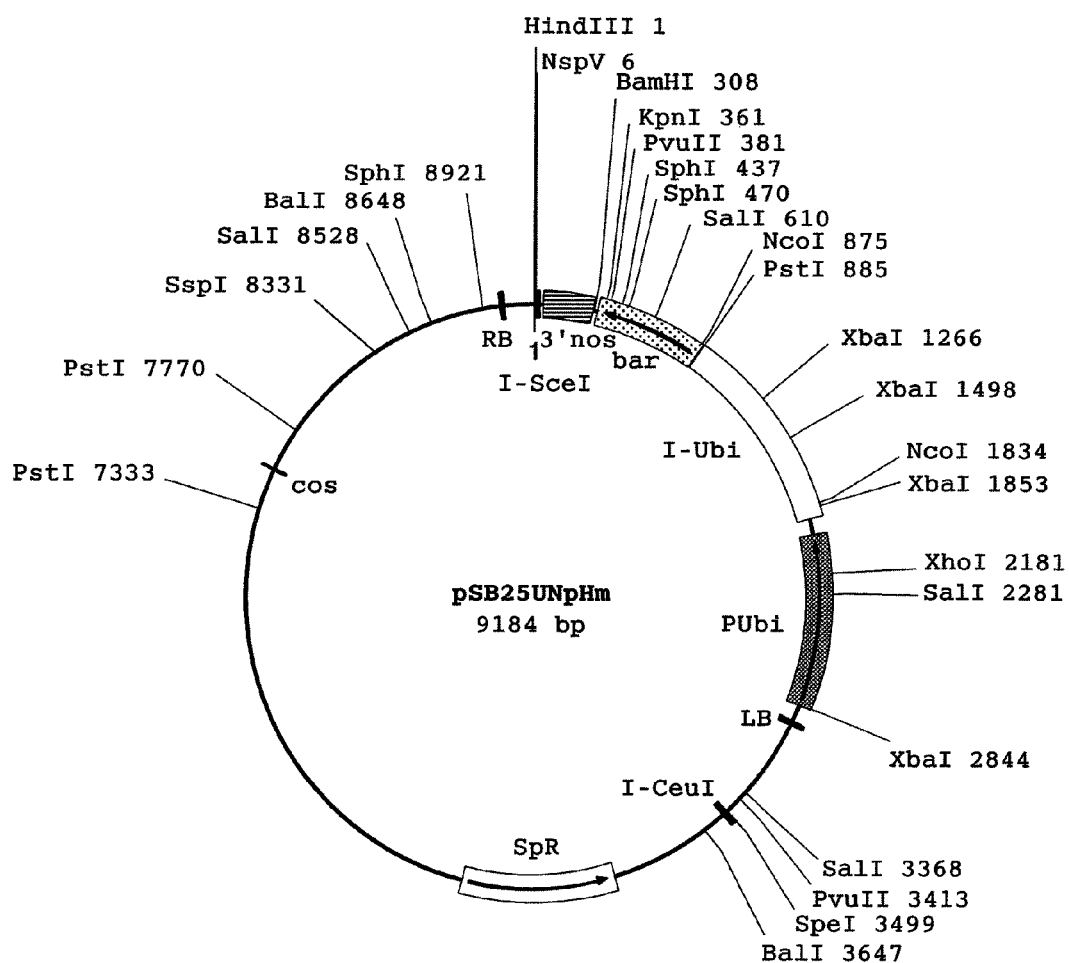
FIG. 2 is a schematic diagram of the vector pSB25UNpHm.

The adapters SpeICeuRV and SpeICeuFW containing a homing endonuclease I-CeuI site (Table 1) were inserted into the SpeI site of pSB200 PacHm1 and pSB25UNpHm1. This operation generated the vector pSB200PcHm containing homing endonuclease sites I-SceI and I-CeuI inserted into the SadI and SpeI sites respectively of pSB200 Pac (FIG. 1), and the vector pSB25UNpHm containing homing endonuclease sites I-SceI (+NspV site) and I-CeuI inserted into the HindIII and SpeI sites respectively of pSB25U (FIG. 2). Excision by I-SceI and I-CeuI was verified, and the nucleotide sequences were checked by using ABI PRISM Fluorescent Sequencer (Model 310 Genetic Analyzer, from Perkin Elmer) to confirm that a single adapter had been inserted. In these vectors, the I-SceI-selectable marker unit-LB-I-CeuI can be excised.

TABLE 1

| Primer Name | Sequence | Length |
| --- | --- | --- |
| HinNspISceRV | 5'-AgC TTT CgA ATA ggg ATA ACA ggg TAA T-3' | 28 mer |
| HinNspISceFW | 5'-AgC TAT TAC CCT gTT ATC CCT ATT CgA A-3' | 28 mer |
| SpeICeuRV | 5'-CTA gTA ACT ATA ACg gTC CTA Agg TAg CgA C-3' | 31 mer |
| SpeICeuFW | 5'-CTA ggT CgC TAC CTT Agg ACC gTT ATA gTT A-3' | 31 mer |

SEQ ID NOs: 23-26 in order from the top.

Then, pSB200PcHm was digested with BamHI to remove the hygromycin resistance gene (hpt), and then blunt-ended. This was ligated to the aatR1-ccdB-Cm-aatR fragment (Invitrogen), and transferred into E. coli DB3.1 to select a chloramphenicol-resistant colony, thereby generating the destination vector pDEST3342. Then, the following primers containing an aatB sequence were synthesized (aatB sequences are shown in uppercase) in order to introduce a marker gene into the pDONR/Zeo plasmid (Invitrogen) by the BP reaction.

TABLE 2

| Primer Name | Sequence | Length |
| --- | --- | --- |
| aatB1-HPT | ggg gAC AAG TTT GTA CAA AAA AGC AGG CTc aat gag ata tga aaa agc c | 49 mer |
| HPT-aatB2 | ggg gAC CAC TTT GTA CAA GAA AGC TGG GTc tat tcc ttt gcc ctc gga cga g | 52 mer |
| aatB1-bar | ggg gAC AAG TTT GTA CAA AAA AGC AGG CTc cat gga ccc aga acg acg c | 49 mer |
| bar-aatB2 | ggg gAC CAC TTT GTA CAA GAA AGC TGG GTt cct aga cgc gtg aga tca g | 49 mer |

SEQ ID NOs: 27-30 in order from the top.

For the amplification of the Hpt gene, the hpt gene described in Bilang et al. (1991) Gene 100: 247-250 was used as a template DNA along with aatB1-HPT and HPT-aatB2 as primers. For the amplification of the phosphinotricin resistance gene (bar), pSB25 (Ishida et al. 1996) was used as a template DNA along with aatB1-bar and bar-aatB2 as primers (Table 2). In 100 μl of a reaction solution containing 10 ng of each template DNA and 25 pmoles of the primers, 35 cycles of PCR was performed. After the completion of the reaction, the products were recovered by ethanol precipitation and used for the BP reaction (25° C., 6 hrs) according to the protocol attached to BP Clonase Enzyme Mix kit (Invitrogen), and then transferred into E. coli DH5a and E. coli cells harboring plasmids of interest were selected on a low salt LA plate containing the antibiotics Zeocin. The nucleotide sequences of the finally obtained plasmids were confirmed by restriction endonuclease analysis, thereby generating pENT-HPTwt and pENT-bar, respectively.

Figure 3:
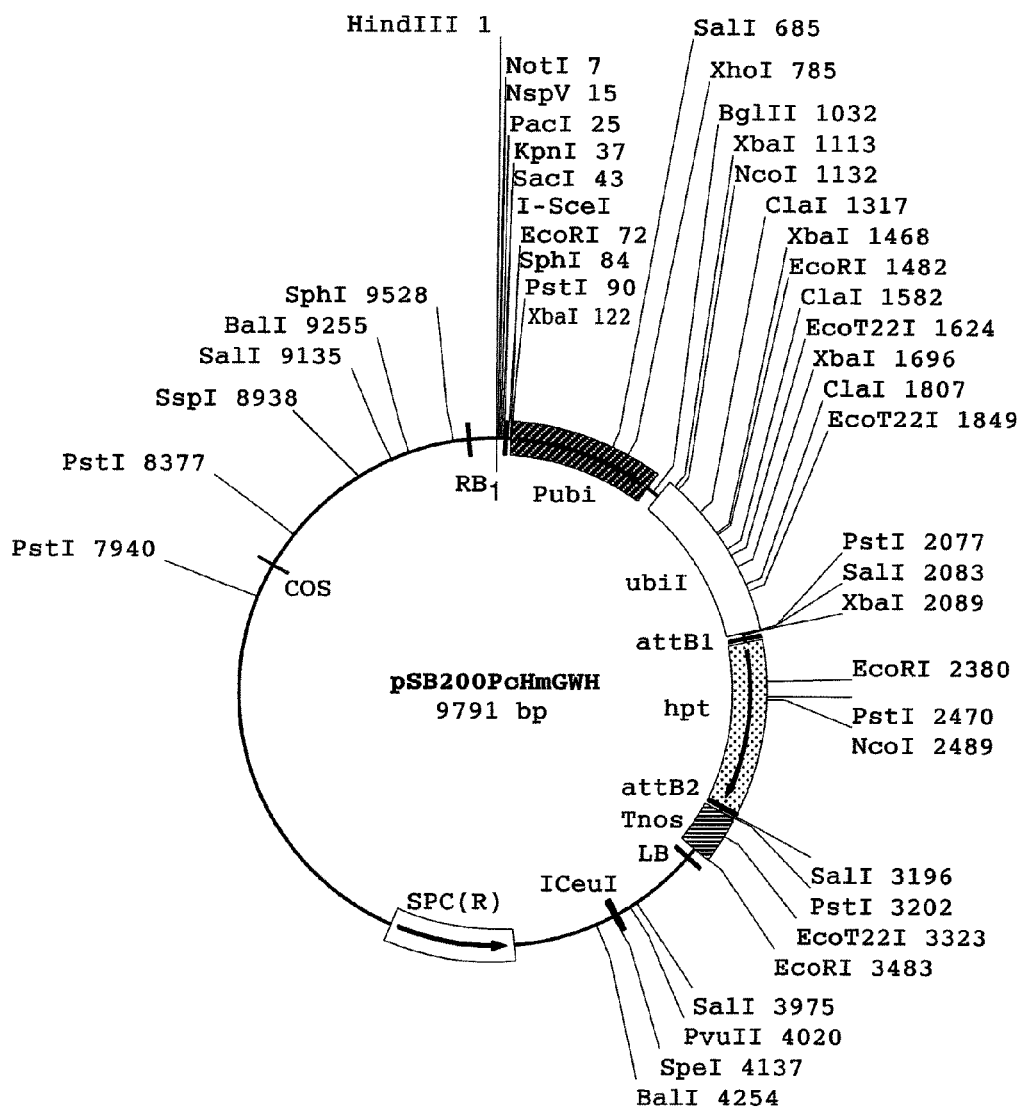
FIG. 3 is a schematic diagram of the vector pSB200PcHmGWH.
Figure 4:
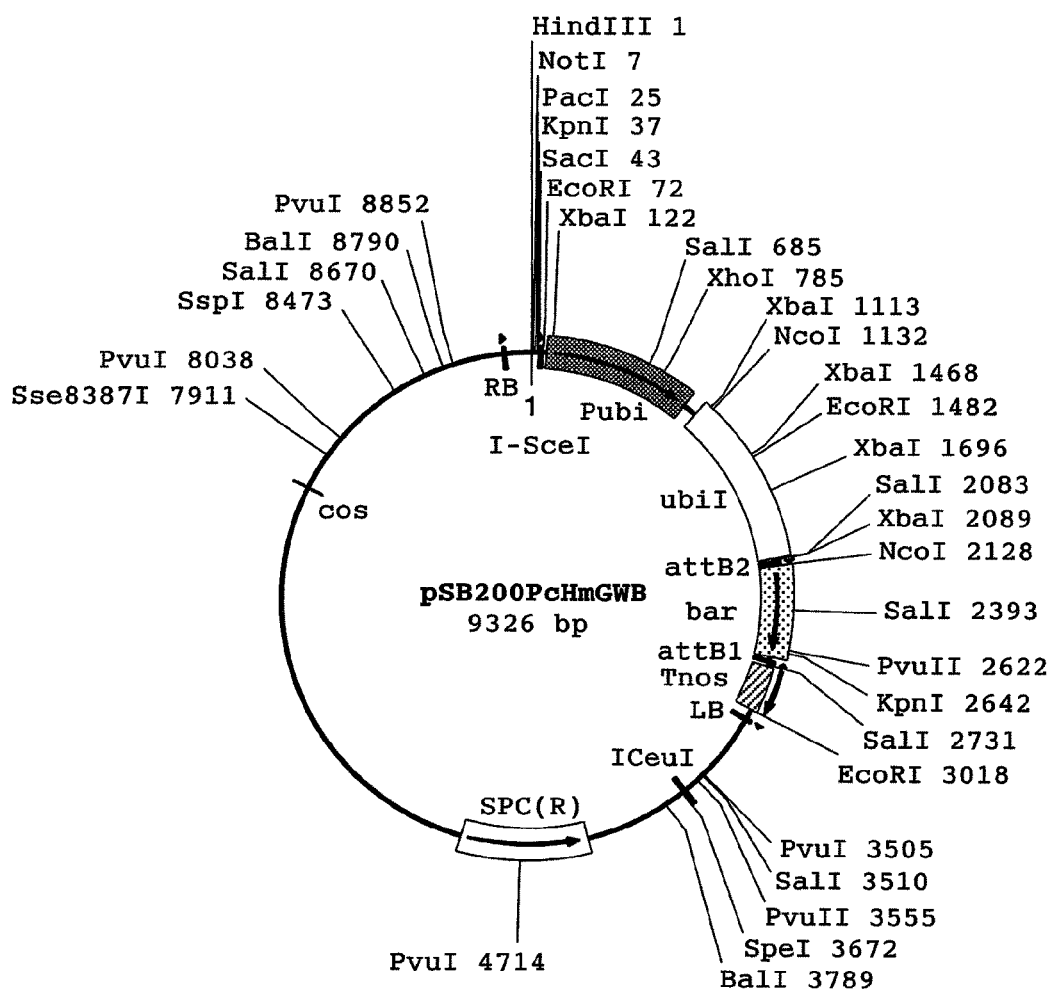
FIG. 4 is a schematic diagram of the vector pSB200PcHmGWB.

The destination vector (pDEST3342) prepared before and the entry vectors (pENT-HPTwt and pENT-bar) were used to prepare final plasmids of interest by the LR reaction. After the reaction in 20 μl of a reaction solution (containing 300 ng each of the destination vector and entry vectors) at 25° C. for 4 hours according to the protocol attached to GATEWAY LR Clonase Enzyme Mix, the reaction products were transferred into E. coli DH5a by electroporation. Plasmid DNAs were prepared from colonies grown on an LA plate containing spectinomycin and candidate clones were selected by restriction fragment patterns. They were confirmed by nucleotide sequence analysis to contain an aatB sequence and the sequence of the HPT gene or bar gene and designated as pSB200PcHmGWH (FIG. 3) and pSB200PcHmGWB (FIG. 4), respectively.

2) Construction of the Cosmid Vector pLC40

A PCR reaction was performed using Pyrobest DNA Polymerase (Takara) along with OriV3'ClaFW, OriV5'PvNhEc, OriT5'BglRV, OriT3'SpEcFW, InC5'XbRV, InC3'BgEcFW, R5'XhoIRV, R3'BmEcFW, 121KIII5'NspV, 121KIII3'SalI, COS 5'BmRV and COS 3'MunFW designed as PCR primers for amplifying a DNA fragment containing oriV, a DNA fragment containing oriT, a DNA fragment containing the incC2 gene, a DNA fragment containing the trfA1 gene, all of which are derived from the IncP plasmid pVK102 (Knauf and Nester, Plasmid 8: 45-54, 1982), a DNA fragment containing the nptIII gene from pBI121 and a DNA fragment containing cos from pSB11 (Table 3).

Each primer contains a restriction endonuclease site for later use. The PCR products other than the trfA1 gene, i.e., the DNA fragment containing oriV from pVK102 (884 bp), the DNA fragment containing oriT (810 bp), the DNA fragment containing the incC1 gene (2118 bp), the DNA fragment containing the nptIII gene from pBI121 (1087 bp), and the DNA fragment containing cos from pSB11 were each cloned into the vector pCR2.1Topo Blunt (from Invitrogen). As a result, the DNA fragment containing oriV was found to contain two nucleotide substitutions and one nucleotide addition as compared with the corresponding nucleotide sequence in a public database (Genbank accession L27758). These mutations were also found in the template plasmid, showing that they were not introduced by PCR but that the template plasmid had a nucleotide sequence different from the sequence in the public database. The nucleotide sequences of oriT, the incC1 gene, and cos were completely identical to those in the database. However, the trfA1 gene could not be cloned alone. Thus, the construction was pursued by the method described below.

The plasmid into which the DNA fragment containing oriV had been cloned was digested with the restriction endonucleases EcoRI and ClaI, and a 0.9 kb fragment was purified. Similarly, the DNA fragment containing oriT was digested with EcoRI and BglII, and the DNA fragment containing nptIII was digested with NspV and SalI, and the digests were purified. The PCR product of the DNA fragment containing the trfA1 gene was precipitated with ethanol, and then digested with XhoI and BamHI, and purified. These 4 fragments (oriV, the trfA1 gene, nptIII, oriT) were ligated at a time and cloned together. The nucleotide sequence of the resulting plasmid (designated as pVRKT) was analyzed to reveal a frameshift mutation in the DNA fragment containing the trfA1 gene as compared with the corresponding nucleotide sequence in the public database (Genbank accession L27758), but the same mutation was also found in pVK102 used as the template, thereby concluding that the mutation was not introduced by PCR and that pVK102 used as the template contained a nucleotide sequence different from the sequence in the public database.

Figure 5:
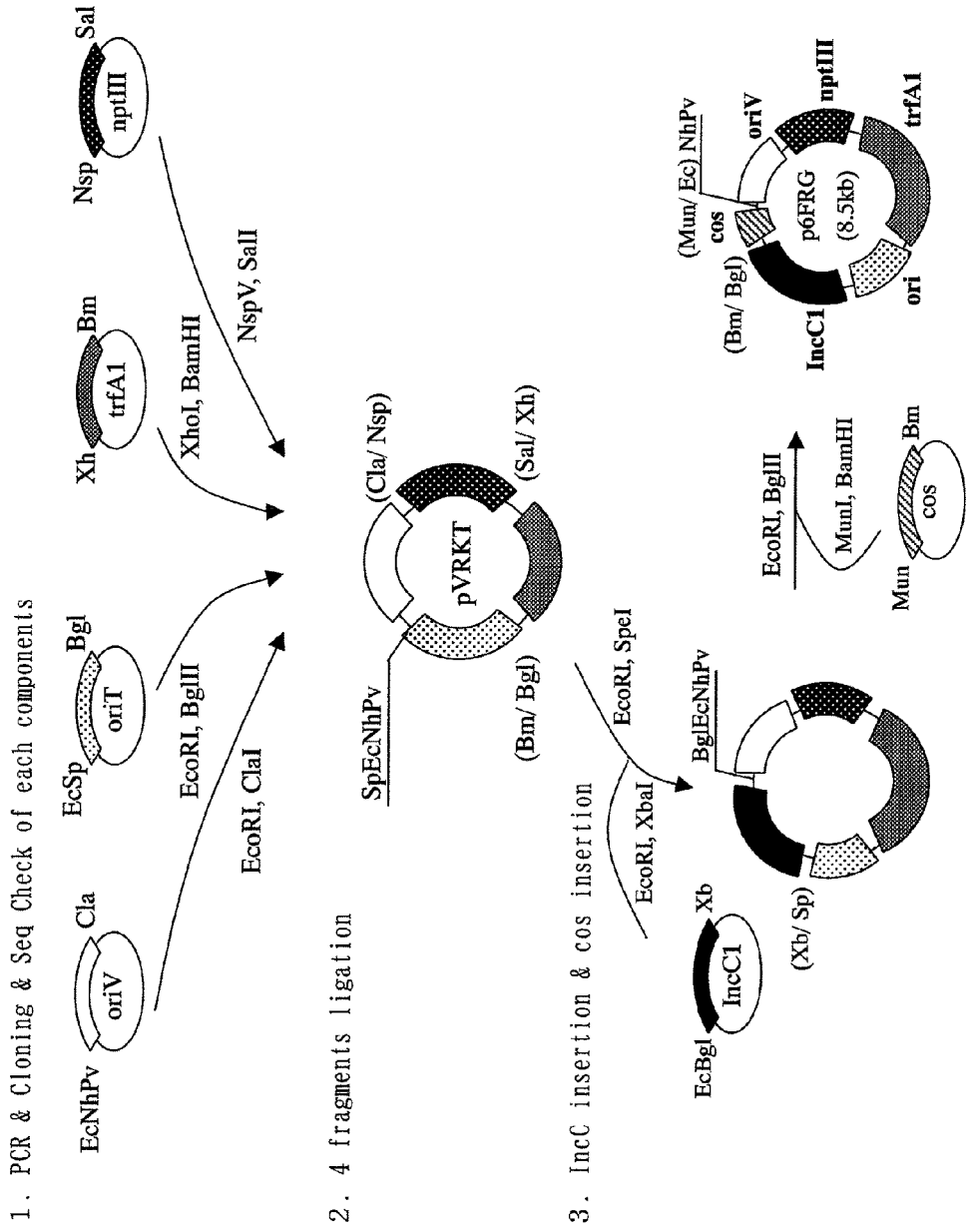
FIG. 5 is a diagram showing a procedure for constructing the vector pLC40.
Figure 5:
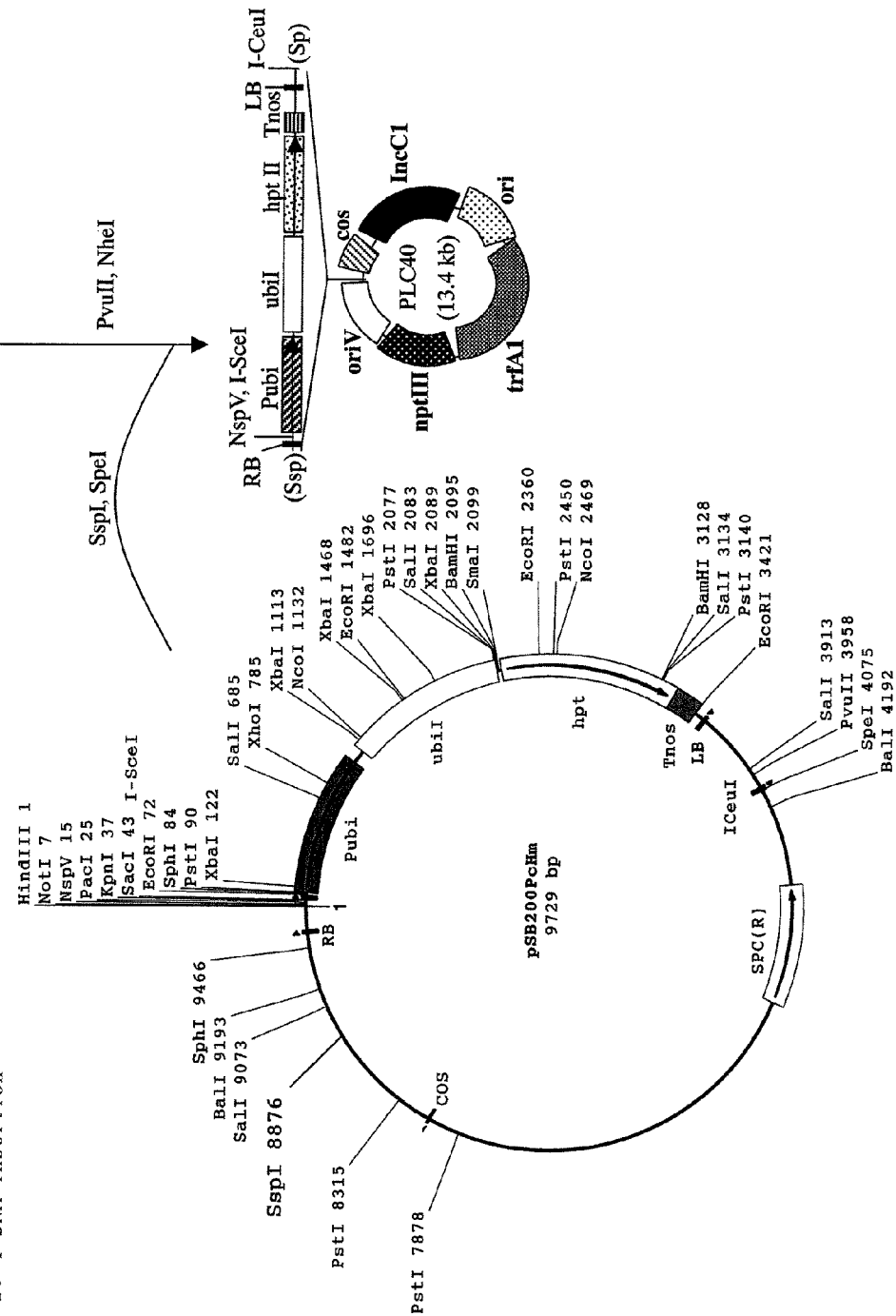
Figure 6:
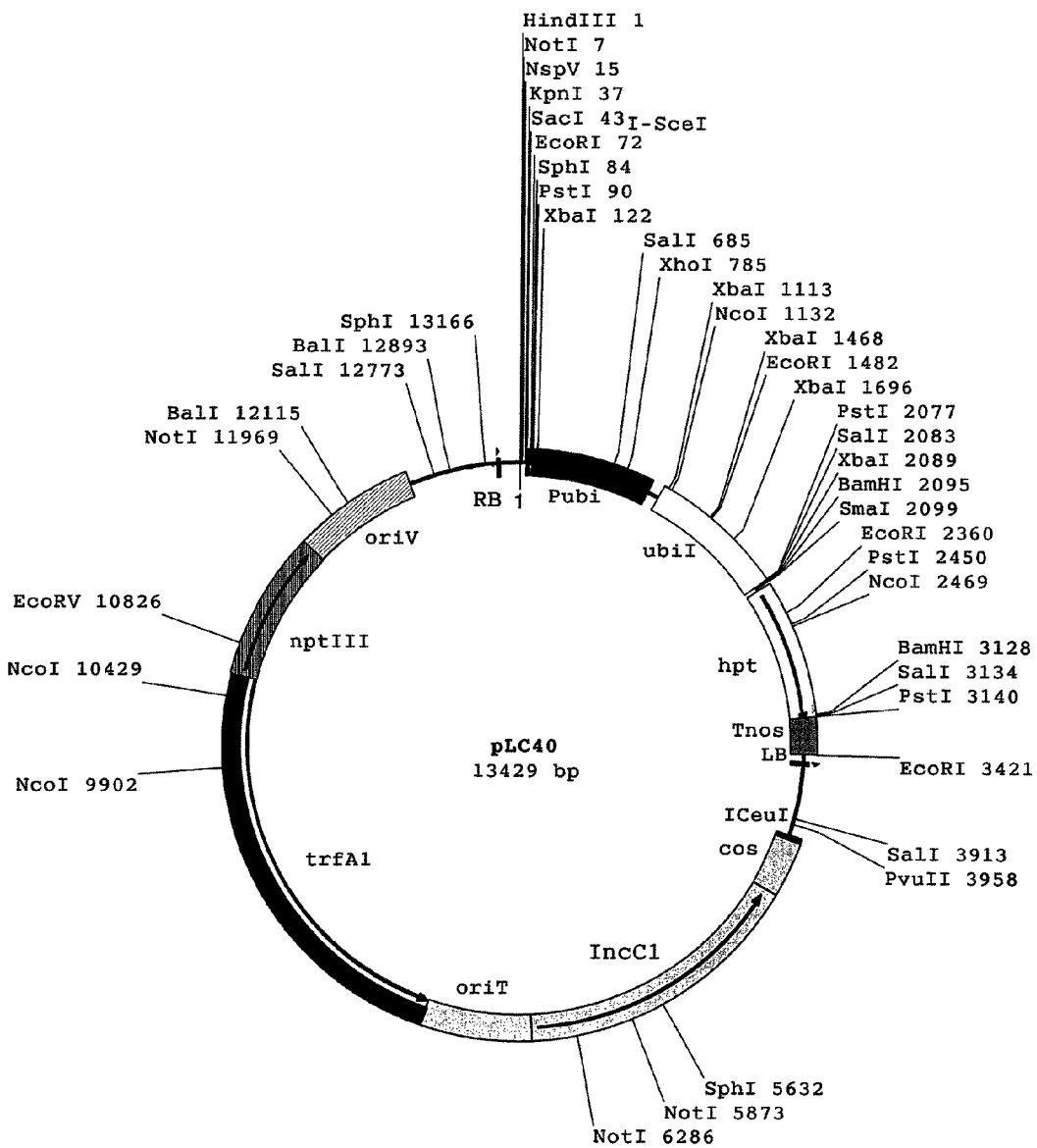
FIG. 6 is a schematic diagram of the vector pLC40.
Figure 8:
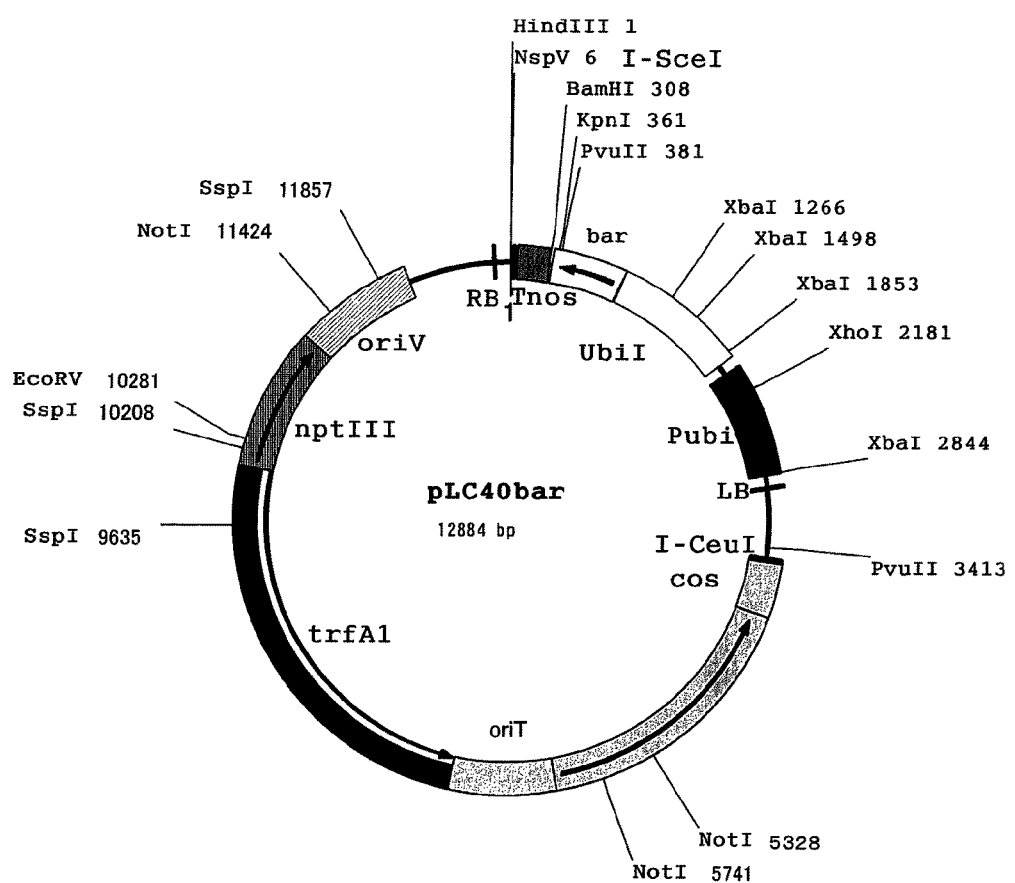
FIG. 8 is a schematic diagram of the vector pLC40 bar.
Figure 9:
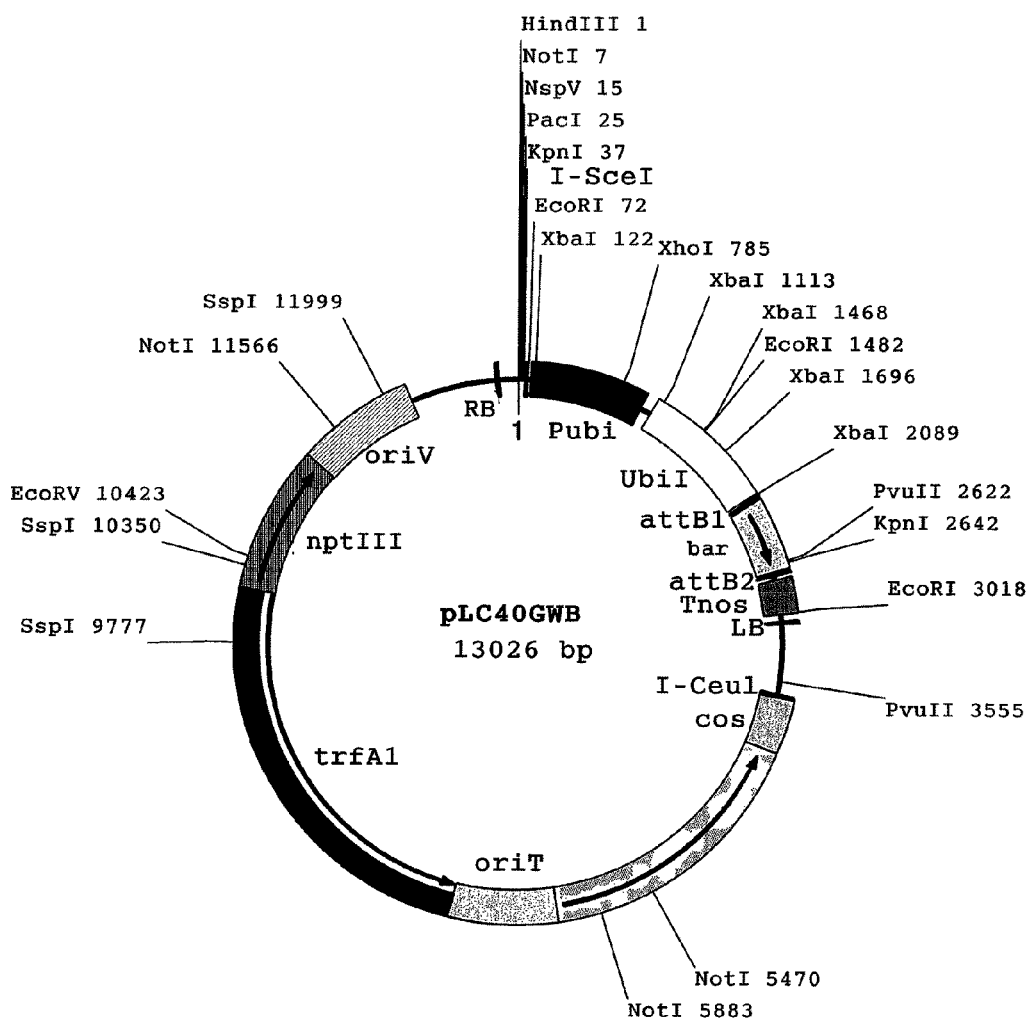
FIG. 9 is a schematic diagram of the vector pLC40GWB.

The resulting plasmid pVRKT containing the 4 fragments were digested with EcoRI and SpeI, and the DNA fragment containing the incC1 gene recovered by digesting the plasmid containing the incC1 gene with EcoRI and XbaI was inserted into it. The resulting plasmid was further digested with EcoRI and BglII, and the DNA fragment containing cos recovered by digesting the plasmid containing the DNA fragment containing cos with MunI and BamHI was inserted into it to generate the low-copy vector backbone p6FRG (about 8.5 kb) consisting of the 6 fragments, i.e., the DNA fragment containing oriV, the DNA fragment containing the trfA1 gene, the DNA fragment containing nptIII, the DNA fragment containing oriT, the DNA fragment containing the incC1 gene, and the DNA fragment containing cos(SEQ ID NO: 1 in the Sequence Listing). The foregoing cloning procedure was summarized in a schematic diagram shown in FIG. 5. The T-DNA region (SspI-SpeI fragment) of pSB200PcHm was inserted into the PvuII, NheI sites of the p6FRG plasmid to generate the vector pLC40 (FIG. 6, SEQ ID NO: 2 in the Sequence Listing).

ing). This differs from pLC40 by insertions of attB1, 2 sequences and a deletion of a 317 bp SspI-BalI region upstream of the RB.

pLC40 bar, pLC40GWB, pLC40GWBSW pSB25UNpHm and pSB200PcHmGWB were digested with the restriction endonucleases SpeI and SspI, and fragments containing the T-DNA were recovered. These fragments were cloned into the PvuII, NheI sites of p6FRG to generate pLC40 bar (FIG. 8, SEQ ID NO: 4 in the Sequence Listing) and pLC40GWB (FIG. 9, SEQ ID NO: 5 in the Sequence Listing), respectively. pSB200PcHmGWB was treated with NspV, blunt-ended, and dephosphorylated. A pSwaI linker (Table 4) was inserted into this site (pSB200PcHmGWBSW). This plasmid was digested with the restriction endonucleases SpeI and SspI, and a fragment containing the T-DNA was recovered. These fragments were cloned into the PvuII, NheI sites of p6FRG to generate pLC40GWBSW.

pLC40:35S-IGUS, pLC40GWB:35S-IGUS

The vector pSB24 (Komari et al. 1996) was treated with the restriction endonucleases HindIII and EcoRI to excise a DNA fragment consisting of 35S promoter-1-GUS gene-NOS terminator. This fragment was further blunt-ended by Klenow treatment, and then a 3.1 kb fragment was purified and recovered. The cosmid vector pLC40 described above was treated with the restriction endonuclease NspV, blunt-ended with Klenow enzyme, and then dephosphorylated and purified. On the other hand, pLC40GWBSW was treated with the restriction endonuclease SwaI, dephosphorylated and then gel-purified. The DNA fragment containing the GUS gene described

TABLE 3

| Primer Name | Sequence | Target gene | Length |
|---|---|---|---|
| 121KIII5'NspV | 5'-TCg TTC gAA TCg ATA CTA TgT TAT ACg CCA AC-3' | nptII | 32 mer |
| 121KIII3'SalI | 5'-ATC gTC gAC TgC ACg AAT ACC AgC gAC CC-3' | | 29 mer |
| COS5'BmRV | 5'-ggg ggA TCC TTC CAT TgT TCA TTC GAC ggA C-3' | cos | 31 mer |
| COS3'MunFW | 5'-ggg CAA TTg ACA TgA ggT TgC CCC gTA TTC-3' | | 30 mer |
| OriV3'ClaFW | 5'-gAT ATC gAT AgC gTg gAC TCA Agg CTC TC-3' | oriV | 29 mer |
| OriV5'PvNhEc | 5'-AAA gAA TTC gCT AgC CAg CTg gCg CTg CCA TTT TTg ggg Tg-3' | | 41 mer |
| R5'XhoIRV | 5'-AAA CTC gAg CAg CCg AgA ACA TTg gTT CC-3' | trfA1 | 29 mer |
| R3'BmEcFW | 5'-TAg gAA TTC ggA TCC AAA ACA ACT gTC AAA gCg CAC-3' | | 36 mer |
| OriT5'BglRV | 5'-CgT AgA TCT ggC gCT Cgg TCT TgC CTT g-3' | oriT | 28 mer |
| OriT3'SpEcFW | 5'-TgT gAA TTC ACT AgT gAT ATT CCA CAA AAC AgC Agg g-3' | | 37 mer |
| InC5'XbRV | 5'-CCg TCT AgA TTC gAg CCA Cgg Tag Cgg C-3' | incC2 | 28 mer |
| InC3'BgEcFW | 5'-CTT gAA TTC AgA TCT TCT Cgg Cgg CgA TCA CgA C-3' | | 34 mer |

SEQ ID NOs: 31-42 in order from the top.

3) Construction of Other pLC Series Cosmid Vectors
pLC40GWH

Figure 7:
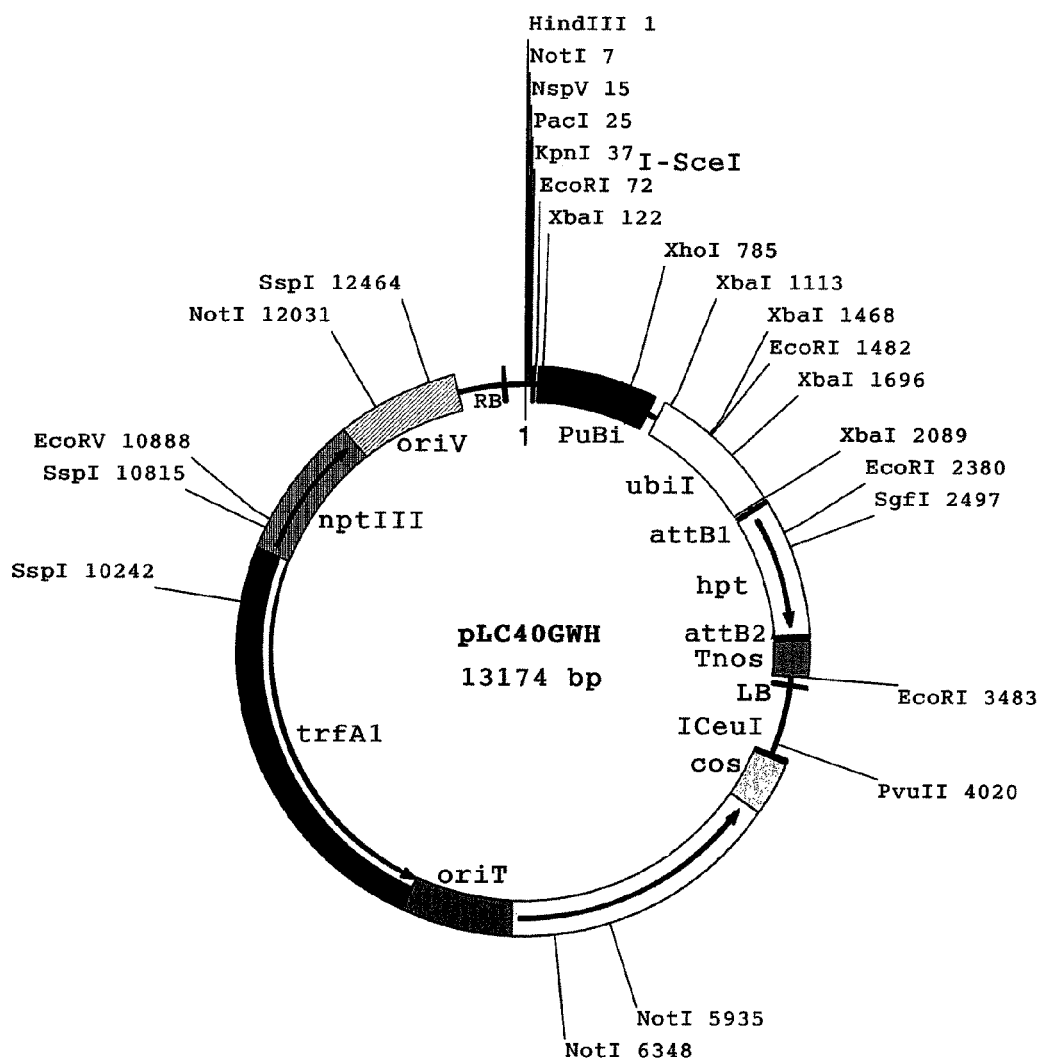
FIG. 7 is a schematic diagram of the vector pLC40GWH.

Of the two BalI sites in the backbone of pSB200PcHmGWH, the one on the left side of the RB is not cleaved because it is methylated. Thus, pSB200PcHmGWH was used in the experiments below after it was once transferred into the *E. coli* strain GM48 to demethylate that site. pSB200PcHmGWH was treated with BalI and SpeI to excise a region containing the T-DNA, which was cloned into the PvuII, NheI sites of 6FRG described above to generate pLC40GWH (FIG. 7, SEQ ID NO: 3 in the Sequence Listabove was inserted into these vectors to prepare pLC40:35S-IGUS and pLC40GWB:35S-IGUS, respectively.

pLC40GWHKorB

The cloned region of IncC1 in the pLC vector was extended, and the vector pLC40GWHKorB containing the korB gene was constructed. IncC3'BgEcFw (described above) and IncC/KorB-Xba#1 (Table 4) were designed as primers for amplifying a DNA fragment containing IncC1-KorB of the IncP-based plasmid pVK102. Each primer contains a restriction endonuclease site for later use. A PCR reaction was performed as follows. In 50 μl of a reaction solution containing 500 ng of the pVK102 plasmid DNA, 5 µl of 10× Pyrobest Buffer II, 4 µl of 2.5 mM each dNTP, 50 pmoles of the primers, and 0.5 µl of Pyrobest DNA Polymerase (from Takara), one cycle of 96° C. for 3 minutes, and 10 cycles of 96° C. for 1 minute, 55° C. for 1 minute, and 72° C. for 2 minutes and 30 seconds were performed by using Mastercycler gradient (eppendorf). The resulting amplified PCR product of IncC1-korB (3065 bp) was cloned into the vector pCR2.1Topo Blunt (from Invitrogen). Ligation reactions were performed following the instructions attached to the vector kit. The DNA was transferred into E. coli DH5a by electroporation, and incubated overnight at 37° C. on a 2×YT agar plate containing the antibiotic Zeocin (25 µg/ml). Colony direct PCR was performed to select candidate clones by using grown colonies as templates along with the same primer set as used for the amplification of IncC1-KorB. PCR conditions included one cycle of 96° C. for 3 minutes, and 30 cycles of 96° C. for 1 minutes, 55° C. for 1 minute, and 72° C. for 2 minutes and 30 seconds using Wastercycler gradient in a suspension of the colony in 20 µl of a reaction solution containing 2 µl of 10× Extaq Buffer, 1.6 µl of 2.5 mM each dNTP, 5 pmoles of the primers, and 0.4 µl of Extaq DNA Polymerase (from Takara). The resulting PCR amplified products of about 3 kb were selected as candidate clones. The nucleotide sequences of these clones were determined by ABI PRISM Fluorescent Sequencer (Model 3100 Genetic Analyzer, from Applied Biosystems). As a result, the nucleotide sequence of IncC1-KorB was completely identical to the sequence in the database.

Figure 10:
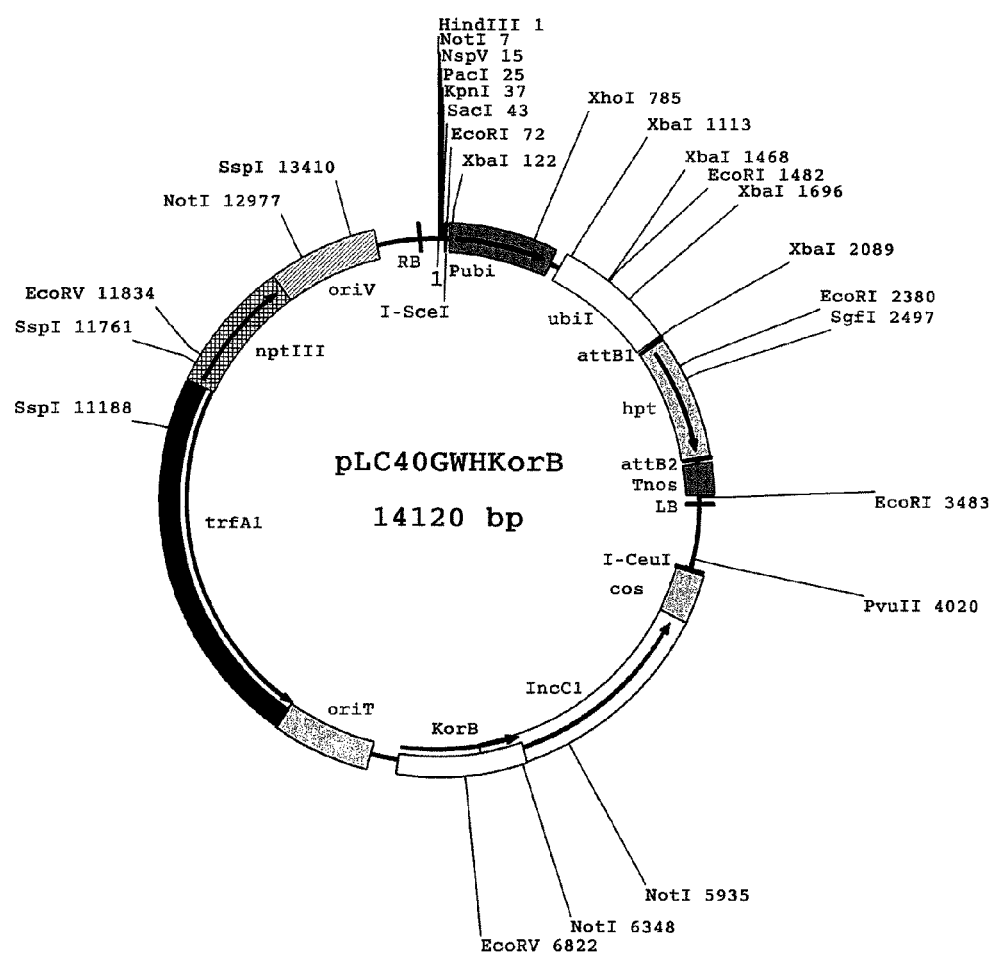
FIG. 10 is a schematic diagram of the vector pLC40GWHkorB.

Then, the plasmid pVRKT described above was digested with EcoRI and SpeI, and the IncC1-KorB fragment recovered by digesting the plasmid containing IncC1-KorB with EcoRI and XbaI was inserted into it. The resulting plasmid was further digested with EcoRI and BglII, and the cos fragment (MunI-BamHI fragment) described above was inserted into it to generate the plasmid p6FRG2 consisting of the 6 fragments, i.e., oriV, trfA1, nptIII, oriT, IncC1-KorB and cos. The T-DNA region (BalI-SpeI fragment) from pSB3342GWH was inserted into the PvuII, NheI sites of the p6FRG2 plasmid to generate the vector pLC40GWHKorB (FIG. 10, SEQ ID NO: 65).

pLC40GWHKorBPI

In order that the cloned large genomic fragment could be excised in its intact form, a recognition site for the homing endonuclease PI-SceI was added upstream of the multicloning site. pLC40GWHKorB was digested with HindIII, and PI-SceI adapters (PI-SceIFw, PI-SceIRv, Table 4) were inserted to generate pLC40GWHKorBPI.

pLC40GWHKorBPIattB3

In order that the promoter of the selectable marker of pLC40GWH could be changed by any other one by a Gateway system, an attB3 site was added upstream of the ubiquitin promoter. pLC40GWHKorBPI was digested with I-SceI and attB3 adapters (attB3Fw, attB3Rv, Table 4) were inserted to prepare pLC40GWHKorBPIattB3.

pLCleo

Figure 11:
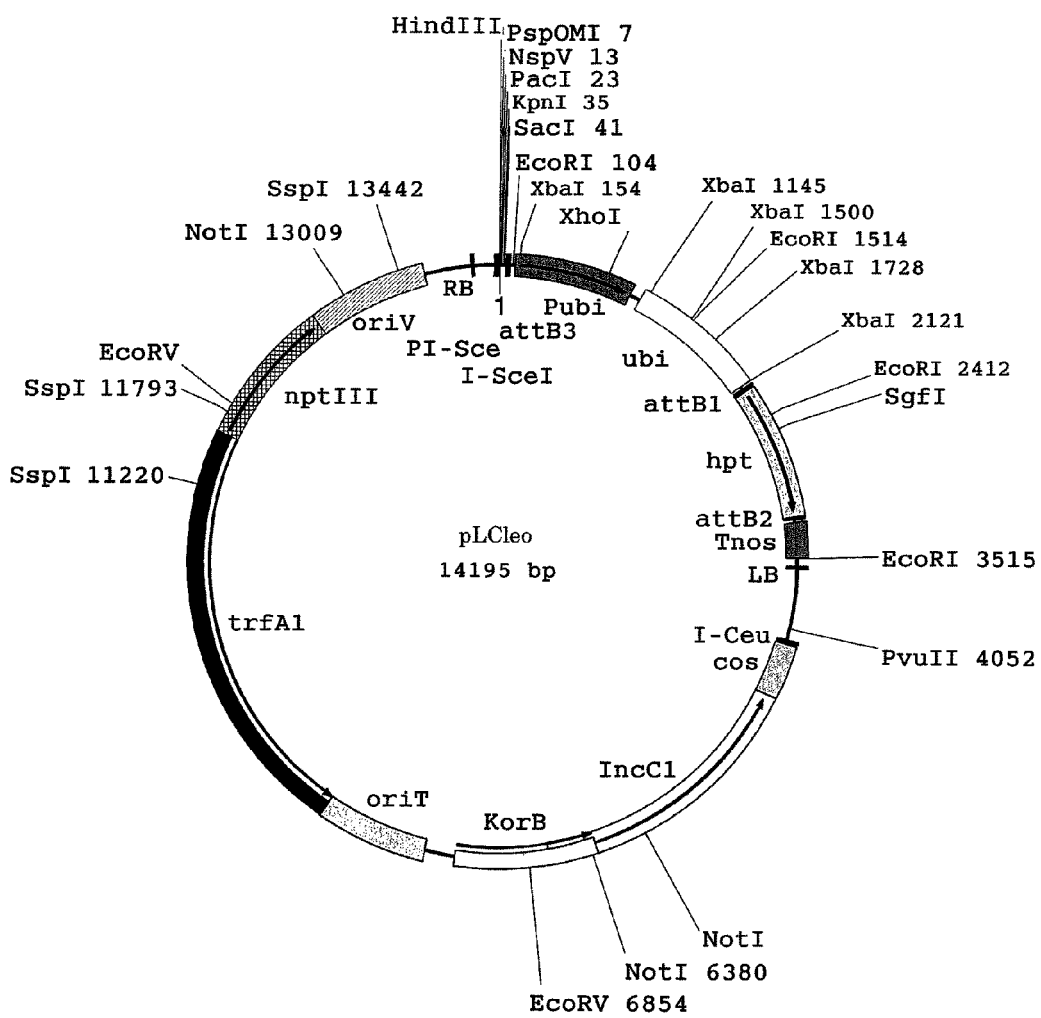
FIG. 11 is a schematic diagram of the vector pLCleo.

In order that an NotI-digested genomic fragment could be cloned, a recognition site for PspOMI (producing the same sticky end as that of NotI) was formed at the multicloning site and simultaneously the recognition site of ApaI (a neoschizomer of PspOMI) in the ubiquitin intron was abolished. pLC40GWHKorBPIattB3 was digested with ApaI and NheI, and ApaIm-NheI adapters (ApaIm-NheIFw, ApaIm-NheIRv, Table 4) were inserted to prepare pLC40GWHKorBPIattB3ApaIm. This plasmid was digested with HindIII and NspV, and HindIII-PspOMI-NspV adapters (HindIII-PspOMI-NspVFw, HindIII-PspOMI-NspVRv, Table 4) were inserted to finally prepare pLCleo (FIG. 11, SEQ ID NO: 66 in the Sequence Listing).

TABLE 4

| Primer/Adapter name | Sequence(5'-3') | Length |
|---|---|---|
| IncC/KorB-Xba#1 | CGG TCT AGA GTG CGC AGC AGC TCG TTA TC | 29 mer |
| PI-SceIFw | AGC TAT CTA TGT CGG GTG CGG AGA AAG AGG TAA TGA AAT GGC A | 43 mer |
| PI-SceIRv | AGC TTG CCA TTT CAT TAC CTC TTT CTC CGC ACC CGA CAT AGA T | 43 mer |
| attB3Fw | CAG GGT AAT CAA CTT TGT ATA ATA AAG TTG ATA A | 34 mer |
| attB3Rv | CAA CTT TAT TAT ACA AAG TTG ATT ACC CTG TTA T | 34 mer |
| ApaIm-NheIFw | GGGTAGTTCTACTTCTGTTCATGTTTGTGTTAGATCCGTGTTTGTGTTAGATCCGTGCTG | 60 mer |
| ApaIm-NheIRv | CTAGCGCCGGATCTAACACAAACACGGATCTAACACAAACATGAACAGAAGTAGAACTACCCGGCC | 66 mer |
| HindIII-PspOMI-NspVFw | AGC TTG GGC CCT T | 13 mer |
| HindIII-PspOMI-NspVRv | AGG GCC CA | 8 mer |

SEQ ID NOs: 68-76 in order from the top.

p6FRGSwKp p6FRG was treated with PvuII and dephosphorylated. The adapter SwaIKpnIRV, SwaIKpnIFW (Table 5) DNAs having recognition sites for SwaI and KpnI were annealed. A part of this was phosphorylated with PNK (Amersham). This SwaI-KpnI linker was inserted into the PvuII site of p6FRG to generate p6FRGSwKp. The KpnI site was designed for cloning a DNA fragment containing the virB gene and the virG gene derived from the Agrobacterium strain A281 in the next step, and the SwaI site was designed for cloning the T-DNA in the step after next.

TABLE 5

| Linker/Adapter name | Sequence | Length |
|---|---|---|
| pSwaI linker | 5'-cca ttt aaa tgg-3' | 12 mer |
| SwaIKpnIRV | 5'-cca ttt aaa tgg tac cgg-3' | 18 mer |
| SwaIKpnIFW | 5'-ccg gta cca ttt aaa tgg-3' | 18 mer |

SEQ ID NOs: 43-45 in order from the top.

p6FRGSVR, p6FRGSVRF

Figure 12:
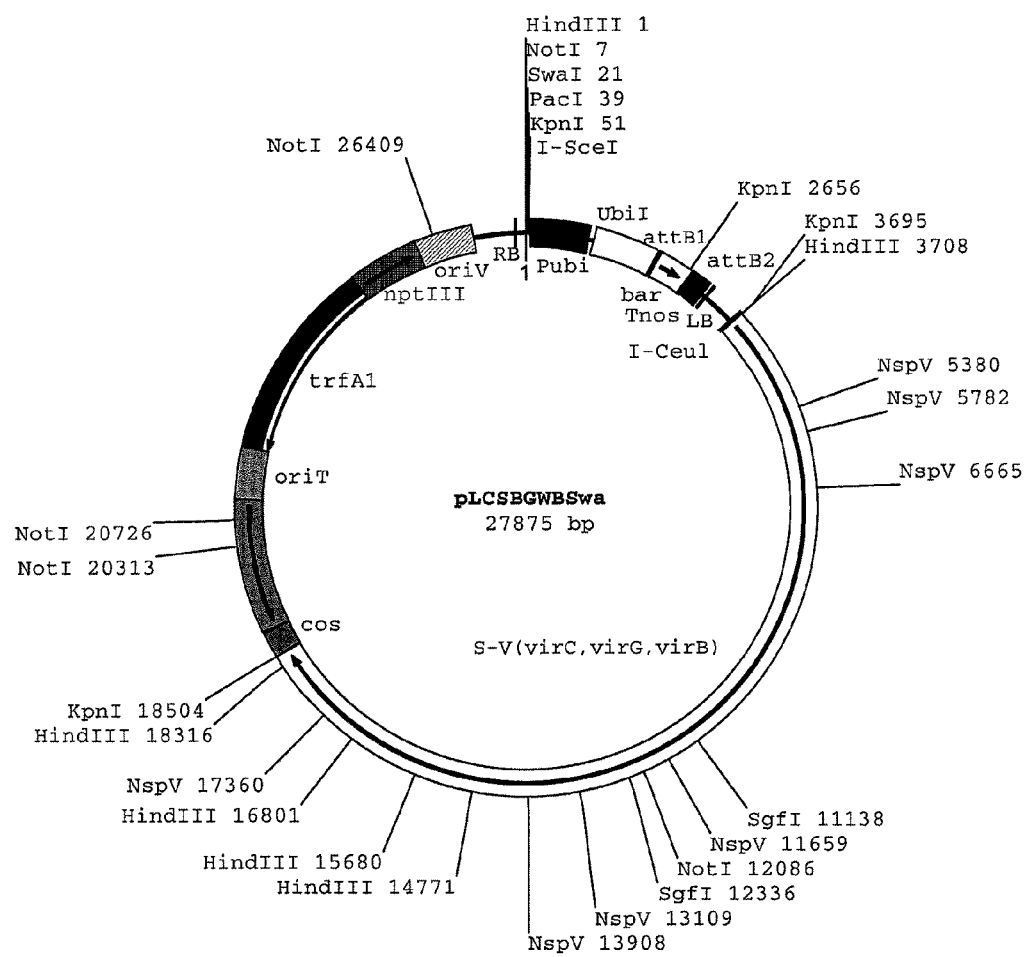
FIG. 12 is a schematic diagram of the vector pLCSBGWB-SWa.

The vector pSB1 (Komari et al. 1996) was digested with KpnI, and a 14.8 kb DNA fragment containing the virB gene and the virG gene was recovered. This fragment was inserted into the KpnI-treated and dephosphorylated vector p6FRGSwKp, thereby generating p6FRGSVR and p6FRGSVF.

pLCSBGWBSW pSB200PcHmGWBSW was digested with SpeI and SspI, and a DNA fragment containing the T-DNA region was blunt-ended with Klenow enzyme. This fragment was inserted into the SwaI-digested and dephosphorylated vector p6FRGSVR, thereby generating pLCSBGWBSW (FIG. 12, SEQ ID NO: 6 in the Sequence Listing). This vector is a low-copy vector having a full length of about 28 kb, which contains the virB gene and the virG gene derived from the *Agrobacterium* strain A281 so that it may be used for transformation of maize. It also contains a cos site, which allows easy cloning of about 10-20 kb of DNA by a packaging reaction.

4) A pLC Vector Containing virG

The vector pLC40GWHvG containing the virG gene in the pLC40GWH vector was constructed by the procedure described below as a means for improving the efficiency of plant transformation with a pLC40 series cosmid vector.

Preparation of the virG Gene

The primers virGProSm and virGTerSm for amplifying the virG gene (including its promoter, the structural gene and the 3' region) were designed and synthesized. These primers, and pTOK47 (Jin et al. 1987 J Bacteriol 169: 4417-4425) as a template DNA, were used to amplify the virG gene by PCR. As a result, the PCR product of about 1 kb was amplified. A part of the product was cloned into the vector pCR2.1Topo (from Invitrogen) in the same manner as described above, and the nucleotide sequence was determined. The DNA sequence of the VirG gene contains an NspV site. This restriction site will be used as a cloning site in a future vector. Thus, this site was removed by PCR mutagenesis. The first adenine in the NspV site (ttcgaa) was changed to guanine (ttcgga) to design and synthesize the primer virGonNspVRV and its complementary sequence virGonNspVFW. PCR was performed with two primer sets, i.e., one consisting of VirGonNspVFW and the primer virGProSpe placed upstream of the virG gene promoter and the other consisting of virGonNspVRV and the primer virGTerSpe placed downstream of the virG gene terminator. The virG gene cloned into pCR2.1Topo was used as a template. As a result, the product of about 400 bp and the product of about 600 bp were amplified by the former and latter sets, respectively. These products were purified and used as templates for the next PCR reaction. A PCR reaction was performed with the purified two PCR products as templates and the previous primers virGProSpe and virGTerSpe. As a result, the PCR product of about 1 kb was amplified. The PCR product was cloned into the pCR2.1Topo vector, and the nucleotide sequence was determined to confirm the mutation (ttcgaa→ttcgga).

Similarly, the unmutated virG gene was amplified by PCR with virGProSpe and virGTerSpe, and cloned into pCR2.1Topo, and the nucleotide sequence was determined. The primers used in PCR are summarized in Table 6.

TABLE 6

| Designation | Sequence 5'-3' | Length |
|---|---|---|
| virGProSm | TCA ATA CCC ggg gTA AGC TCg AAg CgT TTC AC | 32 mer |

TABLE 6-continued

| Designation | Sequence 5'-3' | Length |
|---|---|---|
| virGTerSm | Tgg TgA CCC ggg ACC TAT Cgg AAC CCC TCA C | 31 mer |
| virGProSpe | TCA ATA ACT AgT gTA ACC TCg AAg CgT TTC AC | 32 mer |
| virGTerSpe | Tgg TgA ACT AgT ACC TAT Cgg AAC CCC TCA C | 31 mer |
| virGonNspVRV | CTT gAg ATC gTT Cgg AAT CTg | 21 mer |
| virGonNspVFW | CAg ATT CCg AAC gAT CTC AAg | 21 mer |

SEQ ID NOs: 46-51 in order from the top.

pLC40GWHvG1, pLC40GWHvGC1

Figure 13:
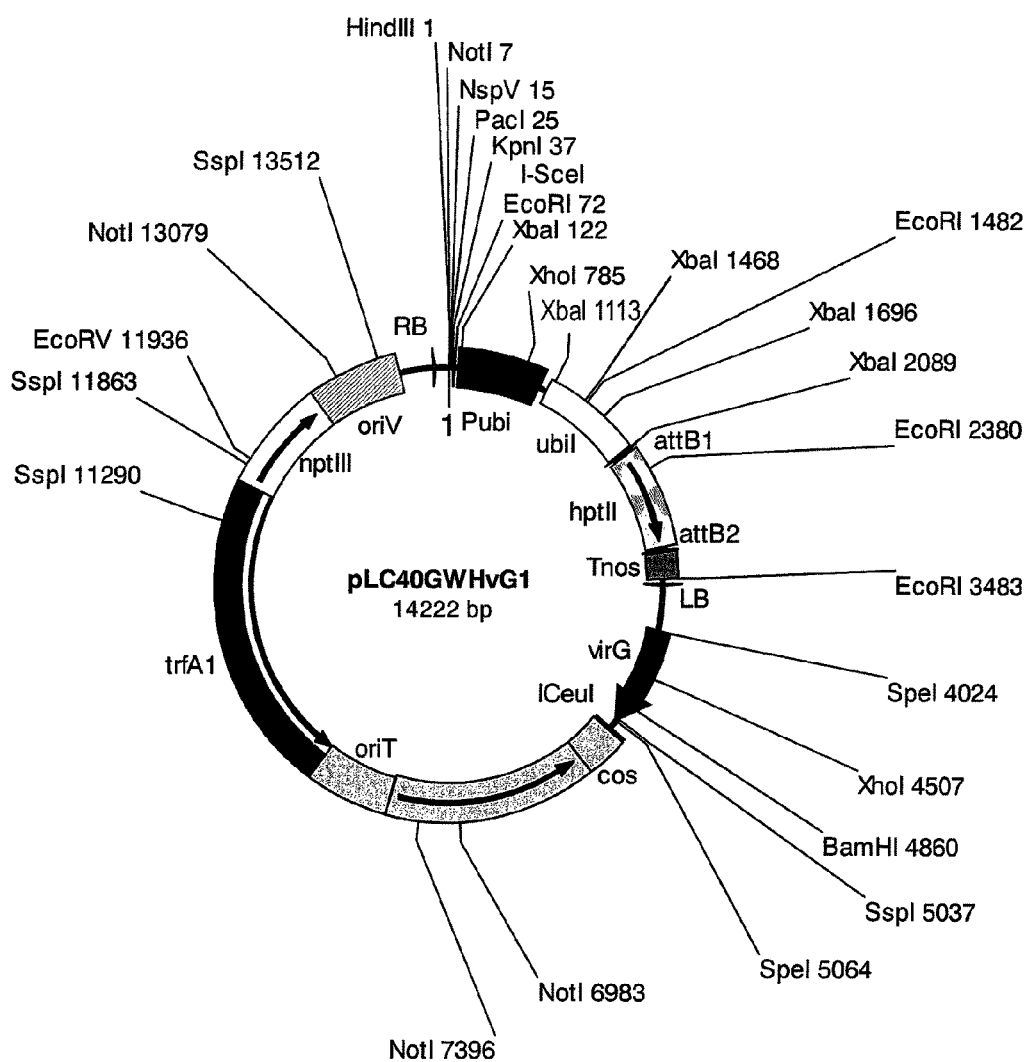
FIG. 13 is a schematic diagram of the vector pLC40GWHvG1.

The vector pLC40GWH was digested with the restriction endonuclease PvuII, and dephosphorylated. An SpeI linker (GACTAGTC, from Takara) was inserted to prepare pLC40GWHSpe. This plasmid was digested with the restriction endonuclease SpeI and dephosphorylated. A fragment of about 1 kb of the mutated virG gene excised with SpeI from the vector was inserted into this plasmid to prepare pLC40GWHvG1 (FIG. 13, SEQ ID NO: 7 in the Sequence Listing). Similarly, the unmutated virG gene was inserted into pLC40GWHSpe to prepare pLC40GWHvGC1.

pLC40GWHvG1:35S-IGUS, pLC40GWHvGC1:35S-IGUS

In the same manner as described above, the vector pSB24 (Komari et al. 1996) was treated with the restriction endonucleases HindIII and EcoRI to excise a DNA fragment containing the GUS gene, which was cloned into a vector having a multicloning site SgfI-HindIII-EcoRI-SgfI. The resulting plasmid was digested with SgfI to recover the DNA fragment containing the GUS gene. At this point, both ends of the DNA fragment containing the GUS gene are SgfI sites. The cosmid vector pLC40GWHvG1 described above was treated with the restriction endonuclease PacI and dephosphorylated. The 3.1 kb SgfI fragment (the DNA fragment containing the GUS gene) was cloned into it to generate pLC40GWHvG1:35S-IGUS. Similarly, 35S-IGUS-NOS was introduced into pLC40GWHvGC1 to prepare pLC40GWHvGC1:35S-IGUS.

5) virG-Containing Vectors Capable of Coexisting with pLC pVGW pTOK47 is a large IncW plasmid of about 28 kb containing virG and virB (Jin et al. 1987 J Bacteriol 169: 4417-4425). Thus, a smaller vector capable of coexisting with a pLC vector and containing the origin of replication IncW ori, the virG gene, and a selectable marker gene (designated as pVGW) was designed and constructed.

The primers pSa5'EcT22 and pSa3'BglII for amplifying a fragment containing IncW on from pTOK47 (Jin et al. 1987 J Bacteriol 169: 4417-4425), and the primers Gm5'Bm and Gm3'Xh-2nd for amplifying the gentamycin resistance gene (gentamycin acetyltransferase) from pPH1JI (Hirsch and Beringer 1984 Plasmid 12: 139-141) were designed (Table 7). Each primer contains a restriction endonuclease site for later use. pTOK47 and pPH1JI were used as templates, respectively. Pyrobest DNA Polymerase (from TaKaRa) was used to perform PCR. As a result, a DNA fragment of about 2.7 kb containing IncW on and a DNA fragment of about 0.7 kb corresponding to the gentamycin resistance gene were amplified.

On the other hand, the primer virGN54DFW for changing the amino acid residue at position 54 of virG derived from pTOK47 from N to D by PCR mutagenesis (virGN54D, Hansen et al. 1994 Proc. Natl. Acad. Sci. USA 91: 7603-7607), and its complementary sequence virGN54DRV were designed. PCR was performed with two primer sets, i.e., one consisting of virGN54DFW and the primer virGProSal placed on the 5' of the virG gene promoter and the other consisting of virGN54DRV and the primer virGTerPst placed on the 3' of the virG gene terminator (Table 7). The pTOK47 plasmid was used as a template. As a result, the product of about 0.4 kb and the product of about 0.7 kb were amplified by the former and latter sets, respectively. These products were purified and used as templates along with the previous primers virGProSal and virGTerPst to further perform a PCR reaction. As a result, the product (virGN54D) of about 1.1 kb was amplified.

The PCR products of the fragment containing IncW ori, the gentamycin resistance gene, and virGN54D were cloned into the pCR-Blunt II-TOPO vector (Invitrogen). The nucleotide sequence was determined and compared with a publicly available sequence (Genbank/EMBL Accession Number: U30471) to reveal a deletion of 6 nucleotides in the fragment containing IncW ori, which was also found in pTOK47 used as a template. However, the nucleotide sequence of the gentamycin resistance gene was completely identical to the sequence in the database. virGN54D was found to contain the mutation at the desired site.

Figure 14:
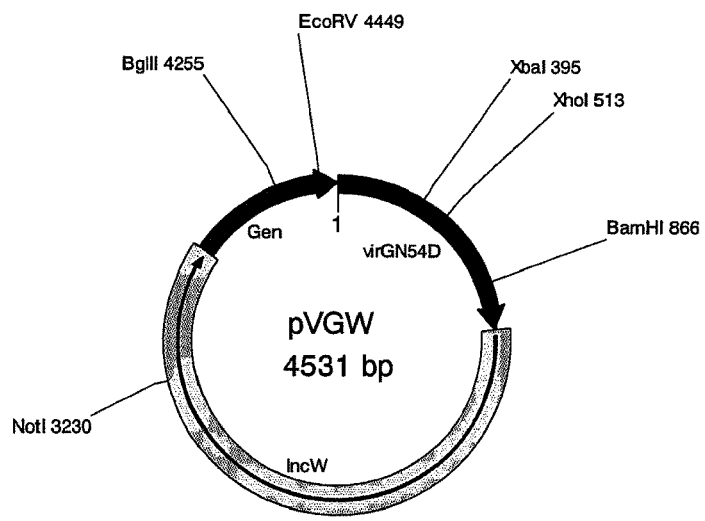
FIG. 14 is a schematic diagram of the vector pVGW.

The plasmid into which the fragment containing IncW on had been cloned was digested with EcoT22I and BglII, and a 2.7 kb fragment was recovered. Similarly, the gentamycin resistance gene was digested with BamHI and XhoI, and virGN54D was digested with SalI and PstI, and each fragment was purified. These three fragments were ligated together (BglII and BamHI, XhoI and SalI, and PstI and EcoT22I produce the same sticky ends) to generate pVGW (FIG. 14, SEQ ID NO: 8 in the Sequence Listing).

TABLE 7

| Designation | Sequence | Length |
|---|---|---|
| pSa5'EcT22 | 5'-aaa atg cat ggc atg ttt aac aga atc tg-3' | 29 mer |
| pSa3'BglII | 5'-ttt aga tct act cgt tcg cgg agc tgg-3' | 27 mer |
| Gm5'Bm | 5'-aaa gga tcc ttc atg gct tgt tat gac tg-3' | 29 mer |
| Gm3'Xh-2$^{nd}$ | 5'-tgc ctc gag aca att tac cga aca act ccg-3' | 30 mer |
| virGN54DFW | 5'-cga cct aaa tct aga tca aca ac-3' | 23 mer |
| viGN54DRV | 5'-gtt gtt gat cta gat tta ggt cg-3' | 23 mer |
| virGProSal | 5'-ttt gtc gac cat agg cga tct cct taa tc-3' | 29 mer |
| virGTerPst | 5'-aaa ctg cag gtg aag agg gac cta tcg g-3' | 28 mer |

SEQ ID NOs: 52-59 in order from the top.

pVGW2

Figure 15:
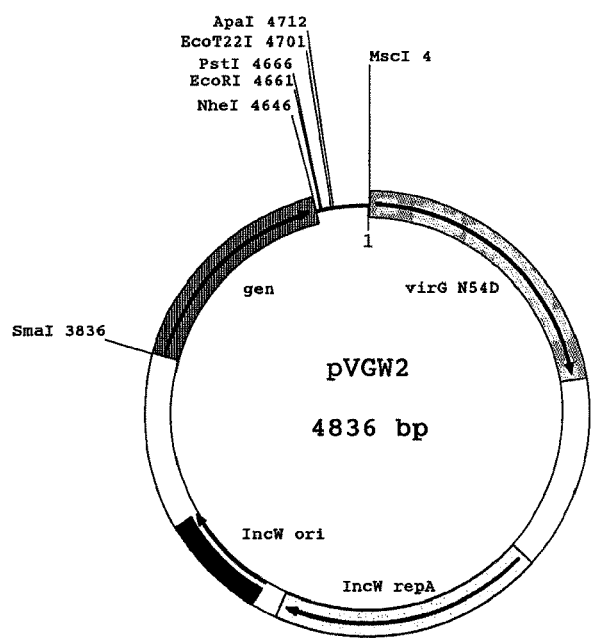
FIG. 15 is a schematic diagram of the vector pVGW2.

To further increase the convenience of pVGW, the promoter region of the gentamycin resistance gene was extended and additional cloning sites were added to construct the vector pVGW2. The primers BamSmaGmPro and NheIsiteG-mRv for amplifying the gentamycin resistance gene of the plasmid pPH1JI, and the primers 'MscIsite-virG5' Fw (for these primers, see Table 8) and pSa3'BglII (described above) for amplifying the virG-IncW region of pVGW were designed. Each primer contains a restriction endonuclease site. A PCR reaction was performed as follows. One cycle of 98° C. for 30 seconds and 35 cycles of 98° C. for 10 seconds, 55° C. for 5 seconds, and 72° C. for 1 minute were performed using Mastercycler gradient (eppendorf) in 50 μl of a reaction solution containing 1 ng of the template plasmid DNA, 25 μl of 2× PrimeSTAR Max Premix (from Takara), and 15 pmoles of the primers. As a result, the PCR products of the gentamycin resistance gene (826 bp) and the virG-IncW region (3840 bp) were amplified. The gentamycin resistance gene was cloned into the vector pCR-Blunt II-TOPO (from Invitrogen), and transferred into E. coli TOP10 (Invitrogen) by electroporation. The cells were incubated on an LB agar plate containing the antibiotics kanamycin (50 μg/ml) at 37° C. overnight, and a plasmid was purified from the resulting colony. The nucleotide sequences of these clones (pCR-Gm) were determined by ABI PRISM Fluorescent Sequencer (Model 3100 Genetic Analyzer, from Applied Biosystems) to confirm that no mutation had been introduced by PCR error. The plasmid pCR-Gm was digested with BamHI and PvuII to recover the Gm fragment, which was ligated to the virG-IncW fragment digested with BglII (having a BglII site at one end and a blunt end at the other). The resulting clone was transferred into E. coli TOP10 by electroporation, and selected on an LB agar plate containing the antibiotics gentamycin (30 μg/ml). A plasmid was purified from the resulting colony and confirmed by the sequencer to contain no PCR error, thereby generating pVGW2 (FIG. 15, SEQ ID NO: 67 in the Sequence Listing).

TABLE 8

| Designation | Sequence | Length |
|---|---|---|
| BamSmaGmPro | 5'-AAA GGA TCC CGG GTT GAC ATA AGC CTG TTC GGT TCG-3' | 36 mer |
| NheIsiteGmRv | 5'-AAA GCT AGC AAT TTA CCG AAC AAC TCC GCG G-3' | 31 mer |
| MscIsite-virG5'Fw | 5'-AAA TGG CCA TAG GCG ATC TCC TTA ATC AAT-3' | 30 mer |

SEQ ID NOs: 77-79 in order from the top.

Example 2

Cloning of Large Fragments by pLC Vectors

The present example describes examples of libraries of Arabidopsis thaliana (ecotype: colombia), wild species of rice (Oryza rufipogon), Sudan grass (Sorghum sudanense), an extremely early maturing variety of Italian millet (Setaria italica), teosinte (Zea diploperennis), pearl millet (Pennisetum typhoideum), Bahia grass (Paspalum notatum Flugge) and sugar cane (Saccharum officinarum) prepared with pLC40, pLC40GWH, pLCleo, pLC40GWHvG1, pSB200, pSB200PcHmGW, or pSB25U.

1) Preparation of Genomic DNA

About 5 g of young leaves of each plant at about one month after seeding grown in a greenhouse was ground in a mortar under liquid nitrogen, and then the genomic DNA was purified by the CTAB method. The yield was about 500-600 μg expressed as DNA. The genomic DNA was partially digested with 0.02-0.06 U/μg of TaqI enzyme. After the partial digestion, fractions containing a genomic DNA fragment of 30-45 kb were recovered by 10-40% sucrose density gradient centrifugation.

2) Preparation of the Vectors

The cosmid vectors pLC40, pLC40GWH, pLCleo, pLC40GWHvG1, pSB200, pSB200PcHmGW, and pSB25U were completely digested with the restriction endonuclease NspV (TOYOBO) and dephosphorylated, and then purified.

3) Cloning by a Packaging Reaction

The vectors prepared as described above were ligated to the genomic DNA fragments, followed by a packaging reaction using GigaPack III XL Packaging extract at room temperature for 2 hours. After the reaction, the clones were incubated with *E. coli* GeneHogs (Invitrogen). As a result, libraries of 1-100,000 cfu (colony-forming-unit) were prepared from all of the combinations of the plant species and vectors (Table 9), as shown in Table 7.

TABLE 9

| Plant species | Vector | Library cfu |
|---|---|---|
| *Arabidopsis thaliana* | pLC40 | ca 80000 |
| | pSB200PcHmGWH | ca 100000 |
| *Oryza rufipogon* | pLC40GWH | ca 20000 |
| | pSB200 | ca 50000 |
| Extremely early maturing Italian millet | pLC40GWH | ca 20000 |
| | pSB200PcHmGWH | ca 20000 |
| Sugar cane | pLC40GWH | ca 50000 |
| | pLC40GWHvG1 | ca 50000 |
| Sudan grass | pLC40GWH | ca 50000 |
| | pSB200PcHmGWH | ca 30000 |
| Pearl millet | pLC40GWH | ca 20000 |
| Teosinte | pLC40GWH | ca 100000 |
| | pSB25UNpHm | ca 20000 |
| Bahia grass | pLCleo | ca 10000 |

4) Analysis of the Cloned Genomic DNA Fragments

Figure 16:
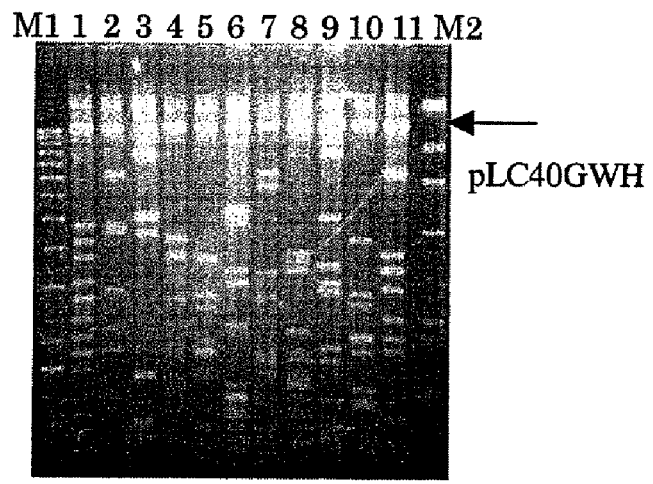
FIG. 16 shows the results of cloning of a genomic DNA fragment by a pLC vector. An example of a teosinte genomic DNA fragment is shown. M1: marker (1 kb ladder), M2: marker (λ-HindIII); the numbers represent clone numbers, and the arrow indicates the size of the band corresponding to pLC40GWH (13.2 kb). Plasmid DNA of eleven clones from a teosinte library was purified. The DNA was cleaved with the restriction endonucleases HindIII and SacI in the multicloning site at each end of the plasmid insert and separated by agarose gel (0.8%) electrophoresis.

Plasmids were purified from 12-24 clones of each library and cleaved with the restriction endonucleases HindIII and SacI in the multicloning site at each end of the insert, thereby yielding bands corresponding to the vectors (9.2-9.8 kb) in all of the clones analyzed in the case of pSB200, pSB25UNpHm and pSB200PcHmGW as well as bands corresponding to the vectors (13.2-14.2 kb) in all of the clones analyzed in the case of pLC40, pLC40GWH, pLCleo and pLC40GWHvG1. The length of the cloned large fragment is estimated to be in the range of 25 kb-45 kb from the total length of the restriction fragments of the insert of each clone, with an average of about 40 kb in the case of the pSB vectors and an average of about 35 kb in the case of the pLC vectors. FIG. 16 shows an example of teosinte genomic DNA/pLC40GWH.

Then, the human genome (Human Genomic DNA, Male, from Promega, Catalog No.: G1471) was partially digested with TaqI to prepare a 30-40 kb fragment, which was then cloned into the vector pLC40GWH. Plasmid DNA was purified from *E. coli* containing the human genomic fragment from arbitrary 12 clones, and the nucleotide sequences at both ends of the insert were analyzed and searched through a database. Homology searches were performed by BLAST through the database of GenBank at NCBI (http://www.ncbi.nlm.nih.gov/BLAST/). The results showed that 11 of the 12 clones isolated are included in 11 single clones containing the human genomic fragment in the database. Ten clones excluding one containing repeated sequences were analyzed for homology to the human genome sequence in the database, whereby the lengths of the cloned human genomic fragments were estimated to be 28023 bp, 31645 bp, 38265 bp, 39599 bp, 31965 bp, 32631 bp, 34727 bp, 36925 bp, 38794 bp, and 34364 bp. The average length was 34693.8 bp, which agreed well with the value obtained by cloning the plant genomes.

Then, the nucleotide sequences at both ends of the cloned plant genomic DNA fragments were determined. Homology searches were performed by BLAST on thus obtained sequence data of 300-600 nucleotides through the database of GenBank at NCBI (http://www.ncbi.nlm.nih.gov/BLAST/) and the database of Beijing Genomics Institute (http://btn.genomics.org.cn:8080/rice/). As a result, *Oryza rufipogon* and *Arabidopsis* showed a homology of 87-100% to the genome sequence of rice and *Arabidopsis*, respectively, over the range of at least 100 bp or more. The libraries of the other plant species also showed significant homologies to the sequences of rice, *Arabidopsis*, maize, sorghum, etc.

Example 3

Transfer into *Agrobacterium* Via Triparental Mating

1) Transfer into *Agrobacterium* Via Triparental Mating and its Efficiency

Each vector containing a plant genomic fragment was transferred into *Agrobacterium* via triparental mating as follows.

i) pLC40 Series Cosmid Vectors pLC40 series cosmid vectors are resistant to kanamycin (Km) and hygromycin (Hm). GeneHogs™ (Invitrogen) was used as host *E. coli*. pRK2073 (spectinomycin (Sp)-resistant) was used as a helper plasmid for triparental mating. HB101 was used as host *E. coli* for the helper plasmid. The *Agrobacterium* strain LBA4404 (no drug resistance) was used.

Initially, *E. coli* GeneHogs™ was infected with an appropriate amount of a dilution of a packaging reaction, spread on an LA plate containing Km (50 μg/mL), and incubated at 23° C. for 3 days. *E. coli* cells in a colony that appeared were streaked with a toothpick on an LA plate containing Km, and incubated at 28° C. for 2 nights. On the other hand, LBA4404 was spread on an AB plate, and incubated at 25° C. for 5 days. HB101/pRK2073 was spread on an LA plate containing Sp (50 μg/mL), and incubated at 37° C. for 2 nights. The cultures of the three strains, i.e., GeneHogs™ harboring a pLC40 series cosmid vector containing a cloned genomic fragment, LBA4404 and HB101/pRK2073 were mixed on an NA plate and incubated at 28° C. overnight. The entire amount of the mixture of the three strains was suspended in 250 μl of sterile water, and 5 μl of the suspension was spread on an AB plate containing Km (50 μg/mL) and Hm (25 μg/mL), and incubated at 28° C. for 7 days. The resulting recombinant *Agrobacterium* was used in plant transformation experiments. This single colony was reincubated on an AB plate containing Km and Hm and a part of the grown colony was spread on an LA with drugs, showing that few *E. coli* cells have been grown.

ii) pSB200 Series Cosmid Vectors pSB200 series cosmid vectors are Sp- and Hm-resistant. GeneHogs™ (Invitrogen) was used as host *E. coli*. pRK2013 (Km-resistant) was used as a helper plasmid. HB101 was used as host *E. coli* for the helper plasmid. The *Agrobacterium* strain LBA4404 harboring pSB1 (tetracycline (Tc) resistance) was used.

Initially, *E. coli* GeneHogs was infected with an appropriate amount of a dilution of a packaging reaction, spread on an LA plate containing Sp (50 μg/mL), and incubated at 23° C. for 3 days. A colony was picked with a toothpick and streaked on an LA plate containing Sp, and incubated at 28° C. for further 2 nights. On the other hand, LBA4404/pSB1 was spread on an AB plate containing Tc (15 μg/mL), and incubated at 25° C. for 5 days. HB101/pRK2013 was spread on an LA plate containing Km (50 μg/mL) and incubated at 37° C. for 2 nights. The cultures of the three strains, i.e., Gene-Hogs™ harboring a pSB200 series cosmid vector containing a cloned genomic fragment, LBA4404/pSB1 and HB101/pRK2013 were mixed on an NA plate and incubated at 28° C. overnight. The entire amount of the mixture of the three strains was suspended in 250 μl of sterile water, and 25 μl of the suspension was spread on an AB plate containing Sp (50 μg/mL) and Hm (25 μg/mL), and incubated at 28° C. for 7 days. The resulting recombinant *Agrobacterium* was used in plant transformation experiments.

iii) pCLD04541

Two genome libraries (the genomes of the rice variety $CO_{39}$ and *Arabidopsis* ecotype Colombia, both having an average insert length of 110 kb in host *E. coli* DH10B) prepared with the vector pCLD04541 provided from Dr. Hongbin Zhang of Texas A&M University were used for triparental mating. The pCLD04541 vector is Km- and Tc-resistant. pRK2073 was used as a helper plasmid, and HB101 was used as host *E. coli* for the helper plasmid. The *Agrobacterium* strain LBA4404 was used.

*E. coli* harboring each clone of the pCLD04541 libraries was spread on an LA containing Tc (10 μg/mL), and incubated at 28° C. for 2 nights. On the other hand, LBA4404 was spread on an AB plate, and incubated at 25° C. for 5 days. HB101/pRK2073 was spread on an LA containing Sp (50 μg/mL) and incubated at 37° C. for 2 nights. The cultures of the three strains, i.e., DH10B harboring pCLD04541 containing a cloned genomic fragment, LBA4404 and HB101/pRK2073 were mixed on an NA plate and incubated at 28° C. overnight. The entire amount of the mixture of the three strains was suspended in 250 μl of sterile water, and a few microliters of the suspension was spread on an AB plate containing Km (25 μg/mL), and incubated at 28° C. for 7 days. The resulting recombinant *Agrobacterium* was used in plant transformation experiments.

As described above, genome clones included in the libraries prepared with pLC40 series cosmid vectors, pSB200 series cosmid vectors and the pCLD04541 vector were transferred into *Agrobacterium*. A summary of these triparental mating systems and the triparental mating efficiencies are shown in Table 7. The triparental mating efficiencies were 97% in pLC series vectors, 79% in pSB series vectors, and 93% in pCLD04541, respectively, showing that the pLC series vectors were the most efficient (Table 10).

TABLE 10

| DNA donor plant | Vector | # of clones used for triparental mating (a) | # of clones giving recombinant *Agrobacterium* (b) | Efficiency(%) b/a |
|---|---|---|---|---|
| <pLC40 series cosmid vectors> | | | | |
| *Oryza rufipogon* | pLC40 GWH | 5657 | 5469 | 96.7 |
| *Arabidopsis thaliana* | pLC40 | 1532 | 1410 | 92.0 |
| Sudan grass | pLC40 GWH | 2301 | 2201 | 95.7 |
| Italian millet | pLC40 GWH | 2521 | 2405 | 95.4 |
| Teosinte | pLC40 GWH | 10739 | 10593 | 98.6 |
| Bahia grass | pLCleo | 384 | 383 | 99.7 |
| Total | | 23134 | 22461 | 97.1 |
| <pSB200 series cosmid vectors> | | | | |
| *Oryza rufipogon* | pSB200 | 10375 | 7504 | 72.3 |
| *Arabidopsis thaliana* | pSB200PcHmGWH | 1332 | 1179 | 88.5 |
| Sudan grass | pSB200PcHmGWH | 2096 | 2031 | 96.9 |
| Italian millet | pSB200PcHmGWH | 2336 | 2032 | 87.0 |
| Total | | 16139 | 12746 | 79.0 |
| <pCLD04541> | | | | |
| Indica riceCO39 | pCLD04541 | 149. | 127 | 85.2 |
| *Arabidopsis thaliana* | pCLD04541 | 192 | 190 | 99.0 |
| Total | | 341 | 317 | 93.0 |

2) Stability of Genomic DNA

To analyze whether or not the genomic DNA fragment carried on each clone has been transferred to *Agrobacterium*, Southern hybridization was performed using the entire genomic DNA fragment as a probe. Plasmid DNAs were conventionally extracted from *E. coli* and *Agrobacterium*, and digested with the restriction endonucleases HindIII and SacI. Then, a part of the digests were fractionated by agarose gel electrophoresis, and transferred to the nylon membrane filter HybondN+. Then, a part of the HindIII and SacI digest (precipitated with ethanol and redissolved in TE) of the *E. coli*-derived plasmid was labeled with an ECL labelling kit (Amersham) and hybridized to this membrane as a probe. Hybridization, washing and signal detection were performed following the instructions attached to the ECL kit. All of four plasmids containing a rufipogon fragment cloned into pLC40GWH showed the transfer of the genomic DNA fragment from *E. coli* to *Agrobacterium*.

Example 4

Transformation of Large Fragments into Rice with pLC Vectors

1) Rice Transformation and its Efficiency
i) Method for Rice Transformation

Immature embryos of the rice variety Yukihikari were infected with *Agrobacterium*. Rice transformation was performed by the method described in the Japanese Patent Application No. 2003-293125, except that all of the aseptically dissected immature embryos were centrifuged as a pretreatment before *Agrobacterium* inoculation. Specifically, the immature embryos were centrifuged in an eppendorf tube containing 1 ml of sterile water at 20000×g for 10 minutes (25° C.). Hygromycin B was used as a selective drug and added at 50 mg/l each in the selective medium, regeneration medium and rooting medium. In the case of pLC40 series cosmid vectors and pSB200 series cosmid vectors, one immature embryo was inoculated with one *Agrobacterium* strain (one type of DNA fragment). In the case of pCLD04541, however, two immature embryos were inoculated with one *Agrobacterium* strain (one type of DNA fragment). Paromomycin was used as a selective drug and added at a concentration of 400-800 mg/l in the selective medium, regeneration medium and rooting medium.

ii) Transfer of Plant Genomic Fragments into Rice

The results of transformation are shown in Table 11. In the case of pSB200 series cosmid vectors, hygromycin-resistant individuals were obtained from 59.1%-62.7% of the strain. In contrast, pLC40 series cosmid vectors gave the transformants from 86.6%-95.4% of the strain. In all of the three donor plants of genomic DNA (*Oryza rufipogon*, Sudan grass, and an extremely early maturing variety of Italian millet), the efficiency was 24%-36% higher when pLC40 series cosmid vectors were used. In the case of the pCLD04541 vector, however, the efficiency was as low as 41-53.4%. These results suggested that pLC40 series cosmid vectors allow transfer of genomic DNA fragments into rice more efficiently than pSB200 series cosmid vectors and pLCD04541.

To evaluate the transformation efficiency of normal size gene expression units, vectors were tested by comparison in the transformation with a DNA fragment containing the GUS gene. When 25 Yukihikari immature embryos were used for each vector, pSB134 (WO2005/017169) gave an average of 11.7 hygromycin-resistant regenerated individuals per immature embryo while pLC40:35S-IGUS gave an average of 11.5 regenerated individuals.

TABLE 11

Results of the transformation of randomized plant genomic fragments into rice using a pSB or pLC vector

| Genome donor plant | Vector | # of genomic fragments used for Agrobacterium-mediated transformation (A) | # of genomic fragments that regenerated hygromycin-resistant individuals (B) | B/A (%) |
|---|---|---|---|---|
| *Oryza rufipogon* | pSB200 | 2246 | 1327 | 59.1 |
| *Oryza rufipogon* | pLC40GWH | 2271 | 2166 | 95.4 |
| Sudan grass | pSB200PcHmGWH | 1997 | 1252 | 62.7 |
| Sudan grass | pLC40GWH | 1760 | 1524 | 86.6 |
| Italian millet | pSB200PcHmGWH | 1940 | 1200 | 61.9 |
| Italian millet | pLC40GWH | 2285 | 1986 | 86.9 |
| Bahia grass | pLCleo | 18 | 16 | 88.9 |
| Indica rice CO39 | pCLD04541 | 156 | 64 | 41.0 |
| *Arabidopsis thaliana* | pCLD04541 | 189 | 101 | 53.4 |

2) Verification of the Transfer of Large Fragments i) PCR of Flanking Regions of Fragments Genomic DNAs were extracted from 11 transformants and young leaves of Yukihikari by the method described above. PCR was performed on these DNAs with 2 sets of the primers shown in the table below. pSB200-9531F and pSB200-4R are primers for amplifying a 139 bp region from the RB to the genomic DNA fragment. HPTinRV and HPTinFW are primers for amplifying an internal region of the hygromycin resistance gene (Table 12). Thirty-five cycles of PCR were performed. As a result, the products were amplified with HPTinRV and HPTinFW in all of the 11 transformants, while no PCR product was obtained with either primer set in the control Yukihikari. When pSB200-9531F and pSB200-4R were used, PCR products were obtained in 10 of the 11 individuals. These results show that the flanking regions of the genomic DNA fragments were transferred into most of the plants transformed with pLC vectors, thus verifying the transfer of the genomic DNA fragments.

TABLE 12

| Designation | Sequence | Length |
|---|---|---|
| pSB200-9531F | 5'-ctg aag gcg gga aac gac aat ctg-3' | 24 mer |
| pSB200-4R | 5'-gct tgc tga gtg gct cct tca acg-3' | 24 mer |
| pSB200-170R | 5'-aac tgc act tca aac aag tgt gac-3' | 24 mer |
| HPTinRV | 5'-tat gtc ctg cgg gta aat ag-3' | 20 mer |
| HPTinFW | 5'-ttg ttg gag ccg aaa tcc g-3' | 19 mer |

SEQ ID NOs: 60-64 in order from the top.

ii) PCR of Both Terminal and Internal Sequences of Fragments

For each of three *Oryza rufipogon* fragments (called A, B, and C) used for the transformation into Yukihikari with the pLC40GWH vector, two individuals of T0 plant were analyzed by PCR to determine whether or not both ends and the center region of each fragment had been introduced. PCR conditions included a treatment at 94° C. for 2 minutes, followed by 35 cycles of thermal denaturation at 94° C. for 30 seconds, annealing at 60° C. for 30 seconds and extension at 60° C. for 30 seconds, and finally a treatment at 72° C. for 2 minutes.

To detect the RB side of fragment A, PCR (PCR1) was performed with pSB200-9531F and a primer specific to fragment A (5'-gtt aat ttc ttg tga tcg aag gac-3' (SEQ ID NO: 11)). To detect the center region of fragment A, a PCR assay was performed by the CAPS method (Konieczny and Ausubel 1993 Plant Journal 4: 403-410) using nucleotide sequence polymorphisms found between the sequence of Nipponbare AP004667 corresponding to fragment A (identified by database searches) and the sequence of *Oryza rufipogon*. Specifically, PCR (PCR2) was performed with two primers (5'-ggg att ctt tat gct ggg ttt agg-3' (SEQ ID NO: 12) and 5'-gca agc aat acc tct gtt atg ctg-3' (SEQ ID NO: 13)), and the product was digested with SspI. To detect the HPT side, PCR (PCR3) was performed with pSB200-170R and a primer specific to fragment A (5'-gtt ttc aga tgg cga cct cag ctt tg-3' (SEQ ID NO: 14)).

Similar marker assays were performed on fragment B and fragment C. Thus, to detect the RB side of fragment B, PCR was performed with pSB200-9531F and a primer specific to fragment B (5'-cag gtg gct tta ttc ctc ctc tca-3' (SEQ ID NO: 15)). To detect the center region of fragment B, a PCR assay was performed by the CAPS method using nucleotide sequence polymorphisms found between the sequence of Nipponbare AP005967 corresponding to fragment B (identified by database searches) and the sequence of *Oryza rufipogon*. Specifically, PCR was performed with two primers (5'-ccg aaa gtt cgt ggg caa tgc cta-3' (SEQ ID NO: 16) and 5'-gcc atc ctt agc ata tga gtg gca-3' (SEQ ID NO: 17)), and the product was digested with HaeIII. To detect the HPT side of fragment B, PCR was performed with pSB200-170R and a primer specific to fragment B (5'-ggc tat tta cgt ggc atg tta cgt-3' (SEQ ID NO: 18)). To detect the RB side of fragment C, PCR was performed with pSB200-9531F and a primer specific to fragment C (5'-tcg taa gtc tac ttc cct tta cga-3' (SEQ ID NO: 19)). To detect the center region of fragment C, a PCR assay was performed by the CAPS method using nucleotide sequence polymorphisms found between the sequence of Nipponbare AL713907 corresponding to fragment C (identified by database searches) and the sequence of *Oryza rufipogon*. Specifically, PCR was performed with two primers (5'-cca aac cac atc ctt ata gtg tgc-3' (SEQ ID NO: 20) and 5'-cct cat tgc atg cgg tca cta c-3' (SEQ ID NO: 21)), and the product was digested with HaeIII. To detect the HPT side of fragment C, PCR was performed with pSB200-170R and a primer specific to fragment C (5'-gca ggg tat taa tcg atc aac acc-3' (SEQ ID NO: 22)).

Figure 17:
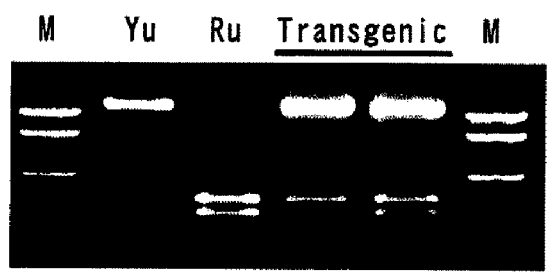
FIG. 17 shows the results of transformation of a genomic DNA fragment into rice (in the center region of fragment B). M: markers, Yu: Yukihikari, Ru: *Oryza rufipogon*, Transgenic: transformed rice (two individuals). In the transformed rice, a band derived from *Oryza rufipogon* was detected in addition to a band derived from Yukihikari.

Analytical results of fragment B are shown in FIG. 17, and analytical results of fragments A-C are summarized in Table 13. Of the two transformants tested for fragment A, no individual containing the entire large fragment was obtained but an individual containing the center region and one end, or both ends was obtained. However, one of the two individuals tested for fragment B and fragment C was shown to contain the entire *Oryza rufipogon* fragment, i.e., both ends and the center region. These results verified that plant genomic fragments of 25-40 kb in size can be transferred into plants by pLC vectors.

TABLE 13

| Fragment | T0 plant | RB side | center | HPT side |
|---|---|---|---|---|
| A | 1 | − | + | + |
|   | 2 | + | − | + |
| B | 1 | + | + | − |
|   | 2 | + | + | + |
| C | 1 | − | − | − |
|   | 2 | + | + | + |

+: An *oryza rufipogon* fragment was detected.
−: An *oryza rufipogon* fragment was not detected.

Example 5

Transformation of Maize with pLC40 Series Cosmid Vectors

1) Combination of pLC with pTOK47 or pLC with pVGW

A vector containing a vir gene is required for maize transformation to increase the transformation efficiency (Ishida et al. 1996 Nat Biotechnol 14:745-50) because the efficiency with ordinary binary vectors is very low except for special methods (Frame et al. (2002) Plant Physiol 129: 13-22). pLC40 series cosmid vectors are ordinary binary vectors so that they should be modified by using a vir gene to improve the transformation efficiency. Thus, the vector pTOK47 capable of coexisting with pLC40 series cosmid vectors (IncP plasmids) in bacteria and expressing a vir gene (Jin et al. 1987 J Bacteriol 169: 4417-4425), and a vector newly constructed by the present invention, pVGW were initially used in combination with pLC. pTOK47 is an IncW plasmid carrying a DNA fragment (KpnI 14.8 kb fragment) containing the virB gene and the virG gene derived from the *Agrobacterium* strain A281, and capable of coexisting with IncP plasmids. pVGW is a plasmid containing a variant virG (virGN54D) and IncW ori.

pTOK47 (tetracycline-resistant) was transferred into the *Agrobacterium* LBA4404 or EHA105 (a kind gift from Dr. Stanton Gelvin of Purdue University) via triparental mating. A plasmid was extracted from this *Agrobacterium* and confirmed by restriction endonuclease analysis to contain pTOK47. Further, pLC40:35S-IGUS or pLC40GWB:35S-IGUS was introduced into the resulting LBA4404/pTOK47 or EHA105/pTOK47 (Tc-resistant) via triparental mating. These *Agrobacteria* are described as LBA4404/pTOK47/ pLC40:35S-IGUS, LBA4404/pTOK47/pLC40GWB:35S-IGUS, EHA105/pTOK47/pLC40:35S-IGUS, and EHA105/ pTOK47/pLC40GWB:35S-IGUS. Plasmid DNAs were extracted from the *Agrobacteria* and analyzed by PCR to confirm the presence of the VirG, RB, hpt or bar, and GUS genes.

In the same manner, pVGW was transferred into the *Agrobacterium* LBA4404 by electroporation, and a colony was selected by gentamycin (Gm 50 μg/mL). pLC40:35S-IGUS or pLC40GWB:35S-IGUS was introduced into the resulting LBA4404/pVGW via triparental mating. These *Agrobacteria* are described as LBA4404/pVGW/pLC40:35S-IGUS and LBA4404/pVGW/pLC40GWB:35S-IGUS. *Agrobacterium* colonies (Km- and Gm-resistant) were directly analyzed by PCR to confirm the presence of the VirG, hpt or bar, and GUS genes.

Moreover, pIG121Hm derived from the IncP plasmid pBI121 (Hiei et al. (1994) Plant J 6: 271-282) was introduced into LB4404/pTOK47 to prepare *Agrobacterium* LB4404/ pTOK47/pIG121Hm, which was used as a control in maize transformation experiments.

2) Transformation of Maize

Maize immature embryos having a size of about 1.2 mm (variety: A188) were aseptically removed from a plant grown in a greenhouse, and immersed in a liquid medium for suspending *Agrobacterium* (LS-inf, Ishida et al. 1996). After thermal treatment at 46° C. for 3 minutes, the immature embryos were washed with the same liquid medium. After centrifugation at 15,000 rpm, 4° C., for 10 minutes, the immature embryos were then immersed in a suspension of each strain at about $1 \times 10^9$ cfu/ml in LS-inf medium (containing 100 μM acetosyringon) and then plated on a coculture medium (LS-AS (Ishida et al. 1996 Nat Biotechnol 14:745-50) containing $AgNO_3$, $CuSO_4$). After incubation at 25° C. in darkness for 3 days, the immature embryos were partially used for GUS analysis.

The cocultured immature embryos were plated on a selective medium containing hygromycin or phosphinothricin (Ishida et al. (2003) Plant Biotechnology 20:57-66) and incubated. A callus grown was excised and plated on a regeneration medium containing hygromycin (Hm) or phosphinothricin (PPT) (Ishida et al. 1996 Nat Biotechnol 14:745-50), and incubated under illumination. After two weeks, regenerated plants showing resistance to Hm or PPT were investigated.

Initially, A188 immature embryos were inoculated with various strains and observed for the transient expression of the GUS gene on day 3 of coculture. Immature embryos inoculated with the control LBA4404/pSB134 showed the expression of the GUS gene over a wide range. However, few immature embryos inoculated with LBA4404/pLC40:35S-IGUS showed the expression except for limited ones showing the expression in very small spots. No increase in expression was found when EHA105 was used as a host. Most of immature embryos inoculated with LBA4404/pTOK47/pLC40: 35S-IGUS, LBA4404/pLC40GWHvG1:35S-IGUS, LBA4404/pVGW/pLC40:35S-IGUS and LBA4404/pVGW/pLC40GWB:35S-IGUS showed spots representing the expression of the GUS gene to a lesser extent than with LBA4404/pSB134, thus verifying that the gene transfer efficiency is improved by the coexistence with a plasmid containing the virB gene and virG gene derived from the *Agrobacterium* strain A281, or the coexistence with a plasmid containing virGN54D, or the addition of the virG gene. On the other hand, there is no difference in the expression of the GUS gene between pLC40GWHvG1:35S-IGUS and pLC40GWHvGC1:35S-IGUS, showing that a single nucleotide substitution for removing an NspV recognition site does not influence the virG activity.

Then, we tried to create transformed plants by incubating the cocultured immature embryos in a selective medium containing Hm or PPT and a regeneration medium. When EHA105 was used as a host, the pLCSBGWBSW vector gave no PPT-resistant plant. When LBA4404 was used as a host, however, the pLCSBGWBSW vector gave plants showing resistance to PPT at an efficiency comparable to that of the superbinary vector pSB131 (containing the GUS gene and the bar gene in the T-DNA region, Ishida et al. 1996 Nat Biotechnol 14:745-50) using the same strain as a host (Table 14). LBA4407/pTOK47/pLC40GWB:35S-IGUS was also shown to give PPT-resistant plants at a high efficiency comparable to that of the superbinary vector pSB131. When the hygromycin resistance gene was used as a selectable marker gene, a pLC40 series cosmid vector (pLC40:35S-IGUS) combined with pTOK47 also gave hygromycin-resistant plants (Table 13). pLC40GWHvG1 containing the virG gene also achieved an efficiency comparable to that of the superbinary vector SB134 (containing the GUS gene and the hygromycin resistance gene in the T-DNA region, Hiei and Komari 2006 Plant Cell, Tissue and Organ Culture 85: 271-283) (Table 14).

TABLE 14

Results of transformation of maize

| Experiment | Strain | Selective drug | # of immature embryos Inoculated (A) | # of immature embryos redifferentiated (B) | Redifferentiation ratio (B/A, %) |
|---|---|---|---|---|---|
| 1 | LBA4404 (pLCSBGWBSW) | PPT | 46 | 10 | 21.7 |
|  | EHA105 (pLCSBGWBSW) | PPT | 46 | 0 | 0 |
|  | LBA4404 (pSB131) | PPT | 45 | 9 | 20.0 |
| 2 | LBA4404 (pLC40GWB:35S-IGUS) | PPT | 56 | 0 | 0 |
|  | LBA4404 (pLC40GWB:35S-IGUS/pTOK47) | PPT | 57 | 14 | 24.6 |
|  | LBA4404 (pSB131) | PPT | 59 | 19 | 32.2 |
| 3 | LBA4404(pLC40:35S-IGUS) | Hm | 43 | 0 | 0 |
|  | LBA4404(pLC40:35S-IGUS/pTOK47) | Hm | 44 | 2 | 4.5 |
|  | LBA4404(pIG121Hm) | Hm | 42 | 0 | 0 |
|  | LBA4404(pIG121Hm/pTOK47) | Hm | 42 | 0 | 0 |
| 4 | LBA4404(pLC40GWHvG1) | Hm | 59 | 5 | 8.5 |
|  | LBA4404(pSB134) | Hm | 57 | 5 | 8.8 |

PPT: phosphinothricin,
Hm: hygromicin

In order to examine the influence of pVGW on maize transformation, maize was then transformed with LBA4404/pLC40:35S-IGUS, LBA4404/pVGW/pLC40:35S-IGUS, LBA4404/pVGW/pLC40GWB:35S-IGUS, and LBA4404/pSB134, and the regenerated individuals were analyzed for GUS expression. As a result, the proportion of the number of GUS-expressing individuals in pLC40:35S-IGUS was 0% (0/16), while the proportion of the number of GUS-expressing individuals per inoculated immature embryo in pLC40:35S-IGUS and pLC40GWB:35S-IGUS both combined with pVGW reached 40% (6/15) and 30% (6/20), respectively, which were comparable to 41.2% (7/17) in the superbinary vector pSB134. Thus, the transformation of maize with pLC vectors could be achieved at high efficiency by using pVGW.

We further tried to transform plant genomic fragments into maize by combining a pLC vector and the pVGW vector. A genomic fragment (30-35 kb) of Sudan grass was randomly cloned into the NspV site of the vector pLC40GWB. The resulting *E. coli* plasmid was transferred to *Agrobacterium* harboring pVGW (LBA4404) via triparental mating. In this manner, *Agrobacterium* harboring both of the plasmids pLC40GWB containing the genomic fragment of Sudan grass and pVGW was prepared, and inoculated into maize immature embryos (variety: A188). Transformed cells were selected to show that 17 of the 27 fragments inoculated gave redifferentiated plants (Table 15). This showed that plant genomic fragments can be efficiently transformed into maize by the combination of pLC and pVGW.

These results demonstrated that maize transformation can be efficiently achieved by the combination with a plasmid carrying a DNA fragment containing the virB gene and virG gene derived from the *Agrobacterium* strain A281 such as pTOK47, or the combination with a plasmid containing the virGN54D gene such as pVGW, or the incorporation of the virG gene into a pLC vector such as pLC40GWHvG1.

TABLE 15

Results of the transformation of randomized plant genomic fragments into maize using a pLC/pVGW vector system

| Genome donor plant | Strain | # of genomic fragments used for Agrobacterium-mediated transformation (A) | # of genomic fragments that regenerated PPT-resistant individuals (B) | B/A(%) |
|---|---|---|---|---|
| Sudan grass | LBA4404(pLC40GWB/pVGW) | 27 | 17 | 63.0 |

Example 6

Isolation of a Gene of Interest from BAC Clones Using pLC Vectors

Komori et al. (2004) (Plant J 37: 315-325) found that a cytoplasmic male sterile strain restores fertility when it is transformed with the PPR791 gene isolated from the rice variety IR24, thus demonstrating that PPR791 is the fertility restorer gene Rf-1. The PRR791 gene was identical with the PPR8-1 gene of the rice variety Milyang 23 that had been previously reported as a candidate for Rf-1 by Kazama and Toriyama (2003) (FEBS Lett 544: 99-102). Thus, the BAC clone OSIMBb0046F08 of Milyang 23 from which the PPR8-1 gene had been derived was obtained from Clemson University, and a model experiment was performed for isolating Rf-1 from the BAC.

Initially, a plasmid was extracted from OSIMBb0046F08 using High Purity Plasmid Midiprep System (Marligen). The plasmid was partially digested with TaqI and a DNA fragment around 30 kb was recovered by sucrose density gradient centrifugation. This DNA fragment was ligated to the BstBI-digested and CIP-treated pLC40GWH vector or the BstBI-digested and CIP-treated pSB200 vector using DNA Ligation Kit <Mighty Mix> (Takara Bio Inc.). The resulting construct was transferred into E. coli by electroporation to give colonies of transformants on an LB plate containing an appropriate antibiotic (50 µg/ml kanamycin or spectinomycin). To determine the presence or absence of the Rf-1 gene in the resulting plasmid, direct PCR (see Examples 1, 3)) was performed by using these colonies as templates along with primers designed for the Rf-1 gene (WSF7T7R1 and IR50226R, Table 16) to select Rf-1 positive clones giving an amplified product of about 2 kb from Rf-1 negative clones showing no amplification of the product. The incidence of positive clones in this PCR screening was 5/39 (12.8%) in the pLC40GWH construct and 6/96 (6.3%) in the pSB200 construct. That is, the cloning efficiency of a gene of interest was about twice higher in the pLC vector than pSB.

One positive clone and two negative clones selected from the pLC40GWH construct, and one positive clone and two negative clones selected from the pSB200 construct were transferred from E. coli to Agrobacterium via triparental mating. The cytoplasmic male sterile strain MS Koshihikari was infected with the resulting Agrobacterium by the method described in Komori et al. (2004). The resulting transformed rice was acclimated and then grown in a greenhouse. During the maturing stage, an average ear was collected from each individual and evaluated for the fertility rate. The results showed that transformants from constructs containing no Rf-1 (pLC-7, pLC-11, pSB-1, pSB-7) were sterile, while constructs containing Rf-1 (pLC-8, pSB-37) gave fertile transformants (Table 17).

These results demonstrated that a gene of interest can be efficiently identified by preparing a library from DNA of BAC containing the gene of interest using a cosmid vector for plant transformation and transferring it into a plant and then selecting a plant showing an expected phenotype.

TABLE 16

| Primer Name | Sequence | Length |
|---|---|---|
| WSF7T7R1 | 5'-AGT GTG TGG CAT GGT GCA TTT CCG-3' | 24 mer |
| IR50226R | 5'-CTC TAG AGG ATA CAC GGT GTA AGG-3' | 24 mer |

SEQ ID NOs: 80-81 in order from the top.

TABLE 17

Fertility restoration by various constructs

| Construct | Presence (+) or absence (−) of Rf-1 | # of individuals analyzed | # of individuals fetile |
|---|---|---|---|
| pLC-8 | + | 6 | 4 |
| pLC-7 | − | 9 | 0 |
| pLC-11 | − | 8 | 0 |
| pSB-37 | + | 9 | 6 |
| pSB-1 | − | 9 | 0 |
| pSB-7 | − | 9 | 0 |

In conclusion, pLC vectors are characterized in that:

1. they allow easy cloning of DNA in the order of 25-40 kb;

2. they are stable in bacteria; and 3. they allow efficient transformation of plants, especially monocotyledons.

pLC vector series are useful for handling medium-size DNA in the field of functional genomics.

The invention claimed is:

1. A cosmid vector having a full length of 15 kb or less characterized in that:
   1) it contains an origin of replication (oriV) of an IncP plasmid but does not contain any origin of replication of other plasmid groups;
   2) it contains the trfA1 gene of an IncP plasmid;
   3) it contains an origin of conjugative transfer (oriT) of an IncP plasmid;
   4) it contains the incC1 gene of an IncP plasmid;
   5) it contains a cos site of lambda phage and the cos site is located outside the T-DNA;
   6) it contains a drug resistance gene expressed in *E. coli* and a bacterium of the genus *Agrobacterium*;
   7) it contains a T-DNA right border sequence of a bacterium of the genus *Agrobacterium*;
   8) it contains a T-DNA left border sequence of a bacterium of the genus *Agrobacterium*;
   9) it contains a selectable marker gene for plant transformation located between 7) and 8) and expressed in a plant; and
   10) it contains restriction endonuclease recognition site(s) located between 7) and 8) for cloning a foreign gene, wherein the cosmid vector is selected from the group consisting of:
   the cosmid vector pLC40 consisting of the nucleotide sequence of SEQ ID NO: 2;
   the cosmid vector pLC40GWH consisting of the nucleotide sequence of SEQ ID NO: 3;
   the cosmid vector pLC40 bar consisting of the nucleotide sequence of SEQ ID NO: 4;
   the cosmid vector pLC40GWB consisting of the nucleotide sequence of SEQ ID NO: 5;
   the cosmid vector pLC40GWHKorB consisting of the nucleotide sequence of SEQ ID NO: 65;
   the cosmid vector pLCleo consisting of the nucleotide sequence of SEQ ID NO: 66; and
   the cosmid vector pLC40GWHvG1 consisting of the nucleotide sequence of SEQ ID NO: 7.

2. A method for transforming a plant, comprising transforming the plant with a bacterium of the genus *Agrobacterium* harboring an expression vector containing a nucleic acid fragment of a plant inserted into the cosmid vector of claim 1.

3. The method of claim 2 wherein the nucleic acid fragment inserted has a size of 25-40 kb.

4. The method of claim 2, wherein said bacterium of the genus *Agrobacterium* harbors the following elements for transforming the plant:
   1a) a vector containing a nucleic acid fragment of a plant and the virG gene of a bacterium of the genus *Agrobacterium* inserted into the cosmid vector of claim 4; or
   1b) a vector containing a nucleic acid fragment of a plant inserted into the cosmid vector of claim 4, and a plasmid capable of coexisting with an IncP plasmid in a cell of a bacterium of the genus *Agrobacterium* and containing the virG gene of a bacterium of the genus *Agrobacterium*, and
   2) a Ti plasmid or Ri plasmid of a bacterium of the genus *Agrobacterium*.

5. The method of claim 4 wherein the virG gene of a bacterium of the genus *Agrobacterium* in 1a) or 1b) is virGN54D.

6. The method of claim 4 wherein the plasmid containing the virG gene of a bacterium of the genus *Agrobacterium* in 1b) contains an origin of replication of an IncW plasmid.

7. The method of claim 6 wherein the plasmid containing the virG gene of a bacterium of the genus *Agrobacterium* in 1b) is pVGW having the structure shown in FIG. 14 or pVGW2 having the structure shown in FIG. 15.

8. The method of claim 4 wherein the plasmid containing the virG gene of a bacterium of the genus *Agrobacterium* in 1b) further contains the virB gene of a bacterium of the genus *Agrobacterium*.

9. The method of claim 8 wherein the plasmid containing the virG gene of a bacterium of the genus *Agrobacterium* in 1b) contains an origin of replication of an IncW plasmid.

10. The method of claim 9 wherein the plasmid containing the virG gene of a bacterium of the genus *Agrobacterium* in 1b) is pTOK47.

11. A map-based cloning method comprising the steps of:
    1) partially or completely digesting BAC clones containing candidate genes responsible for a plant phenotype with a restriction endonuclease;
    2) subcloning DNA fragments obtained in step 1) using a cosmid vector according to claim 4 to construct a library; and
    3) individually transferring clones constituting the library into a plant to evaluate the phenotypes of transformed plants.

12. The map-based cloning method of claim 11 wherein the DNA fragments obtained in step 1) have a size of 25-40 kb.

* * * * *

SEQUENCE LISTING

<160> NUMBER OF SEQ ID NOS: 81

<210> SEQ ID NO 1
<211> LENGTH: 8507
<212> TYPE: DNA
<213> ORGANISM: Artificial Sequence
<220> FEATURE:
<223> OTHER INFORMATION: Synthetic vector: p6FRG
<220> FEATURE:
<221> NAME/KEY: misc_feature
<222> LOCATION: (1)..(816)
<223> OTHER INFORMATION: oriT
<220> FEATURE:
<221> NAME/KEY: misc_feature
<222> LOCATION: (817)..(2935)
<223> OTHER INFORMATION: IncC1
<220> FEATURE:
<221> NAME/KEY: misc_feature
<222> LOCATION: (2936)..(3344)
<223> OTHER INFORMATION: cos
<220> FEATURE:
<221> NAME/KEY: misc_feature
<222> LOCATION: (3345)..(4247)
<223> OTHER INFORMATION: oriV
<220> FEATURE:
<221> NAME/KEY: misc_feature
<222> LOCATION: (4248)..(5340)
<223> OTHER INFORMATION: (complement) nptIII
<220> FEATURE:
<221> NAME/KEY: misc_feature
<222> LOCATION: (5341)..(8507)
<223> OTHER INFORMATION: trfA1

<400> SEQUENCE: 1

```
tggcgctcgg tcttgccttg ctcgtcggtg atgtacttca ccagctccgc gaagtcgctc      60
ttcttgatgg agcgcatggg gacgtgcttg gcaatcacgc gcaccccccg gccgttttag     120
cggctaaaaa agtcatggct ctgccctcgg gcggaccacg cccatcatga ccttgccaag     180
ctcgtcctgc ttctcttcga tcttcgccag cagggcgagg atcgtggcat caccgaaccg     240
cgccgtgcgc gggtcgtcgg tgagccagag tttcagcagg ccgcccaggc ggcccaggtc     300
gccattgatg cgggccagct cgcggacgtg ctcatagtcc acgacgcccg tgattttgta     360
gccctggccg acggccagca ggtaggccga caggctcatg ccggccgccg ccgccttttc     420
ctcaatcgct cttcgttcgt ctggaaggca gtacaccttg ataggtgggc tgcccttcct     480
ggttggcttg gtttcatcag ccatccgctt gccctcatct gttacgccgg cggtagccgg     540
ccagcctcgc agagcaggat tcccgttgag caccgccagg tgcgaataag ggacagtgaa     600
gaaggaacac ccgctcgcgg gtgggcctac ttcacctatc ctgcccggct gacgccgttg     660
gatacaccaa ggaaagtcta cacgaaccct ttggcaaaat cctgtatatc gtgcgaaaaa     720
ggatggatat accgaaaaaa tcgctataat gaccccgaag cagggttatg cagcggaaaa     780
gcgctgcttc cctgctgttt tgtggaatat cactagattc gagccacggt agcggcgggc     840
gccgtgattg atgatatagc ggcccggctg ctcctggttc tcgcgcaccg aaatgggtga     900
cttcaccccg cgctctttga tcgtggcacc gatttccgcg atgctctccg gggaaaagcc     960
ggggttgtcg gccgtccgcg gctgatgcgg atcttcgtcg atcaggtcca ggtccagctc    1020 gataggccg gaaccgccct gagacgccgc aggagcgtcc aggaggctcg acaggtcgcc    1080
gatgctatcc aaccccaggc cggacggctg cgccgcgcct gcggcttcct gagcggccgc    1140
agcggtgttt ttcttggtgg tcttggcttg agccgcagtc attgggaaat ctccatcttc    1200
gtgaacacgt aatcagccag ggcgcgaacc tctttcgatg ccttgcgcgc ggccgttttc    1260
```

```
ttgatcttcc agaccggcac accggatgcg agggcatcgg cgatgctgct gcgcaggcca    1320
acggtggccg gaatcatcat cttggggtac gcggccagca gctcggcttg gtggcgcgcg    1380
tggcgcggat ccgcgcatc gaccttgctg ggcaccatgc caaggaattg cagcttggcg     1440
ttcttctggc gcacgttcgc aatggtcgtg accatcttct tgatgccctg gatgctgtac    1500
gcctcaagct cgatggggga cagcacatag tcggccgcga agagggcggc cgccaggccg    1560
acgccaaggg tcgggccgt gtcgatcagg cacacgtcga agccttggtt cgccagggcc     1620
ttgatgttcg ccccgaacag ctcgcgggcg tcgtccagcg acagccgttc ggcgttcgcc    1680
agtaccgggt tggactcgat gagggcgagg cgcgcggcct ggccgtcgcc ggctgcgggt    1740
gcggtttcgg tccagccgcc ggcagggaca cgcgccgaaca gcttgcttgc atgcaggccg   1800
gtagcaaagt ccttgagcgt gtaggacgca ttgccctggg ggtccaggtc gatcacggca    1860
acccgcaagc cgcgctcgaa aaagtcgaag gcaagatgca caagggtcga agtcttgccg    1920
acgccgcctt tctggttggc cgtgaccaaa gttttcatcg tttggtttcc tgttttttct    1980
tggcgtccgc ttcccacttc cggacgatgt acgcctgatg ttccggcaga accgccgtta    2040
cccgcgcgta cccctcgggc aagttcttgt cctcgaacgc ggcccacacg cgatgcaccg    2100
cttgcgacac tgcgcccctg gtcagtccca gcgacgttgc gaacgtcgcc tgtggcttcc    2160
catcgactaa gacgccccgc gctatctcga tggtctgctg ccccacttcc agcccctgga    2220
tcgcctcctg gaactggctt tcggtaagcc gtttcttcat ggataacacc cataatttgc    2280
tccgcgcctt ggttgaacat agcggtgaca gccgccagca catgagagaa gtttagctaa    2340
acatttctcg cacgtcaaca cctttagccg ctaaaactcg tccttggcgt aacaaaacaa    2400
aagcccggaa accgggcttt cgtctcttgc cgcttatggc tctgcacccg gctccatcac    2460
caacaggtcg cgcacgcgct tcactcggtt gcggatcgac actgccagcc caacaaagcc    2520
ggttgccgcc gccgccagga tcgcgccgat gatgccggcc acaccggcca tcgcccacca    2580
ggtcgccgcc ttccggttcc attcctgctg gtactgcttc gcaatgctgg acctcggctc    2640
accataggct gaccgctcga tggcgtatgc cgcttctccc cttggcgtaa acccagcgc    2700
cgcaggcggc attgccatgc tgcccgccgc tttcccgacc acgacgcgcg caccaggctt   2760
gcggtccaga ccttcggcca cggcgagctg cgcaaggaca taatcagccg ccgacttggc    2820
tccacgcgcc tcgatcagct cttgcactcg cgcgaaatcc ttggcctcca cggccgccat    2880
gaatcgcgca cgcggcgaag gctccgcagg gccggcgtcg tgatcgccgc cgagaagatc    2940
cttccattgt tcattccacg gacaaaaaca gagaaaggaa acgacagagg ccaaaaagct    3000
cgctttcagc acctgtcgtt tcctttcttt tcagagggta ttttaaataa aaacattaag    3060
ttatgacgaa gaagaacgga aacgccttaa accggaaaat tttcataaat agcgaaaacc    3120
cgcgaggtcg ccgccccgta acctgtcgga tcaccggaaa ggacccgtaa agtgataatg    3180
attatcatct acatatcaca acgtgcgtgg aggccatcaa accacgtcaa ataatcaatt    3240
atgacgcagg tatcgtatta attgatctgc atcaacttaa cgtaaaaaca acttcagaca    3300
atacaaatca gcgacactga atacgggca acctcatgtc aattcgctag ccagctggcg    3360
ctgccatttt tggggtgagg ccgttcgcgg ccgaggggcg cagcccctgg ggggatggga    3420
ggcccgcgtt agcgggccgg gagggttcga aaggggggg caccccccctt cggcgtgcgc    3480
ggtcacgcgc acagggcgca gccctggtta aaaacaaggt ttataaatat tggtttaaaa    3540
gcaggttaaa agacaggtta gcggtggccg aaaaacgggc ggaaaccctt gcaaatgctg    3600
gattttctgc ctgtggacag cccctcaaat gtcaataggt gcgcccctca tctgtcagca    3660
```

```
ctctgcccct caagtgtcaa ggatcgcgcc cctcatctgt cagtagtcgc gcccctcaag    3720
tgtcaatacc gcagggcact tatcccaggg cttgtccaca tcatctgtgg gaaactcgcg    3780
taaaatcagg cgttttcgcc gatttgcgag gctggccagc tccacgtcgc cggccgaaat    3840
cgagcctgcc cctcatctgt caacgccgcg ccgggtgagt cggcccctca agtgtcaacg    3900
tccgcccctc atctgtcagt gagggccaag ttttccgcga ggtatccaca acgccggcgg    3960
ccgcggtgtc tcgcacacgg cttcgacggc gtttctggcg cgtttgcagg gccatagacg    4020
gccgccagcc cagcggcgag ggcaaccagc ccggtgagcg tcggaaaggc gctggaagcc    4080
ccgtagcgac gcgagaggg gcgagacaag ccaagggcgc aggctcgatg cgcagcacga    4140
catagccggt tctcgcaagg acgagaattt ccctgcggtg cccctcaagt gtcaatgaaa    4200
gtttccaacg cgagccattc gcgagagcct tgagtccacg ctatcgaatc gatactatgt    4260
tatacgccaa ctttgaaaac aactttgaaa aagctgtttt ctggtattta aggttttaga    4320
atgcaaggaa cagtgaattg gagttcgtct tgttataatt agcttcttgg ggtatcttta    4380
aatactgtag aaagaggaa ggaaataata aatggctaaa atgagaatat caccggaatt    4440
gaaaaaactg atcgaaaaat accgctgcgt aaaagatacg gaaggaatgt ctcctgctaa    4500
ggtatataag ctggtgggag aaaatgaaaa cctatattta aaaatgacgg acagccggta    4560
taaagggacc acctatgatg tggaacggga aaaggacatg atgctatggc tggaaggaaa    4620
gctgcctgtt ccaaaggtcc tgcactttga acggcatgat ggctggagca atctgctcat    4680
gagtgaggcc gatggcgtcc tttgctcgga agagtatgaa gatgaacaaa gccctgaaaa    4740
gattatcgag ctgtatgcgg agtgcatcag gctctttcac tccatcgaca tatcggattg    4800
tccctatacg aatagcttag acagccgctt agccgaattg gattacttac tgaataacga    4860
tctggccgat gtggattgcg aaaactggga agaagacact ccatttaaag atccgcgcga    4920
gctgtatgat tttttaaaga cggaaaagcc cgaagaggaa cttgtctttt cccacgcgga    4980
cctgggagac agcaacatct tgtgaaaga tggcaaagta agtggctttta ttgatcttgg    5040 gagaagcggc agggcggaca agtggtatga cattgccttc tgcgtccggt cgatcaggga    5100
ggatatcggg gaagaacagt atgtcgagct attttttgac ttactgggga tcaagcctga    5160
ttgggagaaa ataaaatatt atattttact ggatgaattg ttttagtacc tagatgtggc    5220
gcaacgatgc cggcgacaag caggagcgca ccgacttctt ccgcatcaag tgttttggct    5280
ctcaggccga ggcccacggc aagtatttgg gcaaggggtc gctggtattc gtgcagtcga    5340
gcagccgaga acattggttc ctgtaggcat cgggattggc ggatcaaaca ctaaagctac    5400
tggaacgagc agaagtcctc cggccgccag ttgccaggcg gtaaaggtga gcagaggcac    5460
gggaggttgc cacttgcggg tcagcacggt tccgaacgcc atggaaaccg ccccgccag    5520 gcccgctgcg acgccgacag gatctagcgc tgcgtttggt gtcaacacca acagcgccac    5580
gcccgcagtt ccgcaaatag cccccaggac cgccatcaat cgtatcgggc tacctagcag    5640
agcggcagag atgaacacga ccatcagcgg ctgcacagcg cctaccgtcg ccgcgacccg    5700
cccggcaggc ggtagaccga aataaacaac aagctccaga atagcgaaat attaagtgcg    5760
ccgaggatga agatgcgcat ccaccagatt cccgttggaa tctgtcggac gatcatcacg    5820
agcaataaac ccgccggcaa cgcccgcagc agcataccgg cgacccctcg gcctcgctgt    5880
tcgggctcca cgaaaacgcc ggacagatgc gccttgtgag cgtccttggg gccgtcctcc    5940
tgtttgaaga ccgacagccc aatgatctcg ccgtcgatgt aggcgccgaa tgccacggca    6000
tctcgcaacc gttcagcgaa cgcctccatg ggcttttttct cctcgtgctc gtaaacggac    6060
```

-continued

```
ccgaacatct ctggagcttt cttcagggcc gacaatcgga tctcgcggaa atcctgcacg   6120
tcggccgctc caagccgtcg aatctgagcc ttaatcacaa ttgtcaattt taatcctctg   6180
tttatcggca gttcgtagag cgcgccgtgc gtcccgagcg atactgagcg aagcaagtgc   6240
gtcgagcagt gcccgcttgt tcctgaaatg ccagtaaagc gctggctgct gaaccccag    6300 ccggaactga ccccacaagg ccctagcgtt tgcaatgcac caggtcatca ttgacccagg   6360
cgtgttccac caggccgctg cctcgcaact cttcgcaggc ttcgccgacc tgctcgcgcc   6420
acttcttcac gcgggtggaa tccgatccgc acatgaggcg aaggtttcc agcttgagcg    6480 ggtacggctc ccggtgcgag ctgaaatagt cgaacatccg tcgggccgtc ggcgacagct   6540
tgcggtactt ctcccatatg aatttcgtgt agtggtcgcc agcaaacagc acgacgattt   6600
cctcgtcgat caggacctgg caacgggacg ttttcttgcc acggtccagg acgcggaagc   6660
ggtgcagcag cgacaccgat tccaggtgcc caacgcggtc ggacgtgaag cccatcgccg   6720
tcgcctgtag gcgcgacagg cattcctcgg ccttcgtgta ataccggcca ttgatcgacc   6780
agcccaggtc ctggcaaagc tcgtagaacg tgaaggtgat cggctcgccg ataggggtgc   6840
gcttcgcgta ctccaacacc tgctgccaca ccagttcgtc atcgtcggcc cgcagctcga   6900
cgccggtgta ggtgatcttc acgtccttgt tgacgtggaa aatgaccttg ttttgcagcg   6960
cctcgcgcgg gattttcttg ttgcgcgtgg tgaacagggc agagcgggcc gtgtcgtttg   7020
gcatcgctcg catcgtgtcc ggccacggcg caatatcgaa caaggaaagc tgcatttcct   7080
tgatctgctg cttcgtgtgt tcagcaacg cggcctgctt ggcctcgctg acctgttttg    7140
ccaggtcctc gccggcggtt tttcgcttct tggtcgtcat agttcctcgc gtgtcgatgg   7200
tcatcgactt cgccaaacct gccgcctcct gttcgagacg acgcgaacgc tccacggcgg   7260
ccgatggcgc gggcagggca gggggagcca gttgcacgct gtcgcgctcg atcttggccg   7320
tagcttgctg gaccatcgag ccgacggact ggaaggtttc gcggggcgca cgcatgacgg   7380
tgcggcttgc gatggtttcg gcatcctcgg cggaaaaccc cgcgtcgatc agttcttgcc   7440
tgtatgcctt ccggtcaaac gtccgattca ttcaccctcc ttgcgggatt gccccgactc   7500
acgccggggc aatgtgccct tattcctgat ttgacccgcc tggtgccttg gtgtccagat   7560
aatccacctt atcggcaatg aagtcggtcc cgtagaccgt ctggccgtcc ttctcgtact   7620
tggtattccg aatcttgccc tgcacgaata ccagcgaccc cttgcccaaa tacttgccgt   7680
gggcctcggc ctgagagcca aaacacttga tgcggaagaa gtcggtgcgc tcctgcttgt   7740
cgccggcatc gttgcgccac tcttcattaa ccgctatatc gaaaattgct gcggcttgt    7800 tagaattgcc atgacgtacc tcggtgtcac gggtaagatt accgataaac tggaactgat   7860 tatgctcat atcgaaagtc tccttgagaa aggagactct agtttagcta acattggtt    7920 ccgctgtcaa gactttagc ggctaaaatt ttgcgggccg cgaccaaagg tgcgaggggc    7980
ggcttccgct gtgtacaacc agatatttt caccaacatc cttcgtctgc tcgatgagcg    8040
gggcatgacg aaacatgagc tgtcggagag ggcagggtt tcaatttcgt ttttatcaga    8100
cttaaccaac ggtaaggcca acccctcgtt gaaggtgatg gaggccattg ccgacgccct   8160
ggaaactccc ctacctcttc tcctggagtc caccgacctt gaccgcgagg cactcgcgga   8220
gattgcgggt catcctttca agagcagcgt gccgccgga tacgaacgca tcagtgtggt    8280
tttgccgtca cataaggcgt ttatcgtaaa gaaatggggc gacgacaccc gaaaaaagct   8340
gcgtggaagg ctctgacgcc aagggttagg cttgcactt ccttctttag ccgctaaaac    8400
ggccccttct ctgcgggccg tcggctcgcg catcatatcg acatcctcaa cggaagccgt   8460
```
gccgcgaatg gcatcgggcg ggtgcgcttt gacagttgtt ttggatc                    8507

<210> SEQ ID NO 2
<211> LENGTH: 13429
<212> TYPE: DNA
<213> ORGANISM: Artificial Sequence
<220> FEATURE:
<223> OTHER INFORMATION: Synthetic vector: pLC40
<220> FEATURE:
<221> NAME/KEY: misc_feature
<222> LOCATION: (48)..(70)
<223> OTHER INFORMATION: I-SceI
<220> FEATURE:
<221> NAME/KEY: misc_feature
<222> LOCATION: (90)..(989)
<223> OTHER INFORMATION: P ubi
<220> FEATURE:
<221> NAME/KEY: misc_feature
<222> LOCATION: (1073)..(2082)
<223> OTHER INFORMATION: UbiI
<220> FEATURE:
<221> NAME/KEY: misc_feature
<222> LOCATION: (2117)..(3239)
<223> OTHER INFORMATION: hpt
<220> FEATURE:
<221> NAME/KEY: misc_feature
<222> LOCATION: (3145)..(3420)
<223> OTHER INFORMATION: Tnos terminater
<220> FEATURE:
<221> NAME/KEY: misc_feature
<222> LOCATION: (3479)..(3503)
<223> OTHER INFORMATION: Left Border of T-DNA
<220> FEATURE:
<221> NAME/KEY: misc_feature
<222> LOCATION: (4045)..(4075)
<223> OTHER INFORMATION: ICeuI
<220> FEATURE:
<221> NAME/KEY: misc_feature
<222> LOCATION: (4082)..(4489)
<223> OTHER INFORMATION: (complement) cos
<220> FEATURE:
<221> NAME/KEY: misc_feature
<222> LOCATION: (4490)..(6608)
<223> OTHER INFORMATION: (complement) IncC1
<220> FEATURE:
<221> NAME/KEY: misc_feature
<222> LOCATION: (6610)..(7431)
<223> OTHER INFORMATION: (complement) oriT
<220> FEATURE:
<221> NAME/KEY: misc_feature
<222> LOCATION: (7426)..(10596)
<223> OTHER INFORMATION: (complement) trfA1
<220> FEATURE:
<221> NAME/KEY: misc_feature
<222> LOCATION: (10593)..(11689)
<223> OTHER INFORMATION: nptIII
<220> FEATURE:
<221> NAME/KEY: misc_feature
<222> LOCATION: (11686)..(12578)
<223> OTHER INFORMATION: (complement) oriV
<220> FEATURE:
<221> NAME/KEY: misc_feature
<222> LOCATION: (13253)..(13277)
<223> OTHER INFORMATION: RB

<400> SEQUENCE: 2
aagcttgcgg ccgcttcgaa gatgttaatt aacatcggta ccgagctcta gggataacag      60
ggtaatagct cgaattctag cttgcatgcc tgcagtgcag cgtgacccgg tcgtgcccct     120
ctctagagat aatgagcatt gcatgtctaa gttataaaaa attaccacat atttttttg     180 tcacacttgt ttgaagtgca gtttatctat ctttatacat atatttaaac tttactctac     240
gaataatata atctatagta ctacaataat atcagtgttt tagagaatca tataaatgaa     300
cagttagaca tggtctaaag gacaattgag tattttgaca acaggactct acagttttat     360

```
cttttttagtg tgcatgtgtt ctcctttttt tttgcaaata gcttcaccta tataatactt    420
catccatttt attagtacat ccatttaggg tttagggtta atggttttta tagactaatt    480
tttttagtac atctatttta ttctatttta gcctctaaat taagaaaact aaaactctat    540
tttagttttt ttatttaata atttagatat aaaatagaat aaaataaagt gactaaaaat    600
taaacaaata cccttttaaga aattaaaaaa actaaggaaa cattttttctt gtttcgagta   660 gataatgcca gcctgttaaa cgccgtcgac gagtctaacg acaccaacc agcgaaccag     720 cagcgtcgcg tcgggccaag cgaagcagac ggcacggcat ctctgtcgct gcctctggac   780
ccctctcgag agttccgctc caccgttgga cttgctccgc tgtcggcatc cagaaattgc   840
gtggcggagc ggcagacgtg agccggcacg gcaggcggcc tcctcctcct ctcacggcac   900
cggcagctac gggggattcc tttcccaccg ctccttcgct ttcccttcct cgcccgccgt   960
aataaataga cacccctcc acacctcttt tccccaacct cgtgttgttc ggagcgcaca   1020
cacacacaac cagatctccc ccaaatccac ccgtcggcac ctccgcttca aggtacgccg   1080
ctcgtcctcc cccccccccc ctctctacct tctctagatc ggcgttccgg tccatggtta   1140
gggcccggta gttctacttc tgttcatgtt tgtgttagat ccgtgtttgt gttagatccg   1200
tgctgctagc gttcgtacac ggatgcgacc tgtacgtcag acacgttctg attgctaact   1260
tgccagtgtt tctcttgggg aatcctggg atggctctag ccgttccgca gacgggatcg   1320
atttcatgat ttttttttgtt tcgttgcata gggtttggtt tgccctttc ctttatttca    1380 atatatgccg tgcacttgtt tgtcgggtca tcttttcatg cttttttttg tcttggttgt   1440
gatgatgtgg tctggttggg cggtcgttct agatcggagt agaattctgt ttcaaactac   1500
ctggtggatt tattaattttt ggatctgtat gtgtgtgcca tacatattca tagttacgaa   1560
ttgaagatga tggatggaaa tatcgatcta ggataggtat acatgttgat gcgggtttta   1620
ctgatgcata tacagagatg cttttttgttc gcttggttgt gatgatgtgg tgtggttggg   1680
cggtcgttca ttcgttctag atcggagtag aatactgttt caaactacct ggtgtattta   1740
ttaattttgg aactgtatgt gtgtgtcata catcttcata gttacgagtt taagatggat   1800
ggaaatatcg atctaggata ggtatacatg ttgatgtggg ttttactgat gcatatacat   1860
gatggcatat gcagcatcta ttcatatgct ctaaccttga gtacctatct attataataa   1920
acaagtatgt tttataatta tttttgatctt gatatacttg gatgatggca tatgcagcag   1980
ctatatgtgg atttttttag ccctgccttc atacgctatt tatttgcttg gtactgtttc   2040
ttttgtcgat gctcaccctg ttgtttggtg ttacttctgc aggtcgactc tagaggatcc   2100 cgggggggcaa tgagatatga aaaagcctga actcaccgcg acgtctgtcg agaagtttct   2160
gatcgaaaag ttcgacagcg tctccgacct gatgcagctc tcgagggcg aagaatctcg   2220 tgctttcagc ttcgatgtag gagggcgtgg atatgtcctg cgggtaaata gctgcgccga   2280
tggtttctac aaagatcgtt atgtttatcg gcactttgca tcggccgcgc tcccgattcc   2340
ggaagtgctt gacattgggg aattcagcga gagcctgacc tattgcatct cccgccgtgc   2400
acagggtgtc acgttgcaag acctgcctga aaccgaactg cccgctgttc tgcagccggt   2460
cgcggaggcc atggatgcga tcgctgcggc cgatcttagc cagacgagcg ggttcggccc   2520
attcggaccg caaggaatcg gtcaatacac tacatggcgt gatttcatat gcgcgattgc   2580
tgatccccat gtgtatcact ggcaaactgt gatggacgac accgtcagtg cgtccgtcgc   2640
gcaggctctc gatgagctga tgctttgggc cgaggactgc cccgaagtcc ggcacctcgt   2700
gcacgcggat ttcggctcca acaatgtcct gacggacaat ggccgcataa cagcggtcat   2760
```

```
tgactggagc gaggcgatgt tcggggattc ccaatacgag gtcgccaaca tcttcttctg    2820
gaggccgtgg ttggcttgta tggagcagca gacgcgctac ttcgagcgga ggcatccgga    2880
gcttgcagga tcgccgcggc tccgggcgta tatgctccgc attggtcttg accaactcta    2940
tcagagcttg gttgacggca atttcgatga tgcagcttgg gcgcagggtc gatgcgacgc    3000
aatcgtccga tccggagccg ggactgtcgg gcgtacacaa atcgcccgca gaagcgcggc    3060
cgtctggacc gatggctgtg tagaagtact cgccgatagt ggaaaccgac gccccagcac    3120
tcgtccggga tccgtcgacc tgcagatcgt tcaaacattt ggcaataaag tttcttaaga    3180
ttgaatcctg ttgccggtct tgcgatgatt atcatataat ttctgttgaa ttacgttaag    3240
catgtaataa ttaacatgta atgcatgacg ttatttatga gatgggtttt tatgattaga    3300
gtcccgcaat tatacattta atacgcgata gaaaacaaaa tatagcgcgc aaactaggat    3360
aaattatcgc gcgcggtgtc atctatgtta ctagatccga tgataagctg tcaaacatga    3420
gaattcagta cattaaaaac gtccgcaatg tgttattaag ttgtctaagc gtcaatttgt    3480
ttacaccaca atatatcctg ccaccagcca gccaacagct ccccgaccgg cagctcggca    3540
caaaatcacc actcgataca ggcagcccat cagtccggga cggcgtcagc gggagagccg    3600
ttgtaaggcg gcagactttg ctcatgttac cgatgctatt cggaagaacg gcaactaagc    3660
tgccgggttt gaaacacgga tgatctcgcg gagggtagca tgttgattgt aacgatgaca    3720
gagcgttgct gcctgtgatc aaatatcatc tccctcgcag agatccgaat tatcagcctt    3780
cttattcatt tctcgcttaa ccgtgacagg ctgtcgatct tgagaactat gccgacataa    3840
taggaaatcg ctggataaag ccgctgagga agctgagtgg cgctatttct ttagaagtga    3900
acgttgacga tcgtcgaccg taccccgatg aattaattcg gacgtacgtt ctgaacacag    3960
ctggatactt acttgggcga ttgtcataca tgacatcaac aatgtacccg tttgtgtaac    4020
cgtctcttgg aggttcgtat gacactaggt cgctacctta ggaccgttat agttactagc    4080
gaattgacat gaggttgccc cgtattcagt gtcgctgatt tgtattgtct gaagttgttt    4140
ttacgttaag ttgatgcaga tcaattaata cgatacctgc gtcataattg attatttgac    4200
gtggtttgat ggcctccacg cacgttgtga tatgtagatg ataatcatta tcactttacg    4260
ggtcctttcc ggtgatccga caggttacgg ggcggcgacc tcgcgggttt tcgctattta    4320
tgaaaatttt ccggtttaag gcgtttccgt tcttcttcgt cataacttaa tgttttattt    4380
taaaataccc tctgaaaaga aaggaaacga caggtgctga aagcgagctt tttggcctct    4440
gtcgtttcct ttctctgttt ttgtccgtgg aatgaacaat ggaaggatct tctcggcggc    4500
gatcacgacg ccggccctgc ggagccttcg ccgcgtgcgc gattcatggc ggccgtggag    4560
gccaaggatt tcgcgcgagt gcaagagctg atcgaggcgc gtggagccaa gtcggcggct    4620
gattatgtcc ttgcgcagct cgccgtggcc gaaggtctgg accgcaagcc tggtgcgcgc    4680
gtcgtggtcg ggaaagcggc gggcagcatg gcaatgccgc ctgcggcgct gggttttacg    4740
ccaaggggag aagcggcata cgccatcgag cggtcagcct atggtgagcc gaggtccagc    4800
attgcgaagc agtaccagca ggaatggaac cggaaggcgg cgacctggtg ggcgatggcc    4860
ggtgtggccg gcatcatcgg cgcgatcctg gcggcggcgg caaccggctt tgttgggctg    4920
gcagtgtcga tccgcaaccg agtgaagcgc gtgcgcgacc tgttggtgat ggagccgggt    4980
gcagagccat aagcggcaag agacgaaagc ccggtttccg ggcttttgtt ttgttacgcc    5040
aaggacgagt tttagcggct aaaggtgttg acgtgcgaga aatgtttagc taaacttctc    5100
tcatgtgctg gcggctgtca ccgctatgtt caaccaaggc gcggagcaaa ttatgggtgt    5160
```

```
tatccatgaa gaaacggctt accgaaagcc agttccagga ggcgatccag gggctggaag    5220
tggggcagca gaccatcgag atagcgcggg gcgtcttagt cgatgggaag ccacaggcga    5280
cgttcgcaac gtcgctggga ctgaccaggg gcgcagtgtc gcaagcggtg catcgcgtgt    5340
gggccgcgtt cgaggacaag aacttgcccg aggggtacgc gcgggtaacg gcggttctgc    5400
cggaacatca ggcgtacatc gtccggaagt gggaagcgga cgccaagaaa aaacaggaaa    5460
ccaaacgatg aaaactttgg tcacggccaa ccagaaaggc ggcgtcggca agacttcgac    5520
ccttgtgcat cttgccttcg acttttcga gcgcggcttg cggggttgccg tgatcgacct    5580 ggacccccag ggcaatgcgt cctacacgct caaggacttt gctaccggcc tgcatgcaag    5640
caagctgttc ggcgctgtcc ctgccggcgg ctggaccgaa accgcacccg cagccggcga    5700
cggccaggcc gcgcgcctcg ccctcatcga gtccaacccg gtactggcga acgccgaacg    5760
gctgtcgctg gacgacgccc gcgagctgtt cggggcgaac atcaaggccc tggcgaacca    5820
aggcttcgac gtgtgcctga tcgacacggc cccgaccctt ggcgtcggcc tggcggccgc    5880
cctcttcgcg gccgactatg tgctgtcccc catcgagctt gaggcgtaca gcatccaggg    5940
catcaagaag atggtcacga ccattgcgaa cgtgcgccag aagaacgcca agctgcaatt    6000
ccttggcatg gtgcccagca aggtcgatgc gcggaatccg cgccacgcgc gccaccaagc    6060
cgagctgctg gccgcgtacc ccaagatgat gattccggcc accgttggcc tgcgcagcag    6120
catcgccgat gccctcgcat ccggtgtgcc ggtctggaag atcaagaaaa cggccgcgcg    6180
caaggcatcg aaagaggttc gcgccctggc tgattacgtg ttcacgaaga tggagatttc    6240
ccaatgactg cggctcaagc caagaccacc aagaaaaaca ccgctgcggc cgctcaggaa    6300
gccgcaggcg cggcgcagcc gtccggcctg gggttggata gcatcggcga cctgtcgagc    6360
ctcctggacg ctcctgcggc gtctcagggc ggttccggcc ctatcgagct ggacctggac    6420
ctgatcgacg aagatccgca tcagccgcgg acgccgaca accccggctt ttccccggag    6480
agcatcgcgg aaatcggtgc cacgatcaaa gagcgcgggg tgaagtcacc catttcggtg    6540
cgcgagaacc aggagcagcc gggccgctat atcatcaatc acggcgcccg ccgctaccgt    6600
ggctcgaatc tagtgatatt ccacaaaaca gcagggaagc agcgcttttc cgctgcataa    6660
ccctgcttcg gggtcattat agcgattttt tcggtatatc catcctttt cgcacgatat    6720 acaggatttt gccaaagggt tcgtgtagac tttccttggt gtatccaacg gcgtcagccg    6780
ggcaggatag gtgaagtagg cccacccgcg agcgggtgtt ccttcttcac tgtcccttat    6840
tcgcacctgg cggtgctcaa cgggaatcct gctctgcgag gctggccggc taccgccggc    6900
gtaacagatg agggcaagcg gatggctgat gaaaccaagc caaccaggaa gggcagccca    6960
cctatcaagg tgtactgcct tccagacgaa cgaagagcga ttgaggaaaa ggcggcggcg    7020
gccggcatga gcctgtcggc ctacctgctg gccgtcggcc agggctacaa aatcacgggc    7080
gtcgtggact atgagcacgt ccgcgagctg gcccgcatca tggcgacct gggccgcctg    7140 ggcggcctgc tgaaactctg gctcaccgac gacccgcgca cggcgcggtt cggtgatgcc    7200
acgatcctcg ccctgctggc gaagatcgaa gagaagcagg acgagcttgg caaggtcatg    7260
atgggcgtgg tccgcccgag ggcagagcca tgactttttt agccgctaaa acggccgggg    7320
ggtgcgcgtg attgccaagc acgtcccccat gcgctccatc aagaagagcg acttcgcgga    7380
gctggtgaag tacatcaccg acgagcaagg caagaccgag cgccagatcc aaaacaactg    7440
tcaaagcgca cccgccgat gccattgcgc gcacggcttc cgttgaggat gtcgatatga    7500
tgcgcgagcc gacggcccgc agagaagggg ccgttttagc ggctaaagaa ggaagtgcaa    7560
```

```
gccctaaccc ttggcgtcag agccttccac gcagcttttt tcgggtgtcg tcgccccatt    7620
tctttacgat aaacgcctta tgtgacggca aaaccacact gatgcgttcg tatccgggcg    7680
gcacgctgct cttgaaagga tgacccgcaa tctccgcgag tgcctcgcgg tcaaggtcgg    7740
tggactccag gagaagaggt aggggagttt ccagggcgtc ggcaatggcc tccatcacct    7800
tcaacgaggg gttggcctta ccgttggtta agtctgataa aaacgaaatt gaaacccctg    7860
ccctctccga cagctcatgt ttcgtcatgc cccgctcatc gagcagacga aggatgttgg    7920 tgaaaatat ctggttgtac acagcggaag ccgcccctcg cacctttggt cgcggcccgc    7980
aaaattttag ccgctaaagt tcttgacagc ggaaccaatg tttagctaaa ctagagtctc    8040
ctttctcaag gagactttcg atatgagcca taatcagttc cagtttatcg gtaatcttac    8100
ccgtgacacc gaggtacgtc atggcaattc taacaagccg caagcaattt tcgatatagc    8160
ggttaatgaa gagtggcgca acgatgccgg cgacaagcag gagcgcaccg acttcttccg    8220
catcaagtgt tttggctctc aggccgaggc ccacggcaag tatttgggca aggggtcgct    8280
ggtattcgtg cagggcaaga ttcggaatac caagtacgag aaggacggcc agacggtcta    8340
cgggaccgac ttcattgccg ataaggtgga ttatctggac accaaggcac caggcgggtc    8400
aaatcaggaa taagggcaca ttgccccggc gtgagtcggg gcaatcccgc aaggagggtg    8460
aatgaatcgg acgtttgacc ggaaggcata caggcaagaa ctgatcgacg cggggttttc    8520
cgccgaggat gccgaaacca tcgcaagccg caccgtcatg cgtgcgcccc gcgaaacctt    8580
ccagtccgtc ggctcgatgg tccagcaagc tacggccaag atcgagcgcg acagcgtgca    8640
actggctccc cctgccctgc ccgcgccatc ggccgccgtg gagcgttcgc gtcgtctcga    8700
acaggaggcg gcaggtttgg cgaagtcgat gaccatcgac acgcgaggaa ctatgacgac    8760
caagaagcga aaaccgccg gcgaggacct ggcaaaacag gtcagcgagg ccaagcaggc    8820
cgcgttgctg aaacacacga agcagcagat caaggaaatg cagctttcct tgttcgatat    8880
tgcgccgtgg ccgacacga tgcgagcgat gccaaacgac acggcccgct ctgccctgtt    8940
caccacgcgc aacaagaaaa tcccgcgcga ggcgctgcaa aacaaggtca ttttccacgt    9000
caacaaggac gtgaagatca cctacaccgg cgtcgagctg cgggccgacg atgacgaact    9060
ggtgtggcag caggtgttgg agtacgcgaa gcgcacccct atcggcgagc cgatcacctt    9120
cacgttctac gagctttgcc aggacctggg ctggtcgatc aatggccggt attacacgaa    9180
ggccgaggaa tgcctgtcgc gcctacaggc gacggcgatg ggcttcacgt ccgaccgcgt    9240
tgggcacctg gaatcggtgt cgctgctgca ccgcttccgc gtcctggacc gtggcaagaa    9300
aacgtcccgt tgccaggtcc tgatcgacga ggaaatcgtc gtgctgtttg ctggcgacca    9360
ctacacgaaa ttcatatggg agaagtaccg caagctgtcg ccgacggccc gacggatgtt    9420
cgactatttc agctcgcacc gggagccgta cccgctcaag ctggaaacct tccgcctcat    9480
gtgcggatcg gattccaccc gcgtgaagaa gtggcgcgag caggtcggcg aagcctgcga    9540
agagttgcga ggcagcggcc tggtggaaca cgcctgggtc aatgatgacc tggtgcattg    9600
caaacgctag ggccttgtgg ggtcagttcc ggctgggggt tcagcagcca gcgctttact    9660
ggcatttcag gaacaagcgg gcactgctcg acgcacttgc ttcgctcagt atcgctcggg    9720
acgcacggcg cgctctacga actgccgata aacagaggat taaaattgac aattgtgatt    9780
aaggctcaga ttcgacggct tggagcggcc gacgtgcagg atttccgcga gatccgattg    9840
tcggccctga gaaagctcc agagatgttc gggtccgttt acgagcacga ggagaaaaag    9900
cccatggagg cgttcgctga acggttgcga gatgccgtgg cattcggcgc ctacatcgac    9960
```

```
ggcgagatca ttgggctgtc ggtcttcaaa caggaggacg gccccaagga cgctcacaag    10020
gcgcatctgt ccggcgtttt cgtggagccc aacagcgag gccgaggggt cgccggtatg    10080
ctgctgcggg cgttgccggc gggtttattg ctcgtgatga tcgtccgaca gattccaacg    10140
ggaatctggt ggatgcgcat cttcatcctc ggcgcactta atatttcgct attctggagc    10200
ttgttgttta tttcggtcta ccgcctgccg ggcgggtcgc ggcgacggta ggcgctgtgc    10260
agccgctgat ggtcgtgttc atctctgccg ctctgctagg tagcccgata cgattgatgg    10320
cggtcctggg ggctatttgc ggaactgcgg gcgtggcgct gttggtgttg acaccaaacg    10380
cagcgctaga tcctgtcggc gtcgcagcgg gcctggcggg ggcggtttcc atggcgttcg    10440
gaaccgtgct gacccgcaag tggcaacctc ccgtgcctct gctcacctt accgcctggc    10500 aactggcggc cggaggactt ctgctcgttc cagtagcttt agtgtttgat ccgccaatcc    10560
cgatgcctac aggaaccaat gttctcggct gctcgactgc acgaatacca gcgacccctt    10620
gcccaaatac ttgccgtggg cctcggcctg agagccaaaa cacttgatgc ggaagaagtc    10680
ggtgcgctcc tgcttgtcgc cggcatcgtt gcgccacatc taggtactaa acaattcat    10740 ccagtaaaat ataatatttt attttctccc aatcaggctt gatccccagt aagtcaaaaa    10800
atagctcgac atactgttct tccccgatat cctccctgat cgaccggacg cagaaggcaa    10860
tgtcatacca cttgtccgcc ctgccgcttc tcccaagatc aataaagcca cttactttgc    10920
catctttcac aaagatgttg ctgtctccca ggtcgccgtg ggaaaagaca agttcctctt    10980
cgggcttttc cgtcttttaa aaatcataca gctcgcgcgg atctttaaat ggagtgtctt    11040
cttcccagtt ttcgcaatcc acatcggcca gatcgttatt cagtaagtaa tccaattcgg    11100
ctaagcggct gtctaagcta ttcgtatagg acaatccga tatgtcgatg gagtgaaaga    11160
gcctgatgca ctccgcatac agctcgataa tctttcagg gctttgttca tcttcatact    11220
cttccgagca aaggacgcca tcggcctcac tcatgagcag attgctccag ccatcatgcc    11280
gttcaaagtg caggaccttt ggaacaggca gctttccttc cagccatagc atcatgtcct    11340
tttcccgttc cacatcatag gtggtcccctt tataccggct gtccgtcatt tttaaatata    11400
ggttttcatt ttctcccacc agcttatata ccttagcagg agacattcct tccgtatctt    11460
ttacgcagcg gtatttttcg atcagttttt tcaattccgg tgatattctc attttagcca    11520
tttattattt ccttcctctt ttctacagta tttaaagata ccccaagaag ctaattataa    11580
caagacgaac tccaattcac tgttccttgc attctaaaac cttaaatacc agaaaacagc    11640
tttttcaaag ttgttttcaa agttggcgta taacatagta tcgattcgat agcgtggact    11700
caaggctctc gcgaatggct cgcgttggaa actttcattg acacttgagg ggcaccgcag    11760
ggaaattctc gtccttgcga gaaccggcta tgtcgtgctg cgcatcgagc ctgcgcccctt    11820 ggcttgtctc gccccctctcc gcgtcgctac ggggcttcca gcgccttttcc gacgctcacc    11880 gggctggttg cctcgccgc tgggctgcg ccgtctatg gccctgcaaa cgcgccagaa    11940
acgccgtcga agccgtgtgc gagacaccgc ggccgccggc gttgtggata cctcgcggaa    12000
aacttggccc tcactgacag atgagggggcg gacgttgaca cttgagggc cgactcaccc    12060 ggcgcggcgt tgacagatga ggggcaggct cgatttcggc cggcgacgtg gagctggcca    12120
gcctcgcaaa tcggcgaaaa cgcctgattt tacgcgagtt tcccacagat gatgtggaca    12180
agcctgggga taagtgccct gcggtattga cacttgaggg gcgcgactac tgacagatga    12240
ggggcgcgat ccttgacact tgagggcag agtgctgaca gatgaggggc gcacctattg    12300
acatttgagg ggctgtccac aggcagaaaa tccagcattt gcaagggttt ccgcccgttt    12360
```

```
ttcggccacc gctaacctgt cttttaacct gcttttaaac caatatttat aaaccttgtt    12420
tttaaccagg gctgcgccct gtgcgcgtga ccgcgcacgc cgaagggggg tgccccccct    12480
tctcgaaccc tcccggcccg ctaacgcggg cctcccatcc ccccaggggc tgcgcccctc    12540
ggccgcgaac ggcctcaccc caaaaatggc agcgccagat tattgaagca tttatcaggg    12600
ttattgtctc atgagcggat acatatttga atgtatttag aaaaataaac aatagggggt    12660
tccgcgcaca tttccccgaa aagtgccacc tgacgtctaa gaaaccatta ttatcatgac    12720
attaacctat aaaaataggc gtatcacgag gccctttcgt cttcaagaat tggtcgacga    12780
tcttgctgcg ttcggatatt tcgtggagt  tcccgccaca gacccggatt gaaggcgaga    12840
tccagcaact cgcgccagat catcctgtga cggaactttg gcgcgtgatg actggccagg    12900
acgtcggccg aaagagcgac aagcagatca cgcttttcga cagcgtcgga tttgcgatcg    12960 aggattttt c ggcgctgcgc tacgtccgcg accgcgttga gggatcaagc cacagcagcc    13020
cactcgacct tctagccgac ccagacgagc caagggatct ttttggaatg ctgctccgtc    13080
gtcaggcttt ccgacgtttg ggtggttgaa cagaagtcat tatcgcacgg aatgccaagc    13140
actcccgagg ggaaccctgt ggttggcatg cacatacaaa tggacgaacg gataaacctt    13200
ttcacgccct tttaaatatc cgattattct aataaacgct cttttctctt aggtttaccc    13260
gccaatatat cctgtcaaac actgatagtt taaactgaag gcgggaaacg acaatctgat    13320
catgagcgga gaattaaggg agtcacgtta tgaccccgc cgatgacgcg ggacaagccg    13380
ttttacgttt ggaactgaca gaaccgcaac gttgaaggag ccactcagc                13429
```

```
<210> SEQ ID NO 3
<211> LENGTH: 13174
<212> TYPE: DNA
<213> ORGANISM: Artificial Sequence
<220> FEATURE:
<223> OTHER INFORMATION: Synthetic vector: pLC40GWH
<220> FEATURE:
<221> NAME/KEY: misc_feature
<222> LOCATION: (48)..(70)
<223> OTHER INFORMATION: I-SceI
<220> FEATURE:
<221> NAME/KEY: misc_feature
<222> LOCATION: (90)..(989)
<223> OTHER INFORMATION: P ubi1
<220> FEATURE:
<221> NAME/KEY: misc_feature
<222> LOCATION: (1073)..(2082)
<223> OTHER INFORMATION: Ubi I
<220> FEATURE:
<221> NAME/KEY: misc_feature
<222> LOCATION: (2103)..(2127)
<223> OTHER INFORMATION: attB1
<220> FEATURE:
<221> NAME/KEY: misc_feature
<222> LOCATION: (2137)..(3162)
<223> OTHER INFORMATION: hpt
<220> FEATURE:
<221> NAME/KEY: misc_feature
<222> LOCATION: (3163)..(3187)
<223> OTHER INFORMATION: (complement) attB2
<220> FEATURE:
<221> NAME/KEY: misc_feature
<222> LOCATION: (3207)..(3482)
<223> OTHER INFORMATION: Tnos
<220> FEATURE:
<221> NAME/KEY: misc_feature
<222> LOCATION: (3541)..(3565)
<223> OTHER INFORMATION: Left Border of T-DNA
<220> FEATURE:
<221> NAME/KEY: misc_feature
<222> LOCATION: (4107)..(4137)
<223> OTHER INFORMATION: ICeuI
<220> FEATURE:
```

```
<221> NAME/KEY: misc_feature
<222> LOCATION: (4144)..(4551)
<223> OTHER INFORMATION: (complement) cos
<220> FEATURE:
<221> NAME/KEY: misc_feature
<222> LOCATION: (4552)..(6670)
<223> OTHER INFORMATION: (complement) IncC1
<220> FEATURE:
<221> NAME/KEY: misc_feature
<222> LOCATION: (6672)..(7493)
<223> OTHER INFORMATION: (complement) oriT
<220> FEATURE:
<221> NAME/KEY: misc_feature
<222> LOCATION: (7488)..(10658)
<223> OTHER INFORMATION: (complement) trfA1
<220> FEATURE:
<221> NAME/KEY: misc_feature
<222> LOCATION: (10655)..(11751)
<223> OTHER INFORMATION: nptIII
<220> FEATURE:
<221> NAME/KEY: misc_feature
<222> LOCATION: (11748)..(12640)
<223> OTHER INFORMATION: (complement) oriV
<220> FEATURE:
<221> NAME/KEY: misc_feature
<222> LOCATION: (12998)..(13022)
<223> OTHER INFORMATION: RB

<400> SEQUENCE: 3
```

| | | | | | |
|---|---|---|---|---|---|
| aagcttgcgg | ccgcttcgaa | gatgttaatt | aacatcggta | ccgagctcta | gggataacag | 60 |
| ggtaatagct | cgaattctag | cttgcatgcc | tgcagtgcag | cgtgacccgg | tcgtgcccct | 120 |
| ctctagagat | aatgagcatt | gcatgtctaa | gttataaaaa | attaccacat | attttttttg | 180 |
| tcacacttgt | ttgaagtgca | gtttatctat | ctttatacat | atatttaaac | tttactctac | 240 |
| gaataatata | atctatagta | ctacaataat | atcagtgttt | tagagaatca | tataaatgaa | 300 |
| cagttagaca | tggtctaaag | gacaattgag | tattttgaca | acaggactct | acagttttat | 360 |
| cttttttagtg | tgcatgtgtt | ctcctttttt | tttgcaaata | gcttcaccta | tataatactt | 420 |
| catccatttt | attagtacat | ccatttaggg | tttaggggtta | atggttttta | tagactaatt | 480 |
| tttttagtac | atctattta | ttctatttta | gcctctaaat | taagaaaact | aaaactctat | 540 |
| tttagttttt | ttatttaata | atttgagtat | aaaatagaat | aaaataaagt | gactaaaaat | 600 |
| taaacaaata | cccttttaaga | aattaaaaaa | actaaggaaa | catttttctt | gtttcgagta | 660 |
| gataatgcca | gcctgttaaa | cgccgtcgac | gagtctaacg | gacaccaacc | agcgaaccag | 720 |
| cagcgtcgcg | tcgggccaag | cgaagcagac | ggcacggcat | ctctgtcgct | gcctctggac | 780 |
| ccctctcgag | agttccgctc | caccgttgga | cttgctccgc | tgtcggcatc | cagaaattgc | 840 |
| gtggcggagc | ggcagacgtg | agccggcacg | gcaggcggcc | tcctcctcct | ctcacggcac | 900 |
| cggcagctac | gggggattcc | tttcccaccg | ctccttcgct | ttcccttcct | cgcccgccgt | 960 |
| aataaataga | caccccctcc | acaccctctt | tccccaacct | cgtgttgttc | ggagcgcaca | 1020 |
| cacacacaac | cagatctccc | ccaaatccac | ccgtcggcac | ctccgcttca | aggtacgccg | 1080 |
| ctcgtcctcc | ccccccccc | ctctctacct | tctctagatc | ggcgttccgg | tccatggtta | 1140 |
| gggcccggta | gttctacttc | tgttcatgtt | tgtgttagat | ccgtgtttgt | gttagatccg | 1200 |
| tgctgctagc | gttcgtacac | ggatgcgacc | tgtacgtcag | acacgttctg | attgctaact | 1260 |
| tgccagtgtt | tctcttttggg | gaatcctggg | atggctctag | ccgttccgca | gacgggatcg | 1320 |
| atttcatgat | ttttttttgtt | tcgttgcata | gggtttggtt | tgcccttttc | ctttatttca | 1380 |
| atatatgccg | tgcacttgtt | tgtcgggtca | tcttttcatg | cttttttttg | tcttggttgt | 1440 |
| gatgatgtgg | tctggttggg | cggtcgttct | agatcggagt | agaattctgt | ttcaaactac | 1500 |

```
ctggtggatt tattaatttt ggatctgtat gtgtgtgcca tacatattca tagttacgaa    1560
ttgaagatga tggatggaaa tatcgatcta ggataggtat acatgttgat gcgggtttta    1620
ctgatgcata tacagagatg cttttttgttc gcttggttgt gatgatgtgg tgtggttggg   1680
cggtcgttca ttcgttctag atcggagtag aatactgttt caaactacct ggtgtattta    1740
ttaattttgg aactgtatgt gtgtgtcata catcttcata gttacgagtt taagatggat    1800
ggaaatatcg atctaggata ggtatacatg ttgatgtggg ttttactgat gcatatacat    1860
gatggcatat gcagcatcta ttcatatgct ctaaccttga gtacctatct attataataa    1920
acaagtatgt tttataatta tttttgatctt gatatacttg gatgatggca tatgcagcag   1980
ctatatgtgg attttttttag ccctgccttc atacgctatt tatttgcttg gtactgtttc   2040
ttttgtcgat gctcaccctg ttgtttggtg ttacttctgc aggtcgactc tagaggatca    2100
tcacaagttt gtacaaaaaa gcaggctcaa tgagatatga aaaagcctga actcaccgcg    2160
acgtctgtcg agaagtttct gatcgaaaag ttcgacagcg tctccgacct gatgcagctc    2220
tcggagggcg aagaatctcg tgctttcagc ttcgatgtag agggcgtgg atatgtcctg    2280 cgggtaaata gctgcgccga tggtttctac aaagatcgtt atgtttatcg gcactttgca    2340
tcggccgcgc tcccgattcc ggaagtgctt gacattgggg aattcagcga gagcctgacc    2400
tattgcatct cccgccgtgc acagggtgtc acgttgcaag acctgcctga aaccgaactg    2460
cccgctgttc tgcagccggt cgcggaggcc atggatgcga tcgctgcggc cgatcttagc    2520
cagacgagcg ggttcggccc attcggaccg caaggaatcg gtcaatacac tacatggcgt    2580
gatttcatat gcgcgattgc tgatccccat gtgtatcact ggcaaactgt gatggacgac    2640
accgtcagtg cgtccgtcgc gcaggctctc gatgagctga tgctttgggc cgaggactgc    2700
cccgaagtcc ggcacctcgt gcacgcggat ttcggctcca acaatgtcct gacggacaat    2760
ggccgcataa cagcggtcat tgactggagc gaggcgatgt tcggggattc ccaatacgag    2820
gtcgccaaca tcttcttctg gaggccgtgg ttggcttgta tggagcagca gacgcgctac    2880
ttcgagcgga ggcatccgga gcttgcagga tcgccgcggc tccgggcgta tatgctccgc    2940
attggtcttg accaactcta tcagagcttg gttgacggca atttcgatga tgcagcttgg    3000
gcgcagggtc gatgcgacgc aatcgtccga tccggagccg ggactgtcgg cgtacacaa    3060 atcgcccgca gaagcgcggc cgtctggacc gatggctgtg tagaagtact cgccgatagt    3120
ggaaaccgac gccccagcac tcgtccgagg gcaaggaat agacccagct ttcttgtaca    3180
aagtggtgat gatccgtcga cctgcagatc gttcaaacat ttggcaataa agtttcttaa    3240
gattgaatcc tgttgccggt cttgcgatga ttatcatata atttctgttg aattacgtta    3300
agcatgtaat aattaacatg taatgcatga cgttatttat gagatgggtt tttatgatta    3360
gagtcccgca attatacatt taatacgcga tagaaaacaa aatatagcgc gcaaactagg    3420
ataaattatc gcgcgcggtg tcatctatgt tactagatcc gatgataagc tgtcaaacat    3480
gagaattcag tacattaaaa acgtccgcaa tgtgttatta agttgtctaa gcgtcaattt    3540
gtttacacca caatatatcc tgccaccagc cagccaacag ctccccgacc ggcagctcgg    3600
cacaaaatca ccactcgata caggcagccc atcagtccgg gacggcgtca gcgggagagc    3660
cgttgtaagg cggcagactt tgctcatgtt accgatgcta ttcggaagaa cggcaactaa    3720
gctgccgggt ttgaaacacg gatgatctcg cggagggtag catgttgatt gtaacgatga    3780
cagagcgttg ctgcctgtga tcaaatatca tctcccctcg cagagatccga attatcagcc    3840 ttcttattca tttctcgctt aaccgtgaca ggctgtcgat cttgagaact atgccgacat    3900
```

```
aataggaaat cgctggataa agccgctgag gaagctgagt ggcgctattt ctttagaagt   3960
gaacgttgac gatcgtcgac cgtacccga tgaattaatt cggacgtacg ttctgaacac    4020
agctggatac ttacttgggc gattgtcata catgacatca acaatgtacc cgtttgtgta   4080
accgtctctt ggaggttcgt atgacactag gtcgctacct taggaccgtt atagttacta   4140
gcgaattgac atgaggttgc cccgtattca gtgtcgctga tttgtattgt ctgaagttgt   4200
ttttacgtta agttgatgca gatcaattaa tacgatacct cgtcataat tgattatttg    4260
acgtggtttg atggcctcca cgcacgttgt gatatgtaga tgataatcat tatcactta    4320
cgggtccttt ccgtgatcc gacaggttac ggggcggcga cctcgcgggt tttcgctatt    4380
tatgaaaatt ttccggttta aggcgtttcc gttcttcttc gtcataactt aatgttttta   4440
tttaaaatac cctctgaaaa gaaggaaac gacaggtgct gaaagcgagc tttttggcct    4500
ctgtcgtttc ctttctctgt ttttgtccgt ggaatgaaca atggaaggat cttctcggcg   4560
gcgatcacga cgccggccct gcggagcctt cgccgcgtgc gcgattcatg gcggccgtgg   4620
aggccaagga tttcgcgcga gtgcaagagc tgatcgaggc gcgtggagcc aagtcggcgg   4680
ctgattatgt ccttgcgcag ctcgccgtgg ccgaaggtct ggaccgcaag cctggtgcgc   4740
gcgtcgtggt cgggaaagcg gcgggcagca tggcaatgcc gcctgcggcg ctgggtttta   4800
cgccaagggg agaagcggca tacgccatcg agcggtcagc ctatggtgag ccgaggtcca   4860
gcattgcgaa gcagtaccag caggaatgga accggaaggc ggcgacctgg tgggcgatgg   4920
ccggtgtggc cggcatcatc ggcgcgatcc tggcggcggc ggcaaccggc tttgttgggc   4980
tggcagtgtc gatccgcaac cgagtgaagc gcgtgcgcga cctgttggtg atggagccgg   5040
gtgcagagcc ataagcggca agagacgaaa gcccggtttc cgggcttttg ttttgttacg   5100
ccaaggacga gttttagcgg ctaaaggtgt tgacgtgcga gaaatgttta gctaaacttc   5160
tctcatgtgc tggcggctgt caccgctatg ttcaaccaag gcgcggagca aattatgggt   5220
gttatccatg aagaaacggc ttaccgaaag ccagttccag gaggcgatcc aggggctgga   5280
agtggggcag cagaccatcg agatagcgcg gggcgtctta gtcgatggga agccacaggc   5340
gacgttcgca acgtcgctgg gactgaccag gggcgcagtg tcgcaagcgg tgcatcgcgt   5400
gtgggccgcg ttcgaggaca agaacttgcc cgaggggtac gcgcgggtaa cggcggttct   5460
gccggaacat caggcgtaca tcgtccggaa gtgggaagcg gacgccaaga aaaacagga    5520
aaccaaacga tgaaaacttt ggtcacggcc aaccagaaag gcggcgtcgg caagacttcg   5580
acccttgtgc atcttgcctt cgactttttc gagcgcggct tgcggttgc cgtgatcgac    5640
ctggaccccc agggcaatgc gtcctacacg ctcaaggact ttgctaccgg cctgcatgca   5700
agcaagctgt tcgcgctgt ccctgccggc ggctggaccg aaaccgcacc cgcagccggc    5760
gacggccagg ccgcgcgcct cgccctcatc gagtccaacc cggtactggc gaacgccgaa   5820
cggctgtcgc tggacgacgc ccgcgagctg ttcggggcga acatcaaggc cctgcgcaac   5880
caaggcttcg acgtgtgcct gatcgacacg gccccgaccc ttggcgtcgg cctggcggcc   5940
gccctcttcg cggccgacta tgtgctgtcc cccatcgagc ttgaggcgta cagcatccag   6000
ggcatcaaga agatggtcac gaccattgcg aacgtgcgcc agaagaacgc caagctgcaa   6060
ttccttggca tggtgcccag caaggtcgat gcgcggaatc cgccacgc gcgccaccaa    6120
gccgagctgc tggccgcgta ccccaagatg atgattccgg ccaccgttgg cctgcgcagc   6180
agcatcgccg atgccctcgc atccggtgtg ccggtctgga agatcaagaa aacggccgcg   6240
cgcaaggcat cgaaagaggt tcgcgccctg gctgattacg tgttcacgaa gatggagatt   6300
```

```
tcccaatgac tgcggctcaa gccaagacca ccaagaaaaa caccgctgcg gccgctcagg   6360
aagccgcagg cgcggcgcag ccgtccggcc tggggttgga tagcatcggc gacctgtcga   6420
gcctcctgga cgctcctgcg gcgtctcagg gcggttccgg ccctatcgag ctggacctgg   6480
acctgatcga cgaagatccg catcagccgc ggacggccga caaccccggc ttttccccgg   6540
agagcatcgc ggaaatcggt gccacgatca agagcgcgg ggtgaagtca cccatttcgg    6600
tgcgcgagaa ccaggagcag ccgggccgct atatcatcaa tcacggcgcc cgccgctacc   6660
gtggctcgaa tctagtgata ttccacaaaa cagcagggaa gcagcgcttt tccgctgcat   6720
aaccctgctt cggggtcatt atagcgattt tttcggtata tccatccttt ttcgcacgat   6780
atacaggatt ttgccaaagg gttcgtgtag actttccttg gtgtatccaa cggcgtcagc   6840
cgggcaggat aggtgaagta ggcccacccg cgagcgggtg ttccttcttc actgtccctt   6900
attcgcacct ggcggtgctc aacgggaatc ctgctctgcg aggctggccg gctaccgccg   6960
gcgtaacaga tgagggcaag cggatggctg atgaaaccaa gccaaccagg aagggcagcc   7020
cacctatcaa ggtgtactgc cttccagacg aacgaagagc gattgaggaa aaggcggcgg   7080
cggccggcat gagcctgtcg gcctacctgc tggccgtcgg ccagggctac aaaatcacgg   7140
gcgtcgtgga ctatgagcac gtccgcgagc tggcccgcat caatggcgac ctgggccgcc   7200
tgggcggcct gctgaaactc tggctcaccg acgaccgcg cacggcgcgg ttcggtgatg    7260
ccacgatcct cgccctgctg gcgaagatcg aagagaagca ggacgagctt ggcaaggtca   7320
tgatgggcgt ggtccgcccg agggcagagc catgactttt ttagccgcta aaacggccgg   7380
ggggtgcgcg tgattgccaa gcacgtcccc atgcgctcca tcaagaagag cgacttcgcg   7440
gagctggtga agtacatcac cgacgagcaa ggcaagaccg agcgccagat ccaaaacaac   7500
tgtcaaagcg cacccgcccg atgccattcg cggcacggct tccgttgagg atgtcgatat   7560
gatgcgcgag ccgacggccc gcagagaagg ggccgtttta gcggctaaag aaggaagtgc   7620
aagccctaac ccttggcgtc agagccttcc acgcagcttt tttcgggtgt cgtcgcccca   7680
tttctttacg ataaacgcct tatgtgacgg caaaaccaca ctgatgcgtt cgtatccggg   7740
cggcacgctg ctcttgaaag gatgaccgc aatctccgcg agtgcctcgc ggtcaaggtc    7800
ggtggactcc aggagaagag gtaggggagt ttccagggcg tcggcaatgg cctccatcac   7860
cttcaacgag gggttggcct taccgttggt taagtctgat aaaaacgaaa ttgaaacccc   7920
tgccctctcc gacagctcat gtttcgtcat gccccgctca tcgagcagac gaaggatgtt   7980
ggtgaaaaat atctggttgt acacagcgga agccgcccct cgcacctttg gtcgcggccc   8040
gcaaattttt agccgctaaa gttcttgaca gcggaaccaa tgtttagcta aactagagtc   8100
tcctttctca aggagacttt cgatatgagc cataatcagt tccagtttat cggtaatctt   8160
acccgtgaca ccgaggtacg tcatggcaat tctaacaagc gcaagcaat  tttcgatata   8220 gcggttaatg aagagtggcg caacgatgcc ggcgacaagc aggagcgcac cgacttcttc   8280
cgcatcaagt gttttggctc tcaggccgag gcccacggca agtatttggg caaggggtcg   8340
ctggtattcg tgcagggcaa gattcggaat accaagtacg agaaggacgg ccagacggtc   8400
tacgggaccg acttcattgc cgataaggtg gattatctgg acaccaaggc accaggcggg   8460
tcaaatcagg aataagggca cattgccccg cgtgagtcg gggcaatccc gcaaggaggg    8520
tgaatgaatc ggacgtttga ccggaaggca tacaggcaag aactgatcga cgcggggttt   8580
tccgccgagg atgccgaaac catcgcaagc cgcaccgtca tgcgtgcgcc ccgcgaaacc   8640
ttccagtccg tcggctcgat ggtccagcaa gctacggcca agatcgagcg cgacagcgtg   8700
```

-continued

```
caactggctc ccctgccct gcccgcgcca tcggccgccg tggagcgttc gcgtcgtctc    8760
gaacaggagg cggcaggttt ggcgaagtcg atgaccatcg acacgcgagg aactatgacg    8820
accaagaagc gaaaaaccgc cggcgaggac ctggcaaaac aggtcagcga ggccaagcag    8880
gccgcgttgc tgaaacacac gaagcagcag atcaaggaaa tgcagctttc cttgttcgat    8940
attgcgccgt ggccggacac gatgcgagcg atgccaaacg cacggcccg ctctgccctg     9000
ttcaccacgc gcaacaagaa aatcccgcgc gaggcgctgc aaaacaaggt cattttccac    9060
gtcaacaagg acgtgaagat cacctacacc ggcgtcgagc tgcgggccga cgatgacgaa    9120
ctggtgtggc agcaggtgtt ggagtacgcg aagcgcaccc ctatcggcga gccgatcacc    9180
ttcacgttct acgagctttg ccaggacctg ggctggtcga tcaatggccg gtattacacg    9240
aaggccgagg aatgcctgtc gcgcctacag gcgacggcga tgggcttcac gtccgaccgc    9300
gttgggcacc tggaatcggt gtcgctgctg caccgcttcc gcgtcctgga ccgtggcaag    9360
aaaacgtccc gttgccaggt cctgatcgac gaggaaatcg tcgtgctgtt tgctggcgac    9420
cactacacga aattcatatg ggagaagtac cgcaagctgt cgccgacggc ccgacggatg    9480
ttcgactatt tcagctcgca ccgggagccg tacccgctca agctggaaac cttccgcctc    9540
atgtgcggat cggattccac ccgcgtgaag aagtggcgcg agcaggtcgg cgaagcctgc    9600
gaagagttgc gaggcagcgg cctggtggaa cacgccgggg tcaatgatga cctggtgcat    9660
tgcaaacgct agggccttgt ggggtcagtt ccggctgggg gttcagcagc cagcgcttta    9720
ctggcatttc aggaacaagc gggcactgct cgacgcactt gcttcgctca gtatcgctcg    9780
ggacgcacgg cgcgctctac gaactgccga taaacagagg attaaaattg acaattgtga    9840
ttaaggctca gattcgacgg cttggagcgg ccgacgtgca ggatttccgc gagatccgat    9900
tgtcggccct gaagaaagct ccagagatgt tcgggtccgt ttacgagcac gaggagaaaa    9960
agcccatgga ggcgttcgct gaacggttgc gagatgccgt ggcattcggc gcctacatcg   10020
acggcgagat cattgggctg tcggtcttca acaggagga cggccccaag gacgctcaca   10080
aggcgcatct gtccgcgtt ttcgtggagc ccgaacagcg aggccgaggg gtcgccggta   10140
tgctgctgcg ggcgttgccg gcgggtttat tgctcgtgat gatcgtccga cagattccaa   10200
cgggaatctg gtggatgcgc atcttcatcc tcggcgcact taatatttcg ctattctgga   10260
gcttgttgtt tatttcggtc taccgcctgc cgggcgggtc gcggcgacgg taggcgctgt   10320
gcagccgctg atggtcgtgt tcatctctgc cgctctgcta ggtagcccga tacgattgat   10380
ggcggtcctg ggggctattt gcggaactgc gggcgtggcc ctgttggtgt tgacaccaaa   10440
cgcagcgcta gatcctgtcg gcgtcgcagc gggcctggcg ggggcggttt ccatggcgtt   10500
cggaaccgtg ctgacccgca gtggcaacc tcccgtgcct ctgctcacct ttaccgcctg    10560
gcaactggcg gccggaggac ttctgctcgt tccagtagct ttagtgtttg atccgccaat   10620
cccgatgcct acaggaacca atgttctcgg ctgctcgact gcacgaatac cagcgacccc   10680
ttgcccaaat acttgccgtg ggcctcggcc tgagagccaa acacttgat gcggaagaag    10740
tcggtgcgct cctgcttgtc gccggcatcg ttgcgccaca tctaggtact aaaacaattc   10800
atccagtaaa atataatatt ttattttctc ccaatcaggc ttgatcccca gtaagtcaaa   10860
aaatagctcg acatactgtt cttccccgat atcctccctg atcgaccgga cgcagaaggc   10920
aatgtcatac cacttgtccg ccctgccgct tctcccaaga tcaataaagc cacttacttt   10980
gccatctttc acaaagatgt tgctgtctcc caggtcgccg tgggaaaaga caagttcctc   11040
ttcgggcttt tccgtctttta aaaaatcata cagctcgcgc ggatctttaa atggagtgtc   11100
```

```
ttcttcccag ttttcgcaat ccacatcggc cagatcgtta ttcagtaagt aatccaattc    11160
ggctaagcgg ctgtctaagc tattcgtata gggacaatcc gatatgtcga tggagtgaaa    11220
gagcctgatg cactccgcat acagctcgat aatcttttca gggctttgtt catcttcata    11280
ctcttccgag caaaggacgc catcggcctc actcatgagc agattgctcc agccatcatg    11340
ccgttcaaag tgcaggacct tggaacagg cagctttcct tccagccata gcatcatgtc     11400
cttttcccgt tccacatcat aggtggtccc tttataccgg ctgtccgtca tttttaaata    11460
taggttttca ttttctccca ccagcttata taccttagca ggagacattc cttccgtatc    11520
ttttacgcag cggtattttt cgatcagttt tttcaattcc ggtgatattc tcattttagc    11580
catttattat ttccttcctc ttttctacag tatttaaaga taccccaaga agctaattat    11640
aacaagacga actccaattc actgttcctt gcattctaaa accttaaata ccagaaaaca    11700 gcttttcaa agttgttttc aaagttggcg tataacatag tatcgattcg atagcgtgga    11760
ctcaaggctc tcgcgaatgg ctcgcgttgg aaactttcat tgacacttga ggggcaccgc    11820
agggaaattc tcgtccttgc gagaaccggc tatgtcgtgc tgcgcatcga gcctgcgccc    11880
ttggcttgtc tcgcccctct ccgcgtcgct acggggcttc cagcgccttt ccgacgctca    11940
ccgggctggt tgccctcgcc gctgggctgg cggccgtcta tggccctgca aacgcgccag    12000
aaacgccgtc gaagccgtgt gcgagacacc gcggccgccg gcgttgtgga tacctcgcgg    12060
aaaacttggc cctcactgac agatgagggg cggacgttga cacttgaggg gccgactcac    12120
ccggcgcggc gttgacagat gaggggcagg ctcgatttcg gccggcgacg tggagctggc    12180
cagcctcgca aatcggcgaa aacgcctgat tttacgcgag tttcccacag atgatgtgga    12240
caagcctggg gataagtgcc ctgcggtatt gacacttgag gggcgcgact actgacagat    12300
gaggggcgcg atccttgaca cttgaggggc agagtgctga cagatgaggg gcgcacctat    12360
tgacatttga ggggctgtcc acaggcagaa aatccagcat ttgcaagggt ttccgcccgt    12420
ttttcggcca ccgctaacct gtcttttaac ctgcttttaa accaatattt ataaaccttg    12480
tttttaacca gggctgcgcc ctgtgcgcgt gaccgcgcac gccgaagggg ggtgccccc     12540 cttctcgaac cctcccggcc cgctaacgcg ggcctcccat cccccagggg gctgcgcccc    12600
tcggccgcga acggcctcac cccaaaaatg gcagcgccag ccaggacgtc ggccgaaaga    12660
gcgacaagca gatcacgctt ttcgacacgc tcggatttgc gatcgaggat ttttcggcgc    12720
tgcgctacgt ccgcgaccgc gttgagggat caagccacag cagcccactc gaccttctag    12780
ccgacccaga cgagccaagg gatcttttg gaatgctgct ccgtcgtcag gctttccgac     12840
gtttgggtgg ttgaacagaa gtcattatcg cacggaatgc caagcactcc cgagggggaac 12900 cctgtggttg gcatgcacat acaaatggac gaacggataa acctttcac gccctttta     12960 atatccgatt attctaataa acgctctttt ctcttaggtt tacccgccaa tatatcctgt    13020
caaacactga tagtttaaac tgaaggcggg aaacgacaat ctgatcatga gcggagaatt    13080
aagggagtca cgttatgacc cccgccgatg acgcgggaca agccgtttta cgtttggaac    13140
tgacagaacc gcaacgttga aggagccact cagc                               13174
```

<210> SEQ ID NO 4
<211> LENGTH: 12884
<212> TYPE: DNA
<213> ORGANISM: Artificial Sequence
<220> FEATURE:
<223> OTHER INFORMATION: Synthetic vector: pLC40bar
<220> FEATURE:
<221> NAME/KEY: misc_feature
<222> LOCATION: (12)..(33)

```
<223> OTHER INFORMATION: I-SceI
<220> FEATURE:
<221> NAME/KEY: misc_feature
<222> LOCATION: (46)..(301)
<223> OTHER INFORMATION: (complement) Tnos
<220> FEATURE:
<221> NAME/KEY: misc_feature
<222> LOCATION: (327)..(878)
<223> OTHER INFORMATION: (complement) bar
<220> FEATURE:
<221> NAME/KEY: misc_feature
<222> LOCATION: (885)..(1898)
<223> OTHER INFORMATION: (complement) UbiI
<220> FEATURE:
<221> NAME/KEY: misc_feature
<222> LOCATION: (1982)..(2849)
<223> OTHER INFORMATION: (complement) P ubi
<220> FEATURE:
<221> NAME/KEY: misc_feature
<222> LOCATION: (2934)..(2958)
<223> OTHER INFORMATION: LB
<220> FEATURE:
<221> NAME/KEY: misc_feature
<222> LOCATION: (3500)..(3531)
<223> OTHER INFORMATION: I-CeuI
<220> FEATURE:
<221> NAME/KEY: misc_feature
<222> LOCATION: (3537)..(3944)
<223> OTHER INFORMATION: (complement) cos
<220> FEATURE:
<221> NAME/KEY: misc_feature
<222> LOCATION: (3946)..(6063)
<223> OTHER INFORMATION: (complement) IncC1
<220> FEATURE:
<221> NAME/KEY: misc_feature
<222> LOCATION: (6065)..(6884)
<223> OTHER INFORMATION: (complement) oriT
<220> FEATURE:
<221> NAME/KEY: misc_feature
<222> LOCATION: (6881)..(10052)
<223> OTHER INFORMATION: (complement) trfA1
<220> FEATURE:
<221> NAME/KEY: misc_feature
<222> LOCATION: (10048)..(11144)
<223> OTHER INFORMATION: nptIII
<220> FEATURE:
<221> NAME/KEY: misc_feature
<222> LOCATION: (11141)..(12033)
<223> OTHER INFORMATION: (complement) oriV
<220> FEATURE:
<221> NAME/KEY: misc_feature
<222> LOCATION: (12708)..(12732)
<223> OTHER INFORMATION: RB

<400> SEQUENCE: 4
aagctttcga ataggggataa caggggtaata gcttgctaga ggatctgcga tctagtaaca    60
tagatgacac cgcgcgcgat aatttatcct agtttgcgcg ctatattttg ttttctatcg   120
cgtattaaat gtataattgc gggactctaa tcataaaaac ccatctcata ataacgtca    180 tgcattacat gttaattatt acatgcttaa cgtaattcaa cagaaattat atgataatca   240
tcgcaagacc ggcaacagga ttcaatctta agaaacttta ttgccaaatg tttgaacgat   300
ctgcttcgga tcctagacgc gtgagatcag atctcggtga cgggcaggac cggacggggc   360
ggtaccggca ggctgaagtc cagctgccag aaacccacgt catgccagtt cccgtgcttg   420
aagccggccg cccgcagcat gccgcggggg gcatatccga gcgcctcgtg catgcgcacg   480
ctcgggtcgt tgggcagccc gatgacagcg accacgctct tgaagccctg tgcctccagg   540
gacttcagca ggtgggtgta gagcgtggag cccagtcccg tccgctggtg gcgggggag    600 acgtacacgg tcgactcggc cgtccagtcg taggcgttgc gtgccttcca ggggcccgcg   660
taggcgatgc cggcgaccctc gccgtccacc tcggcgacga gccagggata gcgctcccgc   720
```

```
agacggacga ggtcgtccgt ccactcctgc ggttcctgcg gctcggtacg gaagttgacc    780
gtgcttgtct cgatgtagtg gttgacgatg gtgcagaccg ccggcatgtc cgcctcggtg    840
gcacggcgga tgtcggccgg gcgtcgttct gggtccatgg cgacctgcag aagtaacacc    900
aaacaacagg gtgagcatcg acaaaagaaa cagtaccaag caaataaata gcgtatgaag    960
gcagggctaa aaaatccac atatagctgc tgcatatgcc atcatccaag tatatcaaga   1020
tcaaaataat tataaaacat acttgtttat tataatagat aggtactcaa ggttagagca   1080
tatgaataga tgctgcatat gccatcatgt atatgcatca gtaaaaccca catcaacatg   1140
tatacctatc ctagatcgat atttccatcc atcttaaact cgtaactatg aagatgtatg   1200
acacacacat acagttccaa aattaataaa taccaccggt agtttgaaac agtattctac   1260
tccgatctag aacgaatgaa cgaccgccca accacaccac atcatcacaa ccaagcgaac   1320
aaaaagcatc tctgtatatg catcagtaaa acccgcatca acatgtatac ctatcctaga   1380
tcgatatttc catccatcat cttcaattcg taactatgaa tatgtatggc acacacatac   1440
agatccaaaa ttaataaatc caccaggtag tttgaaacag aattaattct actccgatct   1500
agaacgaccg cccaaccaga ccacatcatc acaaccaaga caaaaaaaag catgaaaaga   1560
tgacccgaca aacaagtgca cggcatatat tgaaataaag gaaaagggca aaccaaaccc   1620
tatgcaacga aacaaaaaaa atcatgaaat cgatcccgtc tgcggaacgg ctagagccat   1680
cccaggattc cccaaagaga aacactggca agttagcaat cagaacgtgt ctgacgtaca   1740
ggtcgcatcc gtgtacgaac gctagcagca cggatctaac acaaacacgg atctaacaca   1800
aacatgaaca gaagtagaac taccgggccc taaccatgga ccggaacgcc gatctagaga   1860
aggtagagag gggggggggg ggaggacgag cggcgtacct tgaagcggag gtgccgacgg   1920
gtggatttgg gggagatctg gttgtgtgtg tgtgcgctcc gaacaacacg aggttgggga   1980
aagagggtgt ggagggggtg tctatttatt acggcgggcg aggaagggaa agcgaaggag   2040
cggtgggaaa ggaatccccc gtagctgccg gtgccgtgag aggaggagga ggccgcctgc   2100
cgtgccggct cacgtctgcc gctccgccac gcaatttctg gatgccgaca gcggagcaag   2160
tccaacggtg gagcggaact ctcgagaggg gtccagaggc agcgacagag atgccgtgcc   2220
gtctgcttcg cttggcccga cgcgacgctg ctggttcgct ggttggtgtc cgttagactc   2280
gtcgacggcg tttaacaggc tggcattatc tactcgaaac aagaaaaatg tttccttagt   2340 tttttaatt tcttaagggg tatttgttta attttagtc actttatttt attctatttt      2400
atatctaaat tattaaataa aaaactaaa atagagtttt agttttctta atttagaggc    2460
taaaatagaa taaaatagat gtactaaaaa aattagtcta taaaaaccat taaccctaaa   2520
ccctaaatgg atgtactaat aaaatggatg aagtattata taggtgaagc tatttgcaaa   2580
aaaaaaggag aacacatgca cactaaaaag ataaaactgt agagtcctgt tgtcaaaata   2640
ctcaattgtc ctttagacca tgtctaactg ttcatttata tgattctcta aaacactgat   2700
attattgtag tactatagat tatattattc gtagagtaaa gtttaaatat atgtataaag   2760
atagataaac tgcacttcaa acaagtgtga caaaaaaaat atgtggtaat tttttataac   2820
ttagacatgc aatgctcatt atctctagag aggggcacga ccgggtcacg ctgcacaatt   2880
cagtacatta aaaacgtccg caatgtgtta ttaagttgtc taagcgtcaa tttgtttaca   2940
ccacaatata tcctgccacc agccagccaa cagctccccg accggcagct cggcacaaaa   3000
tcaccactcg atacaggcag cccatcagtc cgggacggcg tcagcgggag agccgttgta   3060
aggcggcaga ctttgctcat gttaccgatg ctattcggaa gaacggcaac taagctgccg   3120
```

```
ggtttgaaac acggatgatc tcgcggaggg tagcatgttg attgtaacga tgacagagcg   3180
ttgctgcctg tgatcaaata tcatctccct cgcagagatc cgaattatca gccttcttat   3240
tcatttctcg cttaaccgtg acaggctgtc gatcttgaga actatgccga cataatagga   3300
aatcgctgga taaagccgct gaggaagctg agtggcgcta tttctttaga agtgaacgtt   3360
gacgatcgtc gaccgtaccc cgatgaatta attcggacgt acgttctgaa cacagctgga   3420
tacttacttg ggcgattgtc atacatgaca tcaacaatgt acccgtttgt gtaaccgtct   3480
cttggaggtt cgtatgacac taggtcgcta ccttaggacc gttatagtta ctagcgaatt   3540
gacatgaggt tgccccgtat tcagtgtcgc tgatttgtat tgtctgaagt tgttttttacg   3600 ttaagttgat gcagatcaat taatacgata cctgcgtcat aattgattat ttgacgtggt   3660
ttgatggcct ccacgcacgt tgtgatatgt agatgataat cattatcact ttacgggtcc   3720
tttccggtga tccgacaggt tacggggcgg cgacctcgcg ggttttcgct atttatgaaa   3780 atttttccggt ttaaggcgtt tccgttcttc ttcgtcataa cttaatgttt ttatttaaaa   3840
taccctctga aaagaaagga aacgacaggt gctgaaagcg agcttttttgg cctctgtcgt   3900 ttcctttctc tgtttttgtc cgtggaatga acaatggaag gatcttctcg gcggcgatca   3960
cgacgccggc cctgcggagc cttcgccgcg tgcgcgattc atggcggccg tggaggccaa   4020
ggatttcgcg cgagtgcaag agctgatcga ggcgcgtgga gccaagtcgg cggctgatta   4080
tgtccttgcg cagctcgccg tggccgaagg tctggaccgc aagcctggtg cgcgcgtcgt   4140
ggtcgggaaa gcggcgggca gcatggcaat gccgcctgcg gcgctgggtt ttacgccaag   4200
gggagaagcg gcatacgcca tcgagcggtc agcctatggt gagccgaggt ccagcattgc   4260
gaagcagtac cagcaggaat ggaaccgaa ggcggcgacc tggtgggcga tggccggtgt   4320
ggccggcatc atcggcgcga tcctggcggc ggcggcaacc ggctttgttg ggctggcagt   4380
gtcgatccgc aaccgagtga agcgcgtgcg cgacctgttg gtgatggagc cgggtgcaga   4440
gccataagcg gcaagagacg aaagcccggt ttccgggctt ttgttttgtt acgccaagga   4500
cgagttttag cggctaaagg tgttgacgtg cgagaaatgt ttagctaaac ttctctcatg   4560
tgctggcggc tgtcaccgct atgttcaacc aaggcgcgga gcaaattatg ggtgttatcc   4620
atgaagaaac ggcttaccga aagccagttc caggaggcga tccaggggct ggaagtgggg   4680
cagcagacca tcgagatagc gcggggcgtc ttagtcgatg ggaagccaca ggcgacgttc   4740
gcaacgtcgc tgggactgac caggggcgca gtgtcgcaag cggtgcatcg cgtgtgggcc   4800
gcgttcgagg acaagaactt gcccgagggg tacgcgcggg taacggcggt tctgccggaa   4860
catcaggcgt acatcgtccg gaagtgggaa gcggacgcca agaaaaaaca ggaaaccaaa   4920
cgatgaaaac tttggtcacg gccaaccaga aaggcgcgt cggcaagact cgacccttg    4980 tgcatcttgc cttcgacttt ttcgagcgcg gcttgcgggt tgccgtgatc gacctggacc   5040
cccagggcaa tgcgtcctac acgctcaagg actttgctac cggcctgcat gcaagcaagc   5100
tgttcggcgc tgtccctgcc ggcggctgga ccgaaaccgc acccgcagcc ggcgacggcc   5160
aggccgcgcg cctcgccctc atcgagtcca accggtact ggcgaacgcc gaacggctgt   5220
cgctggacga cgcccgcgag ctgttcgggg cgaacatcaa ggccctggcg aaccaaggct   5280
tcgacgtgtg cctgatcgac acggccccga cccttggcgt cggcctggcg ccgcccctct   5340
tcgcggccga ctatgtgctg tcccccatcg agcttgaggc gtacagcatc cagggcatca   5400
agaagatggt cacgaccatt gcgaacgtgc gccagaagaa cgccaagctg caattccttg   5460
gcatggtgcc cagcaaggtc gatgcgcgga atccgcgcca cgcgcgccac caagccgagc   5520
```

```
tgctggccgc gtacccgaag atgatgattc cggccaccgt tggcctgcgc agcagcatcg   5580
ccgatgccct cgcatccggt gtgccggtct ggaagatcaa gaaaacggcc gcgcgcaagg   5640
catcgaaaga ggttcgcgcc ctggctgatt acgtgttcac gaagatggag atttcccaat   5700
gactgcggct caagccaaga ccaccaagaa aacaccgct  gcggccgctc aggaagccgc   5760
aggcgcggcg cagccgtccg gcctgggggtt ggatagcatc ggcgacctgt cgagcctcct   5820
ggacgctcct gcggcgtctc agggcggttc cggccctatc gagctggacc tggacctgat   5880
cgacgaagat ccgcatcagc cgcggacggc cgacaaccc  ggcttttccc cggagagcat   5940
cgcggaaatc ggtgccacga tcaaagagcg cggggtgaag tcacccattt cggtgcgcga   6000
gaaccaggag cagccgggcc gctatatcat caatcacggc gcccgccgct accgtggctc   6060
gaatctagtg atattccaca aaacagcagg gaagcagcgc ttttccgctg cataaccctg   6120
cttcggggtc attatagcga ttttttcggt atatccatcc tttttcgcac gatatacagg   6180
attttgccaa agggttcgtg tagactttcc ttggtgtatc caacggcgtc agccgggcag   6240
gataggtgaa gtaggcccac ccgcgagcgg gtgttccttc ttcactgtcc cttattcgca   6300
cctggcggtc ctcaacggga atcctgctct gcgaggctgg ccggctaccg ccggcgtaac   6360
agatgagggc aagcggatgg ctgatgaaac caagccaacc aggaagggca gcccacctat   6420
caaggtgtac tgccttccag acgaacgaag agcgattgag gaaaaggcgg cggcggccgg   6480
catgagcctg tcggcctacc tgctggccgt cggccagggc tacaaaatca cgggcgtcgt   6540
ggactatgag cacgtccgcg agctggcccg catcaatggc gacctgggcc gcctgggcgg   6600
cctgctgaaa ctctggctca ccgacgaccc gcgcacggcg cggttcggtg atgccacgat   6660
cctcgccctg ctggcgaaga tcgaagagaa gcaggacgag cttggcaagg tcatgatggg   6720
cgtggtccgc ccgagggcag agccatgact ttttagccg  ctaaacggc cgggggggtgc   6780 gcgtgattgc caagcacgtc cccatgcgct ccatcaagaa gagcgacttc gcggagctgg   6840
tgaagtacat caccgacgag caaggcaaga ccgagcgcca gatccaaaac aactgtcaaa   6900
gcgcacccgc ccgatgccat cgcggcacg  gcttccgttg aggatgtcga tatgatgcgc   6960
gagccgacgg cccgcagaga aggggccgtt ttagcggcta aagaaggaag tgcaagccct   7020
aacccttggc gtcagagcct tccacgcagc ttttttcggg tgtcgtcgcc ccatttcttt   7080
acgataaacg ccttatgtga cggcaaaacc acactgatgc gttcgtatcc gggcggcacg   7140
ctgctcttga aaggatgacc cgcaatctcc gcgagtgcct cgcggtcaag gtcggtggac   7200
tccaggagaa gaggtagggg agtttccagg gcgtcggcaa tggcctccat caccttcaac   7260 gagggggttgg ccttaccgtt ggttaagtct gataaaaacg aaattgaaac ccctgccctc   7320
tccgacagct catgtttcgt catgccccgc tcatcgagca gacgaaggat gttggtgaaa   7380
aatatctggt tgtacacagc ggaagccgcc cctcgcacct ttggtcgcgg cccgcaaaat   7440
tttagccgct aaagttcttg acagcggaac caatgtttag ctaaactaga gtctcctttc   7500
tcaaggagac tttcgatatg agccataatc agttccagtt tatcggtaat cttacccgtg   7560
acaccgaggt acgtcatggc aattctaaca agccgcaagc aattttcgat atagcggtta   7620
atgaagagtg gcgcaacgat gccggcgaca agcaggagcg caccgacttc ttccgcatca   7680
agtgttttgg ctctcaggcc gaggcccacg gcaagtattt gggcaagggg tcgctggtat   7740
tcgtgcaggg caagattcgg aataccaagt acgagaagga cggccagacg gtctacggga   7800
ccgacttcat tgccgataag gtggattatc tggacaccaa ggcaccaggc gggtcaaatc   7860
aggaataagg gcacattgcc ccggcgtgag tcggggcaat cccgcaagga gggtgaatga   7920
```

```
atcggacgtt tgaccggaag gcatacaggc aagaactgat cgacgcgggg ttttccgccg   7980
aggatgccga aaccatcgca agccgcaccg tcatgcgtgc gccccgcgaa accttccagt   8040
ccgtcggctc gatggtccag caagctacgg ccaagatcga gcgcgacagc gtgcaactgg   8100
ctcccctgc cctgcccgcg ccatcggccg ccgtggagcg ttcgcgtcgt ctcgaacagg    8160
aggcggcagg tttggcgaag tcgatgacca tcgacacgcg aggaactatg acgaccaaga   8220
agcgaaaaac cgccggcgag gacctggcaa aacaggtcag cgaggccaag caggccgcgt   8280
tgctgaaaca cacgaagcag cagatcaagg aaatgcagct ttccttgttc gatattgcgc   8340
cgtggccgga cacgatgcga gcgatgccaa acgacacggc ccgctctgcc ctgttcacca   8400
cgcgcaacaa gaaaatcccg cgcgaggcgc tgcaaaacaa ggtcattttc cacgtcaaca   8460
aggacgtgaa gatcacctac accggcgtcg agctgcgggc cgacgatgac gaactggtgt   8520
ggcagcaggt gttggagtac gcgaagcgca cccctatcgg cgagccgatc accttcacgt   8580
tctacgagct ttgccaggac ctgggctggt cgatcaatgg ccggtattac acgaaggccg   8640
aggaatgcct gtcgcgccta caggcgacgg cgatgggctt cacgtccgac cgcgttgggc   8700
acctggaatc ggtgtcgctg ctgcaccgct tccgcgtcct ggaccgtggc aagaaaacgt   8760
cccgttgcca ggtcctgatc gacgaggaaa tcgtcgtgct gtttgctggc gaccactaca   8820
cgaaattcat atgggagaag taccgcaagc tgtcgccgac ggcccgacgg atgttcgact   8880
atttcagctc gcaccggag ccgtacccgc tcaagctgga aaccttccgc ctcatgtgcg    8940
gatcggattc cacccgcgtg aagaagtggc gcgagcaggt cggcgaagcc tgcgaagagt   9000
tgcgaggcag cggcctggtg aacacgcct gggtcaatga tgacctggtg cattgcaaac    9060
gctagggcct tgtgggggtca gttccggctg ggggttcagc agccagcgct ttactggcat   9120
ttcaggaaca agcgggcact gctcgacgca cttgcttcgc tcagtatcgc tcgggacgca   9180
cggcgcgctc tacgaactgc cgataaacag aggattaaaa ttgacaattg tgattaaggc   9240
tcagattcga cggcttggag cggccgacgt gcaggatttc cgcgagatcc gattgtcggc   9300
cctgaagaaa gctccagaga tgttcgggtc cgtttacgag cacgaggaga aaaagcccat   9360
ggaggcgttc gctgaacggt tgcgagatgc cgtggcattc ggcgcctaca tcgacggcga   9420
gatcattggg ctgtcggtct tcaaacagga ggacggcccc aaggacgctc acaaggcgca   9480
tctgtccggc gttttcgtgg agcccgaaca gcgaggccga ggggtcgccg gtatgctgct   9540
gcgggcgttg ccggcgggtt tattgctcgt gatgatcgtc cgacagattc caacgggaat   9600
ctggtggatg cgcatcttca tcctcggcgc acttaatatt tcgctattct ggagcttgtt   9660
gtttatttcg gtctaccgcc tgccgggcgg gtcgcggcga cggtaggcgc tgtgcagccg   9720
ctgatggtcg tgttcatctc tgccgctctg ctaggtagcc cgatacgatt gatgcggtc    9780
ctggggcta tttgcggaac tgcgggcgtg gcgctgttgg tgttgacacc aaacgcagcg    9840
ctagatcctg tcgcgtcgc agcgggcctg gcggggcgg tttccatggc gttcggaacc     9900
gtgctgaccc gcaagtggca acctcccgtg cctctgctca cctttaccgc ctggcaactg   9960
gcggccggag gacttctgct cgttccagta gctttagtgt ttgatccgcc aatcccgatg   10020
cctacaggaa ccaatgttct cggctgctcg actgcacgaa taccagcgac cccttgccca   10080
aatacttgcc gtgggcctcg gcctgagagc caaaacactt gatgcggaag aagtcggtgc   10140
gctcctgctt gtcgccggca tcgttgcgcc acatctaggt actaaaacaa ttcatccagt   10200
aaaatataat attttatttt ctcccaatca ggcttgatcc ccagtaagtc aaaaaatagc   10260
tcgacatact gttcttcccc gatatcctcc ctgatcgacc ggacgcagaa ggcaatgtca   10320
```

```
taccacttgt ccgccctgcc gcttctccca agatcaataa agccacttac tttgccatct   10380
ttcacaaaga tgttgctgtc tcccaggtcg ccgtgggaaa agacaagttc ctcttcgggc   10440
ttttccgtct ttaaaaaatc atacagctcg cgcggatctt taaatggagt gtcttcttcc   10500
cagttttcgc aatccacatc ggccagatcg ttattcagta agtaatccaa ttcggctaag   10560
cggctgtcta agctattcgt atagggacaa tccgatatgt cgatggagtg aaagagcctg   10620
atgcactccg catacagctc gataatcttt tcagggcttt gttcatcttc atactcttcc   10680
gagcaaagga cgccatcggc ctcactcatg agcagattgc tccagccatc atgccgttca   10740
aagtgcagga cctttggaac aggcagcttt ccttccagcc atagcatcat gtcctttttcc   10800
cgttccacat cataggtggt ccctttatac cggctgtccg tcatttttaa atataggttt   10860
tcattttctc ccaccagctt atataccttta gcaggagaca ttccttccgt atcttttacg   10920
cagcggtatt tttcgatcag tttttttcaat tccggtgata ttctcatttt agccatttat   10980
tatttccttc ctcttttcta cagtatttaa agatacccca agaagctaat tataacaaga   11040
cgaactccaa ttcactgttc cttgcattct aaaaccttaa ataccagaaa acagcttttt   11100
caaagttgtt ttcaaagttg gcgtataaca tagtatcgat tcgatagcgt ggactcaagg   11160
ctctcgcgaa tggctcgcgt tggaaacttt cattgacact tgagggcac cgcagggaaa    11220
ttctcgtcct tgcgagaacc ggctatgtcg tgctgcgcat cgagcctgcg cccttggctt   11280
gtctcgcccc tctccgcgtc gctacggggc ttccagcgcc tttccgacgc tcaccgggct   11340
ggttgccctc gccgctgggc tggcggccgt ctatggccct gcaaacgcgc cagaaacgcc   11400
gtcgaagccg tgtgcgagac accgcggccg ccggcgttgt ggatacctcg cggaaaactt   11460
ggccctcact gacagatgag gggcggacgt tgacacttga ggggccgact cacccggcgc   11520
ggcgttgaca gatgaggggc aggctcgatt tcggccggcg acgtggagct ggccagcctc   11580
gcaaatcggc gaaaacgcct gattttacgc gagtttccca cagatgatgt ggacaagcct   11640
ggggataagt gccctgcggt attgacactt gaggggcgcg actactgaca gatgaggggc   11700
gcgatccttg acacttgagg ggcagagtgc tgacagatga ggggcgcacc tattgacatt   11760
tgagggctg tccacaggca gaaaatccag catttgcaag ggtttccgcc cgttttttcgg   11820
ccaccgctaa cctgtcttt aacctgcttt taaaccaata tttataaacc ttgttttaa    11880
ccagggctgc gccctgtgcg cgtgaccgcg cacgccgaag gggggtgccc cccttctcg    11940
aaccctcccg gcccgctaac gcgggcctcc catcccccca ggggctgcgc ccctcggccg   12000
cgaacggcct caccccaaaa atggcagcgc cagattattg aagcatttat cagggttatt   12060
gtctcatgag cggatacata tttgaatgta tttagaaaaa taaacaaata ggggttccgc   12120
gcacatttcc ccgaaaagtg ccacctgacg tctaagaaac cattattatc atgacattaa   12180
cctataaaaa taggcgtatc acgaggccct ttcgtcttca agaattggtc gacgatcttg   12240
ctgccgttcgg atatttcgt ggagttcccg ccacagaccc ggattgaagg cgagatccag   12300
caactcgcgc cagatcatcc tgtgacggaa ctttggcgcg tgatgactgg ccaggacgtc   12360
ggccgaaaga cgacaagca gatcacgctt ttcgacagcg tcggatttgc gatcgaggat    12420
ttttcggcgc tgcgctacgt ccgcgaccgc gttgagggat caagccacag cagcccactc   12480
gaccttctag ccgacccaga cgagccaagg gatctttttg gaatgctgct ccgtcgtcag   12540
gctttccgac gtttgggtgg ttgaacagaa gtcattatcg cacggaatgc caagcactcc   12600
cgaggggaac cctgtggttg gcatgcacat acaaatggac gaacggataa accttttcac   12660
gccccttttaa atatccgatt attctaataa acgctcttt ctcttaggtt tacccgccaa   12720
```

```
tatatcctgt caaacactga tagtttaaac tgaaggcggg aaacgacaat ctgatcatga    12780
gcggagaatt aagggagtca cgttatgacc cccgccgatg acgcgggaca agccgtttta    12840
cgtttggaac tgacagaacc gcaacgttga aggagccact cagc                    12884
```

<210> SEQ ID NO 5
<211> LENGTH: 13026
<212> TYPE: DNA
<213> ORGANISM: Artificial Sequence
<220> FEATURE:
<223> OTHER INFORMATION: Synthetic vector: pLC40GWB
<220> FEATURE:
<221> NAME/KEY: misc_feature
<222> LOCATION: (48)..(70)
<223> OTHER INFORMATION: I-SceI
<220> FEATURE:
<221> NAME/KEY: misc_feature
<222> LOCATION: (90)..(989)
<223> OTHER INFORMATION: Pubi
<220> FEATURE:
<221> NAME/KEY: misc_feature
<222> LOCATION: (1073)..(2082)
<223> OTHER INFORMATION: UbiI
<220> FEATURE:
<221> NAME/KEY: misc_feature
<222> LOCATION: (2103)..(2127)
<223> OTHER INFORMATION: attB1
<220> FEATURE:
<221> NAME/KEY: misc_feature
<222> LOCATION: (2130)..(2681)
<223> OTHER INFORMATION: bar
<220> FEATURE:
<221> NAME/KEY: misc_feature
<222> LOCATION: (2698)..(2722)
<223> OTHER INFORMATION: attB2
<220> FEATURE:
<221> NAME/KEY: misc_feature
<222> LOCATION: (2742)..(3017)
<223> OTHER INFORMATION: Tnos
<220> FEATURE:
<221> NAME/KEY: misc_feature
<222> LOCATION: (3076)..(3100)
<223> OTHER INFORMATION: LB
<220> FEATURE:
<221> NAME/KEY: misc_feature
<222> LOCATION: (3642)..(3672)
<223> OTHER INFORMATION: I-CeuI
<220> FEATURE:
<221> NAME/KEY: misc_feature
<222> LOCATION: (3679)..(4086)
<223> OTHER INFORMATION: (complement) cos
<220> FEATURE:
<221> NAME/KEY: misc_feature
<222> LOCATION: (4088)..(6205)
<223> OTHER INFORMATION: (complement) IncC1
<220> FEATURE:
<221> NAME/KEY: misc_feature
<222> LOCATION: (6207)..(7026)
<223> OTHER INFORMATION: (complement) oriT
<220> FEATURE:
<221> NAME/KEY: misc_feature
<222> LOCATION: (7023)..(10193)
<223> OTHER INFORMATION: (complement) trfA1
<220> FEATURE:
<221> NAME/KEY: misc_feature
<222> LOCATION: (10190)..(11286)
<223> OTHER INFORMATION: nptIII
<220> FEATURE:
<221> NAME/KEY: misc_feature
<222> LOCATION: (11283)..(12175)
<223> OTHER INFORMATION: (complement) oriV
<220> FEATURE:
<221> NAME/KEY: misc_feature
<222> LOCATION: (12850)..(12874)
<223> OTHER INFORMATION: RB

<400> SEQUENCE: 5

-continued

| | | | | | |
|---|---|---|---|---|---|
| aagcttgcgg | ccgcttcgaa | gatgttaatt | aacatcggta | ccgagctcta | gggataacag | 60 |
| ggtaatagct | cgaattctag | cttgcatgcc | tgcagtgcag | cgtgacccgg | tcgtgcccct | 120 |
| ctctagagat | aatgagcatt | gcatgtctaa | gttataaaaa | attaccacat | atttttttg | 180 |
| tcacacttgt | ttgaagtgca | gtttatctat | ctttatacat | atatttaaac | tttactctac | 240 |
| gaataatata | atctatagta | ctacaataat | atcagtgttt | tagagaatca | tataaatgaa | 300 |
| cagttagaca | tggtctaaag | gacaattgag | tattttgaca | acaggactct | acagttttat | 360 |
| cttttagtg | tgcatgtgtt | ctcctttttt | tttgcaaata | gcttcaccta | tataatactt | 420 |
| catccatttt | attagtacat | ccatttaggg | tttagggtta | atggttttta | tagactaatt | 480 |
| tttttagtac | atctattta | ttctatttta | gcctctaaat | taagaaaact | aaaactctat | 540 |
| tttagttttt | ttatttaata | atttagatat | aaaatagaat | aaaatagaaagt | gactaaaaat | 600 |
| taaacaaata | cccctttaaga | aattaaaaaa | actaaggaaa | cattttttctt | gtttcgagta | 660 |
| gataatgcca | gcctgttaaa | cgccgtcgac | gagtctaacg | gacaccaacc | agcgaaccag | 720 |
| cagcgtcgcg | tcgggccaag | cgaagcagac | ggcacggcat | ctctgtcgct | gcctctggac | 780 |
| ccctctcgag | agttccgctc | caccgttgga | cttgctccgc | tgtcggcatc | cagaaattgc | 840 |
| gtggcggagc | ggcagacgtg | agccggcacg | gcaggcggcc | tcctcctcct | ctcacggcac | 900 |
| cggcagctac | gggggattcc | tttcccaccg | ctccttcgct | ttcccttcct | cgcccgccgt | 960 |
| aataaataga | caccccctcc | acaccctctt | tccccaacct | cgtgttgttc | ggagcgcaca | 1020 |
| cacacacaac | cagatctccc | ccaaatccac | ccgtcggcac | ctccgcttca | aggtacgccg | 1080 |
| ctcgtcctcc | ccccccccc | ctctctacct | tctctagatc | ggcgttccgg | tccatggtta | 1140 |
| gggcccggta | gttctacttc | tgttcatgtt | tgtgttagat | ccgtgtttgt | gttagatccg | 1200 |
| tgctgctagc | gttcgtacac | ggatgcgacc | tgtacgtcag | acacgttctg | attgctaact | 1260 |
| tgccagtgtt | tctctttggg | gaatcctggg | atggctctag | ccgttccgca | gacgggatcg | 1320 |
| atttcatgat | ttttttttgtt | tcgttgcata | gggtttggtt | tgcccttttc | ctttatttca | 1380 |
| atatatgccg | tgcacttgtt | tgtcgggtca | tcttttcatg | cttttttttg | tcttggttgt | 1440 |
| gatgatgtgg | tctggttggg | cggtcgttct | agatcggagt | agaattctgt | ttcaaactac | 1500 |
| ctggtggatt | tattaattt | ggatctgtat | gtgtgtgcca | tacatattca | tagttacgaa | 1560 |
| ttgaagatga | tggatggaaa | tatcgatcta | ggataggtat | acatgttgat | gcgggtttta | 1620 |
| ctgatgcata | tacagagatg | cttttttgttc | gcttggttgt | gatgatgtgg | tgtggttggg | 1680 |
| cggtcgttca | ttcgttctag | atcggagtag | aatactgttt | caaactacct | ggtgtattta | 1740 |
| ttaattttgg | aactgtatgt | gtgtgtcata | catcttcata | gttacgagtt | taagatggat | 1800 |
| ggaaatatcg | atctaggata | ggtatacatg | ttgatgtggg | ttttactgat | gcatatacat | 1860 |
| gatggcatat | gcagcatcta | ttcatatgct | ctaaccttga | gtacctatct | attataataa | 1920 |
| acaagtatgt | tttataatta | ttttgatctt | gatatacttg | gatgatggca | tatgcagcag | 1980 |
| ctatatgtgg | atttttttag | ccctgccttc | atacgctatt | tatttgcttg | gtactgtttc | 2040 |
| ttttgtcgat | gctcaccctg | ttgtttggtg | ttacttctgc | aggtcgactc | tagaggatca | 2100 |
| tcacaagttt | gtacaaaaaa | gcaggctcca | tggacccaga | acgacgcccg | gccgacatcc | 2160 |
| gccgtgccac | cgaggcggac | atgccggcgg | tctgcaccat | cgtcaaccac | tacatcgaga | 2220 |
| caagcacggt | caacttccgt | accgagccgc | aggaaccgca | ggagtggacg | gacgacctcg | 2280 |
| tccgtctgcg | ggagcgctat | ccctggctcg | tcgccgaggt | ggacggcgag | gtcgccggca | 2340 |
| tcgcctacgc | gggcccctgg | aaggcacgca | acgcctacga | ctggacggcc | gagtcgaccg | 2400 |

```
tgtacgtctc cccccgccac cagcggacgg gactgggctc cacgctctac acccacctgc    2460
tgaagtccct ggaggcacag ggcttcaaga gcgtggtcgc tgtcatcggg ctgcccaacg    2520
acccgagcgt gcgcatgcac gaggcgctcg gatatgcccc ccgcggcatg ctgcgggcgg    2580
ccggcttcaa gcacgggaac tggcatgacg tgggtttctg gcagctggac ttcagcctgc    2640
cggtaccgcc ccgtccggtc ctgcccgtca ccgagatctg atctcacgcg tctaggaacc    2700
cagctttctt gtacaaagtg gtgatgatcc gtcgacctgc agatcgttca aacatttggc    2760
aataaagttt cttaagattg aatcctgttg ccggtcttgc gatgattatc ataatttc     2820
tgttgaatta cgttaagcat gtaataatta acatgtaatg catgacgtta tttatgagat    2880
gggttttat gattagagtc ccgcaattat acatttaata cgcgatagaa acaaaatat     2940
agcgcgcaaa ctaggataaa ttatcgcgcg cggtgtcatc tatgttacta gatccgatga    3000
taagctgtca acatgagaa ttcagtacat taaaaacgtc cgcaatgtgt tattaagttg    3060
tctaagcgtc aatttgttta caccacaata tatcctgcca ccagccagcc aacagctccc    3120
cgaccggcag ctcggcacaa aatcaccact cgatacaggc agcccatcag tccgggacgg    3180
cgtcagcggg agagccgttg taaggcggca gactttgctc atgttaccga tgctattcgg    3240
aagaacggca actaagctgc cgggtttgaa acacggatga tctcgcggag ggtagcatgt    3300
tgattgtaac gatgacagag cgttgctgcc tgtgatcaaa tatcatctcc ctcgcagaga    3360
tccgaattat cagccttctt attcatttct cgcttaaccg tgacaggctg tcgatcttga    3420
gaactatgcc gacataatag gaaatcgctg gataaagccg ctgaggaagc tgagtggcgc    3480
tatttctta gaagtgaacg ttgacgatcg tcgaccgtac cccgatgaat taattcggac    3540
gtacgttctg aacacagctg gatacttact gggcgattg tcatacatga catcaacaat    3600
gtacccgttt gtgtaaccgt ctcttggagg ttcgtatgac actaggtcgc taccttagga    3660
ccgttatagt tactagcgaa ttgacatgag gttgccccgt attcagtgtc gctgatttgt    3720
attgtctgaa gttgtttta cgttaagttg atgcagatca attaatacga tacctgcgtc    3780
ataattgatt atttgacgtg gtttgatggc ctccacgcac gttgtgatat gtagatgata    3840
atcattatca ctttacgggt cctttccggt gatccgacag gttacgggc ggcgacctcg     3900
cgggttttcg ctatttatga aaattttccg gtttaaggcg tttccgttct tcttcgtcat    3960
aacttaatgt ttttatttaa aatacctct gaaaagaaag gaaacgacag gtgctgaaag    4020
cgagctttt ggcctctgtc gtttcctttc tctgtttttg tccgtggaat gaacaatgga    4080
aggatcttct cggcggcgat cacgacgccg gccctgcgga gccttcgccg cgtgcgcgat    4140
tcatggcggc cgtggaggcc aaggatttcg cgcgagtgca agagctgatc gaggcgcgtg    4200
gagccaagtc ggcggctgat tatgtccttg cgcagctcgc cgtggccgaa ggtctggacc    4260
gcaagcctgg tgcgcgcgtc gtggtcggga agcggcggg cagcatggca atgccgcctg    4320
cggcgctggg ttttacgcca aggggagaag cggcatacgc catcgagcgg tcagcctatg    4380
gtgagccgag gtccagcatt gcgaagcagt accagcagga atggaaccgg aaggcggcga    4440
cctggtgggc gatggccggt gtggccggca tcatcgcgc gatcctggcg gcggcggcaa    4500
ccggctttgt tgggctggca gtgtcgatcc gcaaccgagt gaagcgcgtg cgcgacctgt    4560
tggtgatgga gccgggtgca gagccataag cggcaagaga cgaaagcccg gtttccgggc    4620
ttttgttttg ttacgccaag gacgagtttt agcggctaaa ggtgttgacg tgcgagaaat    4680
gtttagctaa acttctctca tgtgctggcg gctgtcaccg ctatgttcaa ccaaggcgcg    4740
gagcaaatta tgggtgttat ccatgaagaa acggcttacc gaaagccagt tccaggaggc    4800
```

-continued

```
gatccagggg ctggaagtgg ggcagcagac catcgagata gcgcggggcg tcttagtcga    4860
tgggaagcca caggcgacgt tcgcaacgtc gctgggactg accaggggcg cagtgtcgca    4920
agcggtgcat cgcgtgtggg ccgcgttcga ggacaagaac ttgcccgagg ggtacgcgcg    4980
ggtaacggcg gttctgccgg aacatcaggc gtacatcgtc cggaagtggg aagcggacgc    5040
caagaaaaaa caggaaacca acgatgaaa actttggtca cggccaacca gaaaggcggc    5100
gtcggcaaga cttcgaccct tgtgcatctt gccttcgact ttttcgagcg cggcttgcgg    5160
gttgccgtga tcgacctgga ccccagggc aatgcgtcct acacgctcaa ggactttgct    5220
accggcctgc atgcaagcaa gctgttcggc gctgtccctg ccggcggctg gaccgaaacc    5280
gcacccgcag ccggcgacgg ccaggccgcg cgcctcgccc tcatcgagtc caacccggta    5340
ctggcgaacg ccgaacggct gtcgctggac gacgcccgcg agctgttcgg ggcgaacatc    5400
aaggccctgg cgaaccaagg cttcgacgtg tgcctgatcg acacggcccc gacccttggc    5460
gtcggcctgg cggccgccct cttcgcggcc gactatgtgc tgtcccccat cgagcttgag    5520
gcgtacagca tccagggcat caagaagatg gtcacgacca ttgcgaacgt gcgccagaag    5580
aacgccaagc tgcaattcct tggcatggtg cccagcaagg tcgatgcgcg gaatccgcgc    5640
cacgcgcgcc accaagccga gctgctggcc gcgtacccca agatgatgat tccggccacc    5700
gttggcctgc gcagcagcat cgccgatgcc ctcgcatccg gtgtgccggt ctggaagatc    5760
aagaaaacgg ccgcgcgcaa ggcatcgaaa gaggttcgcg ccctggctga ttacgtgttc    5820
acgaagatgg agatttccca atgactgcgg ctcaagccaa gaccaccaag aaaaacaccg    5880
ctgcggccgc tcaggaagcc gcaggcgcgg cgcagccgtc cggcctgggg ttggatagca    5940
tcggcgacct gtcgagcctc ctggacgctc ctgcggcgtc tcagggcggt tccggcccta    6000
tcgagctgga cctggacctg atcgacgaag atccgcatca gccgcggacg gccgacaacc    6060
ccggcttttc cccggagagc atcgcggaaa tcggtgccac gatcaaagag cgcggggtga    6120
agtcacccat ttcggtgcgc gagaaccagg agcagccggg ccgctatatc atcaatcacg    6180
gcgcccgccg ctaccgtggc tcgaatctag tgatattcca caaacagca gggaagcagc    6240 gcttttccgc tgcataaccc tgcttcgggg tcattatagc gattttttcg gtatatccat    6300 ccttttcgc acgatataca ggattttgcc aaagggttcg tgtagacttt ccttggtgta    6360
tccaacggcg tcagccgggc aggataggtg aagtaggccc acccgcgagc gggtgttcct    6420
tcttcactgt cccttattcg cacctggcgg tgctcaacgg gaatcctgct ctgcgaggct    6480
ggccggctac cgccggcgta acagatgagg gcaagcggat ggctgatgaa accaagccaa    6540
ccaggaaggg cagcccacct atcaaggtgt actgccttcc agacgaacga agagcgattg    6600
aggaaaaggc ggcggcggcc ggcatgagcc tgtcggccta cctgctggcc gtcggccagg    6660
gctacaaaat cacgggcgtc gtggactatg agcacgtccg cgagctggcc cgcatcaatg    6720
gcgacctggg ccgcctgggc ggcctgctga aactctggct caccgacgac ccgcgcacgg    6780
cgcggttcgg tgatgccacg atcctcgccc tgctggcgaa gatcgaagag aagcaggacg    6840
agcttggcaa ggtcatgatg ggcgtggtcc gcccgagggc agagccatga cttttttagc    6900
cgctaaaacg gccgggggt gcgcgtgatt gccaagcacg tccccatgcg ctccatcaag    6960
aagagcgact tcgcggagct ggtgaagtac atcaccgacg agcaaggcaa gaccgagcgc    7020
cagatccaaa acaactgtca aagcgcaccc gcccgatgcc attcgcggca cggcttccgt    7080
tgaggatgtc gatatgatgc gcgagccgac ggcccgcaga gaaggggccg ttttagcggc    7140
taaagaagga agtgcaagcc ctaacccttg gcgtcagagc cttccacgca gctttttcg    7200
```

```
ggtgtcgtcg ccccatttct ttacgataaa cgccttatgt gacggcaaaa ccacactgat    7260
gcgttcgtat ccgggcggca cgctgctctt gaaaggatga cccgcaatct ccgcgagtgc    7320
ctcgcggtca aggtcggtgg actccaggag aagaggtagg ggagtttcca gggcgtcggc    7380
aatggcctcc atccttca acgaggggtt ggccttaccg ttggttaagt ctgataaaaa    7440
cgaaattgaa acccctgccc tctccgacag ctcatgtttc gtcatgcccc gctcatcgag    7500
cagacgaagg atgttggtga aaaatatctg gttgtacaca gcggaagccg cccctcgcac    7560
ctttggtcgc ggcccgcaaa attttagccg ctaaagttct tgacagcgga accaatgttt    7620 agctaaaacta gagtctcctt tctcaaggag actttcgata tgagccataa tcagttccag    7680
tttatcggta atcttacccg tgacaccgag gtacgtcatg gcaattctaa caagccgcaa    7740
gcaattttcg atatagcggt taatgaagag tggcgcaacg atgccggcga caagcaggag    7800
cgcaccgact tcttccgcat caagtgtttt ggctctcagg ccgaggccca cggcaagtat    7860
ttgggcaagg ggtcgctggt attcgtgcag ggcaagattc ggaataccaa gtacgagaag    7920
gacggccaga cggtctacgg gaccgacttc attgccgata aggtggatta tctggacacc    7980
aaggcaccag gcgggtcaaa tcaggaataa gggcacattg ccccggcgtg agtcggggca    8040
atcccgcaag gagggtgaat gaatcggacg tttgaccgga aggcatacag gcaagaactg    8100
atcgacgcgg ggttttccgc cgaggatgcc gaaaccatcg caagccgcac cgtcatgcgt    8160 gcgcccgcg aaaccttcca gtccgtcggc tcgatggtcc agcaagctac ggccaagatc    8220
gagcgcgaca cgtgcaact ggctccccct gccctgcccg cgccatcggc cgccgtggag    8280
cgttcgcgtc gtctcgaaca ggaggcggca ggtttggcga agtcgatgac catcgacacg    8340
cgaggaacta tgacgaccaa gaagcgaaaa accgccggcg aggacctggc aaaacaggtc    8400
agcgaggcca agcaggccgc gttgctgaaa cacacgaagc agcagatcaa ggaaatgcag    8460
ctttccttgt tcgatattgc gccgtggccg gacacgatgc gagcgatgcc aaacgacacg    8520
gcccgctctg ccctgttcac cacgcgcaac aagaaaatcc cgcgcgaggc gctgcaaaac    8580
aaggtcattt tccacgtcaa caaggacgtg aagatcacct acaccggcgt cgagctgcgg    8640
gccgacgatg acgaactggt gtggcagcag gtgttggagt acgcgaagcg cacccctatc    8700
ggcgagccga tcaccttcac gttctacgag cttttgccagg acctgggctg gtcgatcaat    8760
ggccggtatt acacgaaggc cgaggaatgc ctgtcgcgcc tacaggcgac ggcgatgggc    8820
ttcacgtccg accgcgttgg gcacctggaa tcggtgtcgc tgctgcaccg cttccgcgtc    8880
ctggaccgtg gcaagaaaac gtcccgttgc caggtcctga tcgacgagga aatcgtcgtg    8940
ctgtttgctg gcgaccacta cacgaaattc atatgggaga agtaccgcaa gctgtcgccg    9000
acggcccgac ggatgttcga ctatttcagc tcgcaccggg agccgtaccc gctcaagctg    9060
gaaaccttcc gcctcatgtg cggatcggat tccacccgcg tgaagaagtg gcgcgagcag    9120
gtcggcgaag cctgcgaaga gttgcgaggc agcggcctgg tggaacacgc ctgggtcaat    9180
gatgacctgg tgcattgcaa acgctagggc cttgtggggt cagttccggc tgggggttca    9240
gcagccagcg ctttactggc atttcaggaa caagcgggca ctgctcgacg cacttgcttc    9300
gctcagtatc gctcgggacg cacggcgcgc tctacgaact gccgataaac agaggattaa    9360
aattgacaat tgtgattaag gctcagattc gacggcttgg agcggccgac gtgcaggatt    9420
tccgcgagat ccgattgtcg gccctgaaga aagctccaga gatgttcggg tccgtttacg    9480
agcacgagga gaaaaagccc atggaggcgt tcgctgaacg gttgcgagat gccgtggcat    9540
tcggcgccta catcgacggc gagatcattg ggctgtcggt cttcaaacag gaggacggcc    9600
```

-continued

```
ccaaggacgc tcacaaggcg catctgtccg gcgttttcgt ggagcccgaa cagcgaggcc   9660
gaggggtcgc cggtatgctg ctgcgggcgt tgccggcggg tttattgctc gtgatgatcg   9720
tccgacagat tccaacggga atctggtgga tgcgcatctt catcctcggc gcacttaata   9780
tttcgctatt ctggagcttg ttgtttattt cggtctaccg cctgccgggc gggtcgcggc   9840
gacggtaggc gctgtgcagc cgctgatggt cgtgttcatc tctgccgctc tgctaggtag   9900
cccgatacga ttgatggcgg tcctgggggc tatttgcgga actgcgggcg tggcgctgtt   9960
ggtgttgaca ccaaacgcag cgctagatcc tgtcggcgtc gcagcgggcc tggcgggggc  10020
ggtttccatg gcgttcggaa ccgtgctgac ccgcaagtgg caacctcccg tgcctctgct  10080
caccttacc gcctggcaac tggcggccgg aggacttctg ctcgttccag tagctttagt  10140
gtttgatccg ccaatcccga tgcctacagg aaccaatgtt ctcggctgct cgactgcacg  10200
aataccagcg acccccttgcc caaatacttg ccgtgggcct cggcctgaga gccaaaacac  10260
ttgatgcgga agaagtcggt gcgctcctgc ttgtcgccgg catcgttgcg ccacatctag  10320
gtactaaaac aattcatcca gtaaaatata atattttatt ttctcccaat caggcttgat  10380
ccccagtaag tcaaaaaata gctcgacata ctgttcttcc ccgatatcct ccctgatcga  10440
ccggacgcag aaggcaatgt cataccactt gtccgccctg ccgcttctcc caagatcaat  10500
aaagccactt actttgccat ctttcacaaa gatgttgctg tctcccaggt cgccgtggga  10560
aaagacaagt tcctcttcgg gcttttccgt ctttaaaaaa tcatacagct cgcgcggatc  10620
tttaaatgga gtgtcttctt cccagttttc gcaatccaca tcggccagat cgttattcag  10680
taagtaatcc aattcggcta agcggctgtc taagctattc gtatagggac aatccgatat  10740
gtcgatggag tgaaagagcc tgatgcactc cgcatacagc tcgataatct tttcagggct  10800
ttgttcatct tcatactctt ccgagcaaag gacgccatcg gcctcactca tgagcagatt  10860
gctccagcca tcatgccgtt caaagtgcag gaccttggaa acaggcagct ttccttccag  10920
ccatagcatc atgtcctttt cccgttccac atcataggtg gtccctttat accggctgtc  10980
cgtcattttt aaatataggt tttcattttc tcccaccagc ttatatacct tagcaggaga  11040
cattccttcc gtatctttta cgcagcggta tttttcgatc agtttttttca attccggtga  11100
tattctcatt ttagccattt attatttcct tcctcttttc tacagtattt aaagataccc  11160
caagaagcta attataacaa gacgaactcc aattcactgt tccttgcatt ctaaaacctt  11220
aaataccaga aaacagcttt ttcaaagttg ttttcaaagt tggcgtataa catagtatcg  11280
attcgatagc gtggactcaa ggctctcgcg aatggctcgc gttggaaact ttcattgaca  11340
cttgaggggc accgcaggga aattctcgtc cttgcgagaa ccggctatgt cgtgctgcgc  11400
atcgagcctg cgcccttggc ttgtctcgcc cctctccgcg tcgctacggg gcttccagcg  11460
cctttccgac gctcaccggg ctggttgccc tcgccgctgg gctggcggcc gtctatggcc  11520
ctgcaaacgc gccagaaacg ccgtcgaagc cgtgtgcgag acaccgcggc cgccggcgtt  11580
gtggatacct cgcggaaaac ttggccctca ctgacagatg agggcggac gttgacactt  11640
gaggggccga ctcacccggc gcggcgttga cagatgaggg gcaggctcga tttcggccgg  11700
cgacgtggag ctggccagcc tcgcaaatcg gcgaaaacgc ctgattttac gcgagtttcc  11760
cacagatgat gtggacaagc ctggggataa gtgccctgcg gtattgacac ttgaggggcg  11820
cgactactga cagatgaggg gcgcgatcct tgacacttga ggggcagagt gctgacagat  11880
gaggggcgca cctattgaca tttgaggggc tgtccacagg cagaaaatcc agcatttgca  11940
agggtttccg cccgttttc ggccaccgct aacctgtctt ttaacctgct tttaaaccaa  12000
```

-continued

```
tatttataaa ccttgttttt aaccagggct gcgccctgtg cgcgtgaccg cgcacgccga    12060 agggggggtgc cccccttct cgaaccctcc cggcccgcta acgcgggcct cccatccccc    12120
caggggctgc gcccctcggc cgcgaacggc ctcaccccaa aaatggcagc gccagattat    12180
tgaagcattt atcagggtta ttgtctcatg agcggataca tatttgaatg tatttagaaa    12240
aataaacaaa tagggggttcc gcgcacattt ccccgaaaag tgccacctga cgtctaagaa    12300
accattatta tcatgacatt aacctataaa aataggcgta tcacgaggcc ctttcgtctt    12360
caagaattgg tcgacgatct tgctgcgttc ggatattttc gtggagttcc cgccacagac    12420
ccggattgaa ggcgagatcc agcaactcgc gccagatcat cctgtgacgg aactttggcg    12480
cgtgatgact ggccaggacg tcggccgaaa gagcgacaag cagatcacgc ttttcgacag    12540
cgtcggattt gcgatcgagg attttcggc gctgcgctac gtccgcgacc gcgttgaggg    12600
atcaagccac agcagcccac tcgaccttct agccgaccca gacgagccaa gggatctttt    12660
tggaatgctg ctccgtcgtc aggctttccg acgtttgggt ggttgaacag aagtcattat    12720
cgcacggaat gccaagcact cccgagggga accctgtggt tggcatgcac atacaaatgg    12780
acgaacggat aaaccttttc acgccctttt aaatatccga ttattctaat aaacgctctt    12840
ttctcttagg tttacccgcc aatatatcct gtcaaacact gatagtttaa actgaaggcg    12900
ggaaacgaca atctgatcat gagcggagaa ttaagggagt cacgttatga ccccgccga    12960 tgacgcggga caagccgttt tacgtttgga actgacagaa ccgcaacgtt gaaggagcca    13020
ctcagc                                                              13026
```

<210> SEQ ID NO 6
<211> LENGTH: 27875
<212> TYPE: DNA
<213> ORGANISM: Artificial Sequence
<220> FEATURE:
<223> OTHER INFORMATION: Synthetic vector: pLCSBGWBSW
<220> FEATURE:
<221> NAME/KEY: misc_feature
<222> LOCATION: (62)..(84)
<223> OTHER INFORMATION: I-SceI
<220> FEATURE:
<221> NAME/KEY: misc_feature
<222> LOCATION: (104)..(1003)
<223> OTHER INFORMATION: Pubi
<220> FEATURE:
<221> NAME/KEY: misc_feature
<222> LOCATION: (1087)..(2096)
<223> OTHER INFORMATION: UbiI
<220> FEATURE:
<221> NAME/KEY: misc_feature
<222> LOCATION: (2117)..(2141)
<223> OTHER INFORMATION: attB1
<220> FEATURE:
<221> NAME/KEY: misc_feature
<222> LOCATION: (2144)..(2695)
<223> OTHER INFORMATION: bar
<220> FEATURE:
<221> NAME/KEY: misc_feature
<222> LOCATION: (2712)..(2736)
<223> OTHER INFORMATION: attB2
<220> FEATURE:
<221> NAME/KEY: misc_feature
<222> LOCATION: (2756)..(3031)
<223> OTHER INFORMATION: Tnos
<220> FEATURE:
<221> NAME/KEY: misc_feature
<222> LOCATION: (3090)..(3114)
<223> OTHER INFORMATION: LB
<220> FEATURE:
<221> NAME/KEY: misc_feature
<222> LOCATION: (3656)..(3686)
<223> OTHER INFORMATION: I-CeuI
<220> FEATURE:

```
<221> NAME/KEY: misc_feature
<222> LOCATION: (3695)..(18509)
<223> OTHER INFORMATION: S-V(virC, virG, virB)
<220> FEATURE:
<221> NAME/KEY: misc_feature
<222> LOCATION: (18522)..(18929)
<223> OTHER INFORMATION: (complement) cos
<220> FEATURE:
<221> NAME/KEY: misc_feature
<222> LOCATION: (18931)..(21048)
<223> OTHER INFORMATION: (complement) IncC1
<220> FEATURE:
<221> NAME/KEY: misc_feature
<222> LOCATION: (21050)..(21869)
<223> OTHER INFORMATION: (complement) oriT
<220> FEATURE:
<221> NAME/KEY: misc_feature
<222> LOCATION: (21866)..(25037)
<223> OTHER INFORMATION: (complement) trfA1
<220> FEATURE:
<221> NAME/KEY: misc_feature
<222> LOCATION: (25033)..(26129)
<223> OTHER INFORMATION: nptIII
<220> FEATURE:
<221> NAME/KEY: misc_feature
<222> LOCATION: (26126)..(27019)
<223> OTHER INFORMATION: (complement)  oriV
<220> FEATURE:
<221> NAME/KEY: misc_feature
<222> LOCATION: (27699)..(27723)
<223> OTHER INFORMATION: RB

<400> SEQUENCE: 6
aagcttgcgg ccgcttcgcc atttaaatgg cgaagatgtt aattaacatc ggtaccgagc    60
tctagggata acagggtaat agctcgaatt ctagcttgca tgcctgcagt gcagcgtgac   120
ccggtcgtgc ccctctctag agataatgag cattgcatgt ctaagttata aaaaattacc   180
acatattttt tttgtcacac ttgtttgaag tgcagtttat ctatctttat acatatattt   240
aaactttact ctacgaataa tataatctat agtactacaa taatatcagt gttttagaga   300
atcatataaa tgaacagtta gacatggtct aaaggacaat tgagtatttt gacaacagga   360
ctctacagtt ttatcttttt agtgtgcatg tgttctcctt ttttttttgca aatagcttca   420 cctatataat acttcatcca ttttattagt acatccattt agggtttagg gttaatggtt   480
tttatagact aattttttta gtacatctat tttattctat tttagcctct aaattaagaa   540
aactaaaact ctatttttagt ttttttattt aataatttag atataaaata gaataaaata   600
aagtgactaa aaattaaaca aataccctt aagaaattaa aaaaactaag gaaacatttt   660
tcttgtttcg agtagataat gccagcctgt taaacgccgt cgacgagtct aacgacaccc   720
aaccagcgaa ccagcagcgt cgcgtcgggc caagcgaagc agacggcacg gcatctctgt   780
cgctgcctct ggacccctct cgagagttcc gctccaccgt tggacttgct ccgctgtcgg   840
catccagaaa ttgcgtggcg gagcggcaga cgtgagccgg cacggcaggc ggcctcctcc   900
tcctctcacg gcaccggcag ctacggggga ttcctttccc accgctcctt cgctttccct   960
tcctcgcccg ccgtaataaa tagacacccc ctccacaccc tctttcccca acctcgtgtt  1020
gttcggagcg cacacacaca caaccagatc tcccccaaat ccacccgtcg gcacctccgc  1080
ttcaaggtac gccgctcgtc ctcccccccc ccccctctct accttctcta gatcggcgtt  1140
ccggtccatg gttagggccc ggtagttcta cttctgttca tgtttgtgtt agatccgtgt  1200
ttgtgttaga tccgtgctgc tagcgttcgt acacggatgc gacctgtacg tcagacacgt  1260
tctgattgct aacttgccag tgtttctctt tggggaatcc tgggatggct ctagccgttc  1320
cgcagacggg atcgatttca tgattttttt tgtttcgttg cataggggttt ggtttgccct  1380
```

```
tttcctttat tcaatatat gccgtgcact tgtttgtcgg gtcatctttt catgcttttt    1440
tttgtcttgg ttgtgatgat gtggtctggt tgggcggtcg ttctagatcg gagtagaatt    1500
ctgtttcaaa ctacctggtg gatttattaa ttttggatct gtatgtgtgt gccatacata    1560
ttcatagtta cgaattgaag atgatggatg gaaatatcga tctaggatag gtatacatgt    1620
tgatgcgggt tttactgatg catatacaga gatgcttttt gttcgcttgg ttgtgatgat    1680
gtggtgtggt tgggcggtcg ttcattcgtt ctagatcgga gtagaatact gtttcaaact    1740
acctggtgta tttattaatt ttggaactgt atgtgtgtgt catacatctt catagttacg    1800
agtttaagat ggatggaaat atcgatctag gataggtata catgttgatg tgggttttac    1860
tgatgcatat acatgatggc atatgcagca tctattcata tgctctaacc ttgagtacct    1920
atctattata taaacaagt atgttttata attattttga tcttgatata cttggatgat    1980
ggcatatgca gcagctatat gtggattttt ttagccctgc cttcatacgc tatttatttg    2040
cttggtactg tttcttttgt cgatgctcac cctgttgttt ggtgttactt ctgcaggtcg    2100
actctagagg atcatcacaa gtttgtacaa aaaagcaggc tccatggacc cagaacgacg    2160
cccggccgac atccgccgtg ccaccgaggc ggacatgccg gcggtctgca ccatcgtcaa    2220
ccactacatc gagacaagca cggtcaactt ccgtaccgag ccgcaggaac cgcaggagtg    2280
gacgacgac ctcgtccgtc tgcgggagcg ctatccctgg ctcgtcgccg aggtggacgg    2340
cgaggtcgcc ggcatcgcct acgcgggccc ctggaaggca cgcaacgcct acgactggac    2400
ggccgagtcg accgtgtacg tctcccccg ccaccagcgg acgggactgg gctccacgct    2460
ctacacccac ctgctgaagt ccctggaggc acagggcttc aagagcgtgg tcgctgtcat    2520
cgggctgccc aacgaccga gcgtgcgcat gcacgaggcg ctcggatatg ccccccgcgg    2580
catgctgcgg gcggccggct tcaagcacgg gaactggcat gacgtgggtt tctggcagct    2640
ggacttcagc ctgccggtac cgccccgtcc ggtcctgccc gtcaccgaga tctgatctca    2700
cgcgtctagg aacccagctt tcttgtacaa agtggtgatg atccgtcgac ctgcagatcg    2760
ttcaaacatt tggcaataaa gtttcttaag attgaatcct gttgccggtc ttgcgatgat    2820
tatcatataa tttctgttga attacgttaa gcatgtaata attaacatgt aatgcatgac    2880
gttatttatg agatgggttt ttatgattag agtcccgcaa ttatacattt aatacgcgat    2940
agaaaacaaa atatagcgcg caaactagga taaattatcg cgcgcggtgt catctatgtt    3000
actagatccg atgataagct gtcaaacatg agaattcagt acattaaaaa cgtccgcaat    3060
gtgttattaa gttgtctaag cgtcaatttg tttacaccac aatatatcct gccaccagcc    3120
agccaacagc tccccgaccg gcagctcggc acaaaatcac cactcgatac aggcagccca    3180
tcagtccggg acggcgtcag cgggagagcc gttgtaaggc ggcagacttt gctcatgtta    3240
ccgatgctat tcggaagaac ggcaactaag ctgccgggtt tgaaacacgg atgatctcgc    3300
ggagggtagc atgttgattg taacgatgac agagcgttgc tgcctgtgat caaatatcat    3360
ctccctcgca gagatccgaa ttatcagcct tcttattcat ttctcgctta accgtgacag    3420
gctgtcgatc ttgagaacta tgccgacata ataggaaatc gctggataaa gccgctgagg    3480
aagctgagtg gcgctatttc tttagaagtg aacgttgacg atcgtcgacc gtaccccgat    3540
gaattaattc ggacgtacgt tctgaacaca gctggatact tacttgggcg attgtcatac    3600
atgacatcaa caatgtaccc gtttgtgtaa ccgtctcttg gaggttcgta tgacactagg    3660
tcgctacctt aggaccgtta tagttactag aaatggtacc tgcggggaag cttacaataa    3720
tgtgtgttgt taagtcttgt tgcctgtcat cgtctgactg actttcgtca taaatcccgg    3780
```

```
cctccgtaac ccagctttgg gcaagctcac ggatttgatc cggcggaacg ggaatatcga    3840
gatgccgggc tgaacgctgc agttccagct ttcccttcg gacaggtac tccagctgat     3900
tgattatctg ctgaagggtc ttggttccac ctcctggcac aatgcgaatg attacttgag    3960
cgcgatcggg catccaattt tctcccgtca ggtgcgtggt caagtgctac aaggcaccttt   4020
tcagtaacga gcgaccgtcg atccgtcgcc gggatacgga caaaatggag cgcagtagtc    4080
catcgagggc ggcgaaagcc tcgccaaaag caatacgttc atctcgcaca gcctccagat    4140
ccgatcgagg gtcttcggcg taggcagata aagcatgga tacattgctt gagagtattc     4200
cgatggactg aagtatggct tccatctttt ctcgtgtgtc tgcatctatt tcgagaaagc    4260
ccccgatgcg gcgcaccgca acgcgaattg ccatactatc cgaaagtccc agcaggcgcg    4320
cttgatagga aaggtttca tactcggccg atcgcagacg ggcactcacg accttgaacc     4380
cttcaacttt cagggatcga tgctggttga tggtagtctc actcgacgtg gctctggtgt    4440
gttttgacat agcttcctcc aaagaaagcg gaaggtctgg atactccagc acgaaatgtg    4500
cccgggtaga cggatggaag tctagccctg ctcaatatga aatcaacagt acatttacag    4560
tcaatactga atatacttgc tacatttgca attgtcttat aacgaatgtg aaataaaaat    4620
agtgtaacaa cgctttact catcgataat cacaaaaaca tttatacgaa caaaaataca    4680
aatgcactcc ggtttcacag gataggcggg atcagaatat gcaactttg acgttttgtt     4740
cttttcaaagg gggtgctggc aaaaccaccg cactcatggg cctttgcgct gctttggcaa   4800
atgacggtaa acgagtggcc ctctttgatg ccgacgaaaa ccggcctctg acgcgatgga    4860
gagaaaacgc cttacaaagc agtactggga tcctcgctgt gaagtctatt ccgccgacga    4920
aatgcccctt cttgaagcag cctatgaaaa tgccgagctc gaaggatttg attatgcgtt    4980
ggccgatacg cgtggcggct cgagcgagct caacaacaca atcatcgcta gctcaaacct    5040
gcttctgatc cccaccatgc taacgccgct cgacatcgat gaggcactat ctacctaccg    5100
ctacgtcatc gagctgctgt tgagtgaaaa tttggcaatt cctacagctg ttttgcgcca    5160
acgcgtcccg gtcggccgat tgacaacatc gcaacgcagg atgtcagaga cgctagagag    5220
ccttccagtt gtaccgtctc ccatgcatga aagagatgca tttgccgcga tgaagaacg     5280
cggcatgttg catcttacat tactaaaacac gggaactgat ccgacgatgc gcctcataga    5340
gaggaatctt cggattgcga tggaggaagt cgtggtcatt tcgaaactga tcagcaaaat    5400
cttggaggct tgaagatggc aattcgcaag cccgcattgt cggtcggcga agcacggcgg    5460
cttgctggtg ctcgacccga gatccaccat cccaaccga cacttgttcc ccagaagctg     5520
gacctccagc acttgcctga aaaagccgac gagaaagacc agcaacgtga gcctctcgtc    5580
gccgatcaca tttacagtcc cgatcgacaa cttaagctaa ctgtggatgc ccttagtcca    5640
cctccgtccc cgaaaaagct ccaggttttt cttccagcgc gaccgcccgc gcctcaagtg    5700
tcgaaaacat atgacaacct cgttcggcaa tacagtccct cgaagtcgct acaaatgatt    5760
ttaaggcgcg cgttggacga tttcgaaagc atgctggcag atggatcatt tcgcgtggcc    5820
ccgaaaagtt atccgatccc ttcaactaca gaaaaatccg ttctcgttca gacctcacgc    5880
atgttcccgg ttgcgttgct cgaggtcgct cgaagtcatt ttgatccgtt ggggttggag    5940
accgctcgag cttcggcca caagctggct accgccgcgc tcgcgtcatt cttgctgga     6000
gagaagccat cgagcaattg gtgaagaggg acctatcgga accctcacc aaatattgag     6060
tgtaggtttg aggccgctgg ccgcgtcctc agtcacctt tgagccagat aattaagagc     6120
caaatgcaat tggctcaggc tgccatcgtc ccccgtgcg aaacctgcac gtccgcgtca     6180
```

```
aagaaataac cggcacctct tgctgttttt atcagttgag ggcttgacgg atccgcctca   6240
agtttgcggc gcagccgcaa aatgagaaca tctatactcc tgtcgtaaac ctcctcgtcg   6300
cgtactcgac tggcaatgag aagttgctcg cgcgatagaa cgtcgcgggg tttctctaaa   6360
aacgcgagga gaagattgaa ctcacctgcc gtaagtttca cctcaccgcc agcttcggac   6420
atcaagcgac gttgcctgag attaagtgtc cagtcagtaa acaaaaaga ccgtcggtct    6480
ttggagcgga caacgttggg gcgcacgcgc aaggcaaccc gaatgcgtgc aagaaactct   6540
ctcgtactaa acggcttagc gataaaatca cttgctccta gctcgagtgc aacaacttta   6600
tccgtctcct caaggcggtc gccactgata attatgattg aatatcaga ctttgccgcc    6660
agatttcgaa cgatctcaag cccatcttca cgacctaaat ttagatcaac aaccacgaca   6720
tcgaccgtcg cggaagagag tactctagtg aactgggtgc tgtcggctac cgcggtcact   6780
ttgaaggcgt ggatcgtaag gtattcgata ataagatgcc gcatagcgac atcgtcatcg   6840
ataagaagaa cgtgtttcaa cggctcacct ttcaatctaa aatctgaacc cttgttcaca   6900
gcgcttgaga aattttcacg tgaaggatgt acaatcatct ccagctaaat gggcagttcg   6960
tcagaattgc ggctgaccgc ggatgacgaa aatgcgaacc aagtatttca atttatgac    7020
aaaagttctc aatcgttgtt acaagtgaaa cgcttcgagg ttacagctac tattgattaa   7080
ggagatcgcc tatggtctcg ccccggcgtc gtgcgtccgc cgcgagccag atctcgccta   7140
cttcataaac gtcctcatag gcacggaatg gaatgatgac atcgatcgcc gtagagagca   7200
tgtcaatcag tgtgcgatct tccaagctag caccttgggc gctacttttg acaagggaaa   7260
acagtttctt gaatccttgg attggattcg cgccgtgtat tgttgaaatc gatcccggat   7320
gtcccgagac gacttcactc agataagccc atgctgcatc gtcgcgcatc tcgccaagca   7380
atatccggtc cggccgcata cgcagacttg cttggagcaa gtgctcggcg ctcacagcac   7440
ccagcccagc accgttcttg gagtagagta gtctaacatg attatcgtgt ggaatgacga   7500
gttcgagcgt atcttctatg gtgattagcc tttcctgggg ggggatggcg ctgatcaagg   7560
tcttgctcat tgttgtcttg ccgcttccgg tagggccaca tagcaacatc gtcagtcggc   7620
tgacgacgca tgcgtgcaga aacgcttcca aatccccgtt gtcaaaatgc tgaaggatag   7680
cttcatcatc ctgattttgg cgtttccttc gtgtctgcca ctggttccac ctcgaagcat   7740
cataacggga ggagacttct ttaagaccag aaacacgcga gcttggccgt cgaatggtca   7800
agctgacggt gcccgaggga acggtcggcg gcagacagat ttgtagtcgt tcaccaccag   7860
gaagttcagt ggcgcagagg gggttacgtg gtccgacatc ctgctttctc agcgcgcccg   7920
ctaaaatagc gatatcttca agatcatcat aagagacggg caaaggcatc ttggtaaaaa   7980
tgccggcttg gcgcacaaat gcctctccag gtcgattgat cgcaatttct tcagtcttcg   8040
ggtcatcgag ccattccaaa atcggcttca gaagaaagcg tagttgcgga tccacttcca   8100
tttacaatgt atcctatctc taagcggaaa tttgaattca ttaagagcgg cggttcctcc   8160
cccgcgtggc gccgccagtc aggcggagct ggtaaacacc aaagaaatcg aggtcccgtg   8220
ctacgaaaat ggaaacggtg tcaccctgat tcttcttcag ggttggcggt atgttgatgg   8280
ttgccttaag ggctgtctca gttgtctgct caccgttatt ttgaaagctg ttgaagctca   8340
tcccgccacc cgagctgccg gcgtaggtgc tagctgcctg gaaggcgcct tgaacaacac   8400
tcaagagcat agctccgcta aaacgctgcc agaagtggct gtcgaccgag cccggcaatc   8460
ctgagcgacc gagttcgtcc gcgcttggcg atgttaacga gatcatcgca tggtcaggtg   8520
tctcggcgcg atcccacaac acaaaaacgc gcccatctcc ctgttgcaag ccacgctgta   8580
```

```
tttcgccaac aacggtggtg ccacgatcaa gaagcacgat attgttcgtt gttccacgaa    8640
tatcctgagg caagacacac tttacatagc ctgccaaatt tgtgtcgatt gcggtttgca    8700
agatgcacgg aattattgtc ccttgcgtta ccataaaatc ggggtgcggc aagagcgtgg    8760
cgctgctggg ctgcagctcg gtgggtttca tacgtatcga caaatcgttc tcgccggaca    8820
cttcgccatt cggcaaggag ttgtcgtcac gcttgccttc ttgtcttcgg cccgtgtcgc    8880
cctgaatggc gcgtttgctg accccttgat cgccgctgct atatgcaaaa atcggtgttt    8940
cttccggccg tggctcatgc cgctccggtt cgcccctcgg cggtagagga gcagcaggct    9000
gaacagcctc ttgaaccgct ggaggatccg cggcacctc aatcggagct ggatgaaatg    9060
gcttggtgtt tgttgcgatc aaagttgacg gcgatgcgtt ctcattcacc ttcttttggc    9120
gcccacctag ccaaatgagg cttaatgata acgcgagaac gacacctccg acgatcaatt    9180
tctgagaccc cgaaagacgc cggcgatgtt tgtcggagac cagggatcca gatgcatcaa    9240
cctcatgtgc cgcttgctga ctatcgttat tcatcccttc gcccccttca ggacgcgttt    9300
cacatcgggc ctcaccgtgc ccgtttgcgg cctttggcca acgggatcgt aagcggtgtt    9360
ccagatacat agtactgtgt ggccatccct cagacgccaa cctcgggaaa ccgaagaaat    9420
ctcgacatcg ctcccttaa ctgaatagtt ggcaacagct tccttgccat caggattgat    9480
ggtgtagatg gagggtatgc gtacattgcc cggaaagtgg aataccgtcg taaatccatt    9540
gtcgaagact tcgagtggca acagcgaacg atcgccttgg gcgacgtagt gccaattact    9600
gtccgccgca ccaagggctg tgacaggctg atccaataaa ttctcagctt tccgttgata    9660
ttgtgcttcc gcgtgtagtc tgtccacaac agccttctgt tgtgcctccc ttcgccgagc    9720
cgccgcatcg tcgcgggt aggcgaattg gacgctgtaa tagagatcgg gctgctcttt    9780
atcgaggtgg gacagagtct tggaacttat actgaaaaca taacggcgca tcccggagtc    9840
gcttgcggtt agcacgatta ctggctgagg cgtgaggacc tggcttgcct tgaaaaatag    9900
ataatttccc cgcggtaggg ctgctagatc tttgctattt gaaacggcaa ccgctgtcac    9960
cgtttcgttc gtggcgaatg ttacgaccaa agtagctcca accgccgtcg agaggcgcac    10020
cacttgatcg ggattgtaag ccaaataacg catgcgcgga tctagcttgc ccgccattgg    10080
agtgtcttca gcctccgcac cagtcgcagc ggcaaataaa catgctaaaa tgaaaagtgc    10140
ttttctgatc atggttcgct gtggcctacg tttgaaacgg tatcttccga tgtctgatag    10200
gaggtgacaa ccagacctgc cgggttggtt agtctcaatc tgccgggcaa gctggtcacc    10260
ttttcgtagc gaactgtcgc ggtccacgta ctcaccacag gcattttgcc gtcaacgacg    10320
agggtccttt tatagcgaat ttgctgcgtg cttggagtta catcatttga agcgatgtgc    10380
tcgacctcca ccctgccgcg tttgccaaga atgacttgag gcgaactggg attgggatag    10440
ttgaagaatt gctggtaatc ctggcgcact gttggggcac tgaagttcga taccaggtcg    10500
taggcgtact gagcggtgtc ggcatcataa ctctcgcgca ggcgaacgta ctcccacaat    10560
gaggcgttaa cgacggcctc ctcttgagtt gcaggcaatc gcgagacaga cacctcgctg    10620
tcaacggtgc cgtccggccg tatccataga tatacgggca caagcctgct caacggcacc    10680
attgtggcta tagcgaacgc ttgagcaaca tttcccaaaa tcgcgatagc tgcgacagct    10740
gcaatgagtt tggagagacg tcgcgccgat ttcgctcgcg cggtttgaaa ggcttctact    10800
tccttatagt gctcggcaag gctttcgcgc gccactagca tggcatattc aggccccgtc    10860
atagcgtcca cccgaattgc cgagctgaag atctgacgga gtaggctgcc atcgccccac    10920
attcagcggg aagatcgggc ctttgcagct cgctaatgtg tcgtttgtct ggcagccgct    10980
```

```
caaagcgaca actaggcaca gcaggcaata cttcatagaa ttctccattg aggcgaattt    11040
ttgcgcgacc tagcctcgct caacctgagc gaagcgacgg tacaagctgc tggcagattg    11100
ggttgcgccg ctccagtaac tgcctccaat gttgccggcg atcgccggca aagcgacaat    11160
gagcgcatcc cctgtcagaa aaacatatc gagttcgtaa agaccaatga tcttggccgc     11220
ggtcgtaccg gcgaaggtga ttacaccaag cataagggtg agcgcagtcg cttcggttag    11280
gatgacgatc gttgccacga ggtttaagag gagaagcaag agaccgtagg tgataagttg    11340
cccgatccac ttagctgcga tgtcccgcgt gcgatcaaaa atatatccga cgaggatcag    11400
aggcccgatc gcgagaagca cttcgtgag aattccaacg gcgtcgtaaa ctccgaaggc     11460
agaccagagc gtgccgtaaa ggacccactg tgcccttgg aaagcaagga tgtcctggtc     11520
gttcatcgga ccgatttcgg atgcgatttt ctgaaaaacg gcctgggtca cggcgaacat    11580
tgtatccaac tgtgccggaa cagtctgcag aggcaagccg gttacactaa actgctgaac    11640
aaagtttggg accgtctttt cgaagatgga accacatag tcttggtagt tagcctgccc     11700
aacaattaga gcaacaacga tggtgaccgt gatcacccga gtgataccgc tacgggtatc    11760
gacttcgccg cgtatgacta aaataccctg aacaataatc aaagagtga cacaggcgat     11820 caatggcgca ctcaccgcct cctggatagt ctcaagcatc gagtccaagc ctgtcgtgaa    11880
ggctacatcg aagatcgtat gaatggccgt aaacggcgcc ggaatcgtga aattcatcga    11940
ttggacctga acttgactgg tttgtcgcat aatgttggat aaaatgagct cgcattcggc    12000
gaggatgcgg gcggatgaac aaatcgccca gccttagggg agggcaccaa agatgacagc    12060 ggtctttga tgctccttgc gttgagcggc cgcctcttcc gcctcgtgaa ggccggcctg     12120
cgcggtagtc atcgttaata ggcttgtcgc ctgtacattt tgaatcattg cgtcatggat    12180
ctgcttgaga agcaaaccat tggtcacggt tgcctgcatg atattgcgag atcgggaaag    12240
ctgagcagac gtatcagcat tcgccgtcaa gcgtttgtcc atcgtttcca gattgtcagc    12300
cgcaatgcca gcgctgtttg cggaaccggt gatctgcgat cgcaacaggt ccgcttcagc    12360
atcactaccc acgactgcac gatctgtatc gctggtgatc gcacgtgccg tggtcgacat    12420
tggcattcgc ggcgaaaaca tttcattgtc taggtccttc gtcgaaggat actgatttt     12480 ctggttgagc gaagtcagta gtccagtaac gccgtaggcc gacgtcaaca tcgtaaccat    12540
cgctatagtc tgagtgagat tctccgcagt cgcgagcgca gtcgcgagcg tctcagcctc    12600
cgttgccggg tcgctaacaa caaactgcgc ccgcgcgggc tgaatatata gaaagctgca    12660
ggtcaaaact gttgcaataa gttgcgtcgt cttcatcgtt tcctaccta tcaatcttct     12720 gcctcgtggt gacgggccat gaattcgctg agccagccag atgagttgcc ttcttgtgcc    12780
tcgcgtagtc gagttgcaaa gcgcaccgtg ttggcacgcc ccgaaagcac ggcgacatat    12840
tcacgcatat cccgcagatc aaattcgcag atgacgcttc cactttctcg tttaagaaga    12900
aacttacggc tgccgaccgt catgtcttca cggatcgcct gaaattcctt ttcggtacat    12960
ttcagtccat cgacataagc cgatcgatct gcggttggtg atggatagaa aatcttcgtc    13020
atacattgcg caaccaagct ggctcctagc ggcgattcca aacatgctc tggttgctgc     13080 gttgccagta ttagcatccc gttgttttt cgaacggtca ggaggaattt gtcgacgaca     13140
gtcgaaaatt taggttttaa caaataggcg cgaaactcat cgcagctcat cacaaaacgg    13200
cggccgtcga tcatggctcc aatccgatgc aggagatatg ctgcagcggg agcgcatact    13260
tcctcgtatt cgagaagatg cgtcatgtcg aagccggtaa tcgacggatc taactttact    13320
tcgtcaactt cgccgtcaaa tgcccagcca agcgcatggc cccggcacca gcgttggagc    13380
```

```
cgcgctcctg cgccttcggc gggcccatgc aacaaaaatt cacgtaaccc cgcgattgaa    13440
cgcatttgtg gatcaaacga gagctgacga tggataccac ggaccagacg gcggttctct    13500
tccggagaaa tcccaccccg accatcactc tcgatgagag ccacgatcca ttcgcgcaga    13560
aaatcgtgtg aggctgctgt gttttctagg ccacgcaacg cgccaaccc  gctgggtgtg    13620 cctctgtgaa gtgccaaata tgttcctcct gtggcgcgaa ccagcaattc gccaccccgg    13680
tccttgtcaa agaacacgac cgtacctgca cggtcgacca tgctctgttc gagcatggct    13740
agaacaaaca tcatgagcgt cgtcttaccc ctcccgatag gcccgaatat tgccgtcatg    13800
ccaacatcgt gctcatgcgg gatatagtcg aaaggcgttc cgccattggt acgaaatcgg    13860
gcaatcgcgt tgccccagtg gcctgagctg cgcccctctg gaaagttttc gaaagagaca    13920
aaccctgcga aattgcgtga agtgattgcg ccagggcgtg tgcgccactt aaaattcccc    13980
ggcaattggg accaataggc cgcttccata ccaataccct cttggacaac cacggcacct    14040
gcatccgcca ttcgtgtccg agcccgcgcg ccctgtccc  caagactatt gagatcgtct    14100
gcatagacgc aaaggctcaa atgatgtgag cccataacga attcgttgct cgcaagtgcg    14160
tcctcagcct cggataattt gccgatttga gtcacggctt tatcgccgga actcagcatc    14220
tggctcgatt tgaggctaag tttcgcgtgc gcttgcgggc gagtcaggaa cgaaaaactc    14280
tgcgtgagaa caagtggaaa atcgagggat agcagcgcgt tgagcatgcc cggccgtgtt    14340
tttgcagggt attcgcgaaa cgaatagatg gatccaacgt aactgtcttt tggcgttctg    14400
atctcgagtc ctcgcttgcc gcaaatgact ctgtcggtat aaatcgaagc gccgagtgag    14460
ccgctgacga ccggaaccgg tgtgaaccga ccagtcatga tcaaccgtag cgcttcgcca    14520
atttcggtga agagcacacc ctgcttctcg cggatgccaa gacgatgcag gccatacgct    14580
ttaagagagc cagcgacaac atgccaaaga tcttccatgt tcctgatctg gcccgtgaga    14640 tcgtttttccc tttttccgct tagcttggtg aacctcctct ttaccttccc taaagccgcc    14700
tgtgggtaga caatcaacgt aaggaagtgt tcattgcgga ggagttggcc ggagagcacg    14760
cgctgttcaa aagcttcgtt caggctagcg gcgaaaacac tacggaagtg tcgcggcgcc    14820
gatgatggca cgtcggcatg acgtacgagg tgagcatata ttgacacatg atcatcagcg    14880
atattgcgca acagcgtgtt gaacgcacga caacgcgcat tgcgcatttc agtttcctca    14940
agctcgaatg caacgccatc aattctcgca atggtcatga tcgatccgtc ttcaagaagg    15000
acgatatggt cgctgaggtg gccaatataa gggagataga tctcaccgga tctttcggtc    15060
gttccactcg cgccgagcat cacaccattc ctctccctcg tgggggaacc ctaattggat    15120
ttgggctaac agtagcgccc ccccaaactg cactatcaat gcttcttccc gcggtccgca    15180
aaaatagcag gacgacgctc gccgcattgt agtctcgctc cacgatgagc cgggctgcaa    15240
accataacgg cacgagaacg acttcgtaga gcgggttctg aacgataacg atgacaaagc    15300
cggcgaacat catgaataac cctgccaatg tcagtggcac cccaagaaac aatgcgggcc    15360
gtgtggctgc gaggtaaagg gtcgattctt ccaaacgatc agccatcaac taccgccagt    15420
gagcgtttgg ccgaggaagc tcgccccaaa catgataaca atgccgccga cgacgccggc    15480
aaccagccca agcgaagccc gcccgaacat ccaggagatc ccgatagcga caatgccgag    15540
aacagcgagt gactggccga acggaccaag gataaacgtg catatattgt taaccattgt    15600
ggcggggtca gtgccgccac ccgcagattg cgctgcggcg ggtccggatg aggaaatgct    15660
ccatgcaatt gcaccgcaca agcttggggc gcagctcgat atcacgcgca tcatcgcatt    15720
cgagagcgag aggcgattta gatgtaaacg gtatctctca aagcatcgca tcaatgcgca    15780
```

```
cctccttagt ataagtcgaa taagacttga ttgtcgtctg cggatttgcc gttgtcctgg  15840
tgtggcggtg gcggagcgat taaaccgcca gcgccatcct cctgcgagcg gcgctgatat  15900
gaccccccaaa catcccacgt ctcttcggat tttagcgcct cgtgatcgtc ttttggaggc  15960
tcgattaacg cgggcaccag cgattgagca gctgtttcaa cttttcgcac gtagccgttt  16020
gcaaaaccgc cgatgaaatt accggtgttg taagcggaga tcgcccgacg aagcgcaaat  16080
tgcttctcgt caatcgtttc gccgcctgca taacgacttt tcagcatgtt tgcagcggca  16140
gataatgatg tgcacgcctg gagcgcaccg tcaggtgtca gaccgagcat agaaaaattt  16200
cgagagttta tttgcatgag gccaacatcc agcgaatgcc gtgcatcgag acggtgcctg  16260
acgacttggg ttgcttggct gtgatcttgc cagtgaagcg tttcgccggt cgtgttgtca  16320
tgaatcgcta aaggatcaaa gcgactctcc accttagcta tcgccgcaag cgtagatgtc  16380
gcaactgatg gggcacactt gcgagcaaca tggtcaaact cagcagatga gagtggcgtg  16440
gcaaggctcg acgaacagaa ggagaccatc aaggcaagag aaagcgaccc cgatctctta  16500
agcataccttt atctccttag ctcgcaacta acaccgcctc tcccgttgga agaagtgcgt  16560
tgttttatgt tgaagattat cgggagggtc ggttactcga aaattttcaa ttgcttcttt  16620
atgatttcaa ttgaagcgag aaacctcgcc cggcgtcttg gaacgcaaca tggaccgaga  16680
accgcgcatc catgactaag caaccggatc gacctattca ggccgcagtt ggtcaggtca  16740
ggctcagaac gaaaatgctc ggcgaggtta cgctgtctgt aaacccattc gatgaacggg  16800
aagcttcctt ccgattgctc ttggcaggaa tattggccca tgcctgcttg cgcttttgcaa  16860
atgctcttat cgcgttggta tcatatgcct tgtccgccag cagaaacgca ctctaagcga  16920
ttatttgtaa aaatgtttcg gtcatgcggc ggtcatgggc ttgacccgct gtcagcgcaa  16980
gacggatcgg tcaaccgtcg gcatcgacaa cagcgtgaat cttggtggtc aaaccgccac  17040
gggaacgtcc catacagcca tcgtcttgat cccgctgttt cccgtcgccg catgttggtg  17100
gacgcggaca caggaactgt caatcatgac gacattctat cgaaagcctt ggaaatcaca  17160
ctcagaatat gatcccagac gtctgcctca cgccatcgta caaagcgatt gtagcaggtt  17220
gtacaggaac cgtatcgatc aggaacgtct gcccagggcg ggcccgtccg gaagcgccac  17280
aagatgacat tgatcacccg cgtcaacgcg cggcacgcga cgcggcttat ttgggaacaa  17340
aggactgaac aacagtccat tcgaaatcgg tgacatcaaa gcggggacgg ttatcagtg   17400
gcctccaagt caagcctcaa tgaatcaaaa tcagaccgat ttgcaaacct gatttatgag  17460
tgtgcggcct aaatgatgaa atcgtccttc tagatcgcct ccgtggtgta gcaacacctc  17520
gcagtatcgc cgtgctgacc ttggccaggg aattgactgg caagggtgct ttcacatgac  17580
cgctcttttg gccgcgatag atgatttcgt tgctgctttg ggcacgtaga aggagagaag  17640
tcatatcgga gaaattcctc ctggcgcgag agcctgctct atcgcgacgg catcccactg  17700
tcgggaacag accggatcat tcacgaggcg aaagtcgtca acacatgcgt tataggcatc  17760
ttcccttgaa ggatgatctt gttgctgcca atctggaggt gcggcagccg caggcagatg  17820
cgatctcagc gcaacttgcg gcaaaacatc tcactcacct gaaaaccact agcgagtctc  17880
gcgatcagac gaaggccttt tacttaacga cacaatatcc gatgtctgca tcacaggcgt  17940
cgctatccca gtcaatacta aagcggtgca ggaactaaag attactgatg acttaggcgt  18000
gccacgaggc ctgagacgac gcgcgtagac agttttttga aatcattatc aaagtgatgg  18060
cctccgctga agcctatcac ctctgcgccg gtctgtcgga gagatgggca agcattatta  18120
cggtcttcgc gcccgtacat gcattggacg attgcagggt caatggatct gagatcatcc  18180
```

```
agaggattgc cgcccttacc ttccgtttcg agttggagcc agcccctaaa tgagacgaca   18240
tagtcgactt gatgtgacaa tgccaagaga gagatttgct taacccgatt tttttgctca   18300
agcgtaagcc tattgaagct tgccggcatg acgtccgcgc cgaaagaata tcctacaagt   18360
aaaacattct gcacaccgaa atgcttggtg tagacatcga ttatgtgacc aagatcctta   18420
gcagtttcgc ttggggaccg ctccgaccag aaataccgaa gtgaactgac gccaatgaca   18480
ggaatccctt ccgtctgcag ataggtaccg gctggctagc gaattgacat gaggttgccc   18540
cgtattcagt gtcgctgatt tgtattgtct gaagttgttt ttacgttaag ttgatgcaga   18600
tcaattaata cgatacctgc gtcataattg attatttgac gtggtttgat ggcctccacg   18660
cacgttgtga tatgtagatg ataatcatta tcactttacg ggtcctttcc ggtgatccga   18720
caggttacgg ggcggcgacc tcgcgggttt tcgctattta tgaaaatttt ccggtttaag   18780
gcgtttccgt tcttcttcgt cataacttaa tgttttatt taaaatacccc tctgaaaaga   18840 aaggaaacga caggtgctga aagcgagctt tttggcctct gtcgtttcct ttctctgttt   18900
ttgtccgtgg aatgaacaat ggaaggatct tctcggcggc gatcacgacg ccggccctgc   18960
ggagccttcg ccgcgtgcgc gattcatggc ggccgtggag gccaaggatt cgcgcgagt   19020 gcaagagctg atcgaggcgc gtggagccaa gtcggcggct gattatgtcc ttgcgcagct   19080
cgccgtggcc gaaggtctgg accgcaagcc tggtgcgcgc gtcgtggtcg ggaaagcggc   19140
gggcagcatg gcaatgccgc ctgcggcgct gggttttacg ccaaggggag aagcggcata   19200
cgccatcgag cggtcagcct atggtgagcc gaggtccagc attgcgaagc agtaccagca   19260
ggaatggaac cggaaggcgg cgacctggtg ggcgatggcc ggtgtggccg gcatcatcgg   19320
cgcgatcctg gcggcggcgg caaccggctt tgttgggctg gcagtgtcga tccgcaaccg   19380
agtgaagcgc gtgcgcgacc tgttggtgat ggagccgggt gcagagccat aagcggcaag   19440
agacgaaagc ccggtttccg ggcttttgtt ttgttacgcc aaggacgagt tttagcggct   19500
aaaggtgttg acgtgcgaga atgtttagc taaacttctc tcatgtgctg gcggctgtca   19560
ccgctatgtt caaccaaggc gcggagcaaa ttatgggtgt tatccatgaa gaaacggctt   19620
accgaaagcc agttccagga ggcgatccag gggctggaag tggggcagca gaccatcgag   19680
atagcgcggg gcgtcttagt cgatgggaag ccacaggcga cgttcgcaac gtcgctggga   19740
ctgaccaggg gcgcagtgtc gcaagcggtg catcgcgtgt gggccgcgtt cgaggacaag   19800
aacttgcccg agggggtacgc gcgggtaacg gcggttctgc cggaacatca ggcgtacatc   19860
gtccggaagt gggaagcgga cgccaagaaa aacaggaaa ccaaacgatg aaaactttgg   19920
tcacggccaa ccagaaaggc ggcgtcggca agacttcgac ccttgtgcat cttgccttcg   19980 acttttcga gcgcggcttg cgggttgccg tgatcgacct ggaccccag gcaatgcgt   20040 cctacacgct caaggacttt gctaccggcc tgcatgcaag caagctgttc ggcgctgtcc   20100
ctgccggcgc ctggaccgaa accgcacccg cagccggcga cggccaggcc gcgcgcctcg   20160
ccctcatcga gtccaacccg gtactggcga acgccgaacg gctgtcgctg gacgacgccc   20220
gcgagctgtt cggggcgaac atcaaggccc tggcgaacca aggcttcgac gtgtgcctga   20280
tcgacacggc cccgacccctt ggcgtcggcc tggcggccgc cctcttcgcg ccgactatg   20340 tgctgtcccc catcgagctt gaggcgtaca gcatccaggg catcaagaag atggtcacga   20400
ccattgcgaa cgtgcgccag aagaacgcca agctgcaatt ccttggcatg gtgcccagca   20460
aggtcgatgc gcggaatccg cgccacgcgc gccaccaagc cgagctgctg gccgcgtacc   20520
ccaagatgat gattccggcc accgttggcc tgcgcagcag catcgccgat gccctcgcat   20580
```

```
ccggtgtgcc ggtctggaag atcaagaaaa cggccgcgcg caaggcatcg aaagaggttc   20640
gcgccctggc tgattacgtg ttcacgaaga tggagatttc ccaatgactg cggctcaagc   20700
caagaccacc aagaaaaaca ccgctgcggc cgctcaggaa gccgcaggcg cggcgcagcc   20760
gtccggcctg gggttggata gcatcggcga cctgtcgagc ctcctggacg ctcctgcggc   20820
gtctcagggc ggttccggcc ctatcgagct ggacctggac ctgatcgacg aagatccgca   20880
tcagccgcgg acgccgaca accccggctt ttccccggag agcatcgcgg aaatcggtgc   20940
cacgatcaaa gagcgcgggg tgaagtcacc catttcggtg cgcgagaacc aggagcagcc   21000
gggccgctat atcatcaatc acggcgcccg ccgctaccgt ggctcgaatc tagtgatatt   21060
ccacaaaaca gcagggaagc agcgcttttc cgctgcataa ccctgcttcg gggtcattat   21120
agcgattttt tcggtatatc catccttttt cgcacgatat acaggatttt gccaaagggt   21180
tcgtgtagac tttccttggt gtatccaacg gcgtcagccg ggcaggatag gtgaagtagg   21240
cccacccgcg agcgggtgtt ccttcttcac tgtcccttat tcgcacctgg cggtgctcaa   21300
cgggaatcct gctctgcgag gctggccggc taccgccggc gtaacagatg agggcaagcg   21360
gatggctgat gaaaccaagc caaccaggaa gggcagccca cctatcaagg tgtactgcct   21420
tccagacgaa cgaagagcga ttgaggaaaa ggcggcggcg gccggcatga gcctgtcggc   21480
ctacctgctg gccgtcggcc agggctacaa aatcacgggc gtcgtggact atgagcacgt   21540
ccgcgagctg gcccgcatca atggcgacct gggccgcctg gcggcctgc tgaaactctg   21600 gctcaccgac gacccgcgca cggcgcggtt cggtgatgcc acgatcctcg ccctgctggc   21660
gaagatcgaa gagaagcagg acgagcttgg caaggtcatg atgggcgtgg tccgcccgag   21720
ggcagagcca tgacttttttt agccgctaaa acggccgggg ggtgcgcgtg attgccaagc   21780
acgtccccat gcgctccatc aagaagagcg acttcgcgga gctggtgaag tacatcaccg   21840
acgagcaagg caagaccgag cgccagatcc aaaacaactg tcaaagcgca cccgcccgat   21900
gccattcgcg gcacggcttc cgttgaggat gtcgatatga tgcgcgagcc gacggcccgc   21960
agagaagggg ccgttttagc ggctaaagaa ggaagtgcaa gccctaaccc ttggcgtcag   22020
agccttccac gcagcttttt tcgggtgtcg tcgccccatt tctttacgat aaacgcctta   22080
tgtgacggca aaaccacact gatgcgttcg tatccgggcg gcacgctgct cttgaaagga   22140
tgacccgcaa tctccgcgag tgcctcgcgg tcaaggtcgg tggactccag gagaagaggt   22200
aggggagttt ccagggcgtc ggcaatggcc tccatcacct tcaacgaggg gttggcctta   22260
ccgttggtta agtctgataa aaacgaaatt gaaacccctg ccctctccga cagctcatgt   22320
ttcgtcatgc cccgctcatc gagcagacga aggatgttgg tgaaaaatat ctggttgtac   22380
acagcggaag ccgcccctcg cacctttggt cgcggcccgc aaaatttag ccgctaaagt   22440 tcttgacagc ggaaccaatg tttagctaaa ctagagtctc cttctcaag gagactttcg   22500 atatgagcca taatcagttc cagtttatcg gtaatcttac ccgtgacacc gaggtacgtc   22560
atggcaattc taacaagccg caagcaattt tcgatatagc ggttaatgaa gagtggcgca   22620
acgatgccgg cgacaagcag gagcgcaccg acttcttccg catcaagtgt tttggctctc   22680
aggccgaggc ccacggcaag tatttgggca aggggtcgct ggtattcgtg cagggcaaga   22740
ttcggaatac caagtacgag aaggacggcc agacggtcta cggaccgac ttcattgccg   22800 ataaggtgga ttatctggac accaaggcac caggcgggtc aaatcaggaa taagggcaca   22860
ttgccccggc gtgagtcggg gcaatccgc aaggagggtg aatgaatcgg acgtttgacc   22920
ggaaggcata caggcaagaa ctgatcgacg cggggttttc cgccgaggat gccgaaacca   22980
```

```
tcgcaagccg caccgtcatg cgtgcgcccc gcgaaacctt ccagtccgtc ggctcgatgg   23040
tccagcaagc tacggccaag atcgagcgcg acagcgtgca actggctccc cctgccctgc   23100
ccgcgccatc ggccgccgtg gagcgttcgc gtcgtctcga acaggaggcg gcaggtttgg   23160
cgaagtcgat gaccatcgac acgcgaggaa ctatgacgac caagaagcga aaaaccgccg   23220
gcgaggacct ggcaaaacag gtcagcgagg ccaagcaggc cgcgttgctg aaacacacga   23280
agcagcagat caaggaaatg cagctttcct tgttcgatat tgcgccgtgg ccggacacga   23340
tgcgagcgat gccaaacgac acggcccgct ctgccctgtt caccacgcgc aacaagaaaa   23400
tcccgcgcga ggcgctgcaa acaaggtca ttttccacgt caacaaggac gtgaagatca   23460
cctacaccgg cgtcgagctg cgggccgacg atgacgaact ggtgtggcag caggtgttgg   23520
agtacgcgaa gcgcacccct atcggcgagc cgatcacctt cacgttctac gagctttgcc   23580
aggacctggg ctggtcgatc aatggccggt attacacgaa ggccgaggaa tgcctgtcgc   23640
gcctacaggc gacggcgatg ggcttcacgt ccgaccgcgt tgggcacctg gaatcggtgt   23700
cgctgctgca ccgcttccgc gtcctggacc gtggcaagaa acgtcccgt tgccaggtcc   23760
tgatcgacga ggaaatcgtc gtgctgtttg ctggcgacca ctacacgaaa ttcatatggg   23820
agaagtaccg caagctgtcg ccgacggccc gacggatgtt cgactatttc agctcgcacc   23880
gggagccgta cccgctcaag ctggaaacct tccgcctcat gtgcggatcg gattccaccc   23940
gcgtgaagaa gtggcgcgag caggtcggcg aagcctgcga agagttgcga ggcagcggcc   24000
tggtggaaca cgcctgggtc aatgatgacc tggtgcattg caaacgctag gccttgtgg   24060
ggtcagttcc ggctggggt tcagcagcca gcgctttact ggcatttcag gaacaagcgg   24120
gcactgctcg acgcacttgc ttcgctcagt atcgctcggg acgcacggcg cgctctacga   24180
actgccgata aacagaggat taaaattgac aattgtgatt aaggctcaga ttcgacggct   24240
tggagcggcc gacgtgcagg atttccgcga gatccgattg tcggccctga agaaagctcc   24300
agagatgttc gggtccgttt acgagcacga ggagaaaaag cccatggagg cgttcgctga   24360
acggttgcga gatgccgtgg cattcggcgc ctacatcgac ggcgagatca ttgggctgtc   24420
ggtcttcaaa caggaggacg gccccaagga cgctcacaag gcgcatctgt ccggcgtttt   24480
cgtggagccc gaacagcgag gccgaggggt cgccggtatg ctgctgcggg cgttgccggc   24540
gggtttattg ctcgtgatga tcgtccgaca gattccaacg ggaatctggt ggatgcgcat   24600
cttcatcctc ggcgcactta atatttcgct attctggagc ttgttgttta tttcggtcta   24660
ccgcctgccg ggcgggtcgc ggcgacggta ggcgctgtgc agccgctgat ggtcgtgttc   24720
atctctgccg ctctgctagg tagcccgata cgattgatgg cggtcctggg ggctatttgc   24780
ggaactgcgg gcgtggcgct gttggtgttg acaccaaacg cagcgctaga tcctgtcggc   24840
gtcgcagcgg gcctggcggg ggcggtttcc atggcgttcg gaaccgtgct gacccgcaag   24900
tgcaacctc ccgtgcctct gctcacctt accgcctggc aactggcggc cggaggactt   24960
ctgctcgttc cagtagcttt agtgtttgat ccgccaatcc cgatgcctac aggaaccaat   25020
gttctcggct gctcgactgc acgaatacca gcgaccccttgcccaaatac ttgccgtggg   25080
cctcggcctg agagccaaaa cacttgatgc ggaagaagtc ggtgcgctcc tgcttgtcgc   25140
cggcatcgtt gcgccacatc taggtactaa aacaattcat ccagtaaaat ataatatttt   25200
attttctccc aatcaggctt gatccccagt aagtcaaaaa atagctcgac atactgttct   25260
tccccgatat cctccctgat cgaccggacg cagaaggcaa tgtcatacca cttgtccgcc   25320
ctgccgcttc tcccaagatc aataaagcca cttactttgc catctttcac aaagatgttg   25380
```

```
ctgtctccca ggtcgccgtg ggaaaagaca agttcctctt cgggcttttc cgtctttaaa   25440
aaatcataca gctcgcgcgg atctttaaat ggagtgtctt cttcccagtt ttcgcaatcc   25500
acatcggcca gatcgttatt cagtaagtaa tccaattcgg ctaagcggct gtctaagcta   25560
ttcgtatagg gacaatccga tatgtcgatg gagtgaaaga gcctgatgca ctccgcatac   25620
agctcgataa tcttttcagg gctttgttca tcttcatact cttccgagca aaggacgcca   25680
tcggcctcac tcatgagcag attgctccag ccatcatgcc gttcaaagtg caggaccttt   25740
ggaacaggca gctttccttc cagccatagc atcatgtcct tttcccgttc cacatcatag   25800
gtggtccctt tataccggct gtccgtcatt tttaaatata ggttttcatt ttctcccacc   25860
agcttatata ccttagcagg agacattcct tccgtatctt ttacgcagcg gtatttttcg   25920
atcagttttt tcaattccgg tgatattctc atttttagcca tttattattt ccttcctctt   25980
ttctacagta tttaaagata ccccaagaag ctaattataa caagacgaac tccaattcac   26040
tgttccttgc attctaaaac cttaaatacc agaaaacagc ttttcaaag ttgttttcaa   26100 agttggcgta taacatagta tcgattcgat agcgtggact caaggctctc gcgaatggct   26160
cgcgttggaa actttcattg acacttgagg ggcaccgcag ggaaattctc gtccttgcga   26220
gaaccggcta tgtcgtgctg cgcatcgagc ctgcgccctt ggcttgtctc gccctctcc   26280 gcgtcgctac ggggcttcca cgcctttcc gacgctcacc gggctggttg ccctcgccgc   26340
tgggctggcg gccgtctatg gccctgcaaa cgcgccagaa acgccgtcga agccgtgtgc   26400
gagacaccgc ggccgccggc gttgtggata cctcgcggaa aacttggccc tcactgacag   26460
atgaggggcg gacgttgaca cttgaggggc cgactcaccc ggcgcggcgt tgacagatga   26520
ggggcaggct cgatttcggc cggcgacgtg gagctggcca gcctcgcaaa tcggcgaaaa   26580
cgcctgattt tacgcgagtt tcccacagat gatgtggaca agcctgggga taagtgccct   26640
gcggtattga cacttgaggg gcgcgactac tgacagatga ggggcgcgat ccttgacact   26700
tgaggggcag agtgctgaca gatgaggggc gcacctattg acatttgagg ggctgtccac   26760
aggcagaaaa tccagcattt gcaagggttt ccgcccgttt ttcggccacc gctaacctgt   26820
cttttaacct gcttttaaac caatatttat aaaccttgtt tttaaccagg gctgcgccct   26880
gtgcgcgtga ccgcgcacgc cgaaggggggg tgccccccct tctcgaaccc tcccggcccg   26940
ctaacgcggg cctcccatcc ccccagggggc tgcgcccctc ggccgcgaac ggcctcaccc   27000
caaaaatggc agcgccagcc atttattatt gaagcattta tcagggttat tgtctcatga   27060
gcggatacat atttgaatgt atttagaaaa ataaacaaat aggggttccg cgcacatttc   27120
cccgaaaagt gccacctgac gtctaagaaa ccattattat catgacatta acctataaaa   27180
ataggcgtat cacgaggccc tttcgtcttc aagaattggt cgacgatctt gctgcgttcg   27240
gatattttcg tggagttccc gccacagacc cggattgaag gcgagatcca gcaactcgcg   27300
ccagatcatc ctgtgacgga actttggcgc gtgatgactg gccaggacgt cggccgaaag   27360
agcgacaagc agatcacgct tttcgacagc gtcggatttg cgatcgagga ttttccggcg   27420
ctgcgctacg tccgcgaccg cgttgaggga tcaagccaca gcagcccact cgaccttcta   27480
gccgacccag acgagccaag ggatcttttt ggaatgctgc tccgtcgtca ggctttccga   27540
cgtttgggtg gttgaacaga agtcattatc gcacggaatg ccaagcactc ccagggggaa   27600
ccctgtggtt ggcatgcaca tacaaatgga cgaacggata aaccttttca cgcccttta   27660 aatatccgat tattctaata aacgctcttt tctcttaggt ttacccgcca atatatcctg   27720
tcaaacactg atagtttaaa ctgaaggcgg gaaacgacaa tctgatcatg agcggagaat   27780
```

```
taagggagtc acgttatgac ccccgccgat gacgcgggac aagccgtttt acgtttggaa    27840
ctgacagaac cgcaacgttg aaggagccac tcagc                               27875
```

<210> SEQ ID NO 7
<211> LENGTH: 14222
<212> TYPE: DNA
<213> ORGANISM: Artificial Sequence
<220> FEATURE:
<223> OTHER INFORMATION: Synthetic vector: pLC40GWHvG1
<220> FEATURE:
<221> NAME/KEY: misc_feature
<222> LOCATION: (48)..(70)
<223> OTHER INFORMATION: I-SceI
<220> FEATURE:
<221> NAME/KEY: misc_feature
<222> LOCATION: (90)..(989)
<223> OTHER INFORMATION: P ubi1
<220> FEATURE:
<221> NAME/KEY: misc_feature
<222> LOCATION: (1073)..(2082)
<223> OTHER INFORMATION: Ubi I
<220> FEATURE:
<221> NAME/KEY: misc_feature
<222> LOCATION: (2103)..(2127)
<223> OTHER INFORMATION: attB1
<220> FEATURE:
<221> NAME/KEY: misc_feature
<222> LOCATION: (2137)..(3162)
<223> OTHER INFORMATION: hpt
<220> FEATURE:
<221> NAME/KEY: misc_feature
<222> LOCATION: (3163)..(3187)
<223> OTHER INFORMATION: (complement) attB2
<220> FEATURE:
<221> NAME/KEY: misc_feature
<222> LOCATION: (3207)..(3482)
<223> OTHER INFORMATION: Tnos
<220> FEATURE:
<221> NAME/KEY: misc_feature
<222> LOCATION: (3541)..(3565)
<223> OTHER INFORMATION: Left Border of T-DNA
<220> FEATURE:
<221> NAME/KEY: misc_feature
<222> LOCATION: (4024)..(5069)
<223> OTHER INFORMATION: virG
<220> FEATURE:
<221> NAME/KEY: misc_feature
<222> LOCATION: (5155)..(5185)
<223> OTHER INFORMATION: ICeuI
<220> FEATURE:
<221> NAME/KEY: misc_feature
<222> LOCATION: (5192)..(5599)
<223> OTHER INFORMATION: (complement) cos
<220> FEATURE:
<221> NAME/KEY: misc_feature
<222> LOCATION: (5600)..(7718)
<223> OTHER INFORMATION: (complement) IncC1
<220> FEATURE:
<221> NAME/KEY: misc_feature
<222> LOCATION: (7720)..(8541)
<223> OTHER INFORMATION: (complement) oriT
<220> FEATURE:
<221> NAME/KEY: misc_feature
<222> LOCATION: (8536)..(11706)
<223> OTHER INFORMATION: (complement) trfA1
<220> FEATURE:
<221> NAME/KEY: misc_feature
<222> LOCATION: (11703)..(12799)
<223> OTHER INFORMATION: nptIII
<220> FEATURE:
<221> NAME/KEY: misc_feature
<222> LOCATION: (12796)..(13688)
<223> OTHER INFORMATION: (complement) oriV
<220> FEATURE:
<221> NAME/KEY: misc_feature
<222> LOCATION: (14046)..(14070)
<223> OTHER INFORMATION: RB

<400> SEQUENCE: 7

```
aagcttgcgg ccgcttcgaa gatgttaatt aacatcggta ccgagctcta gggataacag      60
ggtaatagct cgaattctag cttgcatgcc tgcagtgcag cgtgacccgg tcgtgcccct     120
ctctagagat aatgagcatt gcatgtctaa gttataaaaa attaccacat attttttttg     180
tcacacttgt ttgaagtgca gtttatctat ctttatacat atatttaaac tttactctac     240
gaataatata atctatagta ctacaataat atcagtgttt tagagaatca tataaatgaa     300
cagttagaca tggtctaaag gacaattgag tattttgaca acaggactct acagttttat     360
cttttagtg tgcatgtgtt ctccttttt tttgcaaata gcttcaccta tataatactt      420
catccatttt attagtacat ccatttaggg tttagggtta atggttttta tagactaatt     480
tttttagtac atctatttta ttctattta gcctctaaat taagaaaact aaaactctat     540
tttagttttt ttatttaata atttagatat aaaatagaat aaaataaagt gactaaaaat     600
taaacaaata ccctttaaga aattaaaaaa actaaggaaa cattttttctt gtttcgagta     660
gataatgcca gcctgttaaa cgccgtcgac gagtctaacg gacaccaacc agcgaaccag     720
cagcgtcgcg tcgggccaag cgaagcagac ggcacggcat ctctgtcgct gcctctggac     780
ccctctcgag agttccgctc caccgttgga cttgctccgc tgtcggcatc cagaaattgc     840
gtggcggagc ggcagacgtg agccggcacg gcaggcggcc tcctcctcct ctcacggcac     900
cggcagctac gggggattcc tttcccaccg ctccttcgct ttcccttcct cgcccgccgt     960
aataaataga caccccctcc acaccctctt tccccaacct cgtgttgttc ggagcgcaca    1020
cacacacaac cagatctccc ccaaatccac ccgtcggcac ctccgcttca aggtacgccg    1080
ctcgtcctcc cccccccccc ctctctacct tctctagatc ggcgttccgg tccatggtta    1140
gggcccggta gttctacttc tgttcatgtt tgtgttagat ccgtgtttgt gttagatccg    1200
tgctgctagc gttcgtacac ggatgcgacc tgtacgtcag acacgttctg attgctaact    1260
tgccagtgtt tctctttggg gaatcctggg atggctctag ccgttccgca gacgggatcg    1320
atttcatgat ttttttttgtt tcgttgcata gggtttggtt tgccctttc ctttatttca    1380
atatatgccg tgcacttgtt tgtcgggtca tcttttcatg cttttttttg tcttggttgt    1440
gatgatgtgg tctggttggg cggtcgttct agatcggagt agaattctgt ttcaaactac    1500
ctggtggatt tattaatttt ggatctgtat gtgtgtgcca tacatattca tagttacgaa    1560
ttgaagatga tggatggaaa tatcgatcta ggataggtat acatgttgat gcgggttta     1620
ctgatgcata tacagagatg cttttttgttc gcttggttgt gatgatgtgg tgtggttggg    1680
cggtcgttca ttcgttctag atcggagtag aatactgttt caaactacct ggtgtattta    1740
ttaattttgg aactgtatgt gtgtgtcata catcttcata gttacgagtt taagatggat    1800
ggaaatatcg atctaggata ggtatacatg ttgatgtggg ttttactgat gcatatacat    1860
gatggcatat gcagcatcta ttcatatgct ctaaccttga gtacctatct attataataa    1920
acaagtatgt tttataatta ttttgatctt gatatacttg gatgatggca tatgcagcag    1980
ctatatgtgg attttttag ccctgccttc atacgctatt tatttgcttg gtactgtttc     2040
ttttgtcgat gctcaccctg ttgtttggtg ttacttctgc aggtcgactc tagaggatca    2100
tcacaagttt gtacaaaaaa gcaggctcaa tgagatatga aaaagcctga actcaccgcg    2160
acgtctgtcg agaagtttct gatcgaaaag ttcgacagcg tctccgacct gatgcagctc    2220
tcggagggcg aagaatctcg tgctttcagc ttcgatgtag gagggcgtgg atatgtcctg    2280
cgggtaaata gctgcgccga tggtttctac aaagatcgtt atgtttatcg gcactttgca    2340
```

```
tcggccgcgc tcccgattcc ggaagtgctt gacattgggg aattcagcga gagcctgacc    2400
tattgcatct cccgccgtgc acagggtgtc acgttgcaag acctgcctga aaccgaactg    2460
cccgctgttc tgcagccggt cgcggaggcc atggatgcga tcgctgcggc cgatcttagc    2520
cagacgagcg ggttcggccc attcggaccg caaggaatcg gtcaatacac tacatggcgt    2580
gatttcatat gcgcgattgc tgatccccat gtgtatcact ggcaaactgt gatggacgac    2640
accgtcagtg cgtccgtcgc gcaggctctc gatgagctga tgctttgggc cgaggactgc    2700
cccgaagtcc ggcacctcgt gcacgcggat ttcggctcca acaatgtcct gacggacaat    2760
ggccgcataa cagcggtcat tgactggagc gaggcgatgt cggggattc ccaatacgag    2820 gtcgccaaca tcttcttctg gaggccgtgg ttggcttgta tggagcagca gacgcgctac    2880
ttcgagcgga ggcatccgga gcttgcagga tcgccgcggc tccgggcgta tgctccgc      2940 attggtcttg accaactcta tcagagcttg gttgacggca atttcgatga tgcagcttgg    3000
gcgcagggtc gatgcgacgc aatcgtccga tccggagccg ggactgtcgg gcgtacacaa    3060
atcgcccgca gaagcgcggc cgtctggacc gatggctgtg tagaagtact cgccgatagt    3120
ggaaaccgac gccccagcac tcgtccgagg gcaaaggaat agaccagct tcttgtaca     3180 aagtggtgat gatccgtcga cctgcagatc gttcaaacat ttggcaataa agtttcttaa    3240
gattgaatcc tgttgccggt cttgcgatga ttatcatata atttctgttg aattacgtta    3300
agcatgtaat aattaacatg taatgcatga cgttatttat gagatgggtt tttatgatta    3360
gagtcccgca attatacatt taatacgcga tagaaaacaa aatatagcgc gcaaactagg    3420
ataaattatc gcgcgcggtg tcatctatgt tactagatcc gatgataagc tgtcaaacat    3480
gagaattcag tacattaaaa acgtccgcaa tgtgttatta agttgtctaa gcgtcaattt    3540
gtttacacca caatatatcc tgccaccagc cagccaacag ctccccgacc ggcagctcgg    3600
cacaaaatca ccactcgata caggcagccc atcagtccgg gacggcgtca gcggagagc    3660 cgttgtaagg cggcagactt tgctcatgtt accgatgcta ttcggaagaa cggcaactaa    3720
gctgccgggt ttgaaacacg gatgatctcg cggagggtag catgttgatt gtaacgatga    3780
cagagcgttg ctgcctgtga tcaaatatca tctcccctcgc agagatccga attatcagcc    3840
ttcttattca tttctcgctt aaccgtgaca ggctgtcgat cttgagaact atgccgacat    3900
aataggaaat cgctggataa agccgctgag gaagctgagt ggcgctattt ctttagaagt    3960
gaacgttgac gatcgtcgac cgtaccccga tgaattaatt cggacgtacg ttctgaacac    4020
aggactagtg taacctcgaa gcgtttcact tgtaacaacg attgagaact tttgtcataa    4080
aattgaaata cttggttcgc attttcgtca tccgcggtca gccgcaattc tgacgaactg    4140
cccatttagc tggagatgat tgtacatcct tcacgtgaaa atttctcaag cgctgtgaac    4200
aagggttcag attttagatt gaaaggtgag ccgttgaaac acgttcttct tatcgatgac    4260
gatgtcgcta tgcggcatct tattatcgaa taccttacga tccacgcctt caaagtgacc    4320
gcggtagccg acagcaccca gttcactaga gtactctctt ccgcgacggt cgatgtcgtg    4380
gttgttgatc taaatttagg tcgtgaagat gggcttgaga tcgttcgaaa tctggcggca    4440
aagtctgata ttccaatcat aattatcagt ggcgaccgcc ttgaggagac ggataaagtt    4500
gttgcactcg agctaggagc aagtgatttt atcgctaagc cgtttagtac gagagagttt    4560
cttgcacgca ttcgggttgc cttgcgcgtg cgccccaacg ttgtccgctc caaagaccga    4620
cggtcttttt gttttactga ctggacactt aatctcaggc aacgtcgctt gatgtccgaa    4680
gctggcggtg aggtgaaact tacggcaggt gagttcaatc ttctcctcgc gttttagag     4740
```

```
aaaccccgcg acgttctatc gcgcgagcaa cttctcattg ccagtcgagt acgcgacgag    4800
gaggtttacg acaggagtat agatgttctc attttgcggc tgcgccgcaa acttgaggcg    4860
gatccgtcaa gccctcaact gataaaaaca gcaagaggtg ccggttattt ctttgacgcg    4920
gacgtgcagg tttcgcacgg ggggacgatg gcagcctgag ccaattgcat ttggctctta    4980
attatctggc tcaaaaggtg actgaggacg cggccagcgg cctcaaacct acactcaata    5040
tttggtgagg ggttccgata ggtactagtc ctggatactt acttgggcga ttgtcataca    5100
tgacatcaac aatgtacccg tttgtgtaac cgtctcttgg aggttcgtat gacactaggt    5160
cgctaccttá ggaccgttat agttactagc gaattgacat gaggttgccc cgtattcagt    5220
gtcgctgatt tgtattgtct gaagttgttt ttacgttaag ttgatgcaga tcaattaata    5280
cgatacctgc gtcataattg attatttgac gtggtttgat ggcctccacg cacgttgtga    5340
tatgtagatg ataatcatta tcactttacg ggtccttttcc ggtgatccga caggttacgg    5400
ggcggcgacc tcgcgggttt tcgctattta tgaaaatttt ccggtttaag gcgtttccgt    5460
tcttcttcgt cataacttaa tgttttttatt taaaataccc tctgaaaaga aaggaaacga    5520
caggtgctga aagcgagctt tttggcctct gtcgtttcct ttctctgttt ttgtccgtgg    5580
aatgaacaat ggaaggatct tctcggcggc gatcacgacg ccggccctgc ggagccttcg    5640
ccgcgtgcgc gattcatggc ggccgtggag gccaaggatt tcgcgcgagt gcaagagctg    5700
atcgaggcgc gtggagccaa gtcggcggct gattatgtcc ttgcgcagct cgccgtggcc    5760
gaaggtctgg accgcaagcc tggtgcgcgc gtcgtggtcg ggaaagcggc gggcagcatg    5820
gcaatgccgc ctgcggcgct gggttttacg ccaagggggag aagcggcata cgccatcgag    5880
cggtcagcct atggtgagcc gaggtccagc attgcgaagc agtaccagca ggaatggaac    5940
cggaaggcgg cgacctggtg ggcgatggcc ggtgtggccg gcatcatcgg cgcgatcctg    6000
gcggcggcgg caaccggctt tgttgggctg gcagtgtcga tccgcaaccg agtgaagcgc    6060
gtgcgcgacc tgttggtgat ggagccgggt gcagagccat aagcggcaag agacgaaagc    6120
ccggtttccg ggcttttgtt ttgttacgcc aaggacgagt tttagcggct aaaggtgttg    6180
acgtgcgaga aatgtttagc taaacttctc tcatgtgctg gcggctgtca ccgctatgtt    6240
caaccaaggc gcggagcaaa ttatgggtgt tatccatgaa gaaacggctt accgaaagcc    6300
agttccagga ggcgatccag gggctggaag tggggcagca gaccatcgag atagcgcggg    6360
gcgtcttagt cgatgggaag ccacaggcga cgttcgcaac gtcgctggga ctgaccaggg    6420
gcgcagtgtc gcaagcggtg catcgcgtgt gggccgcgtt cgaggacaag aacttgcccg    6480
aggggtacgc gcgggtaacg gcggttctgc cggaacatca ggcgtacatc gtccggaagt    6540
gggaagcgga cgccaagaaa aaacaggaaa ccaaacgatg aaaactttgg tcacggccaa    6600
ccagaaaggc ggcgtcggca agacttcgac ccttgtgcat cttgccttcg acttttttcga    6660
gcgcggcttg cgggttgccg tgatcgacct ggaccccag gcaatgcgt cctacacgct     6720
caaggacttt gctaccggcc tgcatgcaag caagctgttc ggcgctgtcc ctgccggcgg    6780
ctggaccgaa accgcacccg cagcggcga cggccaggcc gcgcgcctcg ccctcatcga    6840
gtccaacccg gtactggcga acgccgaacg gctgtcgctg gacgacgccc gcgagctgtt    6900
cggggcgaac atcaaggccc tggcgaacca aggcttcgac gtgtgcctga tcgacacggc    6960
cccgacccctt ggcgtcggcc tggcggccgc cctcttcgcg gccgactatg tgctgtcccc    7020
catcgagctt gaggcgtaca gcatccaggg catcaagaag atggtcacga ccattgcgaa    7080
cgtgcgccag aagaacgcca agctgcaatt ccttggcatg gtgcccagca aggtcgatgc    7140
```

```
gcggaatccg cgccacgcgc gccaccaagc cgagctgctg gccgcgtacc ccaagatgat   7200
gattccggcc accgttggcc tgcgcagcag catcgccgat gccctcgcat ccggtgtgcc   7260
ggtctggaag atcaagaaaa cggccgcgcg caaggcatcg aaagaggttc gcgccctggc   7320
tgattacgtg ttcacgaaga tggagatttc ccaatgactg cggctcaagc caagaccacc   7380
aagaaaaaca ccgctgcggc cgctcaggaa gccgcaggcg cggcgcagcc gtccggcctg   7440
gggttggata gcatcggcga cctgtcgagc ctcctggacg ctcctgcggc gtctcagggc   7500
ggttccggcc ctatcgagct ggacctggac ctgatcgacg aagatccgca tcagccgcgg   7560
acggccgaca accccggctt ttccccggag agcatcgcgg aaatcggtgc cacgatcaaa   7620
gagcgcgggg tgaagtcacc catttcggtg cgcgagaacc aggagcagcc gggccgctat   7680
atcatcaatc acggcgcccg ccgctaccgt ggctcgaatc tagtgatatt ccacaaaaca   7740
gcagggaagc agcgcttttc cgctgcataa ccctgcttcg gggtcattat agcgattttt   7800
tcggtatatc catccttttt cgcacgatat acaggatttt gccaaagggt tcgtgtagac   7860
tttccttggt gtatccaacg cgtcagccg ggcaggatag gtgaagtagg cccacccgcg   7920
agcgggtgtt ccttcttcac tgtcccttat tcgcacctgg cggtgctcaa cgggaatcct   7980
gctctgcgag gctggccggc taccgccggc gtaacagatg agggcaagcg gatggctgat   8040
gaaaccaagc caaccaggaa gggcagccca cctatcaagg tgtactgcct tccagacgaa   8100
cgaagagcga ttgaggaaaa ggcggcggcg gccggcatga gcctgtcggc ctacctgctg   8160
gccgtcggcc agggctacaa aatcacgggc gtcgtggact atgagcacgt ccgcgagctg   8220
gcccgcatca atggcgacct gggccgcctg ggcggcctgc tgaaactctg gctcaccgac   8280
gacccgcgca cggcgcggtt cggtgatgcc acgatcctcg ccctgctggc gaagatcgaa   8340
gagaagcagg acgagcttgg caaggtcatg atgggcgtgg tccgcccgag ggcagagcca   8400
tgacttttt agccgctaaa acggccgggg ggtgcgcgtg attgccaagc acgtccccat   8460
gcgctccatc aagaagagcg acttcgcgga gctggtgaag tacatcaccg acgagcaagg   8520
caagaccgag cgccagatcc aaaacaactg tcaaagcgca cccgcccgat gccattcgcg   8580
gcacggcttc cgttgaggat gtcgatatga tgcgcgagcc gacggcccgc agagaagggg   8640
ccgttttagc ggctaaagaa ggaagtgcaa gccctaaccc ttggcgtcag agccttccac   8700
gcagcttttt tcgggtgtcg tcgcccatt tctttacgat aaacgcctta tgtgacggca   8760
aaaccacact gatgcgttcg tatccgggcg gcacgctgct cttgaaagga tgacccgcaa   8820
tctccgcgag tgcctcgcgg tcaaggtcgg tggactccag gagaagaggt aggggagttt   8880
ccagggcgtc ggcaatggcc tccatcacct tcaacgaggg gttggcctta ccgttggtta   8940
agtctgataa aaacgaaatt gaaaccctg ccctctccga cagctcatgt ttcgtcatgc   9000
cccgctcatc gagcagacga aggatgttgg tgaaaaatat ctggttgtac acagcggaag   9060
ccgccctcg cacctttggt cgcggcccgc aaaattttag ccgctaaagt tcttgacagc   9120
ggaaccaatg tttagctaaa ctagagtctc ctttctcaag gagactttcg atatgagcca   9180
taatcagttc cagtttatcg gtaatcttac ccgtgacacc gaggtacgtc atggcaattc   9240
taacaagccg caagcaattt tcgatatagc ggttaatgaa gagtggcgca acgatgccgg   9300
cgacaagcag gagcgcaccg acttcttccg catcaagtgt tttggctctc aggccgaggc   9360
ccacggcaag tatttgggca aggggtcgct ggtattcgtg cagggcaaga ttcggaatac   9420
caagtacgag aaggacggcc agacggtcta cgggaccgac ttcattgccg ataaggtgga   9480
ttatctggac accaaggcac caggcgggtc aaatcaggaa taagggcaca ttgccccggc   9540
```

```
gtgagtcggg gcaatcccgc aaggagggtg aatgaatcgg acgtttgacc ggaaggcata   9600
caggcaagaa ctgatcgacg cggggttttc cgccgaggat gccgaaacca tcgcaagccg   9660
caccgtcatg cgtgcgcccc gcgaaacctt ccagtccgtc ggctcgatgg tccagcaagc   9720
tacgccaag atcgagcgcg acagcgtgca actggctccc cctgccctgc ccgcgccatc    9780
ggccgccgtg gagcgttcgc gtcgtctcga acaggaggcg caggtttgg cgaagtcgat    9840
gaccatcgac acgcgaggaa ctatgacgac caagaagcga aaaccgccg gcgaggacct    9900
ggcaaaacag gtcagcgagg ccaagcaggc cgcgttgctg aaacacacga agcagcagat   9960
caaggaaatg cagctttcct tgttcgatat tgcgccgtgg ccggacacga tgcgagcgat  10020
gccaaacgac acggcccgct ctgccctgtt caccacgcgc aacaagaaaa tcccgcgcga  10080
ggcgctgcaa aacaaggtca ttttccacgt caacaaggac gtgaagatca cctacaccgg  10140
cgtcgagctg cgggccgacg atgacgaact ggtgtggcag caggtgttgg agtacgcgaa  10200
gcgcacccct atcggcgagc cgatcacctt cacgttctac gagctttgcc aggacctggg  10260
ctggtcgatc aatggccggt attacacgaa ggccgaggaa tgcctgtcgc gcctacaggc  10320
gacggcgatg ggcttcacgt ccgaccgcgt tgggcacctg gaatcggtgt cgctgctgca  10380
ccgcttccgc gtcctggacc gtggcaagaa aacgtcccgt tgccaggtcc tgatcgacga  10440
ggaaatcgtc gtgctgtttg ctggcgacca ctacacgaaa ttcatatggg agaagtaccg  10500
caagctgtcg ccgacggccc gacggatgtt cgactatttc agctcgcacc gggagccgta  10560
cccgctcaag ctggaaacct tccgcctcat gtgcggatcg gattccaccc gcgtgaagaa  10620
gtggcgcgag caggtcggcg aagcctgcga agagttgcga ggcagcggcc tggtggaaca  10680
cgcctgggtc aatgatgacc tggtgcattg caaacgctag ggccttgtgg ggtcagttcc  10740
ggctgggggt tcagcagcca gcgctttact ggcatttcag gaacaagcgg gcactgctcg  10800
acgcacttgc ttcgctcagt atcgctcggg acgcacggcg cgctctacga actgccgata  10860
aacagaggat taaaattgac aattgtgatt aaggctcaga ttcgacggct tggagcggcc  10920
gacgtgcagg atttccgcga gatccgattg tcggccctga agaaagctcc agagatgttc  10980
gggtccgttt acgagcacga ggagaaaaag cccatggagg cgttcgctga acggttgcga  11040
gatgccgtgg cattcggcgc ctacatcgac ggcgagatca ttgggctgtc ggtcttcaaa  11100
caggaggacg gccccaagga cgctcacaag gcgcatctgt ccggcgtttt cgtggagccc  11160
gaacagcgag gccgagggt cgccggtatg ctgctgcggg cgttgccggc gggtttattg   11220
ctcgtgatga tcgtccgaca gattccaacg ggaatctggt ggatgcgcat cttcatcctc  11280
ggcgcactta atatttcgct attctggagc ttgttgttta tttcggtcta ccgcctgccg  11340
ggcgggtcgc ggcgacggta ggcgctgtgc agccgctgat ggtcgtgttc atctctgccg  11400
ctctgctagg tagcccgata cgattgatgg cggtcctggg ggctatttgc ggaactgcgg  11460
gcgtggcgct gttggtgttg acaccaaacg cagcgctaga tcctgtcggc gtcgcagcgg  11520
gcctggcggg ggcggtttcc atggcgttcg gaaccgtgct gacccgcaag tggcaacctc  11580
ccgtgcctct gctcaccttt accgcctggc aactggcggc cggaggactt ctgctcgttc  11640
cagtagcttt agtgtttgat ccgccaatcc cgatgcctac aggaaccaat gttctcggct  11700
gctcgactgc acgaatacca gcgacccctt gcccaaatac ttgccgtggg cctcggcctg  11760
agagccaaaa cacttgatgc ggaagaagtc ggtgcgctcc tgcttgtcgc cggcatcgtt  11820
gcgccacatc taggtactaa aacaattcat ccagtaaaat ataatatttt attttctccc  11880
aatcaggctt gatccccagt aagtcaaaaa atagctcgac atactgttct tccccgatat  11940
```

```
cctccctgat cgaccggacg cagaaggcaa tgtcatacca cttgtccgcc ctgccgcttc    12000
tcccaagatc aataaagcca cttactttgc catctttcac aaagatgttg ctgtctccca    12060
ggtcgccgtg ggaaaagaca agttcctctt cgggcttttc cgtctttaaa aaatcataca    12120
gctcgcgcga atctttaaat ggagtgtctt cttcccagtt ttcgcaatcc acatcggcca    12180
gatcgttatt cagtaagtaa tccaattcgg ctaagcggct gtctaagcta ttcgtatagg    12240
gacaatccga tatgtcgatg gagtgaaaga gcctgatgca ctccgcatac agctcgataa    12300
tcttttcagg gctttgttca tcttcatact cttccgagca aaggacgcca tcggcctcac    12360
tcatgagcag attgctccag ccatcatgcc gttcaaagtg caggaccttt ggaacaggca    12420
gctttccttc cagccatagc atcatgtcct tttcccgttc cacatcatag gtggtccctt    12480
tataccggct gtccgtcatt tttaaatata ggttttcatt ttctcccacc agcttatata    12540
ccttagcagg agacattcct tccgtatctt ttacgcagcg gtattttcg atcagttttt    12600 tcaattccgg tgatattctc atttagcca tttattattt ccttcctctt ttctacagta    12660
tttaaagata ccccaagaag ctaattataa caagacgaac tccaattcac tgttccttgc    12720
attctaaaac cttaaatacc agaaaacagc tttttcaaag ttgttttcaa agttggcgta    12780
taacatagta tcgattcgat agcgtggact caaggctctc gcgaatggct cgcgttggaa    12840
actttcattg acacttgagg ggcaccgcag ggaaattctc gtccttgcga gaaccggcta    12900
tgtcgtgctg cgcatcgagc ctgcgccctt ggcttgtctc gccctctcc gcgtcgctac    12960 ggggcttcca gcgccttttcc gacgctcacc gggctggttg ccctcgccgc tgggctggcg    13020
gccgtctatg gccctgcaaa cgcgccagaa acgccgtcga agccgtgtgc gagacaccgc    13080
ggccgccggc gttgtggata cctcgcgaa aacttggccc tcactgacag atgaggggcg    13140
gacgttgaca cttgaggggc cgactcaccc ggcgcggcgt tgacagatga ggggcaggct    13200
cgatttcggc cggcgacgtg gagctggcca gcctcgcaaa tcggcgaaaa cgcctgattt    13260
tacgcgagtt tcccacagat gatgtggaca agcctgggga taagtgccct gcggtattga    13320
cacttgaggg gcgcgactac tgacagatga ggggcgcgat ccttgacact tgaggggcag    13380
agtgctgaca gatgaggggc gcacctattg acatttgagg ggctgtccac aggcagaaaa    13440
tccagcattt gcaagggttt ccgcccgttt ttcggccacc gctaacctgt ctttaacct    13500 gcttttaaac caatatttat aaaccttgtt tttaaccagg gctgcgccct gtgcgcgtga    13560
ccgcgcacgc cgaaggggg tgcccccct tctcgaaccc tcccggcccg ctaacgcggg    13620
cctcccatcc cccaggggc tgcgcccctc ggccgcgaac ggcctcaccc caaaaatggc    13680
agcgccagcc aggacgtcgg ccgaaagagc gacaagcaga tcacgctttt cgacagcgtc    13740
ggatttgcga tcgaggattt ttcggcgctg cgctacgtcc gcgaccgcgt tgagggatca    13800
agccacagca gcccactcga ccttctagcc gacccagacg agccaaggga tctttttgga    13860
atgctgctcc gtcgtcaggc tttccgacgt ttgggtggtt gaacagaagt cattatcgca    13920
cggaatgcca agcactcccg aggggaaccc tgtggttggc atgcacatac aaatggacga    13980
acggataaac cttttcacgc ccttttaaat atccgattat tctaataaac gctcttttct    14040
cttaggttta cccgccaata tatcctgtca aacactgata gtttaaactg aaggcgggaa    14100
acgacaatct gatcatgagc ggagaattaa gggagtcacg ttatgacccc cgccgatgac    14160
gcgggacaag ccgttttacg tttggaactg acagaaccgc aacgttgaag gagccactca    14220
gc                                                                  14222
```

<210> SEQ ID NO 8

```
<211> LENGTH: 4531
<212> TYPE: DNA
<213> ORGANISM: Artificial Sequence
<220> FEATURE:
<223> OTHER INFORMATION: Synthetic vector: pVGW
<220> FEATURE:
<221> NAME/KEY: misc_feature
<222> LOCATION: (1)..(1080)
<223> OTHER INFORMATION: virG N54D
<220> FEATURE:
<221> NAME/KEY: misc_feature
<222> LOCATION: (1081)..(3830)
<223> OTHER INFORMATION: IncW ori-containing region
<220> FEATURE:
<221> NAME/KEY: misc_feature
<222> LOCATION: (1770)..(2741)
<223> OTHER INFORMATION: IncW repA
<220> FEATURE:
<221> NAME/KEY: misc_feature
<222> LOCATION: (2832)..(3214)
<223> OTHER INFORMATION: IncW ori
<220> FEATURE:
<221> NAME/KEY: misc_feature
<222> LOCATION: (3831)..(4531)
<223> OTHER INFORMATION: gen (gentamycin acetyltransferase)

<400> SEQUENCE: 8
```

| | | | | | |
|---|---|---|---|---|---|
| tcgaccatag | gcgatctcct | taatcaatag | tagctgtaac | ctcgaagcgt | ttcacttgta | 60 |
| acaacgattg | agaactttg | tcataaaatt | gaaatacttg | gttcgcattt | tcgtcatccg | 120 |
| cggtcagccg | caattctgac | gaactgccca | tttagctgga | gatgattgta | catccttcac | 180 |
| gtgaaaattt | ctcaagcgct | gtgaacaagg | gttcagattt | tagattgaaa | ggtgagccgt | 240 |
| tgaaacacgt | tcttcttatc | gatgacgatg | tcgctatgcg | gcatcttatt | atcgaatacc | 300 |
| ttacgatcca | cgccttcaaa | gtgaccgcgg | tagccgacag | cacccagttc | actagagtac | 360 |
| tctcttccgc | gacggtcgat | gtcgtggttg | ttgatctaga | tttaggtcgt | gaagatgggc | 420 |
| ttgagatcgt | tcgaaatctg | gcggcaaagt | ctgatattcc | aatcataatt | atcagtggcg | 480 |
| accgccttga | ggagacggat | aaagttgttg | cactcgagct | aggagcaagt | gattttatcg | 540 |
| ctaagccgtt | tagtacgaga | gagttttctt | cacgcattcg | ggttgccttg | cgcgtgcgcc | 600 |
| ccaacgttgt | ccgctccaaa | gaccgacggt | ctttttgttt | tactgactgg | acacttaatc | 660 |
| tcaggcaacg | tcgcttgatg | tccgaagctg | gcggtgaggt | gaaacttacg | gcaggtgagt | 720 |
| tcaatcttct | cctcgcgttt | ttagagaaac | cccgcgacgt | tctatcgcgc | gagcaacttc | 780 |
| tcattgccag | tcgagtacgc | gacgaggagg | tttacgacag | gagtatagat | gttctcattt | 840 |
| tgcggctgcg | ccgcaaactt | gaggcggatc | cgtcaagccc | tcaactgata | aaaacagcaa | 900 |
| gaggtgccgg | ttatttcttt | gacgcggacg | tgcaggtttc | gcacgggggg | acgatggcag | 960 |
| cctgagccaa | ttgcatttgg | ctcttaatta | tctggctcaa | aaggtgactg | aggacgcggc | 1020 |
| cagcggcctc | aaacctacac | tcaatatttg | gtgaggggtt | ccgataggtc | cctcttcacc | 1080 |
| tgcatggcat | gtttaaccga | atctgacgtt | ttccctgcaa | atgccaaaat | actatgccta | 1140 |
| tctccgggtt | tcgcgtgacg | gccaagaccc | ggaaaaccaa | aaatacggtt | tgctcgaata | 1200 |
| cgcgaacgcc | aaaggcttcg | cgccgctaca | gatcgaggaa | gaaattgcca | gcagagcaaa | 1260 |
| ggactggcgc | aagcgcaagc | tcggagcaat | catcgaaaag | gccgagcgtg | gcgacgtgct | 1320 |
| actgacgccg | gagattacgc | gcattgccgg | ttccgccctc | gccgccttgg | aaattctcaa | 1380 |
| agcggcgagc | gagcgcggcc | taatcgtcca | tgtgaccaaa | cagaagatca | tcatggacgg | 1440 |
| cagcctacaa | agcgacatca | tggcaaccgt | gcttggcttg | gctgcacaga | tcgagcggca | 1500 |
| tttcattcag | gcacgtacca | ccgaggcgct | acaagtcgcc | agagagcgcg | gcaagacgct | 1560 |

```
cgggcgaccc aagggcagca aatcgagcgc cttgaagctg gacagccgta ttgatgaagt    1620
acaggcatac gtgaaccttg gcttgccgca aagtcgcgca gccgagttgt taggcgtcag    1680
ccctcacacc ttgcgcctgt tcatcaaacg ccggaacatc aaacccacaa acactagacc    1740
aaccatcacc atgccgggga gggaacaaca tgcctaagaa caacaaagcc cccggccatc    1800
gtatcaacga gatcatcaag acgagcctcg cgctcgaaat ggaggatgcc cgcgaagctg    1860
gcttagtcgg ctacatggcc cgttgccttg tgcaagcgac catgcccccac accgaccca    1920 agaccagcta ctttgagcgc accaatggca tcgtcacctt gtcgatcatg ggcaagccga    1980
gcatcggcct gccctacggt tctatgccgc gcaccttgct tgcttggata tgcaccgagg    2040
ccgtgcgaac gaaagacccc gtgttgaacc ttggccggtc gcaatcggaa tttctacaaa    2100
ggctcggaat gcacaccgat ggccgttaca cggccaccct tcgcaatcag gcgcaacgcc    2160
tgttttcatc catgatttcg cttgccggcg agcaaggcaa tgacttcggc attgagaacg    2220
tcgtcattgc caagcgcgct tttctattct ggaatcccaa gcggccagaa gatcgggcgc    2280
tatgggatag caccctcacc ctcacaggcg atttcttcga ggaagtcacc cgctcaccgg    2340
ttcctatccg aatcgactac ctgcatgcct tgcggcagtc tccgcttgcg atggacattt    2400
acacgtggct gacctatcgc gtgttcctgt tgcgggccaa gggccgcccc ttcgtgcaaa    2460
tcccttgggt cgccctgcaa gcgcaattcg gctcatccta tggcagccgc gcacgcaact    2520
cgcccgaact ggacgataag gcccgagagc gggcagagcg ggcagcactc gccagcttca    2580
aatacaactt caaaaagcgc ctacgcgaag tgttgattgt ctatcccgag gcaagcgact    2640
gcatcgaaga tgacggcgaa tgcctgcgca tcaaatccac acgcctgcat gtcacccgcg    2700
cacccggcaa gggcgctcgc atcggcccc ctccgacttg accaggccaa cgctacgctt    2760
ggcttggtca agccttccca tccaacagcc cgccgtcgag cgggcttttt tatccccgga    2820
agcctgtgga tagagggtag ttatccacgt gaaaccgcta atgccccgca aagccttgat    2880
tcacggggct ttccggcccg ctccaaaaac tatccacgtg aaatcgctaa tcagggtacg    2940
tgaaatcgct aatcggagta cgtgaaatcg ctaataaggt cacgtgaaat cgctaatcaa    3000
aaaggcacgt gagaacgcta atagcccttt cagatcaaca gcttgcaaac ccccctcgct    3060
ccggcaagta gttacagcaa gtagtatgtt caattagctt ttcaattatg aatatatata    3120
tcaattattg gtcgcccttg gcttgtggac aatgcgctac gcgcaccggc tccgcccgtg    3180
gacaaccgca agcggttgcc caccgtcgag cgccttttgcc cacaacccgg cggccgcaac    3240
agatcgtttt ataaattttt tttttgaaa aagaaaaagc ccgaaaggcg gcaacctctc    3300
gggcttctgg atttccgatc aacgcaggag tcgttcggaa agtagctgtt ccagaattat    3360
aggcgcagag acaccagatt ccaagatggc tctgttaaat tgttgtagta tgtagtatca    3420
tacaacatac tacagtacag aggcccgcaa gaatggcaat cactaaacaa gacatttggc    3480
gagcagccga cgaactggac gccgaaggca tccggcccac tttggccgcc gtgcgcaaga    3540
aactcggaag cggtagcttc acaaccattt ccgatgcaat ggctgaatgg aaaaaccgca    3600
agaccgccac cctgccctca tcagacccat tgccggttgc agtcaacgag catcttgccg    3660
agcttggcaa tgcgctatgg gctatcgccc tggcgcacgc caacgcccgg tttgacgaag    3720
atcggaaaca gatcgaggcc gacaaagcgg ccatcagcca gcagcttgcc gaagcaatcg    3780
aactagccga caccttcacc cgcgaaaacg accagctccg cgaacgagta gatccttcat    3840
ggcttgttat gactgttttt ttgtacagtc tatgcctcgg gcatccaagc agcaagcgcg    3900
ttacgccgtg ggtcgatgtt tgatgttatg gagcagcaac gatgttacgc agcagcaacg    3960
```

-continued

```
atgttacgca gcagggcagt cgccctaaaa caaagttagg tggctcaagt atgggcatca     4020
ttcgcacatg taggctcggc cctgaccaag tcaaatccat gcgggctgct cttgatcttt     4080
tcggtcgtga gttcggagac gtagccacct actcccaaca tcagccggac tccgattacc     4140
tcgggaactt gctccgtagt aagacattca tcgcgcttgc tgccttcgac caagaagcgg     4200
ttgttggcgc tctcgcggct tacgttctgc ccaagtttga gcagccgcgt agtgagatct     4260
atatctatga tctcgcagtc tccggcgagc accggaggca gggcattgcc accgcgctca     4320
tcaatctcct caagcatgag gccaacgcgc ttggtgctta tgtgatctac gtgcaagcag     4380
attacggtga cgatcccgca gtggctctct atacaaagtt gggcatacgg gaagaagtga     4440
tgcactttga tatcgaccca agtaccgcca cctaacaatt cgttcaagcc gagatcggct     4500
tcccggccgc ggagttgttc ggtaaattgt c                                    4531
```

```
<210> SEQ ID NO 9
<211> LENGTH: 12
<212> TYPE: DNA
<213> ORGANISM: Artificial Sequence
<220> FEATURE:
<223> OTHER INFORMATION: Synthetic cos sequence

<400> SEQUENCE: 9
aggtcgccgc cc                                                          12

<210> SEQ ID NO 10
<211> LENGTH: 10
<212> TYPE: DNA
<213> ORGANISM: Artificial Sequence
<220> FEATURE:
<223> OTHER INFORMATION: Synthetic vector: pac linker

<400> SEQUENCE: 10
gttaattaac                                                             10

<210> SEQ ID NO 11
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 11
gttaatttct tgtgatcgaa ggac                                             24

<210> SEQ ID NO 12
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 12
gggattcttt atgctgggtt tagg                                             24

<210> SEQ ID NO 13
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 13
gcaagcaata cctctgttat gctg                                             24
```

```
<210> SEQ ID NO 14
<211> LENGTH: 26
<212> TYPE: DNA
<213> ORGANISM: Artificial Sequence
<220> FEATURE:
<223> OTHER INFORMATION: Synthetic primer for amplification

<400> SEQUENCE: 14
gttttcagat ggcgacctca gctttg                                      26

<210> SEQ ID NO 15
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 15
caggtggctt tattcctcct ctca                                        24

<210> SEQ ID NO 16
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 16
ccgaaagttc gtgggcaatg ccta                                        24

<210> SEQ ID NO 17
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 17
gccatcctta gcatatgagt ggca                                        24

<210> SEQ ID NO 18
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 18
ggctatttac gtggcatgtt acgt                                        24

<210> SEQ ID NO 19
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 19
tcgtaagtct acttcccttt acga                                        24

<210> SEQ ID NO 20
<211> LENGTH: 24
<212> TYPE: DNA
<213> ORGANISM: Artificial Sequence
<220> FEATURE:
<223> OTHER INFORMATION: Synthetic primer for amplification
```

```
-continued

<400> SEQUENCE: 20
ccaaaccaca tccttatagt gtgc                                          24

<210> SEQ ID NO 21
<211> LENGTH: 22
<212> TYPE: DNA
<213> ORGANISM: Artificial Sequence
<220> FEATURE:
<223> OTHER INFORMATION: Synthetic primer for amplification

<400> SEQUENCE: 21
cctcattgca tgcggtcact ac                                            22

<210> SEQ ID NO 22
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 22
gcagggtatt aatcgatcaa cacc                                          24

<210> SEQ ID NO 23
<211> LENGTH: 28
<212> TYPE: DNA
<213> ORGANISM: Artificial Sequence
<220> FEATURE:
<223> OTHER INFORMATION: Synthetic primer for amplification

<400> SEQUENCE: 23
agctttcgaa tagggataac agggtaat                                      28

<210> SEQ ID NO 24
<211> LENGTH: 28
<212> TYPE: DNA
<213> ORGANISM: Artificial Sequence
<220> FEATURE:
<223> OTHER INFORMATION: Synthetic primer for amplification

<400> SEQUENCE: 24
agctattacc ctgttatccc tattcgaa                                      28

<210> SEQ ID NO 25
<211> LENGTH: 31
<212> TYPE: DNA
<213> ORGANISM: Artificial Sequence
<220> FEATURE:
<223> OTHER INFORMATION: Synthetic primer for amplification

<400> SEQUENCE: 25
ctagtaacta taacggtcct aaggtagcga c                                  31

<210> SEQ ID NO 26
<211> LENGTH: 31
<212> TYPE: DNA
<213> ORGANISM: Artificial Sequence
<220> FEATURE:
<223> OTHER INFORMATION: Synthetic primer for amplification

<400> SEQUENCE: 26
ctaggtcgct accttaggac cgttatagtt a                                  31

<210> SEQ ID NO 27
<211> LENGTH: 49
<212> TYPE: DNA
```

```
<213> ORGANISM: Artificial Sequence
<220> FEATURE:
<223> OTHER INFORMATION: Synthetic primer for amplification

<400> SEQUENCE: 27
ggggacaagt ttgtacaaaa aagcaggctc aatgagatat gaaaaagcc                49

<210> SEQ ID NO 28
<211> LENGTH: 52
<212> TYPE: DNA
<213> ORGANISM: Artificial Sequence
<220> FEATURE:
<223> OTHER INFORMATION: Synthetic primer for amplification

<400> SEQUENCE: 28
ggggaccact ttgtacaaga aagctgggtc tattcctttg ccctcggacg ag            52

<210> SEQ ID NO 29
<211> LENGTH: 49
<212> TYPE: DNA
<213> ORGANISM: Artificial Sequence
<220> FEATURE:
<223> OTHER INFORMATION: Synthetic primer for amplification

<400> SEQUENCE: 29
ggggacaagt ttgtacaaaa aagcaggctc catggaccca gaacgacgc                49

<210> SEQ ID NO 30
<211> LENGTH: 49
<212> TYPE: DNA
<213> ORGANISM: Artificial Sequence
<220> FEATURE:
<223> OTHER INFORMATION: Synthetic primer for amplification

<400> SEQUENCE: 30
ggggaccact ttgtacaaga aagctgggtt cctagacgcg tgagatcag                49

<210> SEQ ID NO 31
<211> LENGTH: 32
<212> TYPE: DNA
<213> ORGANISM: Artificial Sequence
<220> FEATURE:
<223> OTHER INFORMATION: Synthetic primer for amplification

<400> SEQUENCE: 31
tcgttcgaat cgatactatg ttatacgcca ac                                  32

<210> SEQ ID NO 32
<211> LENGTH: 29
<212> TYPE: DNA
<213> ORGANISM: Artificial Sequence
<220> FEATURE:
<223> OTHER INFORMATION: Synthetic primer for amplification

<400> SEQUENCE: 32
atcgtcgact gcacgaatac cagcgaccc                                      29

<210> SEQ ID NO 33
<211> LENGTH: 31
<212> TYPE: DNA
<213> ORGANISM: Artificial Sequence
<220> FEATURE:
<223> OTHER INFORMATION: Synthetic primer for amplification

<400> SEQUENCE: 33
ggcggatcct tccattgttc attccacgga c                                   31
```

```
<210> SEQ ID NO 34
<211> LENGTH: 30
<212> TYPE: DNA
<213> ORGANISM: Artificial Sequence
<220> FEATURE:
<223> OTHER INFORMATION: Synthetic primer for amplification

<400> SEQUENCE: 34
gggcaattga catgaggttg ccccgtattc                                      30

<210> SEQ ID NO 35
<211> LENGTH: 29
<212> TYPE: DNA
<213> ORGANISM: Artificial Sequence
<220> FEATURE:
<223> OTHER INFORMATION: Synthetic primer for amplification

<400> SEQUENCE: 35
gatatcgata gcgtggactc aaggctctc                                       29

<210> SEQ ID NO 36
<211> LENGTH: 41
<212> TYPE: DNA
<213> ORGANISM: Artificial Sequence
<220> FEATURE:
<223> OTHER INFORMATION: Synthetic primer for amplification

<400> SEQUENCE: 36
aaagaattcg ctagccagct ggcgctgcca tttttggggt g                         41

<210> SEQ ID NO 37
<211> LENGTH: 29
<212> TYPE: DNA
<213> ORGANISM: Artificial Sequence
<220> FEATURE:
<223> OTHER INFORMATION: Synthetic primer for amplification

<400> SEQUENCE: 37
aaactcgagc agccgagaac attggttcc                                       29

<210> SEQ ID NO 38
<211> LENGTH: 36
<212> TYPE: DNA
<213> ORGANISM: Artificial Sequence
<220> FEATURE:
<223> OTHER INFORMATION: Synthetic primer for amplification

<400> SEQUENCE: 38
taggaattcg gatccaaaac aactgtcaaa gcgcac                               36

<210> SEQ ID NO 39
<211> LENGTH: 28
<212> TYPE: DNA
<213> ORGANISM: Artificial Sequence
<220> FEATURE:
<223> OTHER INFORMATION: Synthetic primer for amplification

<400> SEQUENCE: 39
cgtagatctg gcgctcggtc ttgccttg                                        28

<210> SEQ ID NO 40
<211> LENGTH: 37
<212> TYPE: DNA
<213> ORGANISM: Artificial Sequence
<220> FEATURE:
<223> OTHER INFORMATION: Synthetic primer for amplification
```

-continued

```
<400> SEQUENCE: 40
tgtgaattca ctagtgatat tccacaaaac agcaggg                                37

<210> SEQ ID NO 41
<211> LENGTH: 28
<212> TYPE: DNA
<213> ORGANISM: Artificial Sequence
<220> FEATURE:
<223> OTHER INFORMATION: Synthetic primer for amplification

<400> SEQUENCE: 41
ccgtctagat tcgagccacg gtagcggc                                          28

<210> SEQ ID NO 42
<211> LENGTH: 34
<212> TYPE: DNA
<213> ORGANISM: Artificial Sequence
<220> FEATURE:
<223> OTHER INFORMATION: Synthetic primer for amplification

<400> SEQUENCE: 42
cttgaattca gatcttctcg gcggcgatca cgac                                   34

<210> SEQ ID NO 43
<211> LENGTH: 12
<212> TYPE: DNA
<213> ORGANISM: Artificial Sequence
<220> FEATURE:
<223> OTHER INFORMATION: Synthetic vector: pSwaI linker

<400> SEQUENCE: 43
ccatttaaat gg                                                           12

<210> SEQ ID NO 44
<211> LENGTH: 18
<212> TYPE: DNA
<213> ORGANISM: Artificial Sequence
<220> FEATURE:
<223> OTHER INFORMATION: Synthetic adaptor: SwaIKpnIRV

<400> SEQUENCE: 44
ccatttaaat ggtaccgg                                                     18

<210> SEQ ID NO 45
<211> LENGTH: 18
<212> TYPE: DNA
<213> ORGANISM: Artificial Sequence
<220> FEATURE:
<223> OTHER INFORMATION: Synthetic adaptor: SwaIKpnIFW

<400> SEQUENCE: 45
ccggtaccat ttaaatgg                                                     18

<210> SEQ ID NO 46
<211> LENGTH: 32
<212> TYPE: DNA
<213> ORGANISM: Artificial Sequence
<220> FEATURE:
<223> OTHER INFORMATION: Synthetic primer for amplification

<400> SEQUENCE: 46
tcaatacccg gggtaacctc gaagcgtttc ac                                     32

<210> SEQ ID NO 47
<211> LENGTH: 31
<212> TYPE: DNA
```

```
<213> ORGANISM: Artificial Sequence
<220> FEATURE:
<223> OTHER INFORMATION: Synthetic primer for amplification

<400> SEQUENCE: 47
tggtgacccg ggacctatcg gaacccctca c                              31

<210> SEQ ID NO 48
<211> LENGTH: 32
<212> TYPE: DNA
<213> ORGANISM: Artificial Sequence
<220> FEATURE:
<223> OTHER INFORMATION: Synthetic primer for amplification

<400> SEQUENCE: 48
tcaataacta gtgtaacctc gaagcgtttc ac                             32

<210> SEQ ID NO 49
<211> LENGTH: 31
<212> TYPE: DNA
<213> ORGANISM: Artificial Sequence
<220> FEATURE:
<223> OTHER INFORMATION: Synthetic primer for amplification

<400> SEQUENCE: 49
tggtgaacta gtacctatcg gaacccctca c                              31

<210> SEQ ID NO 50
<211> LENGTH: 21
<212> TYPE: DNA
<213> ORGANISM: Artificial Sequence
<220> FEATURE:
<223> OTHER INFORMATION: Synthetic primer for amplification

<400> SEQUENCE: 50
cttgagatcg ttcggaatct g                                         21

<210> SEQ ID NO 51
<211> LENGTH: 21
<212> TYPE: DNA
<213> ORGANISM: Artificial Sequence
<220> FEATURE:
<223> OTHER INFORMATION: Synthetic primer for amplification

<400> SEQUENCE: 51
cagattccga acgatctcaa g                                         21

<210> SEQ ID NO 52
<211> LENGTH: 29
<212> TYPE: DNA
<213> ORGANISM: Artificial Sequence
<220> FEATURE:
<223> OTHER INFORMATION: Synthetic primer for amplification

<400> SEQUENCE: 52
aaaatgcatg gcatgtttaa cagaatctg                                 29

<210> SEQ ID NO 53
<211> LENGTH: 27
<212> TYPE: DNA
<213> ORGANISM: Artificial Sequence
<220> FEATURE:
<223> OTHER INFORMATION: Synthetic primer for amplification

<400> SEQUENCE: 53
tttagatcta ctcgttcgcg gagctgg                                   27
```

<210> SEQ ID NO 54
<211> LENGTH: 29
<212> TYPE: DNA
<213> ORGANISM: Artificial Sequence
<220> FEATURE:
<223> OTHER INFORMATION: Synthetic primer for amplification

<400> SEQUENCE: 54
aaaggatcct tcatggcttg ttatgactg                                29

<210> SEQ ID NO 55
<211> LENGTH: 30
<212> TYPE: DNA
<213> ORGANISM: Artificial Sequence
<220> FEATURE:
<223> OTHER INFORMATION: Synthetic primer for amplification

<400> SEQUENCE: 55
tgcctcgaga caatttaccg aacaactccg                               30

<210> SEQ ID NO 56
<211> LENGTH: 23
<212> TYPE: DNA
<213> ORGANISM: Artificial Sequence
<220> FEATURE:
<223> OTHER INFORMATION: Synthetic primer for amplification

<400> SEQUENCE: 56
cgacctaaat ctagatcaac aac                                      23

<210> SEQ ID NO 57
<211> LENGTH: 23
<212> TYPE: DNA
<213> ORGANISM: Artificial Sequence
<220> FEATURE:
<223> OTHER INFORMATION: Synthetic primer for amplification

<400> SEQUENCE: 57
gttgttgatc tagatttagg tcg                                      23

<210> SEQ ID NO 58
<211> LENGTH: 29
<212> TYPE: DNA
<213> ORGANISM: Artificial Sequence
<220> FEATURE:
<223> OTHER INFORMATION: Synthetic primer for amplification

<400> SEQUENCE: 58
tttgtcgacc ataggcgatc tccttaatc                                29

<210> SEQ ID NO 59
<211> LENGTH: 28
<212> TYPE: DNA
<213> ORGANISM: Artificial Sequence
<220> FEATURE:
<223> OTHER INFORMATION: Synthetic primer for amplification

<400> SEQUENCE: 59
aaactgcagg tgaagaggga cctatcgg                                 28

<210> SEQ ID NO 60
<211> LENGTH: 24
<212> TYPE: DNA
<213> ORGANISM: Artificial Sequence
<220> FEATURE:
<223> OTHER INFORMATION: Synthetic primer for amplification -continued

```
<400> SEQUENCE: 60
ctgaaggcgg gaaacgacaa tctg                                              24

<210> SEQ ID NO 61
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 61
gcttgctgag tggctccttc aacg                                              24

<210> SEQ ID NO 62
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 62
aactgcactt caaacaagtg tgac                                              24

<210> SEQ ID NO 63
<211> LENGTH: 20
<212> TYPE: DNA
<213> ORGANISM: Artificial Sequence
<220> FEATURE:
<223> OTHER INFORMATION: Synthetic primer for amplification

<400> SEQUENCE: 63
tatgtcctgc gggtaaatag                                                   20

<210> SEQ ID NO 64
<211> LENGTH: 19
<212> TYPE: DNA
<213> ORGANISM: Artificial Sequence
<220> FEATURE:
<223> OTHER INFORMATION: Synthetic primer for amplification

<400> SEQUENCE: 64
ttgttggagc cgaaatccg                                                    19

<210> SEQ ID NO 65
<211> LENGTH: 14120
<212> TYPE: DNA
<213> ORGANISM: Artificial Sequence
<220> FEATURE:
<223> OTHER INFORMATION: Synthetic vector: pLC40GWHkorB
<220> FEATURE:
<221> NAME/KEY: misc_feature
<222> LOCATION: (54)..(66)
<223> OTHER INFORMATION: I-SceI
<220> FEATURE:
<221> NAME/KEY: misc_feature
<222> LOCATION: (90)..(989)
<223> OTHER INFORMATION: Pubi
<220> FEATURE:
<221> NAME/KEY: misc_feature
<222> LOCATION: (1073)..(2082)
<223> OTHER INFORMATION: ubiI
<220> FEATURE:
<221> NAME/KEY: misc_feature
<222> LOCATION: (2103)..(2127)
<223> OTHER INFORMATION: attB1
<220> FEATURE:
<221> NAME/KEY: misc_feature
<222> LOCATION: (2127)..(3162)
<223> OTHER INFORMATION: hpt
<220> FEATURE:
```

```
<221> NAME/KEY: misc_feature
<222> LOCATION: (3166)..(3186)
<223> OTHER INFORMATION: attB2
<220> FEATURE:
<221> NAME/KEY: misc_feature
<222> LOCATION: (3207)..(3482)
<223> OTHER INFORMATION: Tnos
<220> FEATURE:
<221> NAME/KEY: misc_feature
<222> LOCATION: (3541)..(3565)
<223> OTHER INFORMATION: LB
<220> FEATURE:
<221> NAME/KEY: misc_feature
<222> LOCATION: (4107)..(4137)
<223> OTHER INFORMATION: I-CeuI
<220> FEATURE:
<221> NAME/KEY: misc_feature
<222> LOCATION: (4144)..(4551)
<223> OTHER INFORMATION: (complement) cos
<220> FEATURE:
<221> NAME/KEY: misc_feature
<222> LOCATION: (4553)..(6670)
<223> OTHER INFORMATION: (complement) IncC1
<220> FEATURE:
<221> NAME/KEY: misc_feature
<222> LOCATION: (6306)..(7382)
<223> OTHER INFORMATION: (complement) KorB
<220> FEATURE:
<221> NAME/KEY: misc_feature
<222> LOCATION: (7618)..(8439)
<223> OTHER INFORMATION: (complement) oriT
<220> FEATURE:
<221> NAME/KEY: misc_feature
<222> LOCATION: (8434)..(11604)
<223> OTHER INFORMATION: (complement) trfA1
<220> FEATURE:
<221> NAME/KEY: misc_feature
<222> LOCATION: (11601)..(12697)
<223> OTHER INFORMATION: nptIII
<220> FEATURE:
<221> NAME/KEY: misc_feature
<222> LOCATION: (12694)..(13586)
<223> OTHER INFORMATION: (complement) oriV
<220> FEATURE:
<221> NAME/KEY: misc_feature
<222> LOCATION: (13944)..(13968)
<223> OTHER INFORMATION: RB

<400> SEQUENCE: 65
aagcttgcgg ccgcttcgaa gatgttaatt aacatcggta ccgagctcta gggataacag      60
ggtaatagct cgaattctag cttgcatgcc tgcagtgcag cgtgacccgg tcgtgcccct     120
ctctagagat aatgagcatt gcatgtctaa gttataaaaa attaccacat atttttttg      180 tcacacttgt ttgaagtgca gtttatctat ctttatacat atatttaaac tttactctac    240
gaataatata atctatagta ctacaataat atcagtgttt tagagaatca tataaatgaa    300
cagttagaca tggtctaaag gacaattgag tattttgaca acaggactct acagttttat    360 cttttagtg tgcatgtgtt ctccttttt tttgcaaata gcttcaccta tataatactt      420
catccatttt attagtacat ccatttaggg tttagggtta atggttttta tagactaatt    480
tttttagtac atctatttta ttctatttta gcctctaaat taagaaaact aaaactctat    540
tttagttttt ttatttaata atttagatat aaaatagaat aaaataaagt gactaaaaat    600
taaacaaata cccctttaaga aattaaaaaa actaaggaaa cattttctt gtttcgagta    660 gataatgcca gcctgttaaa cgccgtcgac gagtctaacg acaccaacc agcgaaccag    720 cagcgtcgcg tcgggccaag cgaagcagac ggcacggcat ctctgtcgct gcctctggac    780
ccctctcgag agttccgctc caccgttgga cttgctccgc tgtcggcatc cagaaattgc    840
gtggcggagc ggcagacgtg agccggcacg gcaggcggcc tcctcctcct ctcacggcac    900
```

```
cggcagctac gggggattcc tttcccaccg ctccttcgct ttcccttcct cgcccgccgt    960
aataaataga cacccctcc acacctctt tccccaacct cgtgttgttc ggagcgcaca     1020
cacacacaac cagatctccc ccaaatccac ccgtcggcac ctccgcttca aggtacgccg   1080
ctcgtcctcc cccccccccc ctctctacct tctctagatc ggcgttccgg tccatggtta   1140
gggcccggta gttctacttc tgttcatgtt tgtgttagat ccgtgtttgt gttagatccg   1200
tgctgctagc gttcgtacac ggatgcgacc tgtacgtcag acacgttctg attgctaact   1260
tgccagtgtt tctctttggg gaatcctggg atggctctag ccgttccgca gacgggatcg   1320
atttcatgat ttttttttgtt tcgttgcata gggtttggtt tgcccttttc ctttatttca   1380
atatatgccg tgcacttgtt tgtcgggtca tcttttcatg cttttttttg tcttggttgt   1440
gatgatgtgg tctggttggg cggtcgttct agatcggagt agaattctgt ttcaaactac   1500
ctggtggatt tattaatttt ggatctgtat gtgtgtgcca tacatattca tagttacgaa   1560
ttgaagatga tggatggaaa tatcgatcta ggataggtat acatgttgat gcgggtttta   1620
ctgatgcata tacagagatg cttttttgttc gcttggttgt gatgatgtgg tgtggttggg   1680
cggtcgttca ttcgttctag atcggagtag aatactgttt caaactacct ggtgtattta   1740
ttaattttgg aactgtatgt gtgtgtcata catcttcata gttacgagtt taagatggat   1800
ggaaatatcg atctaggata ggtatacatg ttgatgtggg ttttactgat gcatatacat   1860
gatggcatat gcagcatcta ttcatatgct ctaaccttga gtacctatct attataataa   1920
acaagtatgt tttataatta ttttgatctt gatatacttg gatgatggca tatgcagcag   1980
ctatatgtgg atttttttag ccctgccttc atacgctatt tatttgcttg gtactgtttc   2040
ttttgtcgat gctcaccctg ttgttggtg ttacttctgc aggtcgactc tagaggatca   2100
tcacaagttt gtacaaaaaa gcaggctcaa tgagatatga aaaagcctga actcaccgcg   2160
acgtctgtcg agaagtttct gatcgaaaag ttcgacagcg tctccgacct gatgcagctc   2220
tcggagggcg aagaatctcg tgctttcagc ttcgatgtag agggcgtgg atatgtcctg   2280
cgggtaaaata gctgcgccga tggttttctac aaagatcgtt atgtttatcg gcactttgca   2340
tcggccgcgc tcccgattcc ggaagtgctt gacattgggg aattcagcga gagcctgacc   2400
tattgcatct cccgccgtgc acagggtgtc acgttgcaag acctgcctga accgaactg    2460
cccgctgttc tgcagccggt cgcggaggcc atggatgcga tcgctgcggc cgatcttagc   2520
cagacgagcg ggttcggccc attcggaccg caaggaatcg gtcaatacac tacatggcgt   2580
gatttcatat gcgcgattgc tgatccccat gtgtatcact ggcaaactgt gatggacgac   2640
accgtcagtg cgtccgtcgc gcaggctctc gatgagctga tgctttgggc cgaggactgc   2700
cccgaagtcc ggcacctcgt gcacgcggat ttcggctcca acaatgtcct gacggacaat   2760
ggccgcataa cagcggtcat tgactggagc gaggcgatgt tcggggattc ccaatacgag   2820
gtcgccaaca tcttcttctg gaggccgtgg ttggcttgta tggagcagca gacgcgctac   2880
ttcgagcgga ggcatccgga gcttgcagga tcgccgcggc tccgggcgta tatgctccgc   2940
attggtcttg accaactcta tcagagcttg gttgacggca atttcgatga tgcagcttgg   3000
gcgcagggtc gatgcgacgc aatcgtccga tccggagccg ggactgtcgg gcgtacacaa   3060
atcgcccgca gaagcgcggc cgtctggacc gatggctgtg tagaagtact cgccgatagt   3120
ggaaaccgac gccccagcac tcgtccgagg gcaaaggaat agacccagct tcttgtaca   3180
aagtggtgat gatccgtcga cctgcagatc gttcaaacat ttggcaataa agtttcttaa   3240
gattgaatcc tgttgccggt cttgcgatga ttatcatata atttctgttg aattacgtta   3300
```

```
agcatgtaat aattaacatg taatgcatga cgttatttat gagatgggtt tttatgatta   3360
gagtcccgca attatacatt taatacgcga tagaaaacaa atatagcgcg caaactaggg   3420
ataaattatc gcgcgcggtg tcatctatgt tactagatcc gatgataagc tgtcaaacat   3480
gagaattcag tacattaaaa acgtccgcaa tgtgttatta agttgtctaa gcgtcaattt   3540
gtttacacca caatatatcc tgccaccagc cagccaacag ctccccgacc ggcagctcgg   3600
cacaaaatca ccactcgata caggcagccc atcagtccgg gacggcgtca gcgggagagc   3660
cgttgtaagg cggcagactt tgctcatgtt accgatgcta ttcggaagaa cggcaactaa   3720
gctgccgggt tgaaacacg dgatgatctcg cggagggtag catgttgatt gtaacgatga   3780
cagagcgttg ctgcctgtga tcaaatatca tctccctcgc agagatccga attatcagcc   3840
ttcttattca tttctcgctt aaccgtgaca ggctgtcgat cttgagaact atgccgacat   3900
aataggaaat cgctggataa agccgctgag gaagctgagt ggcgctattt ctttagaagt   3960
gaacgttgac gatcgtcgac cgtaccccga tgaattaatt cggacgtacg ttctgaacac   4020
agctggatac ttacttgggc gattgtcata catgacatca acaatgtacc cgtttgtgta   4080
accgtctctt ggaggttcgt atgacactag gtcgctacct taggaccgtt atagttacta   4140
gcgaattgac atgaggttgc cccgtattca gtgtcgctga tttgtattgt ctgaagttgt   4200
ttttacgtta agttgatgca gatcaattaa tacgatacct gcgtcataat tgattatttg   4260
acgtggtttg atggcctcca cgcacgttgt gatatgtaga tgataatcat tatcacttta   4320
cgggtccttt ccggtgatcc gacaggttac ggggcggcga cctcgcgggt tttcgctatt   4380
tatgaaaatt ttccggttta aggcgtttcc gttcttcttc gtcataactt aatgttttta   4440
tttaaaatac cctctgaaaa gaaaggaaac gacaggtgct gaaagcgagc ttttttggcct   4500 ctgtcgtttc ctttctctgt ttttgtccgt ggaatgaaca atggaaggat cttctcggcg   4560
gcgatcacga cgccggccct gcggagcctt cgccgcgtgc gcgattcatg gcggccgtgg   4620
aggccaagga tttcgcgcga gtgcaagagc tgatcgaggc gcgtggagcc aagtcggcgg   4680
ctgattatgt ccttgcgcag ctcgccgtgg ccgaaggtct ggaccgcaag cctggtgcgc   4740
gcgtcgtggt cgggaaagcg gcgggcagca tggcaatgcc gcctgcggcg ctgggttta   4800 cgccaagggg agaagcggca tacgccatcg agcggtcagc ctatggtgag ccgaggtcca   4860
gcattgcgaa gcagtaccag caggaatgga accggaaggc ggcgacctgg tgggcgatgg   4920
ccggtgtggc cggcatcatc ggcgcgatcc tggcggcggc ggcaaccggc tttgttgggc   4980
tggcagtgtc gatccgcaac cgagtgaagc gcgtgcgcga cctgttggtg atggagccgg   5040
gtgcagagcc ataagcggca agagacgaaa gcccggtttc cgggcttttg ttttgttacg   5100
ccaaggacga gttttagcgg ctaaaggtgt tgacgtgcga gaaatgttta gctaaacttc   5160
tctcatgtgc tggcggctgt caccgctatg ttcaaccaag gcgcggagca aattatgggt   5220
gttatccatg aagaaacggc ttaccgaaag ccagttccag gaggcgatcc aggggctgga   5280
agtggggcag cagaccatcg agatagcgcg gggcgtctta gtcgatggga agccacaggc   5340
gacgttcgca acgtcgctgg gactgaccag gggcgcagtg tcgcaagcgg tgcatcgcgt   5400
gtgggccgcg ttcgaggaca agaacttgcc cgaggggtac gcgcgggtaa cggcggttct   5460
gccggaacat caggcgtaca tcgtccggaa gtgggaagcg gacgccaaga aaaacagga   5520 aaccaaacga tgaaaacttt ggtcacggcc aaccagaaag gcggcgtcgg caagacttcg   5580
acccttgtgc atcttgcctt cgactttttc gagcgcggct tgcgggttgc cgtgatcgac   5640
ctggaccccc agggcaatgc gtcctacacg ctcaaggact tgctaccgg cctgcatgca   5700
```

```
agcaagctgt tcggcgctgt ccctgccggc ggctggaccg aaaccgcacc cgcagccggc    5760
gacggccagg ccgcgcgcct cgccctcatc gagtccaacc cggtactggc gaacgccgaa    5820
cggctgtcgc tggacgacgc ccgcgagctg ttcggggcga acatcaaggc cctggcgaac    5880
caaggcttcg acgtgtgcct gatcgacacg gccccgaccc ttggcgtcgg cctggcggcc    5940
gccctcttcg cggccgacta tgtgctgtcc cccatcgagc ttgaggcgta cagcatccag    6000
ggcatcaaga agatggtcac gaccattgcg aacgtgcgcc agaagaacgc caagctgcaa    6060
ttccttggca tggtgcccag caaggtcgat gcgcggaatc cgcgccacgc gcgccaccaa    6120
gccgagctgc tggccgcgta ccccaagatg atgattccgg ccaccgttgg cctgcgcagc    6180
agcatcgccg atgccctcgc atccggtgtg ccggtctgga agatcaagaa aacggccgcg    6240
cgcaaggcat cgaaagaggt tcgcgccctg gctgattacg tgttcacgaa gatggagatt    6300
tcccaatgac tgcggctcaa gccaagacca ccagaaaaa caccgctgcg ccgctcagg    6360 aagccgcagg cgcggcgcag ccgtccggcc tggggttgga tagcatcggc gacctgtcga    6420
gcctcctgga cgctcctgcg gcgtctcagg gcggttccgg ccctatcgag ctggacctgg    6480
acctgatcga cgaagatccg catcagccgc ggacggccga caaccccggc ttttccccgg    6540
agagcatcgc ggaaatcggt gccacgatca agagcgcgg ggtgaagtca cccatttcgg    6600
tgcgcgagaa ccaggagcag ccgggccgct atatcatcaa tcacggcgcc cgccgctacc    6660
gtggctcgaa gtgggccggc aagaagtcca tcccggcgtt catcgacaac gactacaacg    6720
aagccgacca ggttatcgag aacctgcaac gcaacgagct gaccccgcgc gaaattgccg    6780
acttcattgg ccgcgagctg gcgaagggca agaagaaagg cgatatcgcc aaggaaatcg    6840
gcaagtcgcc ggcgttcatc acccagcacg tcacgctgct ggacctgccg gagaagatcg    6900
ccgatgcgtt caacaccggc cgcgtgcgcg acgtgaccgt ggtgaacgag ctggtgacgg    6960
ccttcaagaa cgcccggag gaagtcgagg cgtggcttga cgacgacacc caggaaatca    7020
cgcgcggcac ggtcaagctg ctgcgcgagt tcctggacga aagggccgc gatcccaaca    7080 ccgtcgatgc cttcaacggc cagactgatg ccgagcgtga cgcggaggcc ggcgacggcc    7140
aggacggcga ggacggcgac caggacggta aggacgccaa ggaaaagggc gcgaaggagc    7200
cggacccgga caagctgaaa aaggccatcg tccaggtcga gcacgacgag cgccctgccc    7260
gccttatcct caaccgtcgg ccgccggcgg aaggctatgc ctggttgaag tacgaggacg    7320
acggccagga gttcgaggcg aaccttgccg acgtgaaact ggtcgcgctc atcgagggct    7380
gatccccaaa gacagcggcg cgggccaccc gcgccgcaca gacaacggtt ccgctacaag    7440
gaggaccgaa gaatgaatcc gatgctgttc tacatcgcgg gaggcgtagg cgcggcgttg    7500
ctgctggttt ccgcgatcat gctgttcaag ctgcgcgagc cgaagaagga acaccgaccg    7560
cagcgcaagg cggcggcccc gacgccgcag ccggtcgata acgagctgct gcgcactcta    7620
gtgatattcc acaaaacagc agggaagcag cgcttttccg ctgcataacc ctgcttcggg    7680
gtcattatag cgattttttc ggtatatcca tcctttttcg cacgatatac aggattttgc    7740
caaagggttc gtgtagactt tccttggtgt atccaacggc gtcagccggg caggataggt    7800
gaagtaggcc cacccgcgag cgggtgttcc ttcttcactg tccccttattc gcacctggcg    7860 gtgctcaacg ggaatcctgc tctgcgaggc tggccggcta ccgccggcgt aacagatgag    7920
ggcaagcgga tggctgatga aaccaagcca accaggaagg gcagcccacc tatcaaggtg    7980
tactgccttc cagacgaacg aagagcgatt gaggaaaagg cggcggcggc cggcatgagc    8040
ctgtcggcct acctgctggc cgtcggccag ggctacaaaa tcacgggcgt cgtggactat    8100
```

```
gagcacgtcc gcgagctggc ccgcatcaat ggcgacctgg gccgcctggg cggcctgctg   8160
aaactctggc tcaccgacga cccgcgcacg gcgcggttcg gtgatgccac gatcctcgcc   8220
ctgctggcga agatcgaaga gaagcaggac gagcttggca aggtcatgat gggcgtggtc   8280
cgcccgaggg cagagccatg acttttttag ccgctaaaac ggccgggggg tgcgcgtgat   8340
tgccaagcac gtccccatgc gctccatcaa gaagagcgac ttcgcggagc tggtgaagta   8400
catcaccgac gagcaaggca agaccgagcg ccagatccaa acaactgtc aaagcgcacc    8460 cgcccgatgc cattcgcggc acggcttccg ttgaggatgt cgatatgatg cgcgagccga   8520
cggcccgcag agaaggggcc gttttagcgg ctaaagaagg aagtgcaagc cctaaccctt   8580
ggcgtcagag ccttccacgc agcttttttc gggtgtcgtc gccccatttc tttacgataa   8640
acgccttatg tgacggcaaa accacactga tgcgttcgta tccgggcggc acgctgctct   8700
tgaaaggatg acccgcaatc tccgcgagtg cctcgcggtc aaggtcggtg gactccagga   8760
gaagaggtag gggagtttcc agggcgtcgg caatggcctc catcaccttc aacgaggggt   8820
tggccttacc gttggttaag tctgataaaa acgaaattga aaccctgcc ctctccgaca     8880 gctcatgttt cgtcatgccc cgctcatcga gcagacgaag gatgttggtg aaaaatatct   8940
ggttgtacac agcggaagcc gcccctcgca cctttggtcg cggcccgcaa aattttagcc   9000
gctaaagttc ttgacagcgg aaccaatgtt tagctaaact agagtctcct ttctcaagga   9060
gactttcgat atgagccata atcagttcca gtttatcggt aatcttaccc gtgacaccga   9120
ggtacgtcat ggcaattcta acaagccgca agcaattttc gatatagcgg ttaatgaaga   9180
gtggcgcaac gatgccggcg acaagcagga gcgcaccgac ttcttccgca tcaagtgttt   9240
tggctctcag gccgaggccc acggcaagta tttgggcaag gggtcgctgg tattcgtgca   9300
gggcaagatt cggaatacca agtacgagaa ggacggccag acgtctacg ggaccgactt     9360 cattgccgat aaggtggatt atctggacac caaggcacca ggcgggtcaa atcaggaata   9420
agggcacatt gccccggcgt gagtcggggc aatcccgcaa ggagggtgaa tgaatcggac   9480
gtttgaccgg aagcatacag gcaagaact gatcgacgcg gggttttccg ccgaggatgc     9540
cgaaaccatc gcaagccgca ccgtcatgcg tgcgccccgc gaaaccttcc agtccgtcgg   9600
ctcgatggtc cagcaagcta cggccaagat cgagcgcgac agcgtgcaac tggctccccc   9660
tgccctgccc gcgccatcgg ccgccgtgga gcgttcgcgt cgtctcgaac aggaggcggc   9720
aggtttggcg aagtcgatga ccatcgacac gcgaggaact atgacgacca agaagcgaaa   9780
aaccgccggc gaggacctgg caaaacaggt cagcgaggcc aagcaggccg cgttgctgaa   9840
acacacgaag cagcagatca aggaaatgca gctttccttg ttcgatattg cgccgtggcc   9900
ggacacgatg cgagcgatgc caaacgcacac ggcccgctct gccctgttca ccacgcgcaa   9960
caagaaaatc ccgcgcgagg cgctgcaaaa caaggtcatt ttccacgtca acaaggacgt  10020
gaagatcacc tacaccggcg tcgagctgcg ggccgacgat gacgaactgg tgtggcagca  10080
ggtgttggag tacgcgaagc gcaccccctat cggcgagccg atcaccttca cgttctacga  10140
gctttgccag gacctgggct ggtcgatcaa tggccggtat tacacgaagg ccgaggaatg  10200
cctgtcgcgc ctacaggcga cggcgatggg cttcacgtcc gaccgcgttg ggcacctgga  10260
atcggtgtcg ctgctgcacc gcttccgcgt cctggaccgt ggcaagaaaa cgtcccgttg  10320
ccaggtcctg atcgacgagg aaatcgtcgt gctgtttgct ggcgaccact acacgaaatt  10380
catatgggaa aagtacccgca agctgtcgcc gacggcccga cggatgttcg actatttcag  10440
ctcgcaccgg gagccgtacc cgctcaagct ggaaaccttc cgcctcatgt gcggatcgga  10500
```

```
ttccacccgc gtgaagaagt ggcgcgagca ggtcggcgaa gcctgcgaag agttgcgagg   10560
cagcggcctg gtggaacacg cctgggtcaa tgatgacctg gtgcattgca aacgctaggg   10620
ccttgtgggg tcagttccgg ctgggggttc agcagccagc gctttactgg catttcagga   10680
acaagcgggc actgctcgac gcacttgctt cgctcagtat cgctcgggac gcacggcgcg   10740
ctctacgaac tgccgataaa cagaggatta aaattgacaa ttgtgattaa ggctcagatt   10800
cgacggcttg gagcggccga cgtgcaggat ttccgcgaga tccgattgtc ggccctgaag   10860
aaagctccag agatgttcgg gtccgtttac gagcacgagg agaaaaagcc catggaggcg   10920
ttcgctgaac ggttgcgaga tgccgtggca ttcggcgcct acatcgacgg cgagatcatt   10980
gggctgtcgg tcttcaaaca ggaggacggc cccaaggacg ctcacaaggc gcatctgtcc   11040
ggcgttttcg tggagcccga acagcgaggc cgaggggtcg ccggtatgct gctgcgggcg   11100
ttgccggcgg gtttattgct cgtgatgatc gtccgacaga ttccaacggg aatctggtgg   11160
atgcgcatct tcatcctcgg cgcacttaat atttcgctat tctggagctt gttgtttatt   11220
tcggtctacc gcctgccggg cgggtcgcgg cgacggtagg cgctgtgcag ccgctgatgg   11280
tcgtgttcat ctctgccgct ctgctaggta gcccgatacg attgatggcg gtcctggggg   11340
ctatttgcgg aactgcgggc gtggcgctgt tggtgttgac accaaacgca gcgctagatc   11400
ctgtcggcgt cgcagcgggc ctggcggggg cggtttccat ggcgttcgga accgtgctga   11460
cccgcaagtg gcaacctccc gtgcctctgc tcacctttac cgcctggcaa ctggcggccg   11520
gaggacttct gctcgttcca gtagctttag tgtttgatcc gccaatcccg atgcctacag   11580
gaaccaatgt tctcggctgc tcgactgcac gaataccagc gaccccttgc ccaaatactt   11640
gccgtgggcc tcggcctgag agccaaaaca cttgatgcgg aagaagtcgg tgcgctcctg   11700
cttgtcgccg gcatcgttgc gccacatcta ggtactaaaa caattcatcc agtaaaatat   11760
aatattttat tttctcccaa tcaggcttga tccccagtaa gtcaaaaaat agctcgacat   11820
actgttcttc cccgatatcc tccctgatcg accggacgca gaaggcaatg tcataccact   11880
tgtccgccct gccgcttctc ccaagatcaa taaagccact tactttgcca tctttcacaa   11940
agatgttgct gtctcccagg tcgccgtggg aaaagacaag ttcctcttcg ggcttttccg   12000
tcttaaaaa atcatacagc tcgcgcggat ctttaaatgg agtgtcttct tcccagtttt   12060
cgcaatccac atcggccaga tcgttattca gtaagtaatc caattcggct aagcggctgt   12120
ctaagctatt cgtatagggc caatccgata tgtcgatgga gtgaaagagc ctgatgcact   12180
ccgcatacag ctcgataatc ttttcagggc tttgttcatc ttcatactct ccgagcaaa   12240
ggacgccatc ggcctcactc atgagcagat tgctccagcc atcatgccgt tcaaagtgca   12300
ggacctttgg aacaggcagc tttccttcca gccatagcat catgtccttt tcccgttcca   12360
catcataggt ggtccctttta taccggctgt ccgtcatttt taaatatagg ttttcatttt   12420
ctcccaccag cttatatacc ttagcaggag acattcctttc cgtatctttt acgcagcggt   12480
attttttcgat cagtttttttc aattccggtg atattctcat tttagccatt tattatttcc   12540
ttcctctttt ctacagtatt taaagatacc ccaagaagct aattataaca agacgaactc   12600
caattcactg ttccttgcat tctaaaacct taaataccag aaaacagctt tttcaaagtt   12660
gttttcaaag ttggcgtata acatagtatc gattcgatag cgtggactca aggctctcgc   12720
gaatggctcg cgttggaaac tttcattgac acttgagggg caccgcaggg aaattctcgt   12780
ccttgcgaga accggctatg tcgtgctgcg catcgagcct gcgcccttgg cttgtctcgc   12840
ccctctccgc gtcgctacgg ggcttccagc gccttttccga cgctcaccgg gctggttgcc   12900
```

```
ctcgccgctg ggctggcggc cgtctatggc cctgcaaacg cgccagaaac gccgtcgaag    12960
ccgtgtgcga gacaccgcgg ccgccggcgt tgtggatacc tcgcggaaaa cttggccctc    13020
actgacagat gaggggcgga cgttgacact tgaggggccg actcacccgg cgcggcgttg    13080
acagatgagg ggcaggctcg atttcggccg gcgacgtgga gctggccagc ctcgcaaatc    13140
ggcgaaaacg cctgatttta cgcgagtttc ccacagatga tgtggacaag cctggggata    13200
agtgccctgc ggtattgaca cttgaggggc gcgactactg acagatgagg ggcgcgatcc    13260
ttgacacttg aggggcagag tgctgacaga tgagggggcgc acctattgac atttgagggg    13320
ctgtccacag gcagaaaatc cagcatttgc aagggtttcc gcccgttttt cggccaccgc    13380
taacctgtct tttaacctgc ttttaaacca atatttataa accttgtttt taaccagggc    13440
tgcgccctgt gcgcgtgacc gcgcacgccg aaggggggtg cccccccttc tcgaaccctc    13500
ccggcccgct aacgcgggcc tcccatcccc caggggctg cgcccctcgg ccgcgaacgg     13560
cctcacccca aaaatggcag cgccagccag gacgtcggcc gaaagagcga caagcagatc    13620
acgcttttcg acagcgtcgg atttgcgatc gaggattttt cggcgctgcg ctacgtccgc    13680
gaccgcgttg agggatcaag ccacagcagc ccactcgacc ttctagccga cccagacgag    13740
ccaagggatc ttttttggaat gctgctccgt cgtcaggctt tccgacgttt gggtggttga    13800
acagaagtca ttatcgcacg gaatgccaag cactcccgag gggaaccctg tggttggcat    13860
gcacatacaa atggacgaac ggataaacct tttcacgccc ttttaaatat ccgattattc    13920
taataaacgc tcttttctct taggtttacc cgccaatata tcctgtcaaa cactgatagt    13980
ttaaactgaa ggcgggaaac gacaatctga tcatgagcgg agaattaagg gagtcacgtt    14040
atgacccccg ccgatgacgc gggacaagcc gttttacgtt tggaactgac agaaccgcaa    14100
cgttgaagga gccactcagc                                                14120
```

<210> SEQ ID NO 66
<211> LENGTH: 14195
<212> TYPE: DNA
<213> ORGANISM: Artificial Sequence
<220> FEATURE:
<223> OTHER INFORMATION: Synthetic vector: pLCleo
<220> FEATURE:
<221> NAME/KEY: misc_feature
<222> LOCATION: (47)..(64)
<223> OTHER INFORMATION: I-SceI
<220> FEATURE:
<221> NAME/KEY: misc_feature
<222> LOCATION: (65)..(85)
<223> OTHER INFORMATION: attB3
<220> FEATURE:
<221> NAME/KEY: misc_feature
<222> LOCATION: (122)..(1021)
<223> OTHER INFORMATION: Pubi
<220> FEATURE:
<221> NAME/KEY: misc_feature
<222> LOCATION: (1105)..(2114)
<223> OTHER INFORMATION: ubiI
<220> FEATURE:
<221> NAME/KEY: misc_feature
<222> LOCATION: (2135)..(2159)
<223> OTHER INFORMATION: attB1
<220> FEATURE:
<221> NAME/KEY: misc_feature
<222> LOCATION: (2169)..(3194)
<223> OTHER INFORMATION: hpt
<220> FEATURE:
<221> NAME/KEY: misc_feature
<222> LOCATION: (3198)..(3218)
<223> OTHER INFORMATION: attB2
<220> FEATURE:
<221> NAME/KEY: misc_feature
<222> LOCATION: (3239)..(3514)

```
<223> OTHER INFORMATION: Tnos
<220> FEATURE:
<221> NAME/KEY: misc_feature
<222> LOCATION: (3573)..(3597)
<223> OTHER INFORMATION: LB
<220> FEATURE:
<221> NAME/KEY: misc_feature
<222> LOCATION: (4139)..(4169)
<223> OTHER INFORMATION: I-CeuI
<220> FEATURE:
<221> NAME/KEY: misc_feature
<222> LOCATION: (4176)..(4583)
<223> OTHER INFORMATION: (complement) cos
<220> FEATURE:
<221> NAME/KEY: misc_feature
<222> LOCATION: (4584)..(6702)
<223> OTHER INFORMATION: (complement) IncC1
<220> FEATURE:
<221> NAME/KEY: misc_feature
<222> LOCATION: (6338)..(7414)
<223> OTHER INFORMATION: (complement) KorB
<220> FEATURE:
<221> NAME/KEY: misc_feature
<222> LOCATION: (7650)..(8471)
<223> OTHER INFORMATION: (complement) oriT
<220> FEATURE:
<221> NAME/KEY: misc_feature
<222> LOCATION: (8466)..(11636)
<223> OTHER INFORMATION: (complement) trfA1
<220> FEATURE:
<221> NAME/KEY: misc_feature
<222> LOCATION: (11633)..(12729)
<223> OTHER INFORMATION: nptIII
<220> FEATURE:
<221> NAME/KEY: misc_feature
<222> LOCATION: (12726)..(13618)
<223> OTHER INFORMATION: (complement) oriV
<220> FEATURE:
<221> NAME/KEY: misc_feature
<222> LOCATION: (13976)..(14000)
<223> OTHER INFORMATION: RB
<220> FEATURE:
<221> NAME/KEY: misc_feature
<222> LOCATION: (14158)..(14195)
<223> OTHER INFORMATION: PI-SceI

<400> SEQUENCE: 66
aagcttgggc ccttcgaaga tgttaattaa catcggtacc gagctctagg gataacaggg       60
taatcaactt tgtataataa agttgataac agggtaatag ctcgaattct agcttgcatg      120
cctgcagtgc agcgtgaccc ggtcgtgccc ctctctagag ataatgagca ttgcatgtct      180
aagttataaa aaattaccac atatttttt tgtcacactt gtttgaagtg cagtttatct      240
atctttatac atatatttaa actttactct acgaataata taatctatag tactacaata      300
atatcagtgt tttagagaat catataaatg aacagttaga catggtctaa aggacaattg      360
agtattttga caacaggact ctacagtttt atctttttag tgtgcatgtg ttctcctttt      420
tttttgcaaa tagcttcacc tatataatac ttcatccatt ttattagtac atccatttag      480
ggtttagggt taatggtttt tatagactaa tttttttagt acatctattt tattctattt      540
tagcctctaa attaagaaaa ctaaaactct attttagttt ttttatttaa taatttagat      600
ataaaataga ataaaataaa gtgactaaaa attaaacaaa tacccttaa gaaattaaaa      660 aaactaagga acatttttc ttgtttcgag tagataatgc cagcctgtta aacgccgtcg      720
acgagtctaa cggacaccaa ccagcgaacc agcagcgtcg cgtcgggcca agcgaagcag      780
acggcacggc atctctgtcg ctgcctctgg accctctcg agagttccgc tccaccgttg      840
gacttgctcc gctgtcggca tccagaaatt gcgtggcgga gcggcagacg tgagccggca      900
cggcaggcgg cctcctcctc ctctcacggc accggcagct acgggggatt cctttcccac      960
```

```
cgctccttcg ctttcccttc ctcgcccgcc gtaataaata gacacccct ccacaccctc    1020 tttccccaac ctcgtgttgt tcggagcgca cacacacaca accagatctc ccccaaatcc    1080
acccgtcggc acctccgctt caaggtacgc cgctcgtcct cccccccccc ccctctctac    1140
cttctctaga tcggcgttcc ggtccatggt tagggccggg tagttctact tctgttcatg    1200
tttgtgttag atccgtgttt gtgttagatc cgtgctgcta gcgttcgtac acggatgcga    1260
cctgtacgtc agacacgttc tgattgctaa cttgccagtg tttctctttg ggaatcctg    1320 ggatggctct agccgttccg cagacgggat cgatttcatg attttttttg tttcgttgca    1380
tagggttttg tttgcccttt tccttatt caatatatgc cgtgcacttg tttgtcgggt    1440
catcttttca tgctttttt tgtcttggtt gtgatgatgt ggtctggttg ggcggtcgtt    1500
ctagatcgga gtagaattct gtttcaaact acctggtgga tttattaatt ttggatctgt    1560
atgtgtgtgc catacatatt catagttacg aattgaagat gatggatgga aatatcgatc    1620
taggataggt atacatgttg atgcgggttt tactgatgca tatacagaga tgcttttttgt    1680 tcgcttggtt gtgatgatgt ggtgtggttg ggcggtcgtt cattcgttct agatcggagt    1740
agaatactgt ttcaaactac ctggtgtatt tattaattt ggaactgtat gtgtgtgtca    1800
tacatcttca tagttacgag tttaagatgg atggaaatat cgatctagga taggtataca    1860
tgttgatgtg ggttttactg atgcatatac atgatggcat atgcagcatc tattcatatg    1920
ctctaacctt gagtacctat ctattataat aaacaagtat gttttataat tattttgatc    1980
ttgatatact tggatgatgg catatgcagc agctatatgt ggattttttt agccctgcct    2040
tcatacgcta tttatttgct tggtactgtt tcttttgtcg atgctcaccc tgttgtttgg    2100
tgttacttct gcaggtcgac tctagaggat catcacaagt ttgtacaaaa aagcaggctc    2160
aatgagatat gaaaaagcct gaactcaccg cgacgtctgt cgagaagttt ctgatcgaaa    2220
agttcgacag cgtctccgac ctgatgcagc tctcggaggg cgaagaatct cgtgctttca    2280
gcttcgatgt aggagggcgt ggatatgtcc tgcgggtaaa tagctgcgcc gatggttct    2340 acaaagatcg ttatgtttat cggcactttg catcggccgc gctcccgatt ccggaagtgc    2400
ttgacattgg ggaattcagc gagagcctga cctattgcat ctcccgccgt gcacagggtg    2460
tcacgttgca agacctgcct gaaaccgaac tgcccgctgt tctgcagccg gtcgcggagg    2520
ccatggatgc gatcgctgcg gccgatctta gccagacgag cgggttcggc ccattcggac    2580
cgcaaggaat cggtcaatac actacatggc gtgatttcat atgcgcgatt gctgatcccc    2640
atgtgtatca ctggcaaact gtgatggacg acaccgtcag tgcgtccgtc gcgcaggctc    2700
tcgatgagct gatgctttgg gccgaggact gccccgaagt ccggcacctc gtgcacgcgg    2760
atttcggctc caacaatgtc ctgacggaca atggccgcat aacagcggtc attgactgga    2820
gcgaggcgat gttcggggat tcccaatacg aggtcgccaa catcttcttc tggaggccgt    2880
ggttggcttg tatggagcag cagacgcgct acttcgagcg gaggcatccg gagcttgcag    2940
gatcgccgcg gctccgggcg tatatgctcc gcattggtct tgaccaactc tatcagagct    3000
tggttgacgg caatttcgat gatgcagctt gggcgcaggg tcgatgcgac gcaatcgtcc    3060
gatccggagc cgggactgtc gggcgtacac aaatcgcccg cagaagcgcg gccgtctgga    3120
ccgatggctg tgtagaagta ctcgccgata gtggaaaccg acgccccagc actcgtccga    3180
gggcaaagga atagacccag ctttcttgta caaagtggtg atgatccgtc gacctgcaga    3240
tcgttcaaac atttggcaat aaagtttctt aagattgaat cctgttgccg gtcttgcgat    3300
gattatcata taatttctgt tgaattacgt taagcatgta ataattaaca tgtaatgcat    3360
```

```
gacgttattt atgagatggg tttttatgat tagagtcccg caattataca tttaatacgc    3420
gatagaaaac aaaatatagc gcgcaaacta ggataaatta tcgcgcgcgg tgtcatctat    3480
gttactagat ccgatgataa gctgtcaaac atgagaattc agtacattaa aaacgtccgc    3540
aatgtgttat taagttgtct aagcgtcaat ttgtttacac cacaatatat cctgccacca    3600
gccagccaac agctccccga ccggcagctc ggcacaaaat caccactcga tacaggcagc    3660
ccatcagtcc gggacggcgt cagcgggaga gccgttgtaa ggcggcagac tttgctcatg    3720
ttaccgatgc tattcggaag aacggcaact aagctgccgg gtttgaaaca cggatgatct    3780
cgcggagggt agcatgttga ttgtaacgat gacagagcgt tgctgcctgt gatcaaatat    3840
catctccctc gcagagatcc gaattatcag ccttcttatt catttctcgc ttaaccgtga    3900
caggctgtcg atcttgagaa ctatgccgac ataataggaa atcgctggat aaagccgctg    3960
aggaagctga gtggcgctat ttctttagaa gtgaacgttg acgatcgtcg accgtacccc    4020
gatgaattaa ttcggacgta cgttctgaac acagctggat acttacttgg gcgattgtca    4080
tacatgacat caacaatgta cccgtttgtg taaccgtctc ttggaggttc gtatgacact    4140
aggtcgctac cttaggaccg ttatagttac tagcgaattg acatgaggtt gccccgtatt    4200
cagtgtcgct gatttgtatt gtctgaagtt gttttacgt taagttgatg cagatcaatt    4260
aatacgatac ctgcgtcata attgattatt tgacgtggtt tgatggcctc cacgcacgtt    4320
gtgatatgta gatgataatc attatcactt tacgggtcct ttccggtgat ccgacaggtt    4380
acggggcggc gacctcgcgg gttttcgcta tttatgaaaa ttttccggtt taaggcgttt    4440
ccgttcttct tcgtcataac ttaatgtttt tatttaaaat accctctgaa agaaaggaa     4500
acgacaggtg ctgaaagcga gcttttggc ctctgtcgtt tcctttctct gtttttgtcc     4560
gtggaatgaa caatggaagg atcttctcgg cggcgatcac gacgccggcc ctgcggagcc    4620
ttcgccgcgt gcgcgattca tggcggccgt ggaggccaag gatttcgcgc gagtgcaaga    4680
gctgatcgag gcgcgtggag ccaagtcggc ggctgattat gtccttgcgc agctcgccgt    4740
ggccgaaggt ctggaccgca agcctggtgc gcgtcgtg gtcggaaag cggcgggcag       4800
catggcaatg ccgcctgcgg cgctgggttt tacgccaagg ggagaagcgg catacgccat    4860
cgagcggtca gcctatggtg agccgaggtc cagcattgcg aagcagtacc agcaggaatg    4920
gaaccggaag gcggcgacct ggtgggcgat ggccggtgtg gccggcatca tcggcgcgat    4980
cctggcggcg gcggcaaccg gctttgttgg gctggcagtg tcgatccgca accgagtgaa    5040
gcgcgtgcgc gacctgttgg tgatggagcc gggtgcagag ccataagcgg caagagcga    5100
aagcccggtt tccgggcttt tgttttgtta cgccaaggac gagttttagc ggctaaaggt    5160
gttgacgtgc gagaaatgtt tagctaaact tctctcatgt gctggcggct gtcaccgcta    5220
tgttcaacca aggcgcggag caaattatgg gtgttatcca tgaagaaacg gcttaccgaa    5280
agccagttcc aggaggcgat ccaggggctg gaagtgggc agcagaccat cgagatagcg    5340
cggggcgtct tagtcgatgg gaagccacag gcgacgttcg caacgtcgct gggactgacc    5400
aggggcgcag tgtcgcaagc ggtgcatcgc gtgtgggccg cgttcgagga caagaacttg    5460
cccgaggggt acgcgcgggt aacggcggtt ctgccggaac atcaggcgta catcgtccgg    5520
aagtgggaag cggacgccaa gaaaaaacag gaaaccaaac gatgaaaact ttggtcacgg    5580
ccaaccagaa aggcggcgtc ggcaagactt cgacccttgt gcatcttgcc ttcgactttt    5640
tcgagcgcgg cttgcgggtt gccgtgatcg acctggaccc ccaggcaat gcgtcctaca    5700
cgctcaagga ctttgctacc ggcctgcatg caagcaagct gttcggcgct gtccctgccg    5760
```

```
gcggctggac cgaaaccgca cccgcagccg gcgacggcca ggccgcgcgc ctcgccctca    5820
tcgagtccaa cccggtactg gcgaacgccg aacggctgtc gctggacgac gcccgcgagc    5880
tgttcggggc gaacatcaag gccctggcga accaaggctt cgacgtgtgc ctgatcgaca    5940
cggccccgac ccttggcgtc ggcctggcgg ccgccctctt cgcggccgac tatgtgctgt    6000
cccccatcga gcttgaggcg tacagcatcc agggcatcaa gaagatggtc acgaccattg    6060
cgaacgtgcg ccagaagaac gccaagctgc aattccttgg catggtgccc agcaaggtcg    6120
atgcgcggaa tccgcgccac gcgcgccacc aagccgagct gctggccgcg taccccaaga    6180
tgatgattcc ggccaccgtt ggcctgcgca gcagcatcgc cgatgccctc gcatccggtg    6240
tgccggtctg gaagatcaag aaaacggccg cgcgcaaggc atcgaaagag gttcgcgccc    6300
tggctgatta cgtgttcacg aagatggaga tttcccaatg actgcggctc aagccaagac    6360
caccaagaaa aacaccgctg cggccgctca ggaagccgca ggcgcggcgc agccgtccgg    6420
cctggggttg gatagcatcg gcgacctgtc gagcctcctg gacgctcctg cggcgtctca    6480
gggcggttcc ggccctatcg agctggacct ggacctgatc gacgaagatc cgcatcagcc    6540
gcggacggcc gacaaccccg gcttttcccc ggagagcatc gcggaaatcg gtgccacgat    6600
caaagagcgc ggggtgaagt cacccatttc ggtgcgcgag aaccaggagc agccgggccg    6660
ctatatcatc aatcacggcg cccgccgcta ccgtggctcg aagtgggccg gcaagaagtc    6720
catcccggcg ttcatcgaca acgactacaa cgaagccgac caggttatcg agaacctgca    6780
acgcaacgag ctgaccccgc gcgaaattgc cgacttcatt ggccgcgagc tggcgaaggg    6840
caagaagaaa ggcgatatcg ccaaggaaat cggcaagtcg ccggcgttca tcacccagca    6900
cgtcacgctg ctggacctgc cggagaagat cgccgatgcg ttcaacaccg gccgcgtgcg    6960
cgacgtgacc gtggtgaacg agctggtgac ggccttcaag aagcgcccgg aggaagtcga    7020
ggcgtggctt gacgacgaca cccaggaaat cacgcgcggc acggtcaagc tgctgcgcga    7080
gttcctggac gagaagggcc gcgatcccaa caccgtcgat gccttcaacg gccagactga    7140
tgccgagcgt gacgcggagg ccggcgacgg ccaggacggc gaggacggcg accaggacgg    7200
taaggacgcc aaggaaaagg gcgcgaagga gccggacccg gacaagctga aaaaggccat    7260
cgtccaggtc gagcacgacg agcgccctgc ccgccttatc ctcaaccgtc ggccgccggc    7320
ggaaggctat gcctggttga agtacgagga cgacggccag gagttcgagg cgaaccttgc    7380
cgacgtgaaa ctggtcgcgc tcatcgaggg ctgatcccca agacagcgg cgcgggccac    7440 ccgcgccgca cagacaacgg ttccgctaca aggaggaccg aagaatgaat ccgatgctgt    7500
tctacatcgc gggaggcgta ggcgcggcgt tgctgctggt ttccgcgatc atgctgttca    7560
agctgcgcga gccgaagaag gaacaccgac cgcagcgcaa ggcggcggcc ccgacgccgc    7620
agccggtcga taacgagctg ctgcgcactc tagtgatatt ccacaaaaca gcaggaagc     7680 agcgcttttc cgctgcataa ccctgcttcg gggtcattat agcgattttt tcggtatatc    7740
catccttttt cgcacgatat acaggatttt gccaaagggt tcgtgtagac tttccttggt    7800
gtatccaacg gcgtcagccg ggcaggatag gtgaagtagg cccacccgcg agcgggtgtt    7860
ccttcttcac tgtcccttat tcgcacctgg cggtgctcaa cgggaatcct gctctgcgag    7920 gctgccggc taccgccggc gtaacagatg agggcaagcg gatggctgat gaaaccaagc     7980
caaccaggaa gggcagccca cctatcaagg tgtactgcct tccagacgaa cgaagagcga    8040
ttgaggaaaa ggcggcggcg gccggcatga gcctgtcggc ctacctgctg gccgtcggcc    8100
agggctacaa aatcacgggc gtcgtggact atgagcacgt ccgcgagctg gcccgcatca    8160
```

```
atggcgacct gggccgcctg ggcggcctgc tgaaactctg gctcaccgac gacccgcgca   8220
cggcgcggtt cggtgatgcc acgatcctcg ccctgctggc gaagatcgaa gagaagcagg   8280
acgagcttgg caaggtcatg atgggcgtgg tccgcccgag ggcagagcca tgactttttt   8340
agccgctaaa acggccgggg ggtgcgcgtg attgccaagc acgtccccat cgctccatc    8400 aagaagagcg acttcgcgga gctggtgaag tacatcaccg acgagcaagg caagaccgag   8460
cgccagatcc aaaacaactg tcaaagcgca cccgcccgat gccattcgcg cacggcttc    8520 cgttgaggat gtcgatatga tgcgcgagcc gacggcccgc agagaagggg ccgttttagc   8580
ggctaaagaa ggaagtgcaa gccctaaccc ttggcgtcag agccttccac gcagcttttt   8640
tcgggtgtcg tcgccccatt tctttacgat aaacgcctta tgtgacggca aaccacact    8700 gatgcgttcg tatccgggcg gcacgctgct cttgaaagga tgacccgcaa tctccgcgag   8760
tgcctcgcgg tcaaggtcgg tggactccag gagaagaggt aggggagttt ccagggcgtc   8820
ggcaatggcc tccatcacct caacgaggg gttggcctta ccgttggtta agtctgataa    8880
aaacgaaatt gaaaccctg ccctctccga cagctcatgt ttcgtcatgc cccgctcatc     8940
gagcagacga aggatgttgg tgaaaaatat ctggttgtac acagcggaag ccgcccctcg   9000 caccttggt cgcggcccgc aaaattttag ccgctaaagt tcttgacagc ggaaccaatg     9060
tttagctaaa ctagagtctc ctttctcaag gagactttcg atatgagcca taatcagttc   9120
cagtttatcg gtaatcttac ccgtgacacc gaggtacgtc atggcaattc taacaagccg   9180
caagcaattt tcgatatagc ggttaatgaa gagtggcgca acgatgccgg cgacaagcag   9240
gagcgcaccg acttcttccg catcaagtgt tttggctctc aggccgaggc ccacggcaag   9300
tatttgggca aggggtcgct ggtattcgtg cagggcaaga ttcggaatac caagtacgag   9360
aaggacggcc agacggtcta cgggaccgac ttcattgccg ataaggtgga ttatctggac   9420
accaaggcac caggcgggtc aaatcaggaa taagggcaca ttgccccggc gtgagtcggg   9480
gcaatcccgc aaggagggtg aatgaatcgg acgtttgacc ggaaggcata caggcaagaa   9540
ctgatcgacg cggggttttc cgccgaggat gccgaaacca tcgcaagccg caccgtcatg   9600
cgtgcgcccc gcgaaacctt ccagtccgtc ggctcgatgg tccagcaagc tacggccaag   9660
atcgagcgcg acagcgtgca actggctccc cctgccctgc ccgcgccatc ggccgccgtg   9720
gagcgttcgc gtcgtctcga acaggaggcg gcaggtttgg cgaagtcgat gaccatcgac   9780
acgcgaggaa ctatgacgac caagaagcga aaaaccgccg gcgaggacct ggcaaaacag   9840
gtcagcgagg ccaagcaggc cgcgttgctg aaacacacga agcagcagat caaggaaatg   9900 cagcttttcct tgttcgatat tgcgccgtgg ccggacacga tgcgagcgat gccaaacgac   9960
acggcccgct ctgccctgtt caccacgcgc aacaagaaaa tcccgcgcga ggcgctgcaa   10020
aacaaggtca ttttccacgt caacaaggac gtgaagatca cctacaccgg cgtcgagctg   10080
cgggccgacg atgacgaact ggtgtggcag caggtgttgg agtacgcgaa cgcgcacccct   10140 atcggcgagc cgatcaccct cacgttctac gagctttgcc aggacctggg ctggtcgatc   10200 aatgccggg attacacgaa ggccgaggaa tgcctgtcgc gcctacaggc gacggcgatg   10260
ggcttcacgt ccgaccgcgt tgggcacctg gaatcggtgt cgctgctgca ccgcttccgc   10320
gtcctggacc gtggcaagaa aacgtcccgt tgccaggtcc tgatcgacga ggaaatcgtc   10380
gtgctgtttg ctggcgacca ctacacgaaa ttcatatggg agaagtaccg caagctgtcg   10440
ccgacggccc gacggatgtt cgactatttc agctcgcacc gggagccgta cccgctcaag   10500
ctggaaacct tccgcctcat gtgcggatcg gattccaccc gcgtgaagaa gtggcgcgag   10560
```

```
caggtcggcg aagcctgcga agagttgcga ggcagcggcc tggtggaaca cgcctgggtc    10620
aatgatgacc tggtgcattg caaacgctag ggccttgtgg ggtcagttcc ggctgggggt    10680
tcagcagcca gcgctttact ggcatttcag gaacaagcgg gcactgctcg acgcacttgc    10740
ttcgctcagt atcgctcggg acgcacggcg cgctctacga actgccgata aacagaggat    10800
taaaattgac aattgtgatt aaggctcaga ttcgacggct tggagcggcc gacgtgcagg    10860
atttccgcga gatccgattg tcggccctga agaaagctcc agagatgttc gggtccgttt    10920
acgagcacga ggagaaaaag cccatggagg cgttcgctga acggttgcga gatgccgtgg    10980
cattcggcgc ctacatcgac ggcgagatca ttgggctgtc ggtcttcaaa caggaggacg    11040
gccccaagga cgctcacaag gcgcatctgt ccggcgtttt cgtggagccc gaacagcgag    11100
gccgaggggt cgccggtatg ctgctgcggg cgttgccggc gggtttattg ctcgtgatga    11160
tcgtccgaca gattccaacg ggaatctggt ggatgcgcat cttcatcctc ggcgcactta    11220
atatttcgct attctggagc ttgttgttta tttcggtcta ccgcctgccg ggcgggtcgc    11280
ggcgacggta ggcgctgtgc agccgctgat ggtcgtgttc atctctgccg ctctgctagg    11340
tagcccgata cgattgatgg cggtcctggg ggctatttgc ggaactgcgg gcgtggcgct    11400
gttggtgttg acaccaaacg cagcgctaga tcctgtcggc gtcgcagcgg gcctggcggg    11460
ggcggtttcc atggcgttcg gaaccgtgct gacccgcaag tggcaacctc ccgtgcctct    11520
gctcaccttt accgcctggc aactggcggc cggaggactt ctgctcgttc cagtagcttt    11580
agtgtttgat ccgccaatcc cgatgcctac aggaaccaat gttctcggct gctcgactgc    11640
acgaatacca gcgacccctt gcccaaatac ttgccgtggg cctcggcctg agagccaaaa    11700
cacttgatgc ggaagaagtc ggtgcgctcc tgcttgtcgc cggcatcgtt gcgccacatc    11760
taggtactaa aacaattcat ccagtaaaat ataatatttt attttctccc aatcaggctt    11820
gatccccagt aagtcaaaaa atagctcgac atactgttct tccccgatat cctccctgat    11880
cgaccggacg cagaaggcaa tgtcatacca cttgtccgcc ctgccgcttc tcccaagatc    11940
aataaagcca cttactttgc catctttcac aaagatgttg ctgtctccca ggtcgccgtg    12000
ggaaaagaca agttcctctt cgggcttttc cgtctttaaa aaatcataca gctcgcgcgg    12060
atctttaaat ggagtgtctt cttcccagtt ttcgcaatcc acatcggcca gatcgttatt    12120
cagtaagtaa tccaattcgg ctaagcggct gtctaagcta ttcgtatagg gacaatccga    12180
tatgtcgatg gagtgaaaga gcctgatgca ctccgcatac agctcgataa tcttttcagg    12240
gctttgttca tcttcatact cttccgagca aaggacgcca tcggcctcac tcatgagcag    12300
attgctccag ccatcatgcc gttcaaagtg caggacctttt ggaacaggca gctttccttc    12360
cagccatagc atcatgtcct tttccgttc cacatcatag gtggtccctt tataccggct    12420
gtccgtcatt tttaaatata ggttttcatt ttctcccacc agcttatata ccttagcagg    12480
agacattcct tccgtatctt ttacgcagcg gtattttcg atcagttttt tcaattccgg    12540
tgatattctc attttagcca tttattattt ccttcctctt ttctacagta tttaaagata    12600
ccccaagaag ctaattataa caagacgaac tccaattcac tgttccttgc attctaaaac    12660
cttaaatacc agaaaacagc ttttcaaag ttgttttcaa agttggcgta taacatagta    12720
tcgattcgat agcgtggact caaggctctc gcgaatggct cgcgttggaa actttcattg    12780
acacttgagg ggcaccgcag ggaaattctc gtccttgcga gaaccggcta tgtcgtgctg    12840
cgcatcgagc ctgcgccctt ggcttgtctc gcccctctcc gcgtcgctac ggggcttcca    12900
gcgcctttcc gacgctcacc gggctggttg ccctcgccgc tgggctggcg gccgtctatg    12960
```

-continued

```
gccctgcaaa cgcgccagaa acgccgtcga agccgtgtgc gagacaccgc ggccgccggc  13020
gttgtggata cctcgcggaa aacttggccc tcactgacag atgaggggcg gacgttgaca  13080
cttgaggggc cgactcaccc ggcgcggcgt tgacagatga ggggcaggct cgatttcggc  13140
cggcgacgtg gagctggcca gcctcgcaaa tcggcgaaaa cgcctgattt tacgcgagtt  13200
tcccacagat gatgtggaca agcctgggga taagtgccct gcggtattga cacttgaggg  13260
gcgcgactac tgacagatga ggggcgcgat ccttgacact tgaggggcag agtgctgaca  13320
gatgaggggc gcacctattg acatttgagg ggctgtccac aggcagaaaa tccagcattt  13380
gcaagggttt ccgcccgttt ttcggccacc gctaacctgt cttttaacct gcttttaaac  13440
caatatttat aaaccttgtt tttaaccagg gctgcgccct gtgcgcgtga ccgcgcacgc  13500 cgaaggggg tgcccccct tctcgaaccc tcccggcccg ctaacgcggg cctcccatcc  13560
ccccaggggc tgcgcccctc ggccgcgaac ggcctcaccc caaaaatggc agcgccagcc  13620
aggacgtcgg ccgaaagagc gacaagcaga tcacgctttt cgacagcgtc ggatttgcga  13680
tcgaggattt ttcggcgctg cgctacgtcc gcgaccgcgt tgagggatca agccacagca  13740
gcccactcga ccttctagcc gacccagacg agccaaggga tcttttttgga atgctgctcc  13800 gtcgtcaggc tttccgacgt ttgggtggtt gaacagaagt cattatcgca cggaatgcca  13860
agcactcccg aggggaaccc tgtggttggc atgcacatac aaatggacga acggataaac  13920
cttttcacgc cctttaaaat atccgattat tctaataaac gctcttttct cttaggttta  13980
cccgccaata tatcctgtca aacactgata gtttaaactg aaggcgggaa acgacaatct  14040
gatcatgagc ggagaattaa gggagtcacg ttatgacccc cgccgatgac gcgggacaag  14100
ccgttttacg tttggaactg acagaaccgc aacgttgaag gagccactca gcaagctatc  14160
tatgtcgggt gcggagaaag aggtaatgaa atggc                              14195
```

<210> SEQ ID NO 67
<211> LENGTH: 4836
<212> TYPE: DNA
<213> ORGANISM: Artificial Sequence
<220> FEATURE:
<223> OTHER INFORMATION: Synthetic vector: pVGW2
<220> FEATURE:
<221> NAME/KEY: misc_feature
<222> LOCATION: (8)..(1086)
<223> OTHER INFORMATION: virG N54D
<220> FEATURE:
<221> NAME/KEY: misc_feature
<222> LOCATION: (1087)..(3836)
<223> OTHER INFORMATION: IncW ori-containing region
<220> FEATURE:
<221> NAME/KEY: misc_feature
<222> LOCATION: (1772)..(2743)
<223> OTHER INFORMATION: IncW repA
<220> FEATURE:
<221> NAME/KEY: misc_feature
<222> LOCATION: (2832)..(3214)
<223> OTHER INFORMATION: IncW ori
<220> FEATURE:
<221> NAME/KEY: misc_feature
<222> LOCATION: (3837)..(4645)
<223> OTHER INFORMATION: gen(Gentamicin acetyltransferase)

<400> SEQUENCE: 67

```
aaatggccat aggcgatctc cttaatcaat agtagctgta acctcgaagc gtttcacttg    60
taacaacgat tgagaacttt tgtcataaaa ttgaaatact tggttcgcat tttcgtcatc   120
cgcggtcagc cgcaattctg acgaactgcc catttagctg gagatgattg tacatccttc   180
acgtgaaaat ttctcaagcg ctgtgaacaa gggttcagat tttagattga aaggtgagcc   240
```

```
gttgaaacac gttcttctta tcgatgacga tgtcgctatg cggcatctta ttatcgaata    300
ccttacgatc cacgccttca aagtgaccgc ggtagccgac agcacccagt tcactagagt    360
actctcttcc gcgacggtcg atgtcgtggt tgttgatcta gatttaggtc gtgaagatgg    420
gcttgagatc gttcgaaatc tggcggcaaa gtctgatatt ccaatcataa ttatcagtgg    480
cgaccgcctt gaggagacgg ataaagttgt tgcactcgag ctaggagcaa gtgattttat    540
cgctaagccg tttagtacga gagagtttct tgcacgcatt cgggttgcct tgcgcgtgcg    600
ccccaacgtt gtccgctcca aagaccgacg gtcttttttgt tttactgact ggacacttaa    660
tctcaggcaa cgtcgcttga tgtccgaagc tggcggtgag gtgaaactta cggcaggtga    720
gttcaatctt ctcctcgcgt ttttagagaa accccgcgac gttctatcgc gcgagcaact    780
tctcattgcc agtcgagtac gcgacgagga ggtttacgac aggagtatag atgttctcat    840
tttgcggctg cgccgcaaac ttgaggcgga tccgtcaagc cctcaactga taaaaacagc    900
aagaggtgcc ggttatttct ttgacgcgga cgtgcaggtt tcgcacgggg ggacgatggc    960
agcctgagcc aattgcattt ggctcttaat tatctggctc aaaaggtgac tgaggacgcg    1020
gccagcggcc tcaaacctac actcaatatt tggtgagggg ttccgatagg tccctcttca    1080
cctgcatggc atgtttaacc gaatctgacg ttttccctgc aaatgccaaa atactatgcc    1140
tatctccggg tttcgcgtga cggccaagac ccggaaaacc aaaaatacgg tttgctcgaa    1200
tacgcgaacg ccaaaggctt cgcgccgcta cagatcgagg aagaaattgc cagcagagca    1260
aaggactggc gcaagcgcaa gctcggagca atcatcgaaa aggccgagcg tggcgacgtg    1320
ctactgacgc cggagattac gcgcattgcc ggttccgccc tcgccgcctt ggaaattctc    1380
aaagcggcga gcgagcgcgg cctaatcgtc catgtgacca aacagaagat catcatggac    1440
ggcagcctac aaagcgacat catggcaacc gtgcttggct tggctgcaca gatcgagcgg    1500
catttcattc aggcacgtac caccgaggcg ctacaagtcg ccagagagcg cggcaagacg    1560
ctcgggcgac ccaagggcag caaatcgagc gccttgaagc tggacagccg tattgatgaa    1620
gtacaggcat acgtgaacct tggcttgccg caaagtcgcg cagccgagtt gttaggcgtc    1680
agccctcaca ccttgcgcct gttcatcaaa cgccggaaca tcaaacccac aaacactaga    1740
ccaaccatca ccatgccggg gagggaacaa catgcctaag aacaacaaag ccccccggcca    1800 tcgtatcaac gagatcatca agacgagcct cgcgctcgaa atggaggatg cccgcgaagc    1860
tggcttagtc ggctacatgg cccgttgcct tgtgcaagcg accatgcccc acaccgaccc    1920
caagaccagc tactttgagc gcaccaatgg catcgtcacc ttgtcgatca tgggcaagcc    1980
gagcatcggc ctgccctacg gttctatgcc gcgcaccttg cttgcttgga tatgcaccga    2040
ggccgtgcga acgaaagacc ccgtgttgaa ccttggccgg tcgcaatcgg aatttctaca    2100
aaggctcgga atgcacaccg atggccgtta cacggccacc cttcgcaatc aggcgcaacg    2160
cctgttttca tccatgattt cgcttgccgg cgagcaaggc aatgacttcg gcattgagaa    2220
cgtcgtcatt gccaagcgcg ctttttctatt ctggaatccc aagcggccag aagatcgggc    2280
gctatgggat agcacccctca ccctcacagg cgatttcttc gaggaagtca cccgctcacc    2340
ggttcctatc cgaatcgact acctgcatgc cttgcggcag tctccgcttg cgatggacat    2400
ttacacgtgg ctgacctatc gcgtgttcct gttgcgggcc aagggccgcc ccttcgtgca    2460
aatcccttgg gtcgccctgc aagcgcaatt cggctcatcc tatggcagcc gcgcacgcaa    2520
ctcgcccgaa ctgacgata aggcccgaga gcgggcagag cgggcagcac tcgccagctt    2580
caaatacaac ttcaaaaagc gcctacgcga agtgttgatt gtctatcccg aggcaagcga    2640
```

```
ctgcatcgaa gatgacggcg aatgcctgcg catcaaatcc acacgcctgc atgtcacccg    2700 cgcaccggc aagggcgctc gcatcggccc ccctccgact tgaccaggcc aacgctacgc     2760
ttggcttggt caagccttcc catccaacag cccgccgtcg agcgggcttt tttatccccg    2820
gaagcctgtg gatagagggt agttatccac gtgaaaccgc taatgccccg caaagccttg   2880
attcacgggg ctttccggcc cgctccaaaa actatccacg tgaaatcgct aatcagggta   2940
cgtgaaatcg ctaatcggag tacgtgaaat cgctaataag gtcacgtgaa atcgctaatc   3000
aaaaaggcac gtgagaacgc taatagccct ttcagatcaa cagcttgcaa acacccctcg   3060
ctccggcaag tagttacagc aagtagtatg ttcaattagc ttttcaatta tgaatatata   3120
tatcaattat tggtcgccct tggcttgtgg acaatgcgct acgcgcaccg gctccgcccg   3180
tggacaaccg caagcggttg cccaccgtcg agcgcctttg cccacaaccc ggcggccgca   3240
acagatcgtt ttataaattt ttttttttga aaagaaaaa gcccgaaagg cggcaacctc    3300
tcgggcttct ggatttccga tcaacgcagg agtcgttcgg aaagtagctg ttccagaatt   3360
ataggcgcag agacaccaga ttccaagatg gctctgttaa attgttgtag tatgtagtat   3420
catacaacat actacagtac agaggcccgc aagaatggca atcactaaac aagcatttg    3480 gcgagcagcc gacgaactgg acgccgaagg catccggccc actttggccg ccgtgcgcaa   3540
gaaactcgga agcggtagct tcacaaccat ttccgatgca atggctgaat ggaaaaaccg   3600
caagaccgcc accctgccct catcagaccc attgccggtt gcagtcaacg agcatcttgc   3660
cgagcttggc aatgcgctat gggctatcgc cctggcgcac gccaacgccc ggtttgacga   3720
agatcggaaa cagatcgagg ccgacaaagc ggccatcagc cagcagcttg ccgaagcaat   3780
cgaactagcc gacaccttca cccgcgaaaa cgaccagctc cgcgaacgag tagatcccgg   3840
gttgacataa gcctgttcgg ttcgtaaact gtaatgcaag tagcgtatgc gctcacgcaa   3900
ctggtccaga accttgaccg aacgcagcgg tggtaacggc gcagtggcgg ttttcatggc   3960
ttgttatgac tgtttttttg tacagtctat gcctcgggca tccaagcagc aagcgcgtta   4020
cgccgtgggt cgatgtttga tgttatggag cagcaacgat gttacgcagc agcaacgatg   4080
ttacgcagca gggcagtcgc cctaaaacaa agttaggtgg ctcaagtatg gcatcattc    4140 gcacatgtag gctcggccct gaccaagtca aatccatgcg ggctgctctt gatcttttcg   4200
gtcgtgagtt cggagacgta gccacctact cccaacatca gccggactcc gattacctcg   4260
ggaacttgct ccgtagtaag acattcatcg cgcttgctgc cttcgaccaa gaagcggttg   4320
ttggcgctct cgcggcttac gttctgccca gtttgagca gccgcgtagt gagatctata    4380
tctatgatct cgcagtctcc ggcgagcacc ggaggcaggg cattgccacc gcgctcatca   4440
atctcctcaa gcatgaggcc aacgcgcttg gtgcttatgt gatctacgtg caagcagatt   4500
acggtgacga tcccgcagtg gctctctata caaagttggg catacgggaa gaagtgatgc   4560
actttgatat cgacccaagt accgccacct aacaattcgt tcaagccgag atcggcttcc   4620
cggccgcgga gttgttcggt aaattgctag ctttaagggc gaattctgca gatatccatc   4680
acactggcgg ccgctcgagc atgcatctag agggcccaat tcgccctata gtgagtcgta   4740
ttacaattca ctggccgtcg ttttacaacg tcgtgactgg gaaaaccctg gcgttaccca   4800
```

-continued acttaatcgc cttgcagcac atcccccttt cgccag     4836

<210> SEQ ID NO 68
<211> LENGTH: 29
<212> TYPE: DNA
<213> ORGANISM: Artificial Sequence
<220> FEATURE:
<223> OTHER INFORMATION: Synthetic primer for amplification

<400> SEQUENCE: 68
cggtctagag tgcgcagcag ctcgttatc     29

<210> SEQ ID NO 69
<211> LENGTH: 43
<212> TYPE: DNA
<213> ORGANISM: Artificial Sequence
<220> FEATURE:
<223> OTHER INFORMATION: Synthetic primer for amplification

<400> SEQUENCE: 69
agctatctat gtcgggtgcg gagaaagagg taatgaaatg gca     43

<210> SEQ ID NO 70
<211> LENGTH: 43
<212> TYPE: DNA
<213> ORGANISM: Artificial Sequence
<220> FEATURE:
<223> OTHER INFORMATION: Synthetic primer for amplification

<400> SEQUENCE: 70
agcttgccat ttcattacct ctttctccgc acccgacata gat     43

<210> SEQ ID NO 71
<211> LENGTH: 34
<212> TYPE: DNA
<213> ORGANISM: Artificial Sequence
<220> FEATURE:
<223> OTHER INFORMATION: Synthetic primer for amplification

<400> SEQUENCE: 71
cagggtaatc aactttgtat aataaagttg ataa     34

<210> SEQ ID NO 72
<211> LENGTH: 34
<212> TYPE: DNA
<213> ORGANISM: Artificial Sequence
<220> FEATURE:
<223> OTHER INFORMATION: Synthetic primer for amplification

<400> SEQUENCE: 72
caactttatt atacaaagtt gattaccctg ttat     34

<210> SEQ ID NO 73
<211> LENGTH: 60
<212> TYPE: DNA
<213> ORGANISM: Artificial Sequence
<220> FEATURE:
<223> OTHER INFORMATION: Synthetic primer for amplification

<400> SEQUENCE: 73
gggtagttct acttctgttc atgtttgtgt tagatccgtg tttgtgttag atccgtgctg     60

<210> SEQ ID NO 74
<211> LENGTH: 66
<212> TYPE: DNA
<213> ORGANISM: Artificial Sequence
<220> FEATURE:

```
<223> OTHER INFORMATION: Synthetic primer for amplification

<400> SEQUENCE: 74
ctagcgccgg atctaacaca aacacggatc taacacaaac atgaacagaa gtagaactac    60
ccggcc                                                                66

<210> SEQ ID NO 75
<211> LENGTH: 13
<212> TYPE: DNA
<213> ORGANISM: Artificial Sequence
<220> FEATURE:
<223> OTHER INFORMATION: Synthetic primer for amplification

<400> SEQUENCE: 75
agcttgggcc ctt                                                        13

<210> SEQ ID NO 76
<211> LENGTH: 8
<212> TYPE: DNA
<213> ORGANISM: Artificial Sequence
<220> FEATURE:
<223> OTHER INFORMATION: Synthetic primer for amplification

<400> SEQUENCE: 76 agggccca                                                               8

<210> SEQ ID NO 77
<211> LENGTH: 36
<212> TYPE: DNA
<213> ORGANISM: Artificial
<220> FEATURE:
<223> OTHER INFORMATION: Synthetic primer for amplification

<400> SEQUENCE: 77
aaaggatccc gggttgacat aagcctgttc ggttcg                               36

<210> SEQ ID NO 78
<211> LENGTH: 31
<212> TYPE: DNA
<213> ORGANISM: Artificial Sequence
<220> FEATURE:
<223> OTHER INFORMATION: Synthetic primer for amplification

<400> SEQUENCE: 78
aaagctagca atttaccgaa caactccgcg g                                    31

<210> SEQ ID NO 79
<211> LENGTH: 30
<212> TYPE: DNA
<213> ORGANISM: Artificial Sequence
<220> FEATURE:
<223> OTHER INFORMATION: Synthetic primer for amplification

<400> SEQUENCE: 79
aaatggccat aggcgatctc cttaatcaat                                      30

<210> SEQ ID NO 80
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 80
agtgtgtggc atggtgcatt tccg                                            24
```

```
<210> SEQ ID NO 81
<211> LENGTH: 24
<212> TYPE: DNA
<213> ORGANISM: Artificial Sequence
<220> FEATURE:
<223> OTHER INFORMATION: Synthetic primer for amplification

<400> SEQUENCE: 81
ctctacagga tacacggtgt aagg                                          24
```